United States Patent
Bergmanis et al.

(10) Patent No.: US 7,186,743 B2
(45) Date of Patent: Mar. 6, 2007

(54) SUBSTITUTED PYRAZOLYL COMPOUNDS FOR THE TREATMENT OF INFLAMMATION

(75) Inventors: Arija A. Bergmanis, Des Plaines, IL (US); Michael Clare, Skokie, IL (US); Joyce Z. Crich, Glenview, IL (US); Lifeng Geng, Skokie, IL (US); Timothy J. Hagen, Gurnee, IL (US); Gunnar J. Hanson, Skokie, IL (US); Stephen C. Houdek, Des Plaines, IL (US); He Huang, Northbrook, IL (US); Donna M. Iula, Palatine, IL (US); Francis J. Koszyk, Prospect Heights, IL (US); Shuyuan Liao, Northbrook, IL (US); Scott B. Mohler, Chicago, IL (US); Maria Nguyen, Morton Grove, IL (US); Richard A. Partis, Evanston, IL (US); Michael A. Stealey, Libertyville, IL (US); Michael B. Tollefson, Hainesville, IL (US); Richard M. Weier, Lake Bluff, IL (US); Xiangdong Xu, Gurnee, IL (US); Dominique Bonafoux, Saint Louis, MO (US); Theresa R. Fletcher, Kirkwood, MO (US); Bruce C Hamper, Kirkwood, MO (US); Patrick J. Lennon, Webster Groves, MO (US); Subo Liao, Ballwin, MO (US); Suzanne Metz, Chesterfield, MO (US); David S. Oburn, Ferguson, MO (US); Thomas J. Owen, Chesterfield, MO (US); Angela M. Scates, Des Peres, MO (US); Michael L. Vazquez, Ballwin, MO (US); Serge G. Wolfson, Chesterfield, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 11/113,926

(22) Filed: Apr. 25, 2005

(65) Prior Publication Data

US 2005/0256180 A1    Nov. 17, 2005

Related U.S. Application Data

(62) Division of application No. 10/247,096, filed on Sep. 19, 2002, now Pat. No. 6,956,052.

(60) Provisional application No. 60/379,090, filed on May 9, 2002, provisional application No. 60/323,423, filed on Sep. 19, 2001.

(51) Int. Cl.
  *A61K 31/416*   (2006.01)
  *A61K 31/454*   (2006.01)
  *A61K 31/5395*  (2006.01)
  *A61K 31/429*   (2006.01)
  *A61K 31/433*   (2006.01)
  *A61K 31/506*   (2006.01)
  *A61K 31/496*   (2006.01)

(52) U.S. Cl. .............. 514/406; 514/338; 514/364; 514/370; 514/362; 514/274; 514/253.09; 514/232.8

(58) Field of Classification Search ............ 514/406, 514/338, 364, 370, 362, 274, 253.09, 232.8
See application file for complete search history.

(56) References Cited

U.S. PATENT DOCUMENTS 6,956,052 B2 * 10/2005 Bergmanis et al. ......... 514/406

* cited by examiner

*Primary Examiner*—Kamal A. Saeed
*Assistant Examiner*—Michael Barker
(74) *Attorney, Agent, or Firm*—Philip B. Polster, II

(57) ABSTRACT

The present invention relates to substituted pyrazolyl derivatives, compositions comprising such, intermediates, methods of making substituted pyrazolyl derivatives, and methods for treating cancer, inflammation, and inflammation-associated disorders, such as arthritis.

27 Claims, No Drawings

SUBSTITUTED PYRAZOLYL COMPOUNDS FOR THE TREATMENT OF INFLAMMATION

This application is a divisional application of U.S. application Ser. No. 10/247,096, filed Sep. 19, 2002, now U.S. Pat. No. 6,956,052 which claims priority under 35 U.S.C. §119 to U.S. Provisional Application Ser. No. 60/323,423, filed Sep. 19, 2001, and U.S. Provisional Application Ser. No. 60/379,090, filed May 9, 2002, which are all incorporated by reference in their entirety as if written herein.

FIELD OF THE INVENTION

The present invention in general is in the field of anti-inflammatory pharmaceutical agents and specifically relates to substituted pyrazolyl derivatives, compositions comprising such, and methods for treating cancer, inflammation, and inflammation-associated disorders, such as arthritis.

BACKGROUND OF THE INVENTION

The following description of the background of the invention is provided to aid in the understanding the invention, but is not admitted to be or describe prior art to the invention.

NF-κB is a ubiquitous transcription factor that plays a prominent role in the activation of the immune system and in stress responses by regulating the transcription of many early, inducible genes including proinflammatory cytokines, adhesion molecules, growth factors, enzymes, and receptors (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Specificity of gene expression is determined at a cellular level by a diverse array of external stimuli such as bacterial products including LPS, as well as cytokines, most importantly tumor necrosis factor-α (TNFα) and interleukin-β (IL1β). Through the synergistic interaction with other transcription factors, further specificity can be achieved while maintaining enormous potential to coordinately induce a large number of functionally related genes. NF-κB is composed of homo and heterodimers of the Rel protein family and is sequestered in an inactive form in the cytoplasm by members of the IκB family of inhibitory proteins (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). IκBs mask the nuclear localization signal on NF-κB, preventing nuclear translocation and hence DNA binding to the promoter regions of responsive genes. Stimulation of cells with an agonist that activates NF-κB leads to a series of biochemical signals, ultimately resulting in the phosphorylation, ubiquitinylation, and degradation of IκBs, thereby releasing NF-κB for nuclear translocation (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Recently, two IκB kinases (IKK1 or IKKα and IKK2 or IKKβ), which phosphorylate IκBs and thereby initiate their degradation, have been cloned and characterized by a number of laboratories (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). The catalytic subunits, IKK1 and IKK2, are similar structurally as well as enzymatically and exist as a heterodimer in a large protein complex referred to as the IKK signalsome (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. And Goeddel, D. V. (1997) *Science* 278, 866–869). A third protein, NEMO (IKKγ, IKKAP1), is a regulatory adapter protein necessary for IKK activation and kinase activity (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538). IKK1 and IKK2 are co-expressed in most human adult tissues as well as in different developmental stages of mouse embryos (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Hu, M. C. T., and Wang, Y. (1998) *Gene* 222, 31–40). This kinase complex appears to represent a critical, common denominator in the activation of NF-κB in a number of signal transduction pathways stimulated by a variety of agonists including cytokines, such as TNFα and IL1β, microbial products such as LPS and viral proteins such as TAX, as well as phorbol esters, oxidizing agents and serine/tyrosine phosphatases (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342).

IKK1 (also termed IKKα, Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. And Roa, A. (1997) *Science* 278, 860–866) was cloned simultaneously by standard biochemical purification of the IκB kinase activity from TNFα stimulated HeLa S3 cells and by its interaction with the MAP3K, NF-κB inducing kinase (NIK), in a yeast two-hybrid screen. IKK1 was identified as the previously cloned serine-threonine kinase, CHUK (Connelly, M. and Marcu, K. (1995) *Cell. Mol. Biol. Res.* 41, 537–549). IKK1 (also termed IKKα) is an 85 kDa, 745 amino acid protein that contains an N-terminal serine/threonine kinase catalytic domain, a leucine zipper-like amphipathic helix, and a C-terminal helix-loop-helix domain. IKK2 (also termed IKKβ) was also cloned by standard biochemical purification, copurifying with IKK1 from TNFα stimulated HeLa S3 cells as well as by being identified in the public database from an EST clone with sequence homology to IKK1 (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. And Goeddel, D. V. (1997) *Science* 278, 866–869). IKK2 is an 87 kDa, 756 amino acid protein with the same over all topology as IKK1 except for the addition of an 11 amino acid extension at the C-terminus. IKK1 and IKK2 are 52% identical overall with 65% identity in the kinase domain and 44% identity in the protein interaction domains in the C-terminus. Data obtained using transient mammalian expression analysis, by in vitro translation experiments and by coexpression in a baculoviral system reveals that IKK1 and IKK2 associate preferentially as a heterodimer through their leucine zipper motifs. Although homodimers have also been described in these systems, the heterodimer is thought to be the physiologic form of the kinase in mammalian cells (Zandi, E. Rothwarf, D. M., Delhase, M., Hayadawa, M and Karin, M. (1997) *Cell* 91, 243–252; Li, J., Peet, G. W., Pullen, S. S., Schembri-King, J., Warren, T. C., Marcu, K. B., Kehry, M. R., Barton, R. and Jakes, S. (1998) *J. Biol. Chem.* 273, 30736–30741). Finally, NEMO (also termed IKKγ) contains three α-helical regions including a leucine zipper, interacts preferentially with IKK2 and is required for activation of the heterodimeric kinase complex perhaps by bringing other proteins into the signalsome complex (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538).

The kinase activities of IKK1 and IKK2 are regulated by phosphorylation and require an intact leucine zipper (LZ) for dimerization as well as an intact helix-loop-helix (HLH) domain, which can exert a positive regulatory effect on kinase activity even when it is expressed in trans with the remainder of the IKK protein (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Delhase, M., Hayakawa, M., Chen, Y., and Karin, M. (1999) *Science* 284, 309–313). Both IKK subunits contain a canonical MAPKK activation loop motif near the N-terminus which is the target for phosphorylation and activation of kinase activity by MAP3Ks such as NIK and MEKK1, although the physiologic regulation by these two upstream kinases awaits further characterization (Zandi, E., and Karin, M. (1999) *Mol. Cell. Biol.* 19, 4547–4551; Karin, M. (1999) *J. Biol. Chem.* 274, 27339–27342; Karin, M., and Delhase, M. (1998) *Proc. Natl. Acad. Sci. USA* 95, 9067–9069). Finally, phosphorylation of serines in the C-terminus of IKK2 results in a decrease in IKK activity and it is postulated to be responsible for the transient kinase activity seen after stimulation of cells with an agonist (Dehase, M., Hayakawa, M., Chen, Y., and Karin, M. (1999) *Science* 284, 309–313).

IKK2 demonstrates a more potent kinase activity compared to IKK1 using IκBα or IκBβ as a substrate (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Delhase, M., Hayakawa, M., Chen, Y., and Karin, M. (1999) *Science* 284,309–313). Mutations of the phospho-acceptor serine residues within the MAPKK activation loop alters IKK2 kinase activity; the serine to alanine substitutions result in decreased kinase activity whereas the serine to glutamic acid substitutions result in a constitutively active kinase. Similar alanine mutations in IKK1 do not result in a decreased stimulation of total IKK activity in response to TNFα or IL1β (Dehase, M., Hayakawa, M., Chen, Y., and Karin, M. (1999) *Science* 284, 309–313). IKK2 being the dominant kinase activity within the IKK complex is further supported by the analysis of fibroblasts from mice deficient in IKK1 or IKK2. Fibroblasts lacking IKK1 retain full IKK activity in response to cytokines and could activate NF-κB. In contrast, fibroblasts lacking IKK2 do not exhibit IKK activity when stimulated with cytokines nor do they activate NF-κB. Furthermore, the phenotypes of each IKK knock out is unique with IKK1 deficiency resulting in skin and skeletal defects and IKK2 knock out being embryonic lethal due to hepatocyte apoptosis (Li, Q., Antwerp, D. V., Mercurio, F., Lee, K., and Verma, I. M. (1999) *Science* 284, 321–325; Takeda, K., Tekeuchi, O., Tsujimura, T., Itami, S., Adachi, O., Kawai, T., Sanjo, H., Yoshikawa, K., Terada, N, and Akira, S. (1999) *Science* 284, 313–316; Hu, Y., Baud, V., Delhase, M., Zhang, P., Deerinck, T., Ellisman, M., Johnson, R., and Karin, M. (1999) *Science* 284, 315–320; Li, Q., Lu, Q., Hwang, J. Y., Buscher, D., Lee, K., Izpisua-Belmonte, J. C., and Verma, I. M. (1999) *Gene and Development* 13, 1322–1328; Tanaka, M., Fuentes, M. E., Yamaguchi, K., Durnin, M. H., Dalrymple, S. A., Hardy, K. L., and Goeddel, D. V. (1999) *Immunity* 10, 421–429).

It is well-known that NF-KB plays a key role in the regulated expression of a large number of pro-inflammatory mediators including cytokines such as IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases. The importance of NF-κB in inflammatory disorders is further strengthened by studies of airway inflammation including asthma in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB. Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α. Such a distribution may be the underlying mechanism for the increased cytokine and eicosanoid production characteristic of this tissue. See Roshak, A. K., et al., J. Biol. Chem., 271, 31496–31501 (1996).

The NF-κB/Rel and IκB proteins are also likely to play a key role in neoplastic transformation. Family members are associated with cell transformation in vitro and in vivo because of overexpression, gene amplification, gene rearrangements, or translocations (Gilmore T D, *Trends Genet* 7:318–322, 1991; Gillmore T D, *Oncogene* 18:6925–6937, 1999; Rayet B. et al., *Oncogene* 18: 6938–6947, 1991). In addition, rearrangement and/or amplification of the genes encoding these proteins are seen in 20–25% of certain human lymphoid tumors. In addition, a role for NF-κB in the regulation of apoptosis, cell cycle progression, invasion, and metastasis has been reported (Bours V. et al., *Biochemical Pharmacology* 60:1085–1090, 2000) strengthening the role of this transcription factor in the control of cell proliferation. The inhibition of NF-κB has been shown to potentiate TNF- and cancer therapy through increased apoptosis (Wang C-Y et al., *Science* 274:784–787, 1996; Wang C-Y et al., *Nat Med* 5:412–417, 1999). It has also been shown that human T-cell leukemia virus type 1 (HTLV1) infected cells (the etiological agent of an aggressive malignancy of activated CD4$^+$ T lymphocytes), IKKα and IKKβ are expressed constitutively, which normally function in a transient manner (Chu Z-L et al., *J of Biological Chemistry* 273:15891–15894, 1998). The HTLV1 transforming and transactivating protein (Tax) has been shown to bind MEKK1 and increases the activity of IKKβ to enhance phosphorylation of serine residues in IκBα that lead to its degradation.

Pyrazoles have been described for use in the treatment of inflammation. U.S. Pat. No. 5,134,142 to Matsuo et al describes 1,5-diaryl pyrazoles, and specifically, 1-(4-fluorophenyl)-5-[4-(methylsulfonyl)phenyl]-3-trifluoromethyl pyrazole, as having anti-inflammatory activity.

U.S. Pat. No. 3,940,418 to R. Hamilton describes tricyclic 4,5-dihydrobenz[g]indazoles as antiinflammatory agents. In addition, R. Hamilton [*J. Heterocyclic Chem.*, 13, 545 (1976)] describes tricyclic 4,5-dihydrobenz[g]indazoles as antiinflammatory agents. U.S. Pat. No. 5,134,155 describes fused tricyclic pyrazoles having a saturated ring bridging the pyrazole and a phenyl radical as HMG-CoA reductase inhibitors. European publication EP 477,049, published Mar. 25, 1992, describes [4,5-dihydro-1-phenyl-1H-benz[g]indazol-3-yl]amides as having antipsychotic activity. European publication EP 347,773, published Dec. 27, 1989, describes [4,5-dihydro-1-phenyl-1H-benz[g]indazol-3-yl]propanamides as immunostimulants. M. Hashem et al [*J. Med. Chem.*, 19, 229 (1976)] describes fused tricyclic pyrazoles, having a saturated ring bridging the pyrazole and a phenyl radical, as antibiotics.

Certain substituted pyrazolyl-benzenesulfonamides have been described in the literature as synthetic intermediates. Specifically, 4-[5-(4-chlorophenyl)-3-phenyl-1H-pyrazol-1-yl]benzenesulfonamide has been prepared from a pyrazoline compound as an intermediate for compounds having hypoglycemic activity [R. Soliman et al, *J. Pharm. Sci.*, 76, 626 (1987)]. 4-[5-[2-(4-Bromophenyl)-2H-1,2,3-triazol-4-yl]-3-methyl-1H-pyrazol-1-yl]benzenesulfonamide has been prepared from a pyrazoline compound and described as potentially having hypoglycemic activity [H. Mokhtar, *Pak. J. Sci. Ind. Res.*, 31, 762 (1988)]. Similarly, 4-[4-bromo-5-[2-(4-chlorophenyl)-2H-1,2,3-triazol-4-yl]-3-methyl-1H-pyrazol-1-yl]benzenesulfonamide has been prepared [H. Mokhtar et al, *Pak. J. Sci. Ind. Res.*, 34, 9 (1991)].

The phytotoxicity of pyrazole derivatives is described [M. Cocco et al, *Il. Farmaco-Ed. Sci.*, 40, 272 (1985)], specifically for 1-[4-(aminosulfonyl)phenyl]-5-phenyl-1H-pyrazole-3,4-dicarboxylic acid.

The use of styryl pyrazole esters for antidiabetes drugs is described [H. Mokhtar et al, *Pharmazie*, 33, 649–651 (1978)]. The use of styryl pyrazole carboxylic acids for antidiabetes drugs is described [R. Soliman et al, *Pharmazie*, 33, 184–5 (1978)]. The use of 4-[3,4,5-trisubstituted-pyrazol-1-yl]benzenesulfonamides as intermediates for sulfonylurea anti-diabetes agents is described, and specifically, 1-[4-(aminosulfonyl)phenyl]-3-methyl-5-phenyl-1H-pyrazole-4-carboxylic acid [R. Soliman et al, *J. Pharm. Sci.*, 72, 1004 (1983)]. A series of 4-[3-substituted methyl-5-phenyl-1H-pyrazol-1-yl]benzenesulfonamides has been prepared as intermediates for anti-diabetes agents, and more specifically, 4-[3-methyl-5-phenyl-1H-pyrazol-1-yl]benzenesulfonamide [H. Feid-Allah, *Pharmazie*, 36, 754 (1981)]. In addition, 1-(4-[aminosulfonyl]phenyl)-5-phenylpyrazole-3-carboxylic acid has been prepared from the above described 4-[3-methyl-5-phenyl-1H-pyrazol-1-yl]benzenesulfonamide compound [R. Soliman et al, *J. Pharm. Sci.*, 70, 602 (1981)].

WO 00/27822 discloses tricyclic pyrazole derivatives, WO 00/59901 discloses dihydroindeno pyrazoles, WO 99/17769 discloses indeno[1,2-c]-, naphtho[1,2-c]- and benzo[6,7]cyclohepta[1,2-c]pyrazole derivatives, U.S. Pat. No. 5,196,445 discloses heteroaryl-3-oxo-propanenitrile derivatives useful in the treatment of rheumatoid arthritis, WO 97/10210 discloses tricyclic pyrrolidine derivatives as calcium channel antagonists, WO 95/15315 discloses diphenyl pyrazole compounds, WO 95/15317 discloses triphenyl pyrazole compounds, WO 95/15318 discloses tri-substituted pyrazole compounds, and WO 96/09293 discloses benz[g]indazolyl derivatives.

WO 95/15316 discloses substituted pyrazolyl benzenesulfonamide derivatives and WO 01/32663 discloses pyrazlecarboxylic acid tricyclic derivatives as CB$_1$ cannabinoid receptor inhibitors.

DETAILED DESCRIPTION OF THE INVENTION

A class of compounds, which are useful in treating cancer, inflammation, and inflammation related disorders, is defined by Formula I:

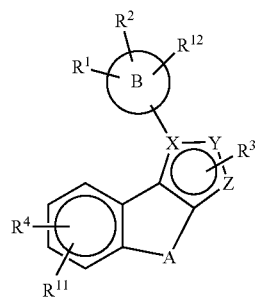

wherein
A is (CH$_2$)$_m$; wherein each CH$_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;
m is 1 to 4;
B is a 5 or 6 membered heteroaryl, aryl, saturated or unsaturated heterocyclic wherein said aryl, heteroaryl, or heterocyclic are optionally substituted with R$^1$, R$^2$, and R$^{12}$;
X is selected from the group consisting of: N and C;
Y and Z are independently selected from the group consisting of: N, CH, CR$^3$, S, and O;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

or isomers, tautomers, carriers, esters, prodrugs, pharmaceutically acceptable salts thereof.

Another class of compounds is defined by formula II

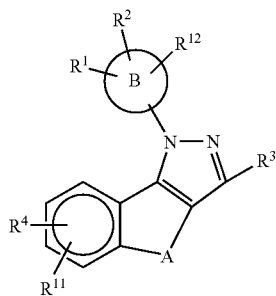

wherein

A is $(CH_2)_m$; wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 to 4;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

or isomers, tautomers, carriers, esters, prodrugs, pharmaceutically acceptable salts thereof.

DEFINITIONS

The present invention includes the use of all hydrates, solvates, complexes and prodrugs of the compounds of this invention. Prodrugs are any covalently bonded compounds, which releases the active parent drug according to Formula I or Formula II in vivo. If a chiral center or another form of an isomeric center is present in a compound of the present invention all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or Formula II or any sub-formula thereof is independent of its meaning, or any other substituents meaning, at any other occurrence, unless specified otherwise.

The term "alkyl" is used, either alone or within other terms such as "haloalkyl" and "alkylsulfonyl"; it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, isoamyl, hexyl, octyl and the like. The term "hydrido" denotes a single hydrogen atom (H). This hydrido radical may be attached, for example, to an oxygen atom to form a hydroxyl radical or two hydrido radicals may be attached to a carbon atom to form a methylene ($-CH_2-$) radical. The term "halo" means halogens such as fluorine, chlorine, and bromine or iodine atoms. The term "haloalkyl" embraces radicals wherein any one or more of the alkyl carbon atoms is substituted with halo as defined above. Specifically embraced are monohaloalkyl, dihaloalkyl, and polyhaloalkyl radicals. A monohaloalkyl radical, for one example, may have a bromo, chloro, or a fluoro atom within the radical. Dihalo radicals may have two or more of the same halo atoms or a combination of different halo radicals and polyhaloalkyl radicals may have more than two of the same halo atoms or a combination of different halo radicals. The term "hydroxyalkyl" embraces linear or branched alkyl radicals having one to about ten carbon atoms any one of which may be substituted with one or more hydroxylradicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro, or bromo, to provide "haloalkoxy" or "haloalkoxyalkyl" radicals. Examples of "alkoxy" radicals include methoxy, butoxy, and trifluoromethoxy. The term "aryl", alone or in combination, means a carbocyclic aromatic system containing one, two, or three rings wherein such rings may be attached together in a pendent manner or may be fused. The term "aryl" embraces aromatic radicals such as phenyl, naphthyl, tetrahydronapthyl, indane, and biphenyl. The term "heterocyclic" embraces saturated, partially saturated, and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" embraces unsaturated heterocyclic radicals. Examples of unsaturated heterocyclic radicals, also termed "heteroaryl" radicals include thienyl, pyrrolyl, furyl, pyridyl, pyrimidyl, pyrazinyl, pyrazolyl, oxazolyl, isoxazolyl, imidazolyl, thiazolyl, and tetrazolyl. The term also embraces radicals where heterocyclic radicals are fused with aryl radicals. Examples of such fused bicyclic radicals include benzofuran, benzothiophene, and the like. The term "heterocyclic alkyl" embraces alkyl attached to the heterocyclic. The term "sulfonyl", whether used alone or linked to other terms such as alkylsulfonyl, denotes respectively divalent radicals $-SO_2-$. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl" or "sulfonamidyl", whether alone or used with terms such as "N-alkylsulfamyl", "N-arylsulfamyl", "N,N-dialkylsulfamyl" and "N-alkyl-N-arylsulfamyl", denotes a sulfonyl radical substituted with an amine radical, forming a sulfonamide ($-SO_2-NH_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted, respectively, with one aryl radical, and one alkyl and one aryl radical. The terms "carboxy" or "carboxyl", whether used alone or with other terms, such as "carboxyalkyl", denotes $-CO_2H$. The term "carboxyalkyl" embraces radicals having a carboxyradical as defined above, attached to an alkyl radical. The term "carbonyl", whether used alone or with other terms, such as "alkylcarbonyl", denotes $-(C=O)-$. The term "alkylcarbonyl" embraces radicals having a carbonyl radical substituted with an alkyl radical. An example of an "allylcarbonyl" radical is $CH_3-(C=O)-$. The term "alkylcarbonylalkyl" denotes an alkyl radical substituted with an "alkylcarbonyl" radical. The term "alkoxycarbonyl" means a radical containing an alkoxy radical, as defined above, attached via an oxygen atom to a carbonyl (C=O)

radical. Examples of such "alkoxycarbonyl" radicals include (CH₃)₃CO—C(═O)— and —(O═)C—OCH₃. The term "alkoxycarbonylalkyl" embraces radicals having "alkoxycarbonyl", as defined above substituted to an alkyl radical. Examples of such "alkoxycarbonylalkyl" radicals include (CH₃)₃COC(═O) (CH₂)₂— and —(CH₂)₂(O═)COCH₃. The term "amido" when used by itself or with other terms such as "amidoalkyl", "N-monoalkylamido", "N-monoarylamido", "N,N-dialkylamido", "N-alkyl-N-arylamido", "N-alkyl-N-hydroxyamido" and "N-alkyl-N-hydroxyamidoalkyl", embraces a carbonyl radical substituted with an amino radical. The terms "N-alkylamido" and "N,N-dialkylamido" denote amido groups which have been substituted with one alkyl radical and with two alkyl radicals, respectively. The terms "N-monoarylamido" and "N-alkyl-N-arylamido" denote amido radicals substituted, respectively, with one aryl radical, and one alkyl and one aryl radical. The term "N-alkyl-N-hydroxyamido" embraces amido radicals substituted with a hydroxyl radical and with an alkyl radical. The term "N-alkyl-N-hydroxyamidoalkyl" embraces alkyl radicals substituted with an N-alkyl-N-hydroxyamido radical. The term "amidoalkyl" embraces alkyl radicals substituted with amido radicals. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(═NH)—NH₂ radical. The term "cyanoamidino" denotes an —C(═N—CN)—NH₂ radical. The term "heterocycloalkyl" embraces heterocyclic-substituted alkyl radicals such as pyridylmethyl and thienylmethyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl, and cycloheptyl. The term "cycloalkenyl" embraces unsaturated radicals having three to ten carbon atoms, such as cylopropenyl, cyclobutenyl, cyclopentenyl, cyclohexenyl, and cycloheptenyl. The term "alkylthio" embraces radicals containing a linear or branched alkyl radical, of one to ten carbon atoms, attached to a divalent sulfur atom. An example of "alkylthio" is methylthio, (CH₃—S—). The term "alkylsulfinyl" embraces radicals containing a linear or branched alkyl radical, of one to ten carbon atoms, attached to a divalent —S(═O)— atom. The terms "N-alkylamino" and "N,N-dialkylamino" denote amino groups which have been substituted with one alkyl radical and with two alkyl radicals, respectively. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino (CH₃C(═O)—NH—).

Compounds of Formula I or Formula II would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I or Formula II would be useful to treat arthritis, including but not limited to rheumatoid arthritis, spondylo arthopathies, gouty arthritis, osteoarthritis, systemic lupus erythematosus, and juvenile arthritis. Such compounds of Formula I or Formula II would be useful in the treatment of asthma, bronchitis, menstrual cramps, tendinitis, bursitis, and skin related conditions such as psoriasis, eczema, burns, and dermatitis. Compounds of Formula I or Formula II also would be useful to treat gastrointestinal conditions such as inflammatory bowel disease, Crohn's disease, gastritis, irritable bowel syndrome, and ulcerative colitis and for the prevention of colorectal cancer. Compounds of Formula I or Formula II would be useful in treating inflammation in such diseases as vascular diseases such as vascularitus, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the present invention may also be used for pain. The compounds are useful as antiinflammatory agents, such as for the treatment of arthritis, with the additional benefit of having significantly less harmful side effects. The compounds of formula I or II are useful as agents for treating cancer or anticancer agents. The compounds of formula I or II may be proapoptotic, antiapoptotic, anticell cycle progressive, antiinvasive, antiproliferative, antiangiogenic, and antimetastatic. The cancer may be colon, ovarian, breast, prostate, gastric, B-cell lymphoma, and multiple myeloma. More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma. Due to the key role of PKs in the regulation of cellular proliferation, these compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. The compounds of formula I or II may be used as an anitviral agent. The compounds of this invention are useful as inhibitors of protein kinases. The compounds of this invention are useful as inhibitors of IKK1 and/or IKK2, IKKα/IKKβ heterodimer, TBK or IKKi. The compounds of the invention may also useful as inhibitors of other protein kinases such as, for instance, protein kinase C in different isoforms, cyclin dependent kinase (cdk), Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases. The present invention preferably includes compounds, which selectively inhibit IKK2 over IKK1. Preferably, the compounds have an IKK2 IC50 of less than 1 μM, and have a selectivity ratio of IKK2 inhibition over IKK1 inhibition of at least 50, and more preferably of at least 100. Even more preferably, the compounds have an IKK1 IC50 of greater than 10 μM, and more preferably of greater than 100 μM. The compounds of formula may also be used to treat angiogenesis associated cardiovascular, ophthalmology and osteoporosis disorders. The compounds of the present invention may also be used for treatment of knee injury such as sport injuries.

While it is possible for an active ingredient to be administered alone as the raw chemical, it is preferable to present it as a pharmaceutical formulation. The present invention comprises a pharmaceutical composition comprising a therapeutically effective amount of a compound of the present invention in association with at least one pharmaceutically acceptable carrier, adjuvant, or diluent. The present invention also comprises a method of treating inflammation or inflammation associated disorders in a subject, the method comprising administering to the subject having such inflammation or disorders a therapeutically effective amount of a compound of the present invention. Also included in the family of compounds of the present invention are the pharmaceutically acceptable salts thereof. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, phydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically acceptable base addition salts of compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compound of the present invention by reacting, for example, the appropriate acid or base with the compound of the present invention.

Also embraced within this invention are pharmaceutical compositions comprising one or more compounds of the present invention in association with one or more non-toxic, pharmaceutically acceptable carriers and/or diluents and/or adjuvants and/or excipient (collectively referred to herein as "carrier" materials) and, if desired, other active ingredients. Accordingly, the compounds of the present invention may be used in the manufacture of a medicament. Pharmaceutical compositions of the compounds of the present invention prepared as herein before described may be formulated as solutions or lyophilized powders for parenteral administration. Powders may be reconstituted by addition of a suitable diluent or other pharmaceutically acceptable carrier prior to use. The liquid formulation may be a buffered, isotonic aqueous solution. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, intravenously, subcutaneously, intramuscularly, intramedullary, orally, or topically. For oral administration, the pharmaceutical composition may be in the form of, for example, a tablet, capsule, suspension, or liquid. The active ingredient may also be administered by injection as a composition wherein, for example, normal isotonic saline solution, standard 5% dextrose in water or buffered sodium or ammonium acetate solution may be used as a suitable carrier. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, or sodium citrate. The pharmaceutical composition is preferably made in the form of a dosage unit containing a particular amount of the active ingredient. Examples of such dosage units are tablets or capsules. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg bodyweight, preferably between about 0.1 and about 50 mg/kg body weight and most preferably between about 1 to 20 mg/kg bodyweight, may be appropriate. The daily dose can be administered in one to four doses per day. For therapeutic purposes, the compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled release formulation as may be provided in a dispersion of active compound in a sustained release material such as glyceryl monostearate, glyceryl distearate, hydroxypropylmethyl cellulose alone or with a wax. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion, or an aqueous or non-aqueous suspension. Such a liquid formulation may be administered orally or filled into a soft gelatin capsule. For rectal administration, the compounds of the present invention may also be combined with excipients such as cocoa butter, glycerin, gelatin, or polyethylene glycols and molded into a suppository. The methods of the present invention include topical administration of the compounds of the present invention. By topical administration is meant non-systemic administration, including the application of a compound of the invention externally to the epidermis, to the buccal cavity and instillation of such a compound into the ear, eye, and nose, wherein the compound does not significantly enter the blood stream. By systemic administration is meant oral, intravenous, intraperitoneal, and intramuscular administration. The amount of a compound of the present invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician.

The topical formulations of the present invention, both for veterinary and for human medical use, comprise an active ingredient together with one or more acceptable carriers therefore, and optionally any other therapeutic ingredients. The carrier must be "acceptable" in the sense of being compatible with the other ingredients of the formulation and not deleterious to the recipient thereof. Formulations suitable for topical administration include liquid or semi-liquid preparations suitable for penetration through the skin to the site of where treatment is required such as: liniments, lotions, creams, ointments or pastes, and drops suitable for administration to the eye, ear or nose. The active ingredient may comprise, for topical administration, from 0.01 to 5.0 wt %. of the formulation.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container, which is then sealed and sterilized by autoclaving, or maintaining at 90–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.00217 c), benzalkonium chloride (0.01%) and chlorhexidine acetate (0.01%). Suitable solvents for the preparation of an oily solution include glycerol, diluted alcohol, and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil. Creams, ointments, or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface-active agent such as an anionic, cationic, or non-ionic surface-active agent such as sorbitan esters or polyoxyethylene derivatives thereof. Suspending agents such as natural gums, cellulose derivatives or inorganic materials such as silicaceous silicas, and other ingredients such as lanolin may also be included. Other adjuvants and modes of administration are well and widely known in the pharmaceutical art. Although this invention has been described with respect to specific embodiments, the details of these embodiments are not to be construed as limitations.

GENERAL SYNTHETIC PROCEDURES

The starting materials used herein are commercially available or are prepared by routine methods well known to those of ordinary skill in the art and can be found in standard reference books, such as the COMPENDIUM OF ORGANIC SYNTHETIC METHODS, Vol. I-VI (published by Wiley-Interscience).

The compounds of the invention can be synthesized according to the following procedures of Schemes I-XI, wherein the $R^1$–$R^{14}$ substituents are as defined for Formula I or Formula II, above, except where further noted.

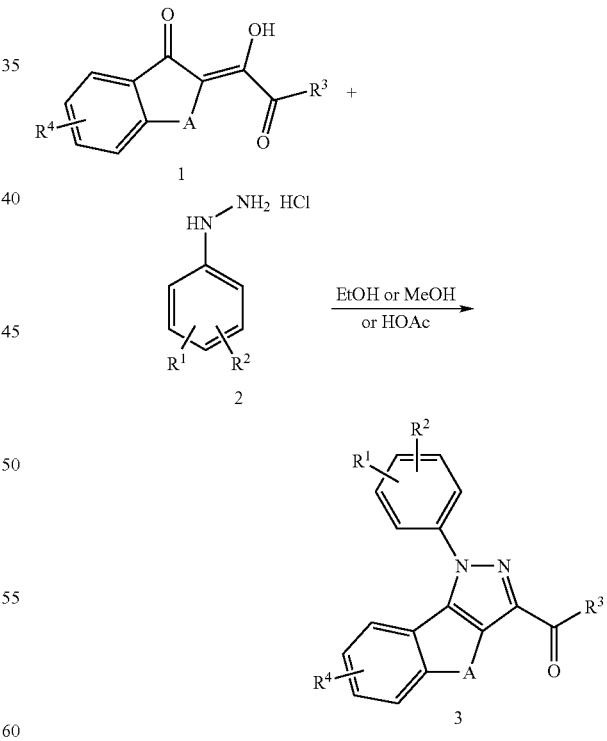

Synthetic Scheme I illustrates the procedure used to prepare the antiinflammatory pyrazoles of the present invention. 1,3-Dicarbonyl compounds such as 1, or the shown enol form which is in equilibrium with the 1,3-diketone, are allowed to react with a substituted hydrazine hydrochloride 2 in warm methanol or ethanol or acetic acid to provide the pyrazoles 3 via a condensation reaction. When A=—CH₂CH₂—, the central ring may be aromatized to provide A=—CH=CH—, by using an oxidant such as DDQ, Pd or Pt on carbon with cyclooctadiene or other H₂ acceptor, or sulfur in an appropriate solvent or without solvent.

SCHEME II

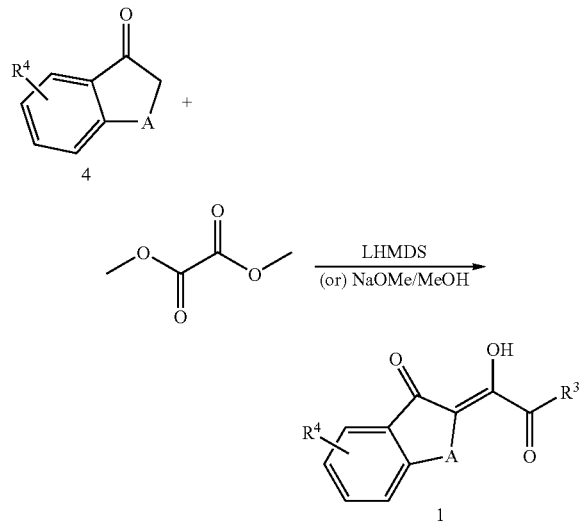

Synthetic Scheme II illustrates the procedure for the preparation of substituted diketones 1. An appropriately substituted ketone 4, including, but not limited to; 1-indanones, 1-tetralones, and 1-benzosuberones, is first treated with base, such as sodium methoxide, lithium bistrimethylsilylamide or lithium diisopropylamide (LDA), followed by condensation with a suitable acylating agent, such as, dimethyl or diethyl oxalate, in an appropriate solvent, such as methanol, diethyl ether or tetrahydrofuran, to provide 1,3-dicarbonyl compounds 1 which are suitable for conversion into antiinflammatory pyrazoles as illustrated in Scheme I. Alternatively, the dicarbonyl compounds 1 can be directly prepared from commercially available cyclic ketones 4.

SCHEME III

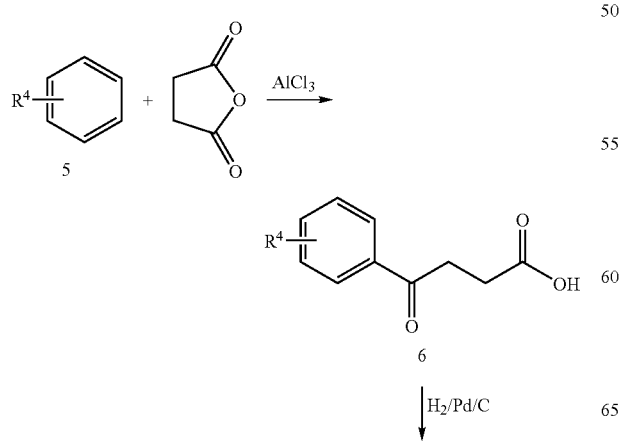

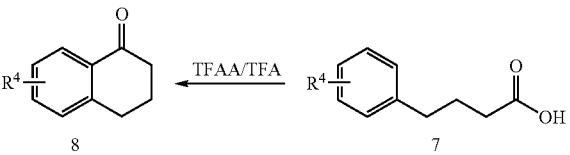

Synthetic Scheme III illustrates a three-step procedure used for the preparation of substituted 1-tetralones. In step one, an appropriate substituted benzene 5 is condensed with succinic anhydride and a catalyst such as aluminum chloride into the corresponding 4-phenyl-4-ketobutanoic acid derivatives 6. In step two, the keto group of the 4-phenyl-4-ketobutanoic acids 6 is reduced using catalytic hydrogenation or Wolff-Kishner type reductions, thus providing 4-phenylbutanoic acids 7. In addition, ketone reductions can be carried out using metal amalgams. In step three, the 4-phenylbutanoic acids are treated with a mixture of trifluoroacetic anhydride, and trifluoroacetic acid to effect intramolecular Friedel-Crafts acylation affording selected tetralones 8. Alternatively, the Friedel-Crafts acylation can be affected with other strong acids such as polyphosphoric acid, sulfuric acid, or aluminum chloride.

SCHEME IV

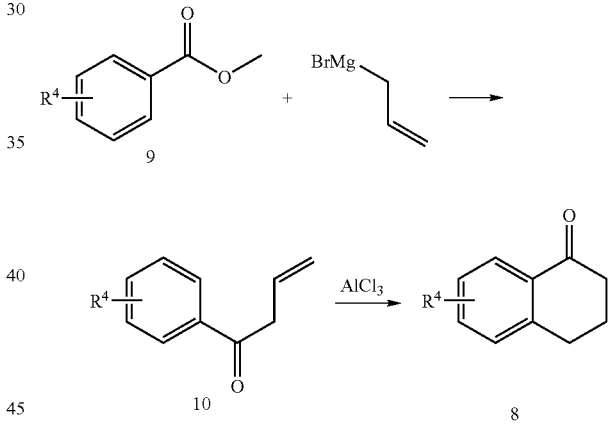

Synthetic Scheme IV describes an alternate synthetic route to 1-tetralones 8. In step one, addition of allylmagnesium bromide in a suitable solvent such as, THF or diethyl ether, to an appropriately substituted benzoate 9 affords the 1-phenylbut-3-ene-1-ones 10. In step two, the 1-phenylbut-3-ene-1-ones 10 can be cyclized under Friedel-Crafts alkylation conditions, provided R4 is a ring activating substituent, using catalysts such as aluminum chloride to produce 1-tetralones 8.

SCHEME V

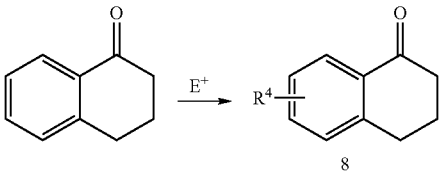

Scheme V describes the direct modification of 1-tetralone to substituted tetralones. Commercially available 1-tetralone may be treated with a variety of electrophilic reagents such as bromine, ammonium nitrite or vinylsilanes, represented by E+, with or without a catalyst to generate directly a substituted tetralone 8, containing bromo, nitro or vinyl groups. Such tetralones 8 can be further embellished to provide the desired substitution patterns. Mixtures may be readily separated using chromatographic techniques.

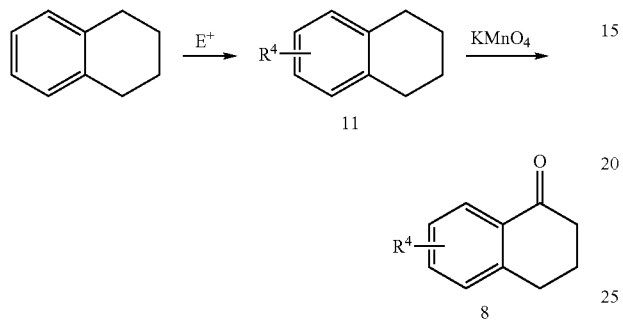

An alternate to Scheme V is Scheme VI wherein an appropriately substituted decaline is subjected to electrophilic addition to generate substituted decalins 11. Substituted decalins may also be prepared by Friedel-Crafts alkylation of substituted benzenes. Substituted decalins 11 can then be oxidized to the tetralones 8 using oxidants such as KMnO₄ or SeO₂.

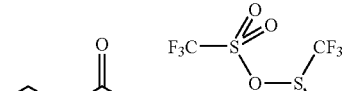

Scheme VII describes the modification of existing tetralones into analogs containing differing functional groups that can also be further modified. By example, hydroxy tetralone (8a where R₄=OH) can be converted to the triflate 8b by treatment with trifluoromethane sulfonic anhydride. Triflate 8b can the be subjected to Pd(OAc)₂ an appropriate phosphine and CO in the presence of methanol to generate tetralone 12 containing a carboxy methyl group. Triflates can be used in a variety of palladium coupling reactions to introduce additional functional groups.

Synthetic Scheme VIII illustrates a three step procedure used for the preparation of substituted 1-indanones 16. In step one, an appropriate substituted benzaldehyde 13 is condensed with methyl acetate and a catalyst such as triethylamine into the corresponding methyl cinnamate derivatives 14. Additionally, commercially available cinnamates may be used in the following steps. In step two the olefin group of the cinnamate 14 is reduced using catalytic hydrogenation and the ester hydrolyzed with base, such as NaOH, thus providing 3-phenylpropanoic acids 15. In step three, the 3-phenylpropanoic acids are treated with a mixture of trifluoroacetic anhydride and trifluoroacetic acid to effect intramolecular Friedel-Crafts acylation affording selected 1-indanones 16. Alternatively, the Friedel-Crafts acylation can be effected with other strong acids such as sulfuric acid or aluminum chloride.

Synthetic Scheme IX illustrates a two-step route for the preparation of substituted 1-indanones 16. Commercially available methyl benzoates 9, or other alkyl esters, may be treated with a vinyl lithium reagent to afford phenylvinyl ketones 17. Alternatively, dimethylamides or N-methyl-O- methylhydroxamides may be used in place of the esters. Also, other vinyl metals, such as; vinylmagnesium bromide may be used in place of the vinyl lithium reagent. The resulting phenylvinyl ketones may be cyclized using Friedel-Crafts alkylating catalysts, such as aluminum chloride.

SCHEME X

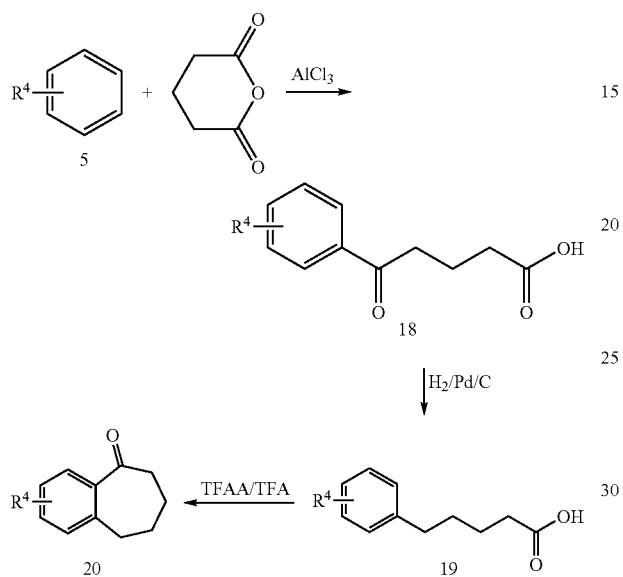

Synthetic Scheme X illustrates a three step procedure used for the preparation of substituted 1-benzosuberones 20. In step one, an appropriate substituted benzene 5 is condensed with glutaric anhydride and a catalyst such as aluminum chloride into the corresponding 5-phenyl-5-ketopentanoic acid derivatives 18. In step two, the keto group of the 5-phenyl-5-ketopentanoic acids 18 is reduced using catalytic hydrogenation or Wolff-Kishner type reductions, thus providing 5-phenylpentanoic acids 19. In addition, ketone reductions can also be carried out using metal amalgams. In step three, the 5-phenylpentanoic acids are treated with a mixture of trifluoroacetic anhydride, and trifluoroacetic acid to effect intramolecular Friedel-Crafts acylation affording selected benzosuberones 20. Alternatively, the Friedel-Crafts acylation can be affected with other strong acids such as polyphosphoric acid, $H_2SO_4$ or $AlCl_3$. Alternatively, 5-phenyl-5-ketopentanoic acids 18, can be prepared from glutaric acid and a phenyllithium or a phenyl Grignard reagent appropriately substituted and compatible with reaction conditions.

Scheme XI

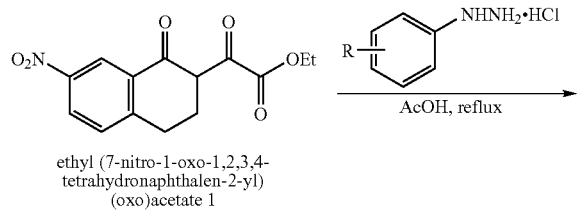

ethyl (7-nitro-1-oxo-1,2,3,4-tetrahydronaphthalen-2-yl)(oxo)acetate 1

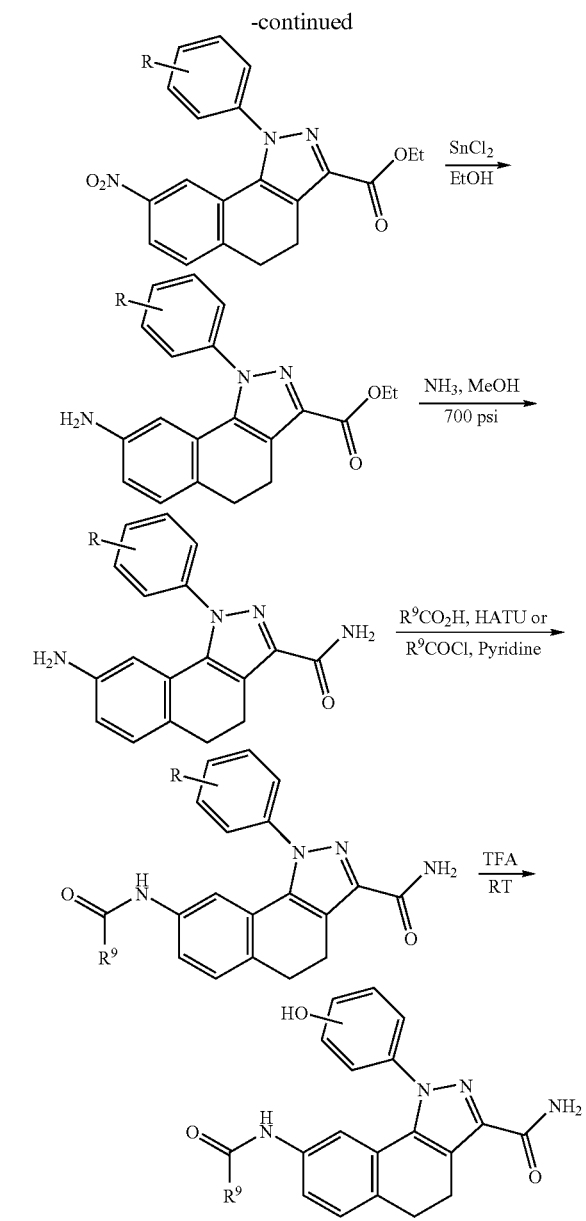

R = 3- or 4-benzyloxyl

Scheme XI describes the synthesis of the pyrazoles with phenols at N-position. In step one; 3- or 4-benzyloxyphenylhydrazine was refluxed with ethyl (7-nitro-1-oxo-1,2,3,4-tetrahydronaphthalen-2-yl)(oxo)acetate 1 in acetic acid to give pyrazole. Then the nitro group was reduced to amine by using tin (II) chloride in ethanol. In the following step, the conversion of ester to amide was achieved by reacting with liquid ammonia in a pressured tube at high temperature. The resulting compound can either react with acid and HATU in DMF or acid chloride in pyridine to give the desired amide. The benzyl group was deprotected by stirring with TFA at room temperature.

The complete content of all publications, patents, and patent applications cited in this disclosure are herein incorporated by reference as if each individual publication, patent, or patent application were specifically and individually indicated to incorporated by reference. Although the foregoing invention has been described in some detail by way of illustration and example for the purposes of clarity of understanding, it will be readily apparent to one skilled in the art in light of the teachings of this invention that changes and modifications can be made without departing from the spirit and scope of the present invention. The following examples are provided for exemplification purposes only and are not intended to limit the scope of the invention, which has been described in broad terms above.

EXAMPLES

Example 1

1-{4-[(aminothio)peroxy]phenyl}-8-nitro-4,5-dihydro-1H-benzo[g]indazole-3-carboxamide

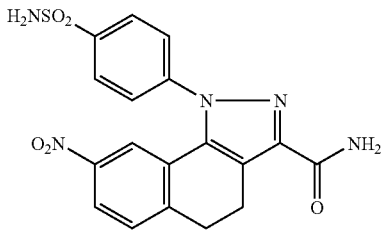

Step 1

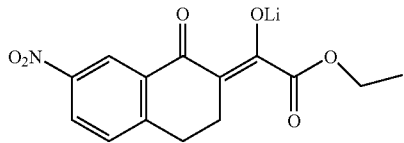

To 7-nitro-1-tetralone (4.6 g, 0.024 mol) and ethyl oxalate (3.5 mL, 0.026 mol) in ether (100 mL) was added dropwise lithium bis(trimethylsilyl)amide (1M in THF, 26 mL). The slurry was stirred overnight and filtered to give the product as an olive green solid, 6.2 g (87% yield). $^1$H NMR (DMSO-$d_6$/300 MHz) 8.45 (d, 1H); 8.05 (d of d, 1H); 7.42 (d, 1H); 4.08 (q, 2H); 2.82–2.72 (m, 2H); 2.51–2.43 (m, 2H); 1.21 (t, 3H).

Step 2

Ethyl 1-{4-[(aminothio)peroxy]phenyl}-8-nitro-4,5-dihydro-1H-benzo[g]indazole-3-carboxylate

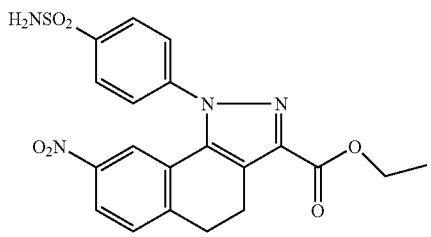

The material of Step 1 (6.2 g, 0.021 mol) and 4-sulfonamidophenylhydrazine hydrochloride (5.1 g; 0.023 mol) were stirred in methanol (100 mL) overnight. Conc. HCl (2 mL) was added to the thick slurry and the contents were heated on a steam bath for 1 hour. Contents were allowed to cool and filtered to give an off-white solid, 6.9 g. NMR and LC/MS analysis show the solid to contain two components, the desired and the hydrated pyrazole. TFA (60 mL) and TFAA (20 mL) were added to the solid and heated on a steam bath for 1 hour. Contents were concentrated in vacuo leaving the product as a solid, 6.4 g (69% yield). FABHRMS m/z 443.1020 (M+H, $C_{20}H_{19}N_4O_6S$ requires 443.1025). $^1$H NMR (DMSO-$d_6$/300 MHz) 8.10 (d of d, 1H); 8.03 (d, 2H); 7.82 (d, 2H); 7.70 (d, 1H); 7.62 (s, 1H); 7.50 (d, 1H); 4.33 (q, 2H); 3.20–2.95 (m, 4H); 1.33 (t, 3H).

Anal. Calcd for $C_{20}H_{18}N_4O_6S$: C, 54.29; H, 4.10; N, 12.66. Found: C, 54.49; H, 4.00; N, 12.52.

Step 3

The material of Step 2 (718 mg, 0.0016 mol), conc. ammonium hydroxide (30 mL), and methanol (15 mL) were stirred in a stoppered flask for 72 hours. Contents were filtered to give a light amber solid (606 mg). The solid was recrystallized from acetonitrile to give the product as a light amber solid, 450 mg (68% yield). FABHRMS m/z 414.0902 (M+H, $C_{18}H_{16}N_5O_5S$ requires 414.0872). $^1$H NMR (DMSO-$d_6$/300 MHz) 8.15–7.95 (m, 3H); 7.83 (d, 2H); 7.80–7.40 (m, 6H); 3.20–2.95 (m, 4H).

Anal. Calcd for $C_{18}H_{15}N_5O_5S$: C, 52.30; H, 3.66; N, 16.94. Found: C, 52.04; H, 3.64; N, 16.61.

Example 2

8-amino-1-{4-[(aminothio)peroxy]phenyl}-4,5-dihydro-1H-benzo[g]indazole-3-carboxamide

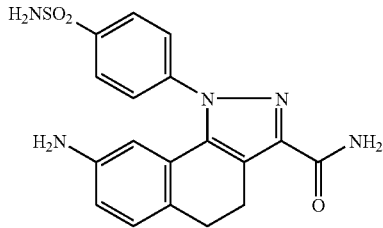

The compound was prepared similarly to Example 1 in 70% yield. FABHRMS m/z 384.1136 (M+H, $C_{18}H_{18}N_5O_3S$ requires 384.1130). $^1$H NMR (DMSO-$d_6$/300 MHz) 7.95 (d, 2H); 7.75 (d, 2H); 7.53 (br s, 1H); 7.43 (br s, 1H); 7.32 (br s, 1H); 7.01 (d, 1H); 6.44 (d of d, 1H); 6.03 (s, 1H); 4.81 (s, 2H); 2.93–2.65 (m, 4H).

Anal. Calcd for $C_{18}H_{17}N_5O_3S$: C, 56.38; H, 4.47; N, 18.27. Found: C, 56.31; H, 4.42; N, 18.31.

Example 3

8-(acetylamino)-1-{4-[(aminothio)peroxy]phenyl}-4,5-dihydro-1H-benzo[g]indazole-3-carboxamide

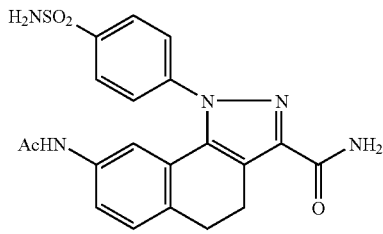

To the material of Example 2 (1.0 g, 0.0026 mol) in DMF (15 mL) was added dropwise a mixture of acetic anhydride (0.283 mL, 0.003 mol) and pyridine (0.243 mL, 0.003 mol) in DMF (5 mL). Contents were stirred overnight, diluted with water (75 mL), and filtered to give the desired as a white solid, 1.0 g (90% yield). FABHRMS m/z 426.1235 (M+H, $C_{20}H_{20}N_5O_4S$ requires 426.1236). $^1$H NMR (DMSO-$d_6$/300 MHz) 9.80 (s, 1H); 8.00 (d, 2H); 7.75 (d, 2H); 7.60 (s, 1H); 7.48 (s, 2H); 7.39 (s, 1H); 7.30 (d, 1H); 7.15 (s, 1H); 2.90 (s, 4H); 1.92 (s, 3H).

Anal. Calcd for $C_{20}H_{19}N_5O_4S$ (1H$_2$O): C, 54.17; H, 4.77; N, 15.79. Found: C, 54.20; H, 4.97; N, 15.77.

Example 4

1-{4-[(aminothio)peroxy]phenyl}-8-{[(methylthio)peroxy]amino}-4,5-dihydro-1H-benzo[g]indazole-3-carboxamide

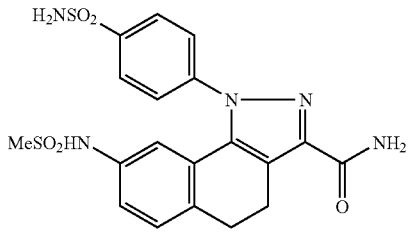

To the material of Example 2 (1.2 g, 0.003 mol) and triethylamine (0.278 mL, 0.0035 mol) in DMF (10 mL) at 0° C., was added dropwise methanesulfonyl chloride (0.278 mL, 0.0035 mol) in CH$_2$Cl$_2$ (2 mL). Contents were stirred overnight, slowly coming to room temperature. Contents were diluted with water (50 mL) and filtered to give the product as an off-white solid, 524 mg (37% yield). FABHRMS m/z 462.0917 (M+H, $C_{19}H_{20}N_5O_5S_2$ requires 462.0906). $^1$H NMR (DMSO-$d_6$/300 MHz) 9.60 (s, 1H); 7.98 (d, 2H); 7.80 (d, 2H); 7.60 (s, 1H); 7.50 (s, 2H); 7.40 (s, 1H); 7.37 (d, 1H); 7.02 (s, 1H); 6.75 (s, 1H); 2.93 (s, 4H); 2.75 (s, 3H).

Anal. Calcd for $C_{19}H_{19}N_5O_5S_2$: C, 49.45; H, 4.15; N, 15.17. Found: C, 49.19; H, 3.77; N, 15.53.

Examples 5–40

Synthesis of the Sulfonamide/Amide/Urea Library

The sulfonamides, amides, and urea were synthesized in a library format by using a Bohdan reaction block. The starting materials are the product of Example 2 (8-amino-1-{4-[(aminothio)peroxy]phenyl}-4,5-dihydro-1H-benzo[g]indazole-3-carboxamide) and appropriate sulfonyl chlorides, acyl chlorides and isocyanates. Thirty-five reactions constituted this library.

The general procedure is as follows: 48 mg of the product of Example 2 (8-amino-1-{4-[(aminothio)peroxy]phenyl}-4,5-dihydro-1h-benzo[g]indazole-3-carboxamide) in 1 mL pyridine was placed in each reaction vessel, then 1.2 eq. of a sulfonyl chloride was added, and the mixture was shaken overnight. Then 3 mL methylene chloride and 300 mg of resin PS-trisamine were added, and then shaken over night. After filtration and washing with 2 mL methanol twice, the filtrates were combined and solvents evaporated. The residue was dissolved in 2 mL dimethylformamide, and MS-TsOH resin (450 mg) was added and shaken for 48 hours. After filtration and washing with 2 mL DMF, the combined filtrate was analyzed by LC-MS and LC. Then the filtrate was evaporated on a SpeedVac and the residue were suspended in 2 mL of H$_2$O/tBuOH, and lyophilized for 2 days. All compounds were obtained in solid form, and the majority of the compounds have about 90% purity. Table 1 shows the substitutions, compound identification, and IKK heterodimer assay values for the compounds from the sulfonamide library. The structures of the compounds of Examples 5–40 were confirmed Mass Spectroscopy and/or NMR analysis.

Synthesis of Compounds of Examples 41–45

Scheme XII

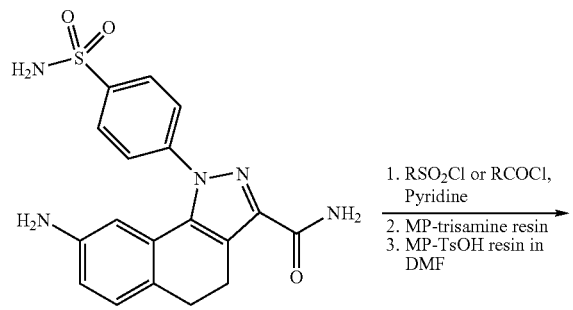

1. RSO$_2$Cl or RCOCl, Pyridine
2. MP-trisamine resin
3. MP-TsOH resin in DMF

Scheme XIII

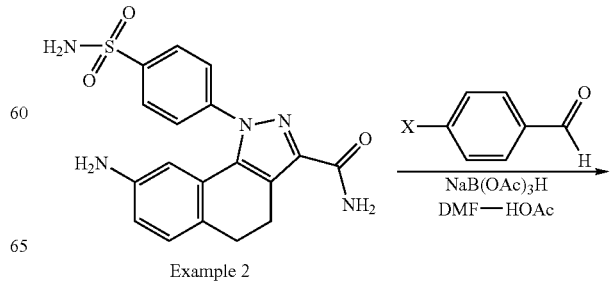

Example 2

-continued

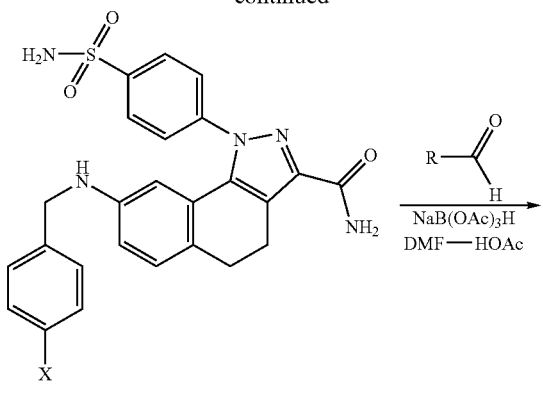

| X = | —H | 70% | Example 41 |
| --- | --- | --- | --- |
| | —CH₃ | 65% | Example 42 |
| | —OCH₃ | 71% | Example 43 |
| | —Cl | 74% | Example 44 |

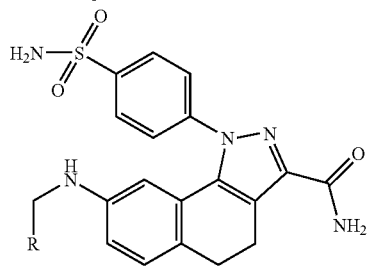

R = —iBu   61%   Example 41

Example 41

1-[4-(aminosulfonyl)phenyl]-8-(benzylamino)-4,5-dihydro-1H-benzo[g]indazole-3-carboxamide

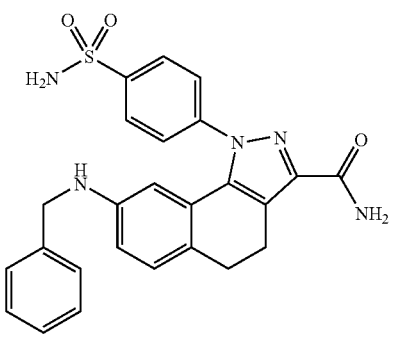

To a mixture of the product of example 2 (8-amino-1-{4-[(aminothio)peroxy]phenyl}-4,5-dihydro-1h-benzo[g]indazole-3-carboxamide) (76 mg, 0.20 mmol), acetic acid (0.3 mL) and sodium triacetoxyborohydride (213 mg, 1.00 mmol) in DMF (3 mL) was added benzaldehyde (64 mg, 0.60 mmol). The resulted mixture was stirred at RT for 18 h, added water (10 mL), extracted with EtOAc (3×10 mL). The combined organic layers was washed with water (3×10 mL), dried over MgSO₄, filtered through a silica gel pad with EtOAc, and concentrated. The crude product was triturated with diethyl ether to give 1-[4-(aminosulfonyl)phenyl]-8-(benzylamino)-4,5-dihydro-1H-benzo[g]indazole-3-car-boxamide as a yellow solid (66 mg, 70%). Its structure was confirmed by ¹H NMR and MS (474, M+1). $C_{25}H_{23}N_5O_3S$, Calc.: C: 63.41; H: 4.90, N: 14.79; Found, C: 63.11; H: 4.70, N: 13.54.

Example 42

1-[4-(aminosulfonyl)phenyl]-8-[(4-methylbenzyl)amino]-4,5-dihydro-1H-benzo[g]indazole-3-carboxamide

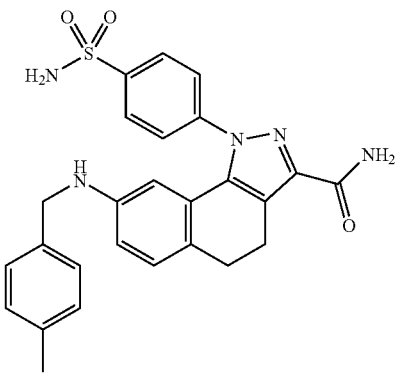

1-[4-(aminosulfonyl)phenyl]-8-[(4-methylbenzyl)amino]-4,5-dihydro-1H-benzo[g]indazole-3-carboxamide (32 mg, 65%) was synthesized by the same procedure as in Example 41, starting with the product of Example 2 (8-amino-1-{4-[(aminothio)peroxy]phenyl}-4,5-dihydro-1H-benzo[g]indazole-3-carboxamide) (38.3 mg, 0.10 mmol) and p-Tolualdehyde (36 mg, 0.30 mmol). Its structure was confirmed by ¹H NMR and MS (488, M+1). $C_{26}H_{25}N_5O_3S$, Calc.: C: 64.05; H: 5.17, N: 14.36; Found, C: 63.78; H: 4.99, N: 14.12.

Example 43

1-[4-(aminosulfonyl)phenyl]-8-[(4-methoxybenzyl)amino]-4,5-dihydro-1H-benzo[g]indazole-3-carboxamide

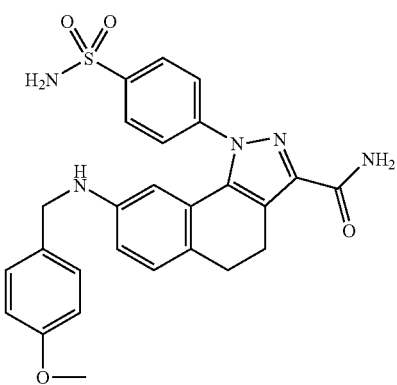

The title compound (36 mg, 71%) was synthesized by the same procedure as in Example 41 starting with the product of Example 2 (8-amino-1-{4-[(aminothio)peroxy]phenyl}-4,5-dihydro-1H-benzo[g]indazole-3-carboxamide) (38.3 mg, 0.10 mmol) and p-anisaldehyde (38 mg, 0.30 mmol). Its structure was confirmed by $^1$H NMR and MS (504, M+1). $C_{26}H_{25}N_5O_4S.(Et_2O)_{0.6}$, Calc.: C: 62.24; H: 5.70, N: 12.78; Found, C: 61.68; H: 5.43, N: 12.54.

Example 44

1-[4-(aminosulfonyl)phenyl]-8-[(4-chlorobenzyl)amino]-4,5-dihydro-1H-benzo[g]indazole-3-carboxamide

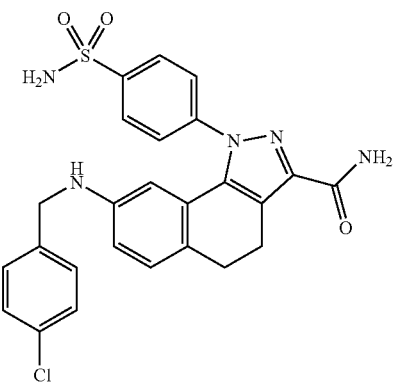

The title compound (37 mg, 74%) was synthesized by the same procedure as in Example 41 starting with the product of Example 2 (8-amino-1-{4-[(aminothio)peroxy]phenyl}-4,5-dihydro-1H-benzo[g]indazole-3-carboxamide) (38.3 mg, 0.10 mmol) and p-chlorobenzaldehyde (42 mg, 0.30 mmol). Its structure was confirmed by $^1$H NMR and MS (508, M+1). $C_{25}H_{22}N_5O_3SCl$, Calc.: C: 59.11; H: 4.37, N: 13.79; Found, C: 58.78; H: 4.25 N: 13.18.

Example 45

1-[4-(aminosulfonyl)phenyl]-8-(isobutylamino)-4,5-dihydro-1H-benzo[g]indazole-3-carboxamide

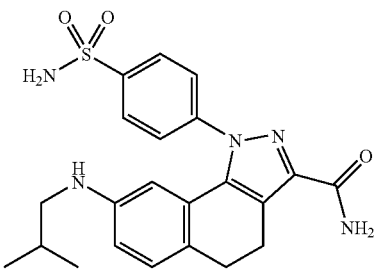

The title compound (27 mg, 61%) was synthesized by the same procedure as in Example 41 starting with the product of Example 2 (8-amino-1-{4-[(aminothio)peroxy]phenyl}-4,5-dihydro-1H-benzo[g]indazole-3-carboxamide) (38.3 mg, 0.10 mmol) and isopropyl aldehyde (22 mg, 0.30 mmol). Its structure was confirmed by $^1$H NMR and MS (440, M+1). $C_{22}H_{25}N_5O_3S.H_2O.(Et_2O)_{0.2}$, Calc.: C: 57.97; H: 6.19, N: 14.83; Found, C: 57.63; H: 5.76 N: 14.04.

Procedures for the Synthesis of Compounds of Example 46 and 47

Scheme XIV

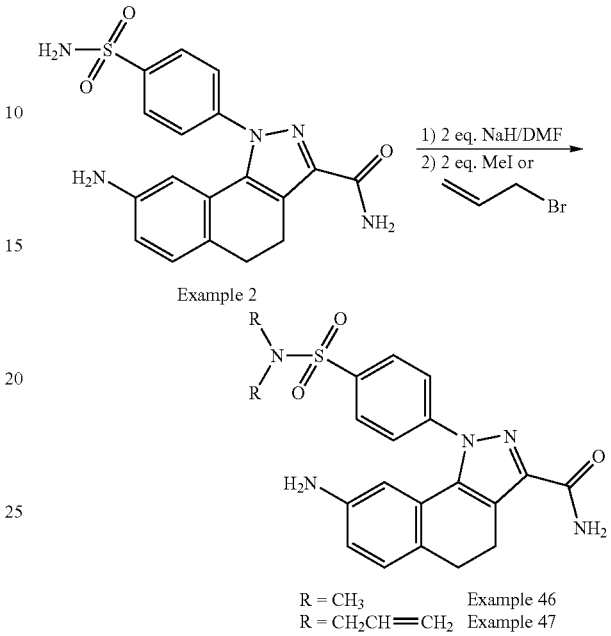

Example 46

8-amino-1-{4-[(dimethylamino)sulfonyl]phenyl}-4,5-dihydro-1H-benzo[g]indazole-3-carboxamide

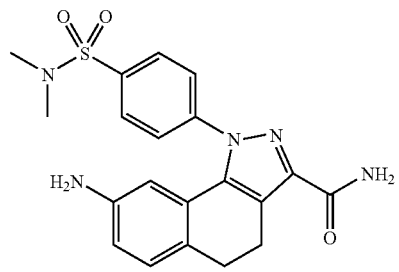

To a stirred solution of the product of Example 2 (8-amino-1-{4-[(aminothio)peroxy]phenyl}-4,5-dihydro-1H-benzo[g]indazole-3-carboxamide) (38 mg, 0.10 mmol) in DMF (1 mL) at RT under Ar was added sodium hydride in mineral oil (60%, 8 mg, 0.20 mmol). After 2 h, iodomethane (28.4 mg, 0.20 mmol) in DMF (1 mL) was added and the resulted mixture was stirred at RT for 18 h, added water (10 mL), extracted with EtOAc (3×10 mL). The combined organic layers was washed with water (3×10 mL), dried over MgSO$_4$, filtered through a silica gel pad with EtOAc, and concentrated. The crude product was triturated with diethyl ether to give 8-amino-1-{4-[(dimethylamino)sulfonyl]phenyl}-4,5-dihydro-1H-benzo[g]indazole-3-carboxamide as a yellow solid (29 mg, 70%). Its structure was confirmed by $^1$H NMR and MS (412, M+1). $C_{20}H_{21}N_5O_3S.(H_2O)_{0.3}(Et_2O)_{0.3}$, Calc.: C: 57.99; H: 5.65, N: 15.95; Found, C: 57.31; H: 5.18, N: 15.26.

Example 47

8-amino-1-{4-[(diallylamino)sulfonyl]phenyl}-4,5-dihydro-1H-benzo[g]indazole-3-carboxamide

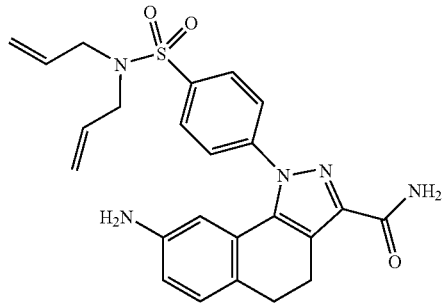

The title compound was synthesized by the same procedure used as for Example 46 except iodomethane was replaced by allyl bromide (24.2 mg, 0.20 mmol). The title compound is a yellow solid (28 mg, 61%). Its structure was confirmed by $^1$H NMR and MS (464, M+1). $C_{24}H_{25}N_5O_3S$, Calc.: C: 62.18; H: 5.44, N: 15.11; Found, C: 61.76; H: 5.10, N: 14.77.

Synthesis of Examples 48 and 49

Scheme XV

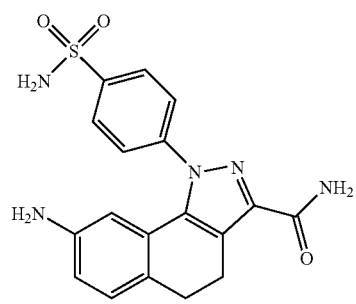
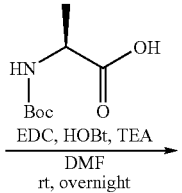

Example 2

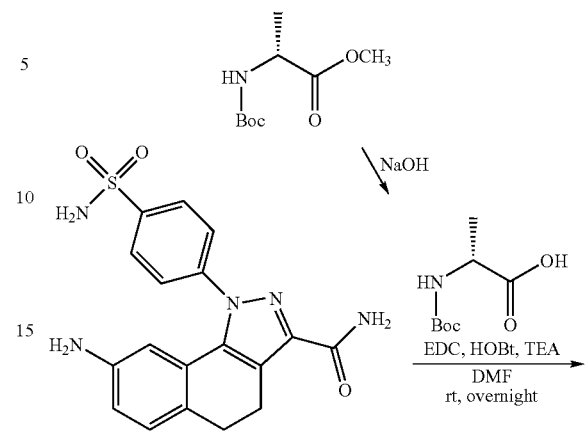

Example 2

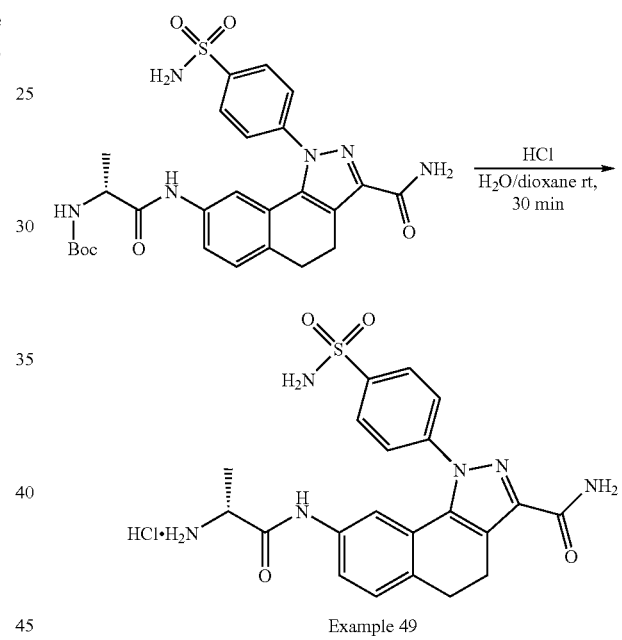

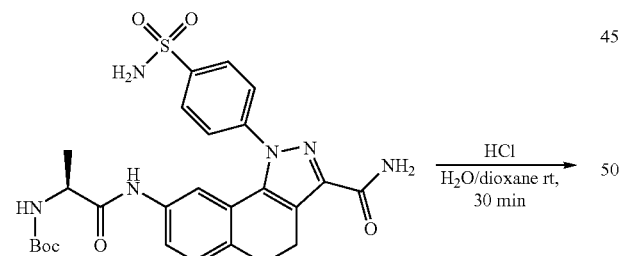
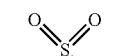

Example 48

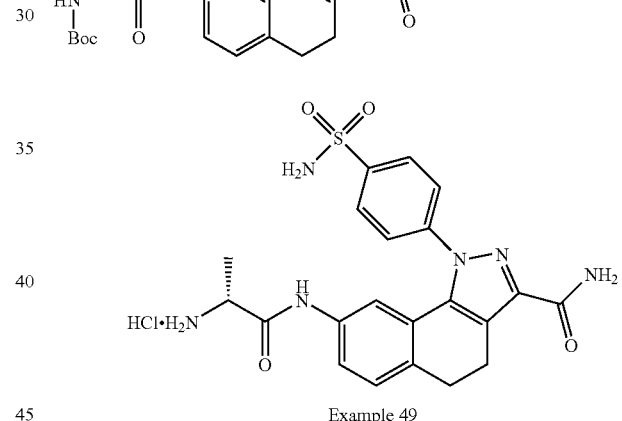

Example 49

Example 48

8-(L-alanylamino)-1-[4-(aminosulfonyl)phenyl]-4,5-dihydro-1H-benzo[g]indazole-3-carboxamide

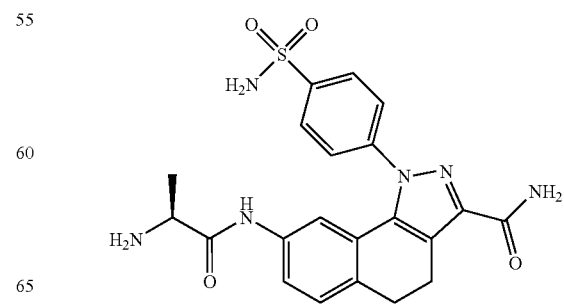

To a stirring solution of 8-amino-1-{4-[(aminothio)peroxy]phenyl}-4,5-dihydro-1H-benzo[g]indazole-3-carboxamide (Example 2) (153 mg, 0.40 mmol) in DMF (6 mL) were added N-Boc-L-alanine (90 mg, 0.48 mmol), EDC (88 mg, 0.46 mmol), HOBt (60 mg, 0.44 mmol), and triethylamine (0.06 mL, 0.44 mmol). The reaction mixture was allowed to stir overnight at room temperature. The DMF was then removed under reduced pressure and the resulting residue was purified by reverse phase preparative HPLC to give a beige powder (83 mg, 38%). The powder was then dissolved in dioxane/water (2 mL, 1:1) and 5 M HCl (1 mL) was added at room temperature. After stirring for 3 hours, the solvent was removed under reduced pressure to give an oily residue. The residue was dissolved in a minimum amount of methanol and ether was added. The resulting precipitate was filtered to give the title compound as a pale yellow solid (66 mg, 90%). $^1$H NMR (400 MHz, d$_6$-DMSO): 1.33 (d, 3H, J=6 Hz), 2.88–2.97 (m, 4H), 3.92 (m, 1H), 7.24–8.15 (7H, m); M+1=456, Anal. Calcd for C$_{21}$H$_{23}$N$_6$O$_4$SCl containing MeOH (1) and CH$_2$Cl$_2$ (1): C, 45.44; H, 4.83; N, 13.82. Found C, 45.37; H, 4.83; N, 13.60.

Example 49

8-(D-alanylamino)-1-[4-(aminosulfonyl)phenyl]-4,5-dihydro-1H-benzo[g]indazole-3-carboxamide

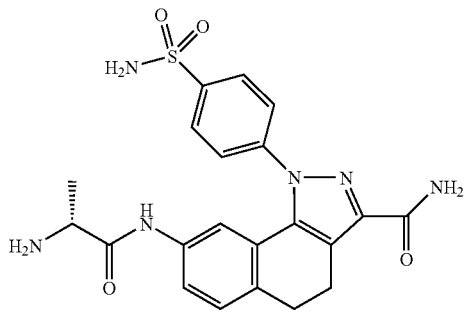

To a stirring solution of 8-amino-1-{4-[(aminothio)peroxy]phenyl}-4,5-dihydro-1H-benzo[g]indazole-3-carboxamide (Example 2) (156 mg, 0.40 mmol) in DMF (6 mL) were added N-Boc-D-alanine (81 mg, 0.43 mmol), EDC (85 mg, 0.44 mmol), HOBt (58 mg, 0.43 mmol), and triethylamine (0.06 mL, 0.44 mmol). The reaction mixture was allowed to stir overnight at room temperature. The DMF was then removed under reduced pressure and the resulting residue was purified by reverse phase preparative HPLC to give a beige powder (122 mg, 56%). The powder was then dissolved in dioxane/water (2 mL, 1:1) and 5 M HCl (1 mL) was added at room temperature. After stirring for 3 hours, the solvent was removed under reduced pressure to give the title compound as a light orange solid (92 mg, 87%). $^1$H NMR (400 MHz, d$_6$-DMSO): 1.35 (d, 3H, J=6 Hz), 2.80–2.94 (m, 4H), 3.91 (m, 1H), 7.13–8.14 (7H, m); M+1=456.

Example 50

8-[(2-chlorobenzoyl)amino]-1-{4-[(dimethylamino)sulfonyl]phenyl}-4,5-dihydro-1H-benzo[g]indazole-3-carboxamide

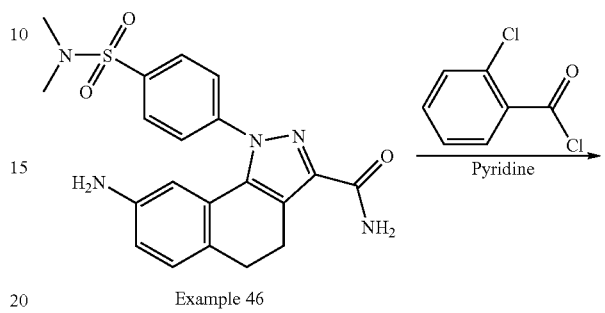

Example 46

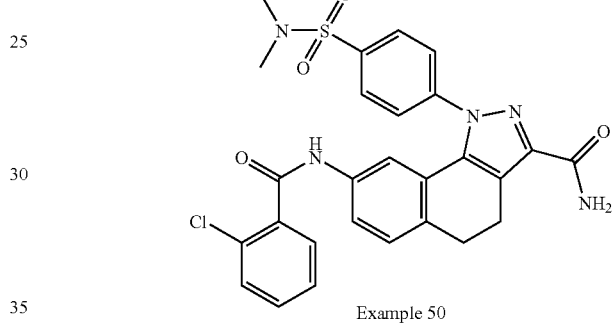

Example 50

To a stirred solution of 8-amino-1-{4-[(dimethylamino)sulfonyl]phenyl}-4,5-dihydro-1H-benzo[g]indazole-3-carboxamide (Example 46) (1.52 g, 3.70 mmol) in pyridine (25 mL) at RT was added 2-chlorobenzoic chloride (970 mg, 5.55 mmol). After 14 h, trisamine (1 g) was added and the mixture was stirred for 2 h. The mixture was filtered through a silica gel pad with EtOAc and concentrated. Column chromatography (silica gel, EtOAc) gave the title compound as a yellow solid (900 mg, 1.63 mmol, 44%). Its structure was confirmed by $^1$H NMR and MS (551, M+1). C$_{27}$H$_{24}$ClN$_5$O$_4$S, Calc.: C: 58.96; H: 4.40, N: 12.73; Found, C: 58.66; H: 4.65, N: 12.58.

Examples 51–91

Synthesis of the Sulfonamide/Amide/Urea Library

The sulfonamides, amides, and ureas of Examples 51–91 were synthesized in a library format as described in Examples 5–40. The starting materials are the product of Example 4 (8-amino-1-{4-[(aminothio)peroxy]phenyl}-4,5-dihydro-1H-benzo[g]indazole-3-carboxamide) and appropriate sulfonyl chlorides, acyl chlorides and isocyanates. Table 1 shows the compound identification, compound, IKK resin assay values, formula weight, and mass spectroscopy characterization for the compounds from the library.

TABLE 1

| COMPOUND | STRUCTURE | EXAMPLE | IKK2-resin | Formula Weight | Mass Spec |
|---|---|---|---|---|---|
| 1-[4-(aminosulfonyl)phenyl]-8-nitro-4,5-dihydro-1H-benzo[g]indazole-3-carboxamide | 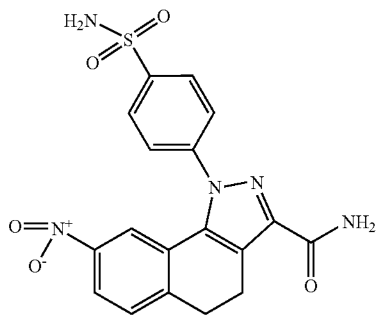 | Example 1 | >100 μM | 413.41 | 414 |
| 8-amino-1-[4-(aminosulfonyl)phenyl]-4,5-dihydro-1H-benzo[g]indazole-3-carboxamide | 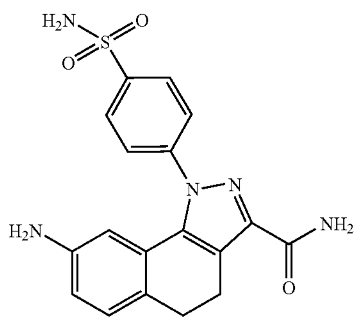 | Example 2 | ≦1 μM | 383.43 | 384 |
| 8-(acetylamino)-1-[4-(aminosulfonyl)phenyl]-4,5-dihydro-1H-benzo[g]indazole-3-carboxamide | 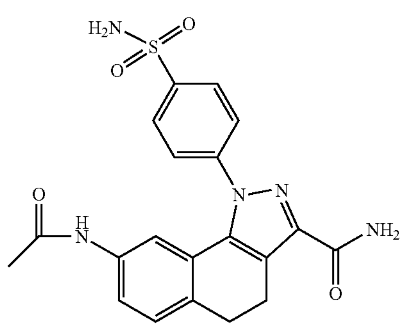 | Example 3 | 10 ≦ 100 μM) | 425.47 | 426 |
| 1-[4-(aminosulfonyl)phenyl]-8-[(methylsulfonyl)amino]-4,5-dihydro-1H-benzo[g]indazole-3-carboxamide | 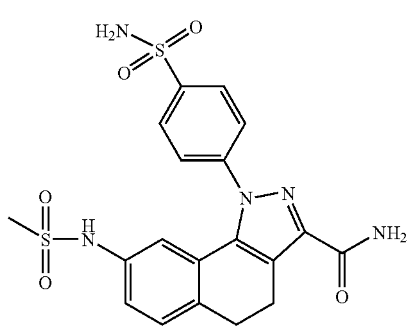 | Example 4 | ≦1 μM | 461.52 | 462 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-{[(trifluoromethyl)sulfonyl]amino}-4,5-dihydro-1H-benzo[g]indazole-3-carboxamide | 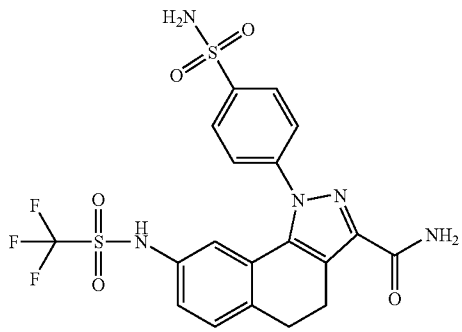 | Example 5 | 10 ≦ 100 μM | 515.49 | 516 |
| 1-[4-(aminosulfonyl)phenyl]-8-[(ethylsulfonyl)amino]-4,5-dihydro-1H-benzo[g]indazole-3-carboxamide | 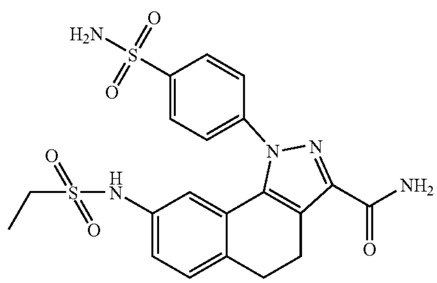 | Example 6 | ≦1 μM | 475.55 | 478 |
| 1-[4-(aminosulfonyl)phenyl]-8-{[(2,2,2-trifluoroethyl)sulfonyl]amino}-4,5-dihydro-1H-benzo[g]indazole-3-carboxamide | 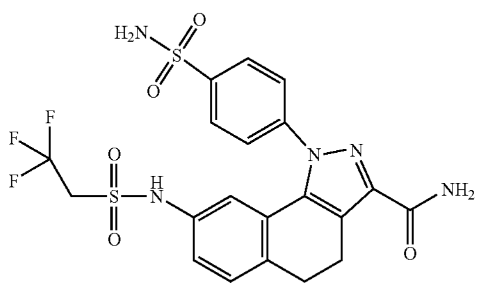 | Example 7 | 1 ≦ 10 μM | 529.52 | 530 |
| 1-[4-(aminosulfonyl)phenyl]-8-[(propylsulfonyl)amino]-4,5-dihydro-1H-benzo[g]indazole-3-carboxamide | 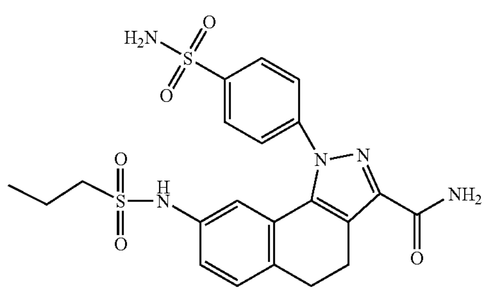 | Example 8 | 1 ≦ 10 μM | 489.58 | 490 |
| 1-[4-(aminosulfonyl)phenyl]-8-[(isopropylsulfonyl)amino]-4,5-dihydro-1H-benzo[g]indazole-3-carboxamide | 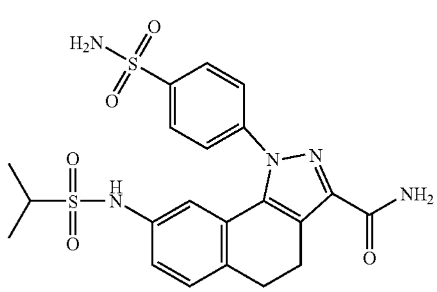 | Example 9 | 1 ≦ 10 μM | 489.58 | 490 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(butylsulfonyl)amino]-4,5-dihydro-1H-benzo[g]indazole-3-carboxamide | 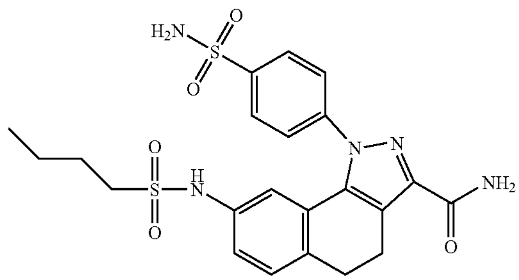 | Example 10 | 1 ≦ 10 μM | 503.60 | 531 |
| 1-[4-(aminosulfonyl)phenyl]-8-[(benzylsulfonyl)amino]-4,5-dihydro-1H-benzo[g]indazole-3-carboxamide | 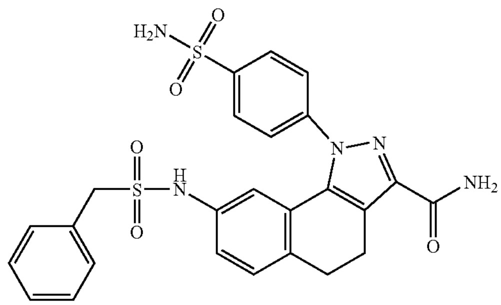 | Example 11 | 1 ≦ 10 μM | 537.62 | 538 |
| 1-[4-(aminosulfonyl)phenyl]-8-[(1-naphthylsulfonyl)amino]-4,5-dihydro-1H-benzo[g]indazole-3-carboxamide | 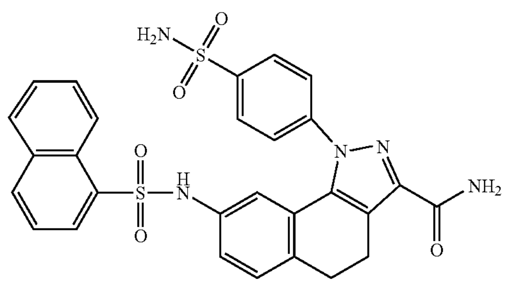 | Example 12 | 10 ≦ 100 μM | 573.65 | 574 |
| 1-[4-(aminosulfonyl)phenyl]-8-({[5-(dimethylamino)-1-naphthyl]sulfonyl}amino)-4,5-dihydro-benzo[g]indazole-3-carboxamide | 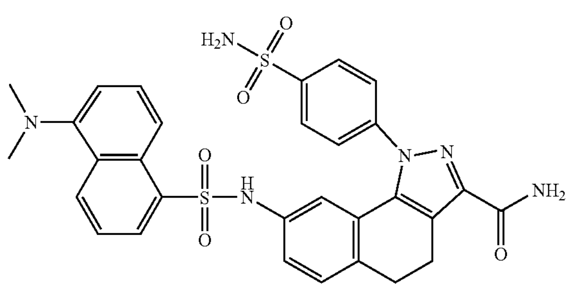 | Example 13 | 1 ≦ 10 μM | 616.72 | 617 |
| 1-[4-(aminosulfonyl)phenyl]-8-[(isoquinolin-5-ylsulfonyl)amino]-4,5-dihydro-1H-benzo[g]indazole-3-carboxamide | 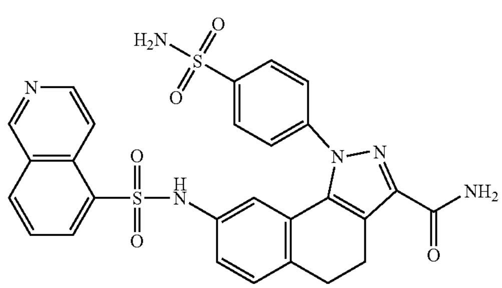 | Example 14 | 1 ≦ 10 μM | 574.64 | 575 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(quinolin-7-ylsulfonyl)amino]-4,5-dihydro-1H-benzo[g]indazole-3-carboxamide | 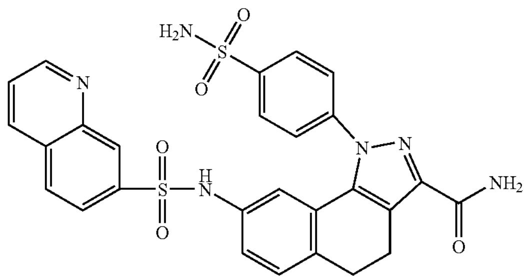 | Example 15 | >100 μM | 574.64 | 575 |
| 1-[4-(aminosulfonyl)phenyl]-8-[(2,1,3-benzoxadiazol-4-ylsulfonyl)amino]-4,5-dihydro-1H-benzo[g]indazole-3-carboxamide | 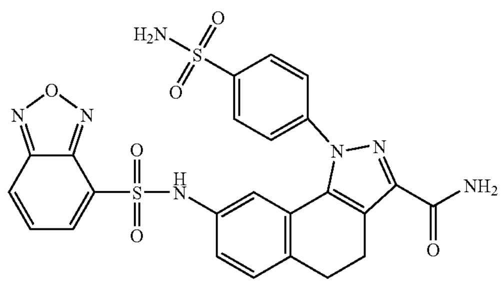 | Example 16 | 1 ≦ 10 μM | 565.59 | 575 |
| 1-[4-(aminosulfonyl)phenyl]-8-[(1,1'-biphenyl-4-ylsulfonyl)amino]-4,5-dihydro-1H-benzo[g]indazole-3-carboxamide | 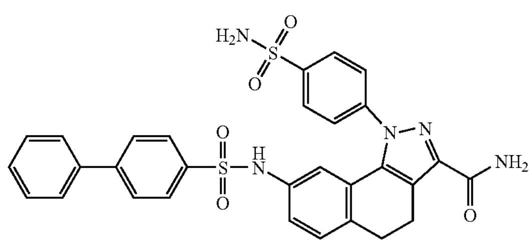 | Example 17 | 1 ≦ 10 μM | 599.69 | 600 |
| 1-[4-(aminosulfonyl)phenyl]-8-{[(5-pyridin-2-ylthien-2-yl)sulfonyl]amino}-4,5-dihydro-1H-benzo[g]indazole-3-carboxamide | 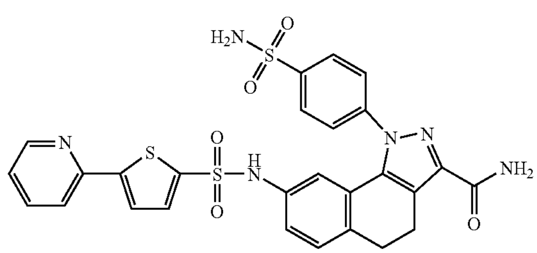 | Example 18 | 10 ≦ 100 μM | 606.71 | 607 |
| 1-[4-(aminosulfonyl)phenyl]-8-{[(1-methyl-1H-imidazol-4-yl)sulfonyl]amino}-4,5-dihydro-1H-benzo[g]indazole-3-carboxamide | 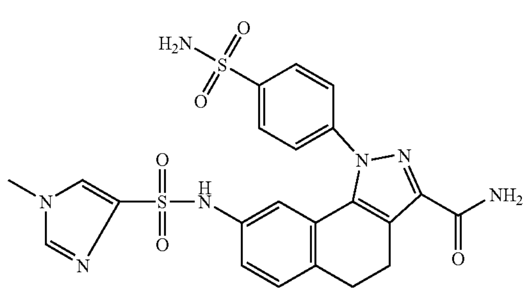 | Example 19 | 10 ≦ 100 μM | 527.58 | 528 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-{[(1,2-dimethyl-1H-imidazol-4-yl)sulfonyl]amino}-4,5-dihydro-1H-benzo[g]indazole-3-carboxamide | 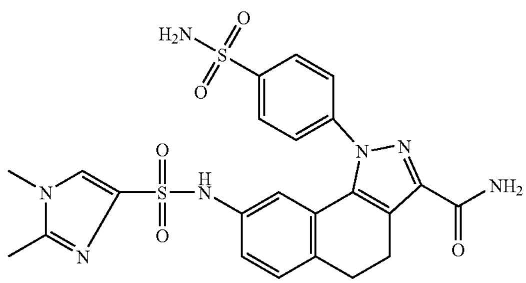 | Example 20 | 10 ≦ 100 μM | 541.61 | 542 |
| 8-({[2-(acetylamino)-4-methyl-1,3-thiazol-5-yl]sulfonyl}amino)-1-[4-(aminosulfonyl)phenyl]-4,5-dihydro-1H-benzo[g]indazole-3-carboxamide | 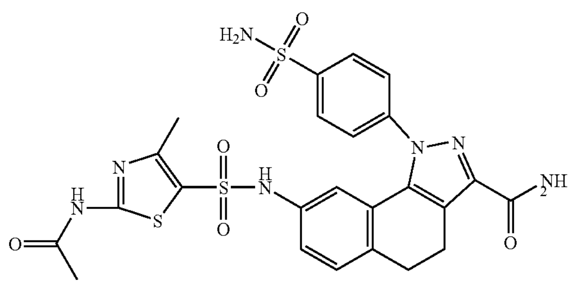 | Example 21 | 1 ≦ 10 μM | 601.69 | 602 |
| 1-[4-(aminosulfonyl)phenyl]-8-{[(4-methylphenyl)sulfonyl]amino}-4,5-dihydro-1H-benzo[g]indazole-3-carboxamide | 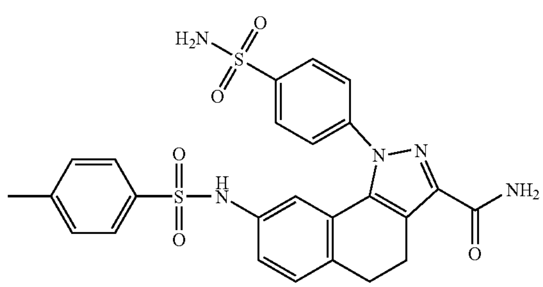 | Example 22 | 10 ≦ 100 μM3) | 537.62 | 538 |
| 1-[4-(aminosulfonyl)phenyl]-8-{[(4-methoxyphenyl)sulfonyl]amino}-4,5-dihydro-1H-benzo[g]indazole-3-carboxamide | 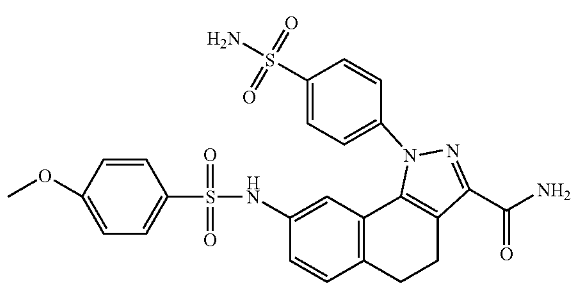 | Example 23 | 10 ≦ 100 μM | 553.62 | 554 |
| 1-[4-(aminosulfonyl)phenyl]-8-{[(4-fluorophenyl)sulfonyl]amino}-4,5-dihydro-1H benzo[g]indazole-3-carboxamide | | Example 24 | 1 ≦ 10 μM | 541.58 | 542 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-{[(4-chlorophenyl)sulfonyl]amino}-4,5-dihydro-1H-benzo[g]indazole-3-carboxamide | 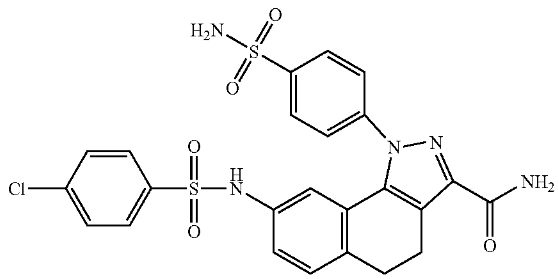 | Example 25 | 1 ≦ 10 μM | 558.04 | 559 |
| 1-[4-(aminosulfonyl)phenyl]-8-{[(4-bromophenyl)sulfonyl]amino}-4,5-dihydro-1H-benzo[g]indazole-3-carboxamide | 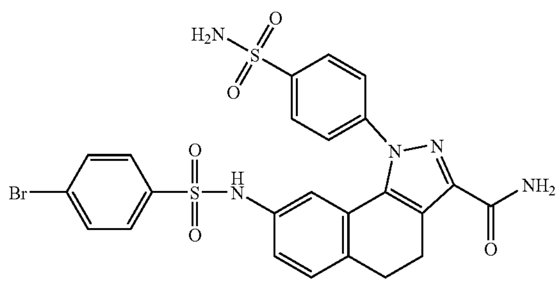 | Example 26 | 1 ≦ 10 μM | 602.49 | 603 |
| 1-[4-(aminosulfonyl)phenyl]-8-({[3-(trifluoromethyl)phenyl]sulfonyl}amino)-4,5-dihydro-1H-benzo[g]indazole-3-carboxamide | 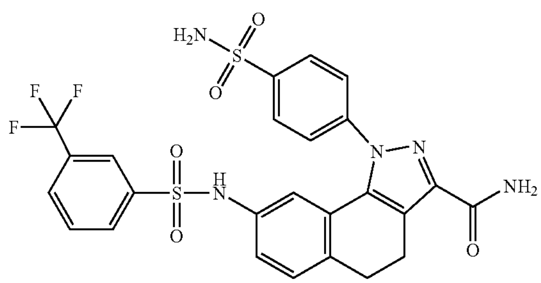 | Example 27 | 10 ≦ 100 μM | 591.59 | 592 |
| 1-[4-(aminosulfonyl)phenyl]-8-{[(3,4-dichlorophenyl)sulfonyl]amino}-4,5-dihydro-1H-benzo[g]indazole-3-carboxamide | 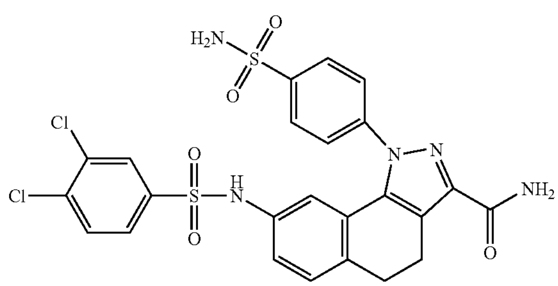 | Example 28 | 1 ≦ 10 μM | 592.48 | 593 |
| 1-[4-(aminosulfonyl)phenyl]-8-{[(2,5-dichlorophenyl)sulfonyl]amino}-4,5-dihydro-1H-benzo[g]indazole-3-carboxamide | 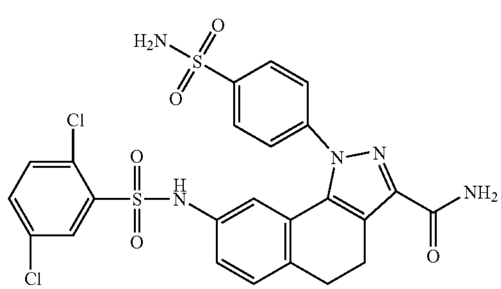 | Example 29 | 1 ≦ 10 μM | 592.48 | 593 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-{[(2,4-dichlorophenyl)sulfonyl]amino}-4,5-dihydro-1H-benzo[g]indazole-3-carboxamide | 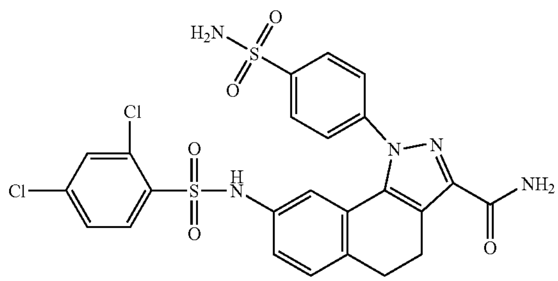 | Example 30 | 1 ≦ 10 μM | 592.48 | 593 |
| 1-[4-(aminosulfonyl)phenyl]-8-{[(2,4-difluorophenyl)sulfonyl]amino}-4,5-dihydro-1H-benzo[g]indazole-3-carboxamide | 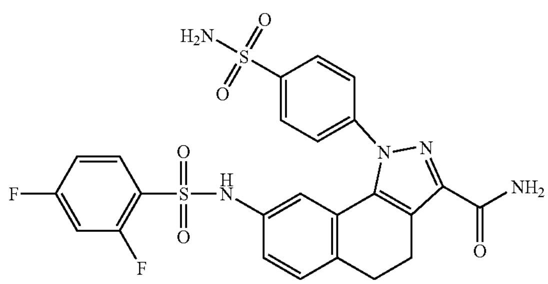 | Example 31 | 10 ≦ 100 μM | 559.57 | 560 |
| 1-[4-(aminosulfonyl)phenyl]-8-{[(3,4-difluorophenyl)sulfonyl]amino}-4,5-dihydro-1H-benzo[g]indazole-3-carboxamide | 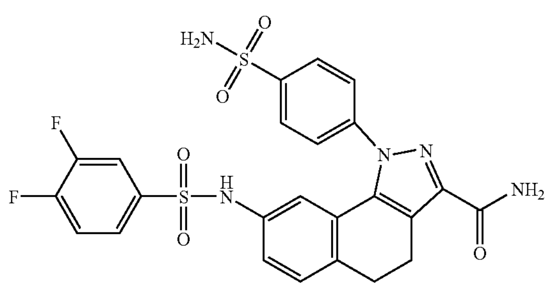 | Example 32 | 10 ≦ 100 μM | 559.57 | 560 |
| 1-[4-(aminosulfonyl)phenyl]-8-{[(4-bromo-2-fluorophenyl)sulfonyl]amino}-4,5-dihydro-1H-benzo[g]indazole-3-carboxamide | 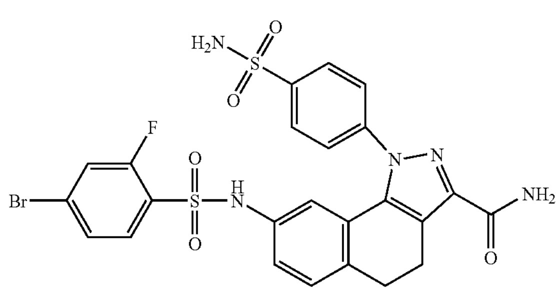 | Example 33 | 1 ≦ 10 μM | 620.48 | 621 |
| 1-[4-(aminosulfonyl)phenyl]-8-{[(3,4-dimethoxyphenyl)sulfonyl]amino}-4,5-dihydro-1H-benzo[g]indazole-3-carboxamide | 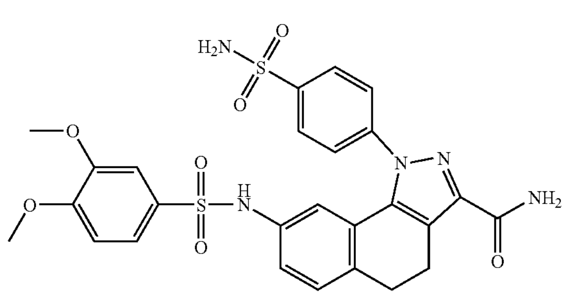 | Example 34 | 10 ≦ 100 μM | 583.64 | 584 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-({[3,5-bis(trifluoromethyl)phenyl]sulfonyl}amino)-4,5-dihydro-1H-benzo[g]indazole-3-carboxamide | 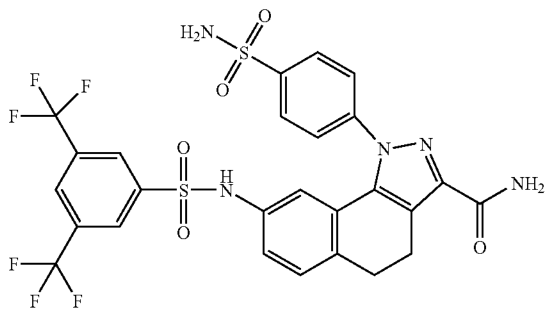 | Example 35 | $1 \leq 10\ \mu M$ | 659.59 | 660 |
| 1-[4-(aminosulfonyl)phenyl]-8-{[(2,4,5-trichlorophenyl)sulfonyl]amino}-4,5-dihydro-1H-benzo[g]indazole-3-carboxamide | 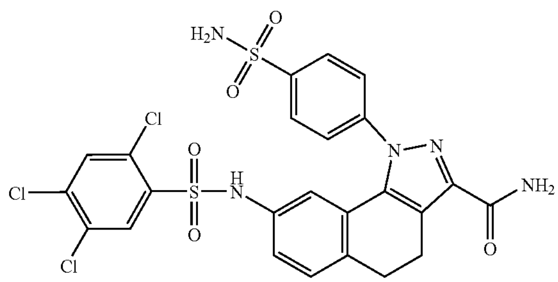 | Example 36 | $1 \leq 10\ \mu M$ | 626.93 | 627 |
| 1-[4-(aminosulfonyl)phenyl]-8-(propionylamino)-4,5-dihydro-1H-benzo[g]indazole-3-carboxamide | 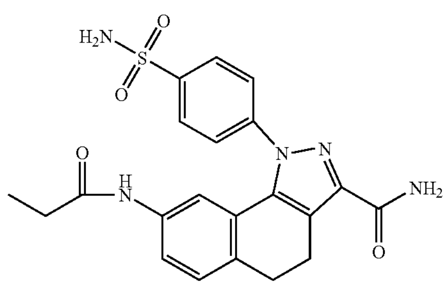 | Example 37 | $1 \leq 10\ \mu M$ | 439.49 | 440 |
| 1-[4-(aminosulfonyl)phenyl]-8-(benzoylamino)-4,5-dihydro-1H-benzo[g]indazole-3-carboxamide | 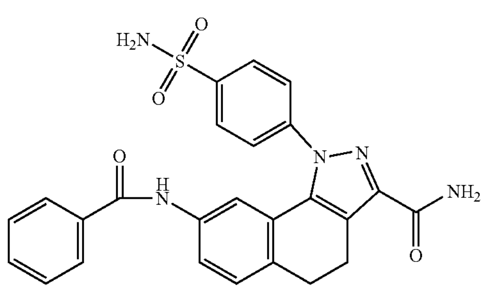 | Example 38 | $1 \leq 10\ \mu M$ | 487.54 | 489 |
| 1-[4-(aminosulfonyl)phenyl]-8-{[(ethylamino)carbonyl]amino}-4,5-dihydro-1H-benzo[g]indazole-3-carboxamide | 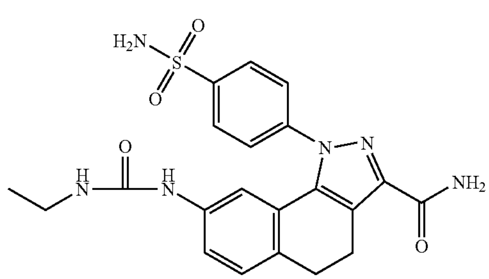 | Example 39 | $1 \leq 10\ \mu M$ | 454.51 | 455 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(anilinocarbonyl)amino] 4,5-dihydro-1H-benzo[g]indazole-3-carboxamide | 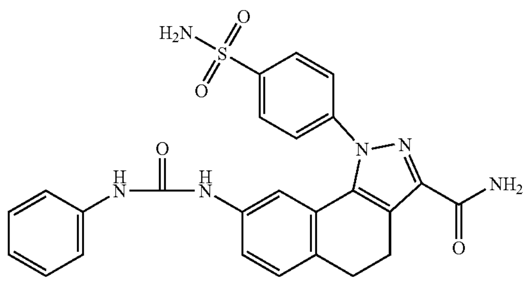 | Example 40 | 1 ≦ 10 μM | 502.55 | 503 |
| 1-[4-(aminosulfonyl)phenyl]-8-(benzylamino)-4,5-dihydro-1H-benzo[g]indazole-3-carboxamide | 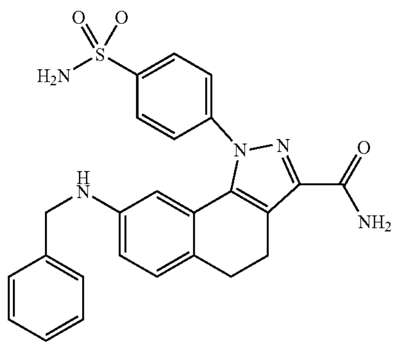 | Example 41 | 1 ≦ 10 μM | 473.56 | 474 |
| 1-[4-(aminosulfonyl)phenyl]-8-[(4-methylbenzyl)amino]-4,5-dihydro-1H-benzo[g]indazole-3-carboxamide | 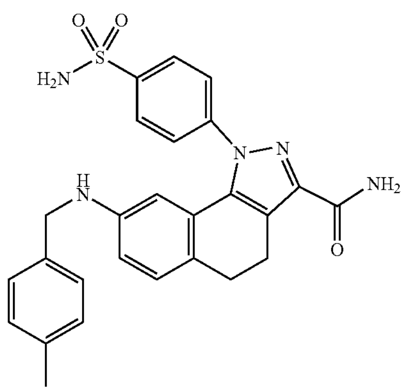 | Example 42 | 10 ≦ 100 μM | 487.58 | 488 |
| 1-[4-(aminosulfonyl)phenyl]-8-[(4-methoxybenzyl)amino]-4,5-dihydro-1H-benzo[g]indazole-3-carboxamide | 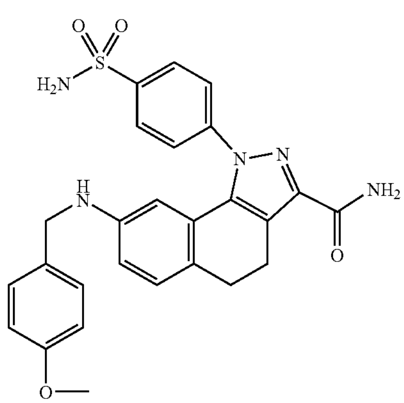 | Example 43 | 1 ≦ 10 μM | 503.58 | |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(4-chlorobenzyl)amino]-4,5-dihydro-1H-benzo[g]indazole-3-carboxamide | 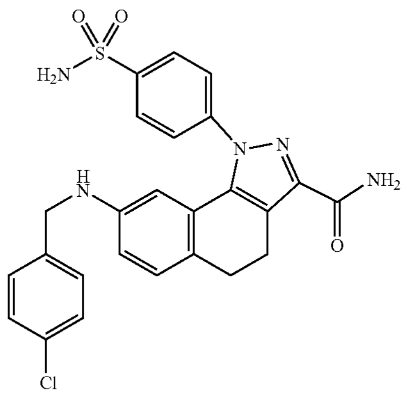 | Example 44 | 10 ≦ 100 μM | 508.00 | 509 |
| 1-[4-(aminosulfonyl)phenyl]-8-(isobutylamino)-4,5-dihydro-1H-benzo[g]indazole-3-carboxamide | 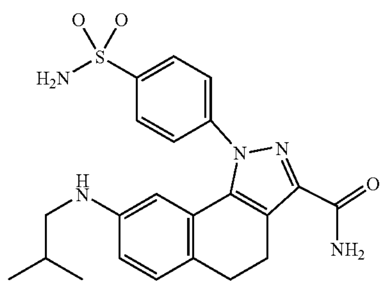 | Example 45 | 10 ≦ 100 μM | 439.54 | 440 |
| 8-amino-1-{4-[(dimethylamino)sulfonyl]phenyl}-4,5-dihydro-1H-benzo[g]indazole-3-carboxamide | 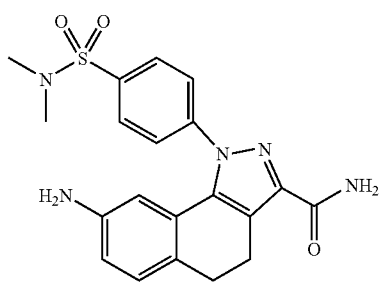 | Example 46 | 1 ≦ 10 μM | 411.48 | 412 |
| 8-amino-1-{4-[(diallylamino)sulfonyl]phenyl}-4,5-dihydro-1H-benzo[g]indazole-3-carboxamide | 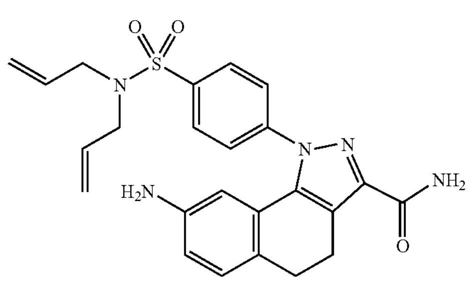 | Example 47 | 1 ≦ 10 μM | 463.56 | 464 |

TABLE 1-continued

| COMPOUND | STRUCTURE | EXAMPLE | IKK2-resin | Formula Weight | Mass Spec |
|---|---|---|---|---|---|
| 8-(L-alanylamino)-1-[4-(aminosulfonyl)phenyl]-4,5-dihydro-1H-benzo[g]indazole-3-carboxamide hydrochloride | 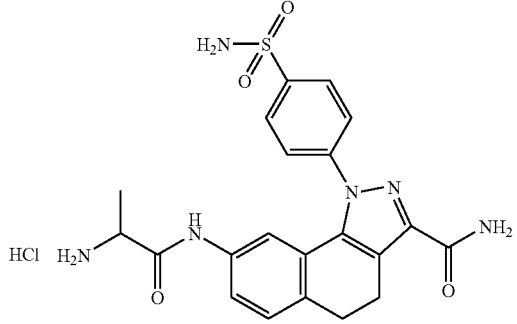 | Example 48 | 1 ≦ 10 μM | 490.97 | 492 |
| 8-(D-alanylamino)-1-[4-(aminosulfonyl)phenyl]-4,5-dihydro-1H-benzo[g]indazole-3-carboxamide hydrochloride | 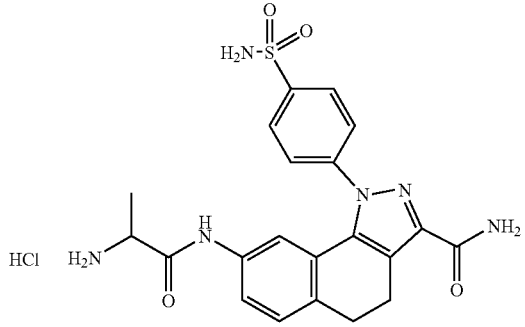 | Example 49 | 1 ≦ 10 μM | 490.97 | 492 |
| 8-[(2-chlorobenzoyl)amino]-1-{4-[(dimethylamino)sulfonyl]phenyl}-4,5-dihydro-1H-benzo[g]indazole-3-carboxamide | 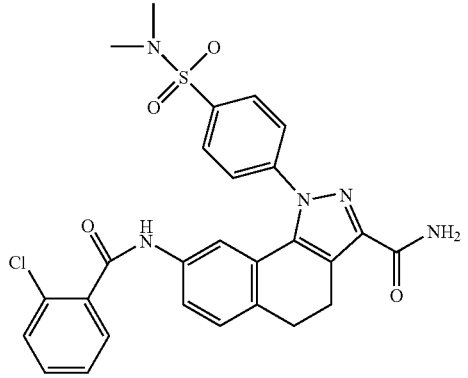 | Example 50 | ≦1 μM | 550.04 | 551 |
| 1-[4-(aminosulfonyl)phenyl]-8-(pentanoylamino)-4,5-dihydro-1H-benzo[g]indazole-3-carboxamide | 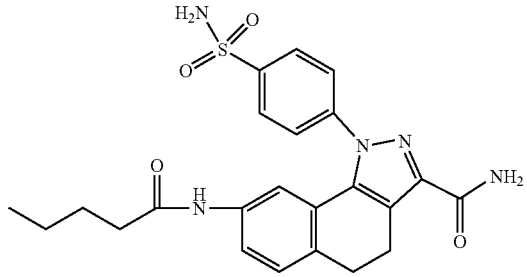 | Example 51 | 1 ≦ 10 μM | 467.55 | 467 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(cyclohexylcarbonyl)amino]-4,5-dihydro-1H-benzo[g]indazole-3-carboxamide | 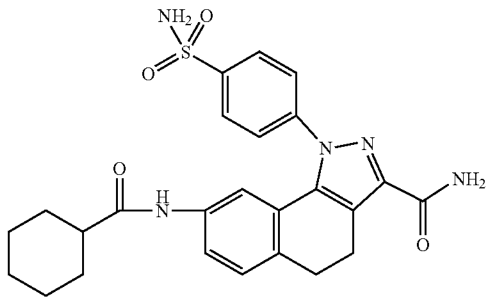 | Example 52 | 1 ≦ 10 μM | 493.59 | 494 |
| 1-[4-(aminosulfonyl)phenyl]-8-[(cyclopentylcarbonyl)amino]-4,5-dihydro-1H-benzo[g]indazole-3-carboxamide | 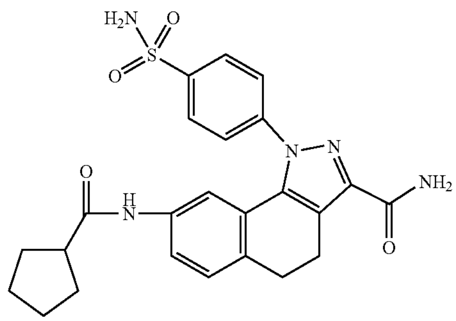 | Example 53 | 1 ≦ 10 μM | 470.56 | 480 |
| 1-[4-(aminosulfonyl)phenyl]-8-[(cyclobutylcarbonyl)amino]-4,5-dihydro-1H-benzo[g]indazole-3-carboxamide | 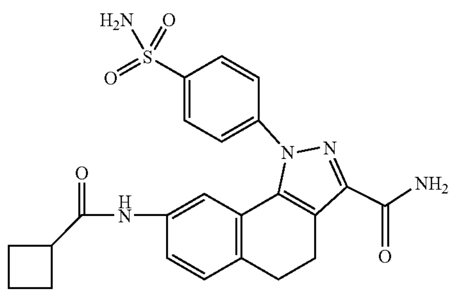 | Example 54 | 1 ≦ 10 μM | 465.53 | 466 |
| 1-[4-(aminosulfonyl)phenyl]-8-[(cyclopropylcarbonyl)amino]-4,5-dihydro-1H-benzo[g]indazole-3-carboxamide | 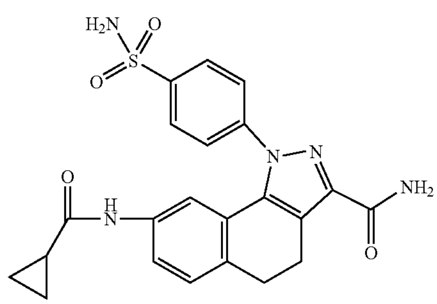 | Example 55 | 1 ≦ 10 μM | 451.51 | 452 |
| 1-[4-(aminosulfonyl)phenyl]-8-(butyrylamino)-4,5-dihydro-1H-benzo[g]indazole-3-carboxamide | 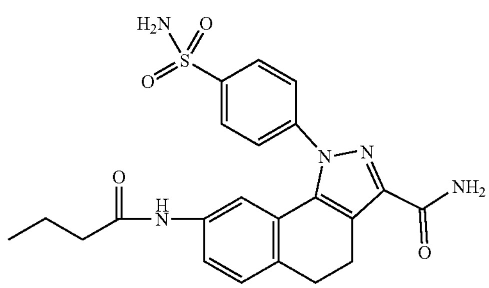 | Example 56 | 1 ≦ 10 μM | 453.52 | 454 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(phenylacetyl)amino]-4,5-dihydro-1H-benzo[g]indazole-3-carboxamide | | Example 57 | 1 ≦ 10 µM | 501.57 | 502 |
| 1-[4-(aminosulfonyl)phenyl]-8-[(methoxyacetyl)amino]-4,5-dihydro-1H-benzo[g]indazole-3-carboxamide | 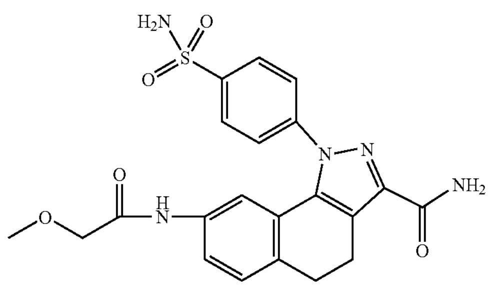 | Example 58 | 1 ≦ 10 µM | 455.49 | 456 |
| 1-[4-(aminosulfonyl)phenyl]-8-(isobutyrylamino)-4,5-dihydro-1H-benzo[g]indazole-3-carboxamide | 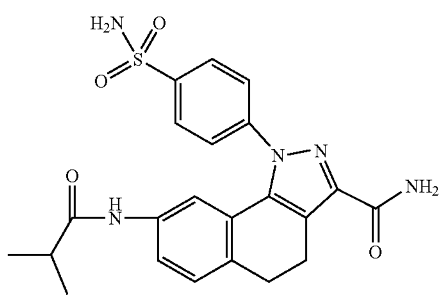 | Example 59 | 1 ≦ 10 µM | 453.52 | 454 |
| 1-[4-(aminosulfonyl)phenyl]-8-{[4-(trifluoromethyl)benzoyl]amino}-4,5-dihydro-1H-benzo[g]indazole-3-carboxainide | 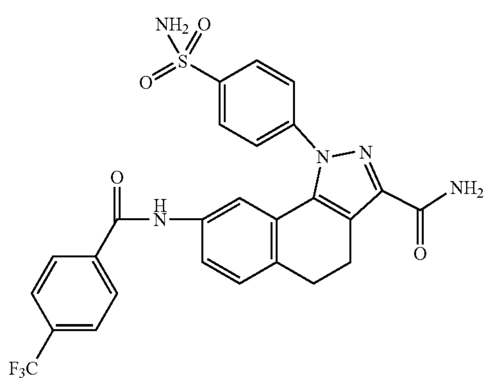 | Example 60 | 1 ≦ 10 µM | 555.54 | 556 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(4-methoxybenzoyl)amino]-4,5-dihydro-1H-benzo[g]indazole-3-carboxamide | 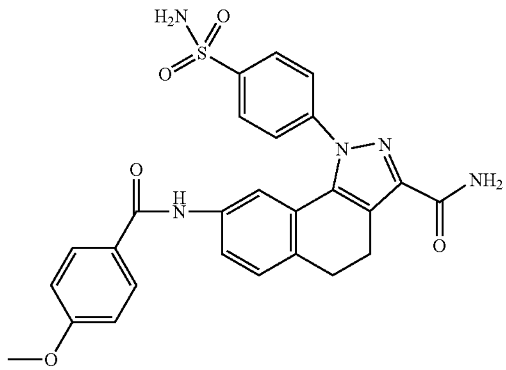 | Example 61 | ≦1 μM | 517.56 | 518 |
| 1-[4-(aminosulfonyl)phenyl]-8-[(4-chlorobenzoyl)amino]-4,5-dihydro-1H-benzo[g]indazole-3-carboxamide | 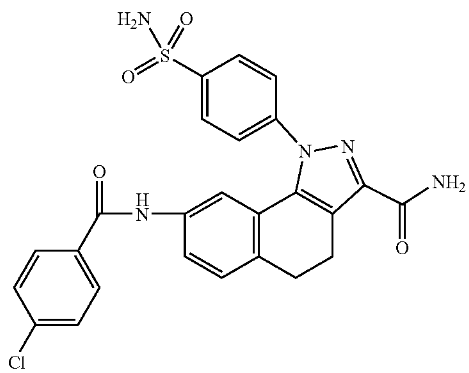 | Example 62 | ≦1 μM | 521.98 | 522 |
| 1-[4-(aminosulfonyl)phenyl]-8-[(4-fluorobenzoyl)amino]-4,5-dihydro-1H-benzo[g]indazole-3-carboxamide | 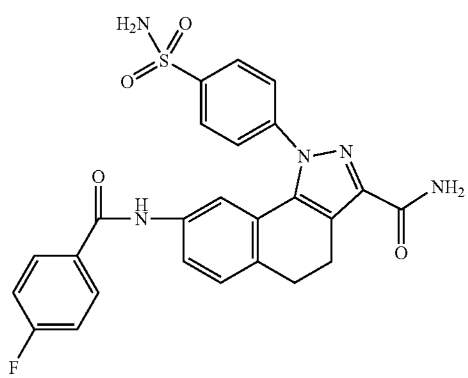 | Example 63 | ≦1 μM | 505.53 | 506 |
| 1-[4-(aminosulfonyl)phenyl]-8-[(3,4-dimethoxybenzoyl)amino]-4,5-dihydro-1H-benzo[g]indazole-3-carboxamide | 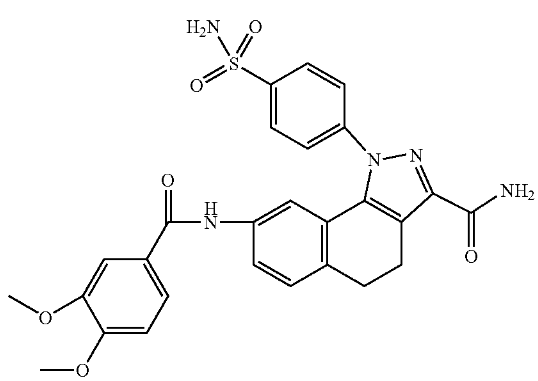 | Example 64 | 1 ≦ 10 μM | 547.59 | 548 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-(2-furoylamino)-4,5-dihydro-1H-benzo[g]indazole-3-carboxamide | 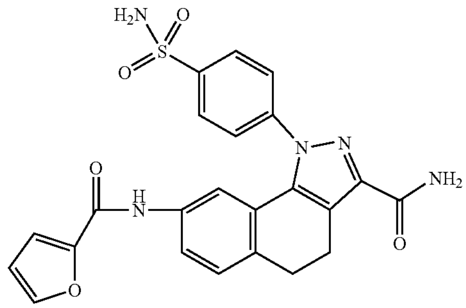 | Example 65 | 10 ≦ 100 μM | 477.5 | 478 |
| 1-[4-(aminosulfonyl)phenyl]-8-[(thien-2-ylcarbonyl)amino]-4,5-dihydro-1H-benzo[g]indazole-3-carboxamide | 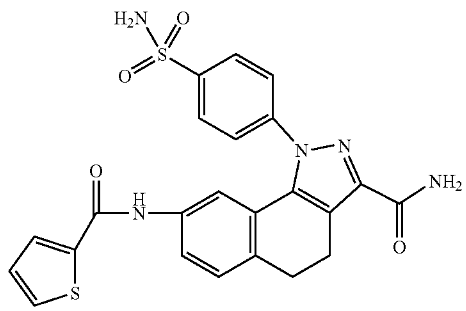 | Example 66 | 10 ≦ 100 μM | 493.57 | 494 |
| 1-[4-(aminosulfonyl)phenyl]-8-(isonicotinoylamino)-4,5-dihydro-1H-benzo[g]indazole-3-carboxamide | 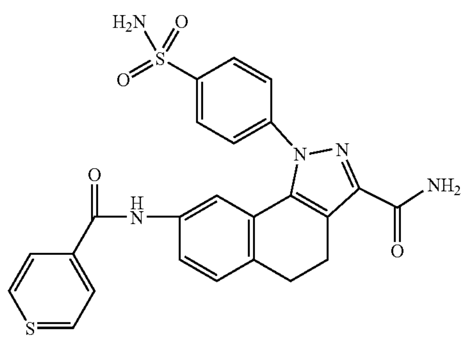 | Example 67 | ≦1 μM | 488.53 | 489 |
| 8-[(1-adamantylcarbonyl)amino]-1-[4-(aminosulfonyl)phenyl]-4,5-dihydro-1H-benzo[g]indazole-3-carboxamide | 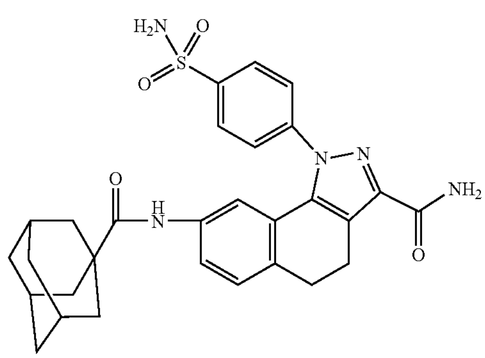 | Example 68 | 1 ≦ 10 μM | 545.66 | 546 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(phenylsulfonyl)amino]-4,5-dihydro-1H-benzo[g]indazole-3-carboxamide | 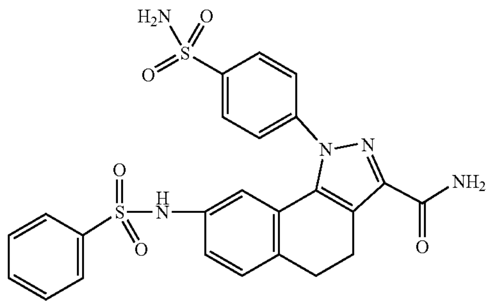 | Example 69 | 1 ≦ 10 μM | 523.59 | 526 |
| 1-[4-(aminosulfonyl)phenyl]-8-{[3-(trifluoromethyl)benzoyl]amino}-4,5-dihydro-1H-benzo[g]indazole-3-carboxamide | 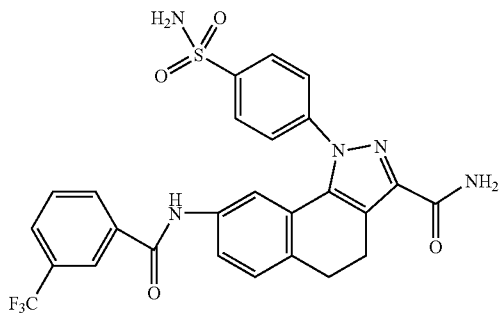 | Example 70 | 1 ≦ 10 μM | 555.54 | 556 |
| 1-[4-(aminosulfonyl)phenyl]-8-[(3-methylbenzoyl)amino]-4,5-dihydro-1H-benzo[g]indazole-3-carboxamide | 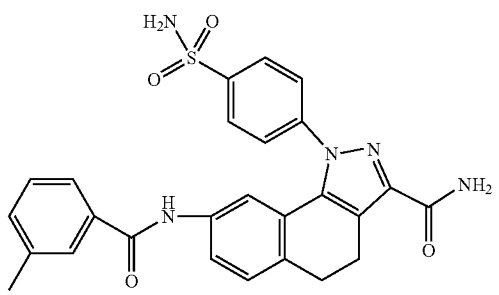 | Example 71 | ≦1 μM | 501.57 | 502 |
| 1-[4-(aminosulfonyl)phenyl]-8-[(3-bromobenzoyl)amino]-4,5-dihydro-1H-benzo[g]indazole-3-carboxamide | 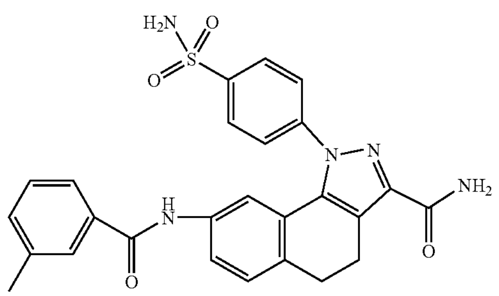 | Example 72 | ≦1 μM | 566.43 | 567 |
| 1-[4-(aminosulfonyl)phenyl]-8-{[(3-methoxyphenyl)acetyl]amino}-4,5-dihydro-1H-benzo[g]indazole-3-carboxamide | 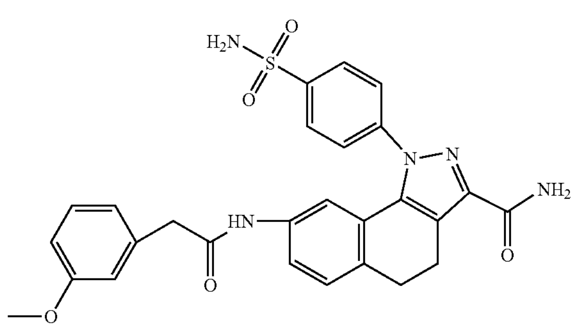 | Example 73 | 1 ≦ 10 μM | 531.59 | 532 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(pyridin-3-ylcarbonyl)amino]-4,5-dihydro-1H-benzo[g]indazole-3-carboxamide | 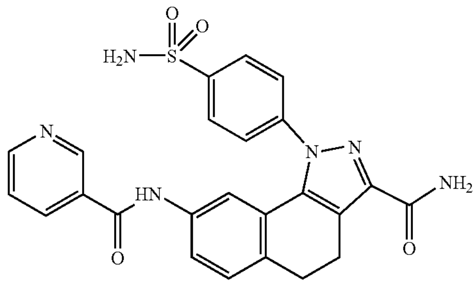 | Example 74 | ≦1 μM | 488.53 | 489 |
| 1-[4-(aminosulfonyl)phenyl]-8-[(2-chlorobenzoyl)amino]-4,5-dihydro-1H-benzo[g]indazole-3-carboxamide | 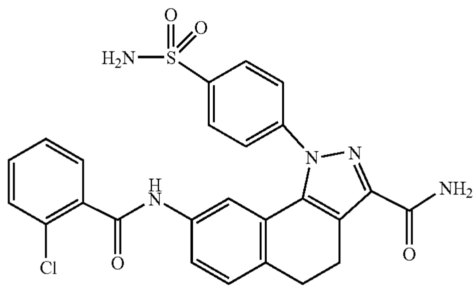 | Example 75 | ≦1 μM | 521.98 | 522 |
| 1-[4-(aminosulfonyl)phenyl]-8-{[(3-bromaphenyl)sulfonyl]amino}-4,5-dihydro-1H-benzo[g]indazole-3-carboxamide | 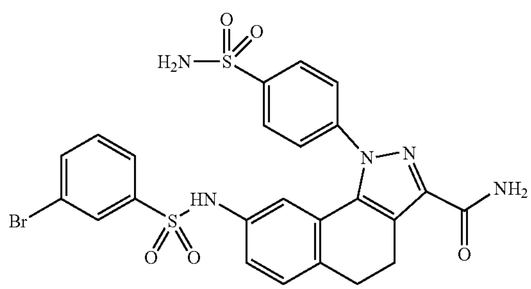 | Example 76 | 1 ≦ 10 μM | 602.49 | 603 |
| 1-[4-(aminosulfonyl)phenyl]-8-{[(3-chlorophenyl)sulfonyl]amino}-4,5-dihydro-1H-benzo[g]indazole-3-carboxamide | 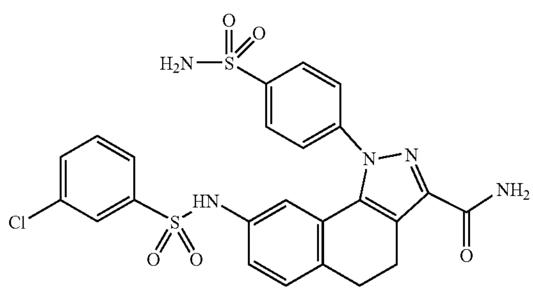 | Example 77 | 1 ≦ 10 μM | 558.04 | 559 |
| 1-[4-(aminosulfonyl)phenyl]-8-[(3-cyanobenzoyl)amino]-4,5-dihydro-1H-benzo[g]indazole-3-carboxamide | 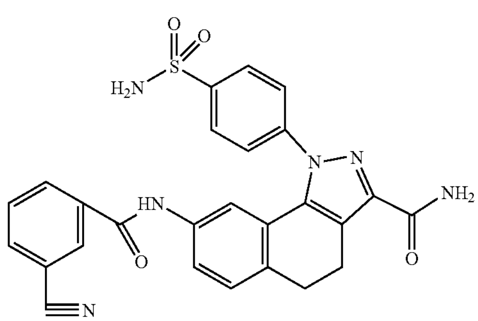 | Example 78 | ≦1 μM | 512.55 | 513 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-methylphenyl)sulfonyl]amino}-4,5-dihydro-1H-benzo[g]indazole-3-carboxamide | 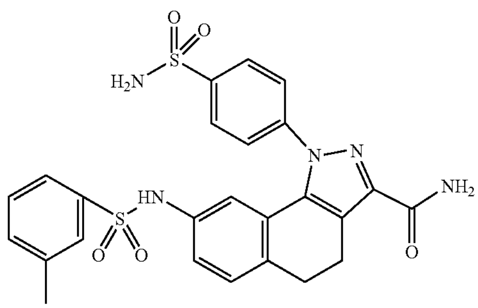 | Example 79 | 10 ≦ 100 μM | 537.62 | 538 |
| 1-[4-(aminosulfonyl)phenyl]-8-[(3-methoxybenzoyl)amino]-4,5-dihydro-1H-benzo[g]indazole-3-carboxamide | 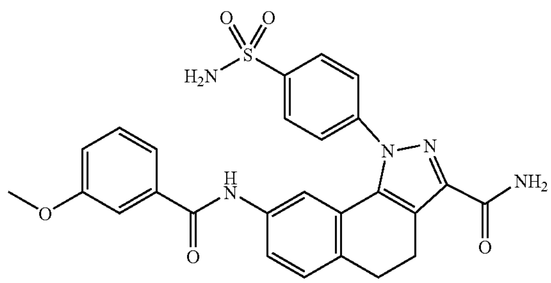 | Example 80 | ≦1 μM | 517.56 | 518 |
| 1-[4-(aminosulfonyl)phenyl]-8-[(3-chlorobenzoyl)amino]-4,5-dihydro-1H-benzo[g]indazole-3-carboxamide | 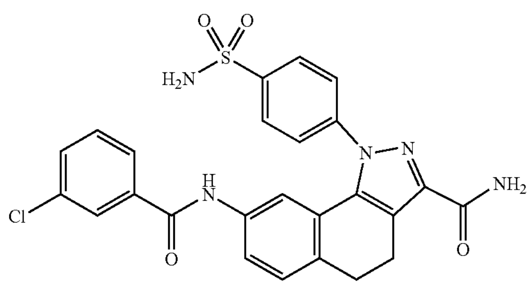 | Example 81 | ≦1 μM | 521.98 | 522 |
| 1-[4-(aminosulfonyl)phenyl]-8-[(2-methoxybenzoyl)amino]-4,5-dihydro-1H-benzo[g]indazole-3-carboxamide | 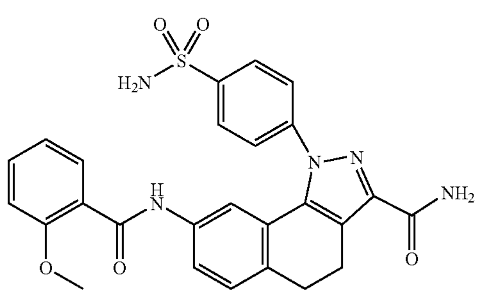 | Example 82 | 10 ≦ 100 μM | 517.56 | 518 |
| 1-[4-(aminosulfonyl)phenyl]-8-{[2-(trifluoromethyl)benzoyl]amino}-4,5-dihydro-1H-benzo[g]indazole-3-carboxamide | 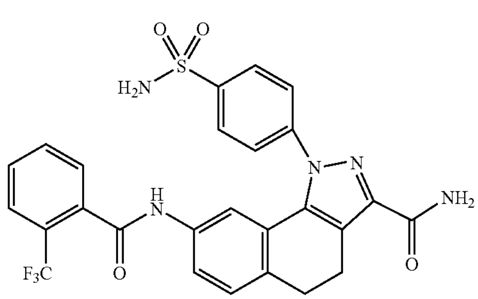 | Example 83 | ≦1 μM | 555.54 | 556 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-[(2-methylbenzoyl)amino]-4,5-dihydro-1H-benzo[g]indazole-3-carboxamide | 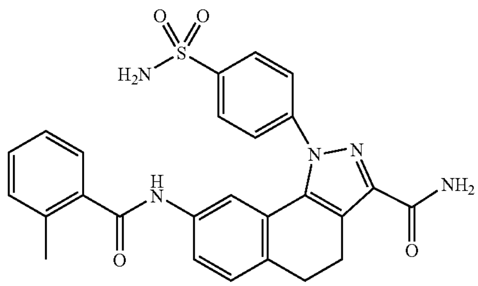 | Example 84 | ≦1 µM | 501.57 | 502 |
| 1-[4-(aminosulfonyl)phenyl]-8-[(2,6-dichlorobenzoyl)amino]-4,5-dihydro-1H-benzo[g]indazole-3-carboxamide | 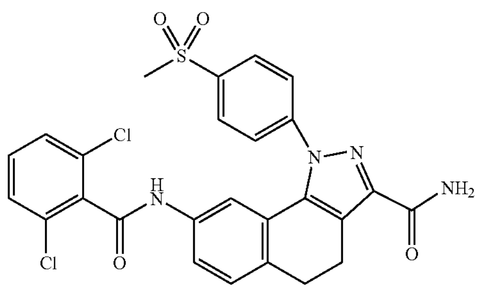 | Example 85 | ≦1 µM | 556.43 | 557 |
| 1-[4-(aminosulfonyl)phenyl]-8-{[2-(trifluoromethoxy)benzoyl]amino}-4,5-dihydro-1H-benzo[g]indazole-3-carboxamide | 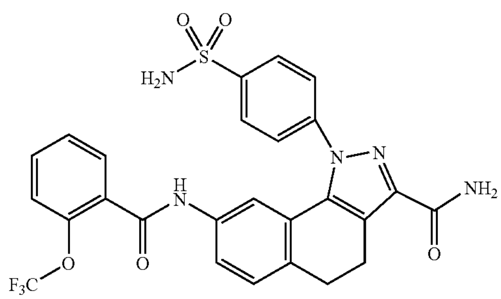 | Example 86 | ≦1 µM | 571.53 | 572 |
| 1-[4-(aminosulfonyl)phenyl]-8-[(2,3-dichlorobenzoyl)amino]-4,5-dihydro-1H-benzo[g]indazole-3-carboxamide | 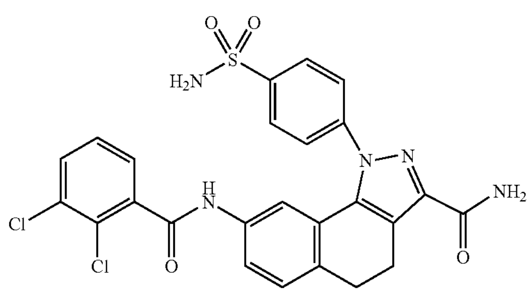 | Example 87 | ≦1 µM | 556.43 | 557 |
| 1-[4-(aminosulfonyl)phenyl]-8-[(2-fluorobenzoyl)amino]-4,5-dihydro-1H-benzo[g]indazole-3-carboxamide | 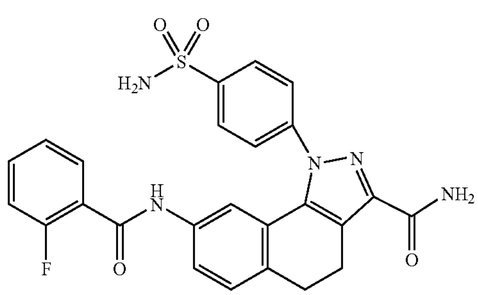 | Example 88 | ≦1 µM | 505.53 | 506 |

TABLE 1-continued

| COMPOUND | STRUCTURE | EXAMPLE | IKK2-resin | Formula Weight | Mass Spec |
|---|---|---|---|---|---|
| 1-[4-(aminosulfonyl)phenyl]-8-{[(2-chloropyridin-3-yl)carbonyl]amino}-4,5-dihydro-1H-benzo[g]indazole-3-carboxamide | 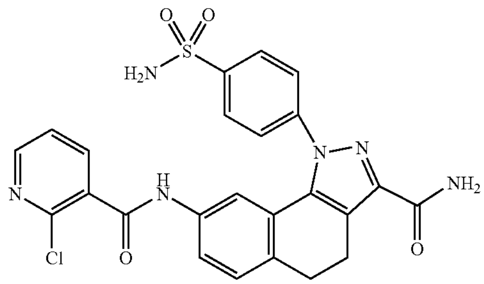 | Example 89 | ≦1 μM | 522.97 | 523 |
| 1-[4-(aminosulfonyl)phenyl]-8-{[(2-chlorophenyl)sulfonyl]amino}-4,5-dihydro-1H-benzo[g]indazole-3-carboxamide | 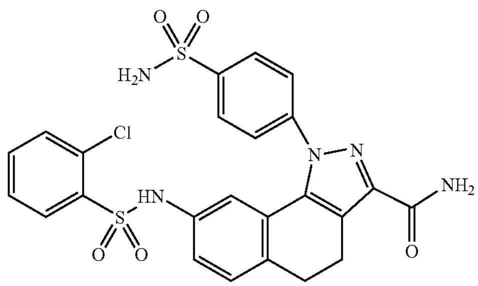 | Example 90 | 10 ≦ 100 μM | 558.04 | 558 |
| 1-[4-(aminosulfonyl)phenyl]-8-[(2-bromobenzoyl)amino]-4,5-dihydro-1H-benzo[g]indazole-3-carboxamide | 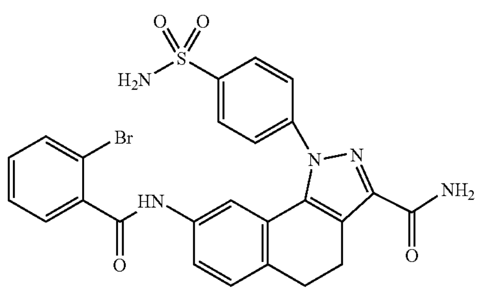 | Example 91 | ≦1 μM | 566.43 | 567 |

Examples 92–125

Examples 92–125 shown in Table 2 were synthesized using the following synthesis procedure similar to scheme I where $R^9$ is the appropriate aryl, substituted aryl, heteroaryl, substituted heteroaryl, substituted arylalkyl, substituted heteroarylalkyl, or cycloalkyl.

Scheme XV

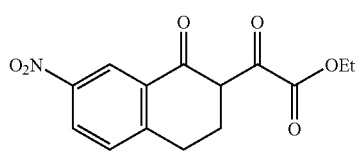

ethyl (7-nitro-1-oxo-1,2,3,4-tetrahydronaphthalen-2-yl)(oxo)acetate 1

-continued

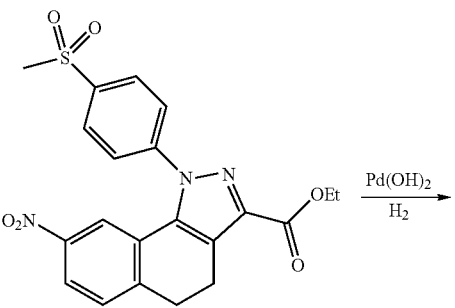

ethyl 1-[4-(methylsulfonyl)phenyl]-8-nitro-4,5-dihydro-1H-benzo[g]indazole-3-carboxylate -continued

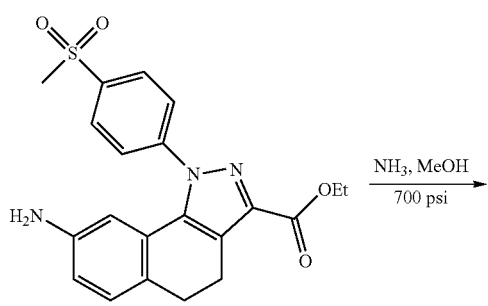

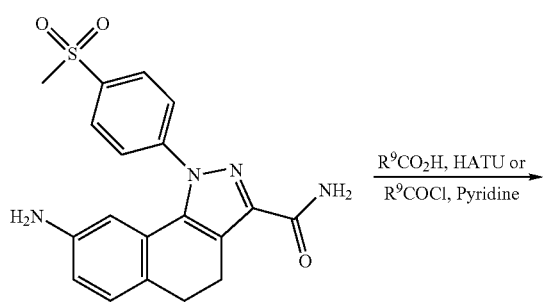

Example 92

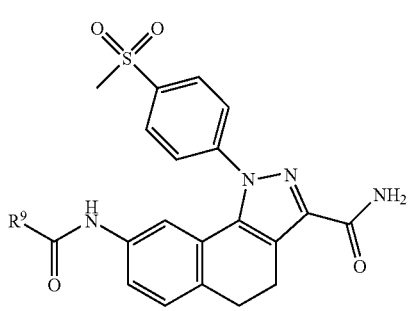

Example 92

8-amino-1-[4-(methylsulfonyl)phenyl]-4,5-dihydro-1H-benzo[g]indazole-3-carboxamide hydrochloride

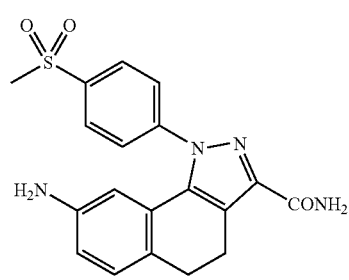

Step 1

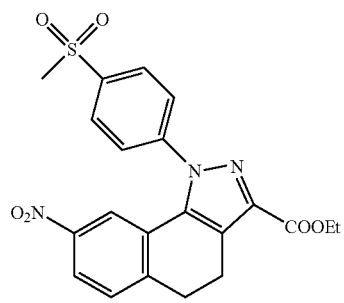

A mixture of (17.2 mmoles) of diketo ester and (17.2 mmoles) 4-(Methylsulfonyl)-phenylhydrazine in 100 ml of acetic acid was refluxed with stirring for 3 h, and then cooled. The mixture was concentrated, and the residue triturated with ethyl acetate affording a brown solid, which was filtered, washed with ethyl acetate, and dried to give the title compound. The structure was supported by $^1$H NMR.

Step 2

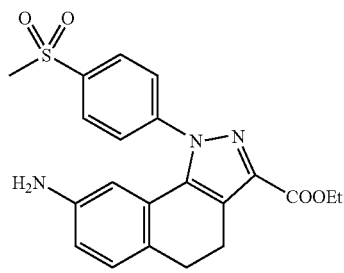

A solution of the title product of Step 1 in acetic acid was treated at room temperature with 5% palladium on carbon under an atmosphere of hydrogen gas at 5 psi. The reaction was followed by LC-MS. When the conversion was complete, the mixture was filtered and concentrated to give the title compound as a brownish oil that was used directly for the next step.

Step 3

8-amino-1-[4-(methylsulfonyl)phenyl]-4,5-dihydro-1H-benzo[g]indazole-3-carboxamide hydrochloride

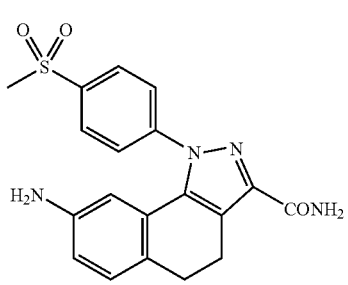

The title product of Step 2 was dissolved in anhydrous ethanol and then an approximately equal volume of liquid ammonia was added. The resulting mixture was sealed in a pressure vessel and then stirred overnight at 100° C. After cooling, the mixture was concentrated. The residue was taken up in dichloromethane-methanol and chromatographed over silica gel using ethyl acetate as eluent to give the title compound, as an oil which crystallized on standing.

TABLE 2

| Structure | Formula Weight | Name | IKK Resin IC$_{50}$ ( | Example |
|---|---|---|---|---|
| 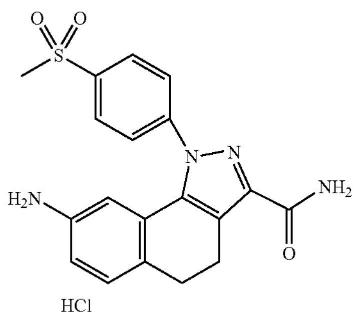 | 418.91 | 8-amino-1-[4-(methylsulfonyl)phenyl]-4,5-dihydro-1H-benzo[g]indazole-3-carboxamide hydrochloride | 1 ≦ 10 μM | 92 |
| 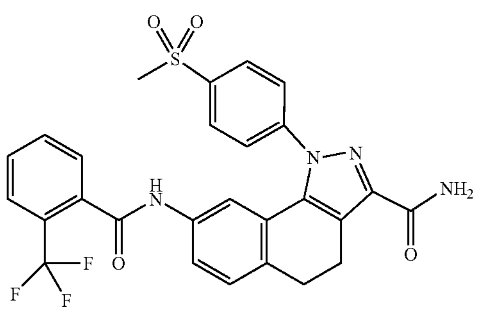 | 554.55 | 1-[4-(methylsulfonyl)phenyl]-8-{[2-(trifluoromethyl)benzoyl]amino}-4,5-dihydro-1H-benzo[g]indazole-3-carboxamide | ≦1 μM | 93 |
| 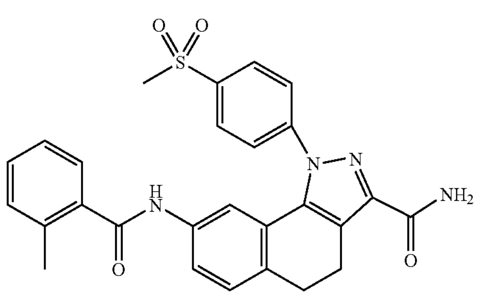 | 500.58 | 8-[(2-methylbenzoyl)amino]-1-[4-(methylsulfonyl)phenyl]-4,5-dihydro-1H-benzo[g]indazole-3-carboxamide | ≦1 μM | 94 |
| 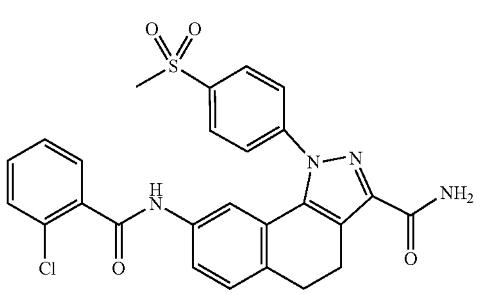 | 521.00 | 8-[(2-chlorobenzoyl)animo]-1-[4-(methylsulfonyl)phenyl]-4,5-dihydro-1H-benzo[g]indazole-3-carboxamide | ≦1 μM | 95 |

TABLE 2-continued

| Structure | Formula Weight | Name | IKK Resin IC$_{50}$ | Example |
|---|---|---|---|---|
| 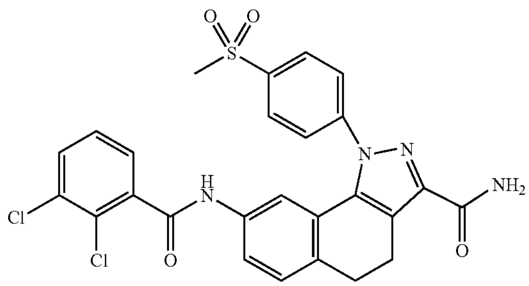 | 555.44 | 8-[(2,3-dichlorobenzoyl)amino]-1-[4-(methylsulfonyl)phenyl]-4,5-dihydro-1H-benzo[g]indazole-3-carboxamide | ≦1 μM | 96 |
| 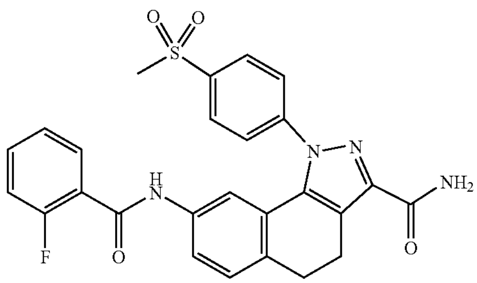 | 504.54 | 8-[(2-fluorobenzoyl)amino]-1-[4-(methylsulfonyl)phenyl]-4,5-dihydro-1H-benzo[g]indazole-3-carboxamide | ≦1 μM | 97 |
| 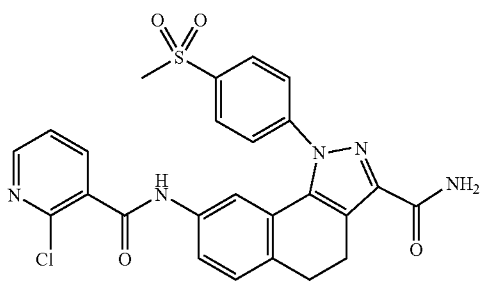 | 521.99 | 8-{[(2-chloropyridin-3-yl)carbonyl]amino}-1-[4-(methylsulfonyl)phenyl]-4,5-dihydro-1H-benzo[g]indazole-3-carboxamide | ≦1 μM | 98 |
| 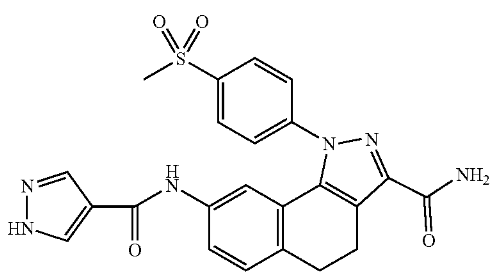 | 476.52 | 1-[4-(methylsulfonyl)phenyl]-8-[(1H-pyrazol-4-ylcarbonyl)amino]-4,5-dihydro-1H-benzo[g]indazole-3-carboxamide | 1 ≦ 10 μM | 99 |
| 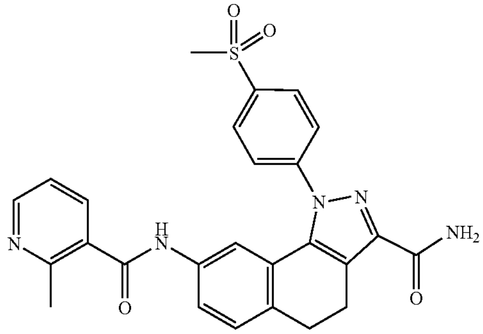 | 501.57 | 8-{[(2-methylpyridin-3-yl)carbonyl]amino}-1-[4-(methylsulfonyl)phenyl]-4,5-dihydro-1H-benzo]g]indazole-3-carboxamide | ≦1 μM | 100 |

TABLE 2-continued

| Structure | Formula Weight | Name | IKK Resin IC$_{50}$ ( | Example |
|---|---|---|---|---|
| 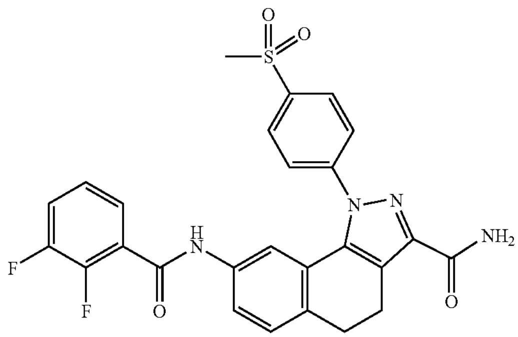 | 522.53 | 8-[(2,3-difluorobenzoyl)amino]-1-[4-(methylsulfonyl)phenyl]-4,5-dihydro-1H-benzo[g]indazole-3-carboxamide | ≦1 μM | 101 |
| 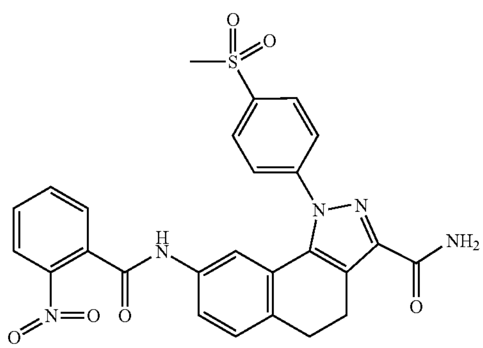 | 531.55 | 1-[4-(methylsulfonyl)phenyl]-8-[(2-nitrobenzoyl)amino]-4,5-dihydro-1H-benzo[g]indazole-3-carboxamide | ≦1 μM | 102 |
| 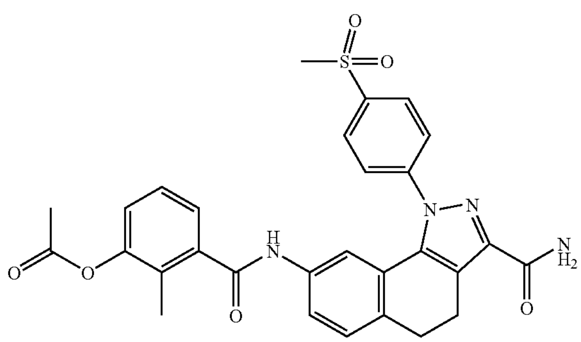 | 558.61 | 3-[({3-(aminocarbonyl)-1-[4-(methylsulfonyl)phenyl]-4,5-dihydro-1H-benzo[g]indazol-8-yl}amino)carbonyl]-2-methylphenyl acetate | 1 ≦ 10 μM | 103 |
| 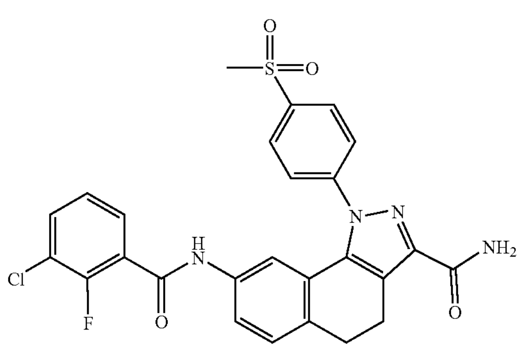 | 538.99 | 8-[(3-chloro-2-fluorobenzoyl)amino]-1-[4-(methylsulfonyl)phenyl]-4,5-dihydro-1H-benzo[g]indazole-3-carboxamide | ≦1 μM | 104 |

TABLE 2-continued

| Structure | Formula Weight | Name | IKK Resin IC$_{50}$ | Example |
|---|---|---|---|---|
| 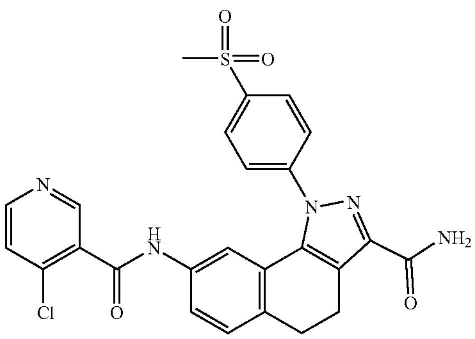 | 521.99 | 8-{[(4-chloropyridin-3-yl)carbonyl]amino}-1-[4-(methylsulfonyl)phenyl]-4,5-dihydro-1H-benzo[g]indazole-3-carboxamide | 1 ≦ 10 μM | 105 |
| 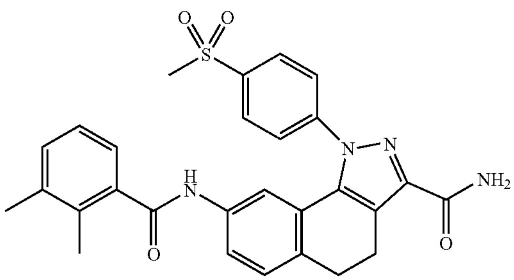 | 514.61 | 8-[(2,3-dimethylbenzoyl)amino]-1-[4-(methylsulfonyl)phenyl]-4,5-dihydro-1H-benzo[g]indazole-3-carboxamide | 1 ≦ 10 μM | 106 |
| 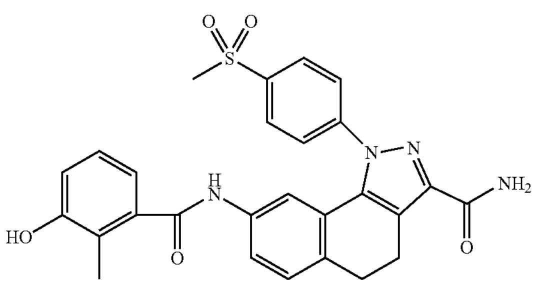 | 516.58 | 8-[(3-hydroxy-2-methylbenzoyl)amino]-1-[4-(methylsulfonyl)phenyl]-4,5-dihydro-1H-benzo[g]indazole-3-carboxamide | ≦1 μM | 107 |
| 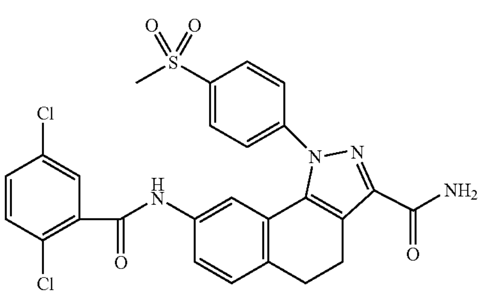 | 555.44 | 8-[(2,5-dichlorobenzoyl)amino]-1-[4-(methylsulfonyl)phenyl]-4,5-dihydro-1H-benzo[g]indazole-3-carboxamide | ≦1 μM | 108 |
| 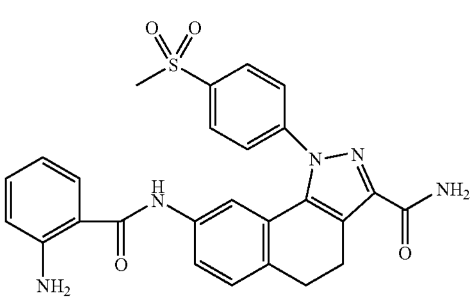 | 501.57 | 8-[(2-aminobenzoyl)amino]-1-[4-(methylsulfonyl)phenyl]-4,5-dihydro-1H-benzo[g]indazole-3-carboxamide | 1 ≦ 10 μM | 109 |

TABLE 2-continued

| Structure | Formula Weight | Name | IKK Resin IC$_{50}$ ( | Example |
|---|---|---|---|---|
| 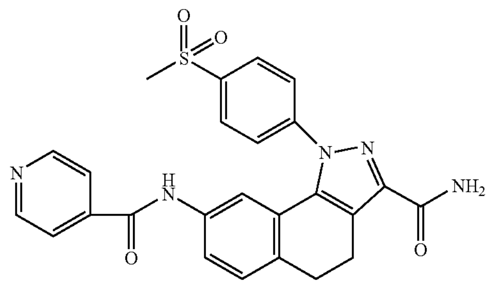 | 487.54 | 8-(isonicotinoylamino)-1-[4-(methylsulfonyl)phenyl]-4,5-dihydro-1H-benzo[g]indazole-3-carboxamide | ≦1 μM | 110 |
| 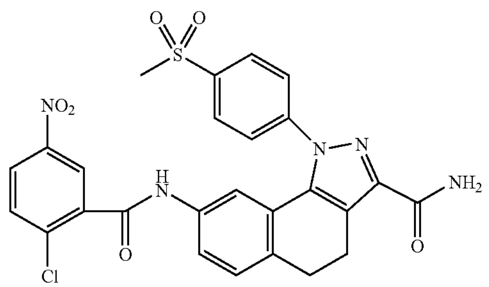 | 566.00 | 8-[(2-chloro-5-nitrobenzoyl)amino]-1-[4-(methylsulfonyl)phenyl]-4,5-dihydro-1H-benzo[g]indazole-3-carboxamide | ≦1 μM | 111 |
| 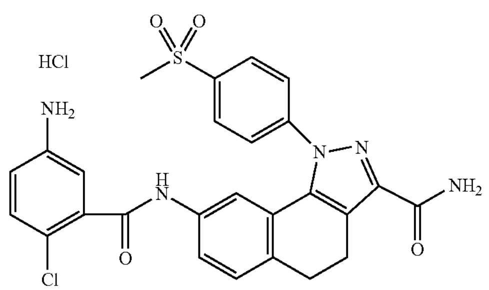 | 572.47 | 8-[(5-amino-2-chlorobenzoyl)amino]-1-[4-(methylsulfonyl)phenyl]-4,5-dihydro-1H-benzo[g]indazole-3-carboxamide hydrochloride | ≦1 μM | 112 |
| | 536.01 | 8-[(3-amino-4-chlorobenzoyl)amino]-1-[4-(methylsulfonyl)phenyl]-4,5-dihydro-1H-benzo[g]indazole-3-carboxamide | ≦1 μM | 113 |
| | 536.01 | 8-[(4-amino-2-chlorobenzoyl)amino]-1-[4-(methylsulfonyl)phenyl]-4,5-dihydro-1H-benzo[g]indazole-3-carboxamide | ≦1 μM | 114 |

TABLE 2-continued

| Structure | Formula Weight | Name | IKK Resin IC$_{50}$ ( | Example |
|---|---|---|---|---|
| | 536.01 | 8-[(2-amino-5-chlorobenzoyl)amino]-1-[4-(methylsulfonyl)phenyl]-4,5-dihydro-1H-benzo[g]indazole-3-carboxamide | 1 ≦ 10 μM | 115 |
| | 536.01 | 8-[(3-amino-2-chlorobenzoyl)amino]-1-[4-(methylsulfonyl)phenyl]-4,5-dihydro-1H-benzo[g]indazole-3-carboxamide | ≦1 μM | 116 |
| | 536.01 | 8-[(2-amino-4-chlorobenzoyl)amino]-1-[4-(methylsulfonyl)phenyl]-4,5-dihydro-1H-benzo[g]indazole-3-carboxamide | ≦1 μM | 117 |
| | 536.01 | 8-[(2-amino-3-chlorobenzoyl)amino]-1-[4-(methylsulfonyl)phenyl]-4,5-dihydro-1H-benzo[g]indazole-3-carboxamide | ≦1 μM | 118 |
| 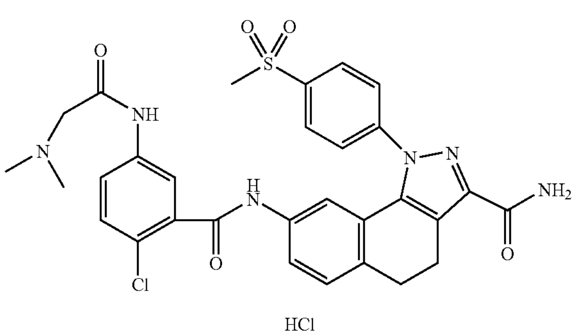 | 657.58 | 8-({2-chloro-5-[(N,N-dimethylglycyl)amino]benzoyl}amino)-1-[4-(methylsulfonyl)phenyl]-4,5-dihydro-1H-benzo[g]indazole-3-carboxamide hydrochloride | ≦1 μM | 119 |

TABLE 2-continued

| Structure | Formula Weight | Name | IKK Resin IC$_{50}$ ( | Example |
|---|---|---|---|---|
| 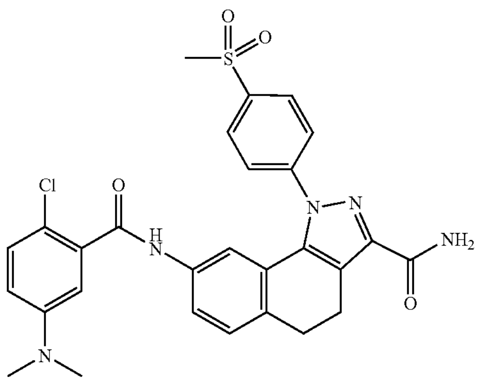 | 564.07 | 8-{[2-chloro-5-(dimethylamino)benzoyl]amino}-1-[4-(methylsulfonyl)phenyl]-4,5-dihydro-1H-benzo[g]indazole-3-carboxamide | ≦1 μM | 120 |
| 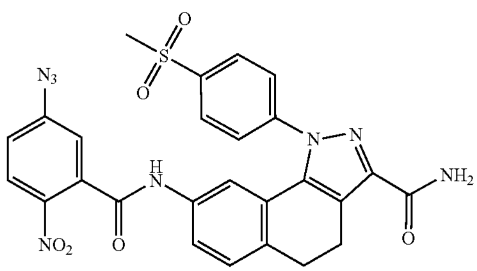 | 572.56 | 8-[(5-azido-2-nitrobenzoyl)amino]-1-[4-(methylsulfonyl)phenyl]-4,5-dihydro-1H-benzo[g]indazole-3-carboxamide | ≦1 μM | 121 |
| 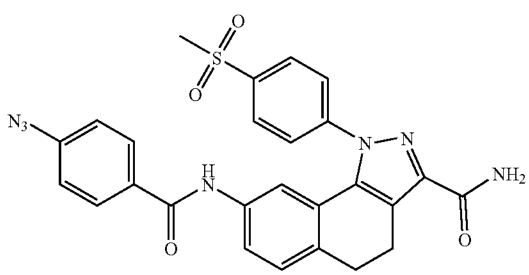 | 527.57 | 8-[(4-azidobenzoyl)amino]-1-[4-(methylsulfonyl)phenyl]-4,5-dihydro-1H-benzo[g]indazole-3-carboxamide | ≦1 μM | 122 |
| 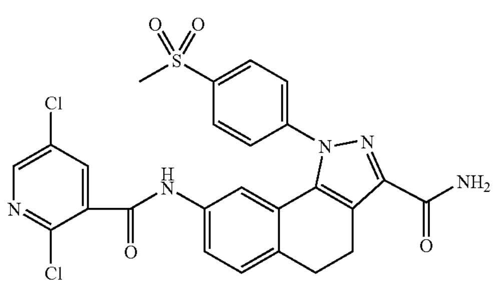 | 556.43 | 8-{[(2,5-dichloropyridin-3-yl)carbonyl]amino}-1-[4-(methylsulfonyl)phenyl]-4,5-dihydro-1H-benzo[g]indazole-3-carboxamide | ≦1 μM | 123 |
| 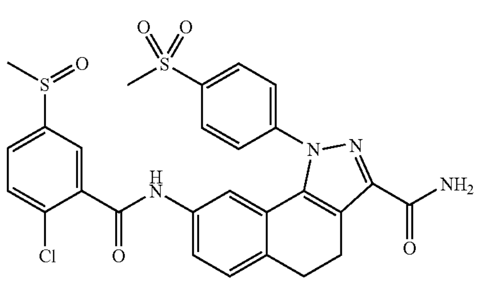 | 583.09 | 8-{[2-chloro-5-(methylsulfinyl)benzoyl]amino}-1-[4-(methylsulfonyl)phenyl]-4,5-dihydro-1H-benzo[g]indazole-3-carboxamide | ≦1 μM | 124 |

TABLE 2-continued

| Structure | Formula Weight | Name | IKK Resin IC$_{50}$ ( | Example |
|---|---|---|---|---|
| 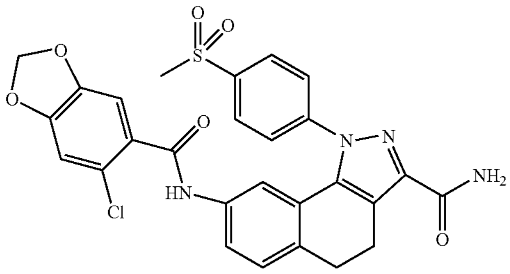 | 565.01 | 8-{[(6-chloro-1,3-benzodioxol-5-yl)carbonyl]amino}-1-[4-(methylsulfonyl)phenyl]-4,5-dihydro-1H-benzo[g]indazole-3-carboxamide | ≦1 µM | 125 |
| 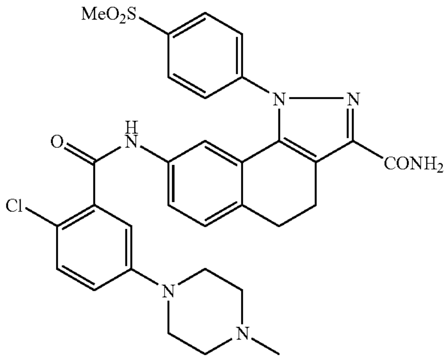 | 619.13 | 8-{[2-chloro-5-(4-methylpiperazin-1-yl)benzoyl]amino}-1-[4-(methylsulfonyl)phenyl]-4,5-dihydro-1H-benzo[g]indazole-3-carboxamide | ≦1 µM | 126 |

Example 126

8-{[2-chloro-5-(4-methylpiperazin-1-yl)benzoyl]amino}-1-[4-(methylsulfonyl)phenyl]-4,5-dihydro-1H-benzo[g]indazole-3-carboxamide Example 126 was synthesized using the following scheme.

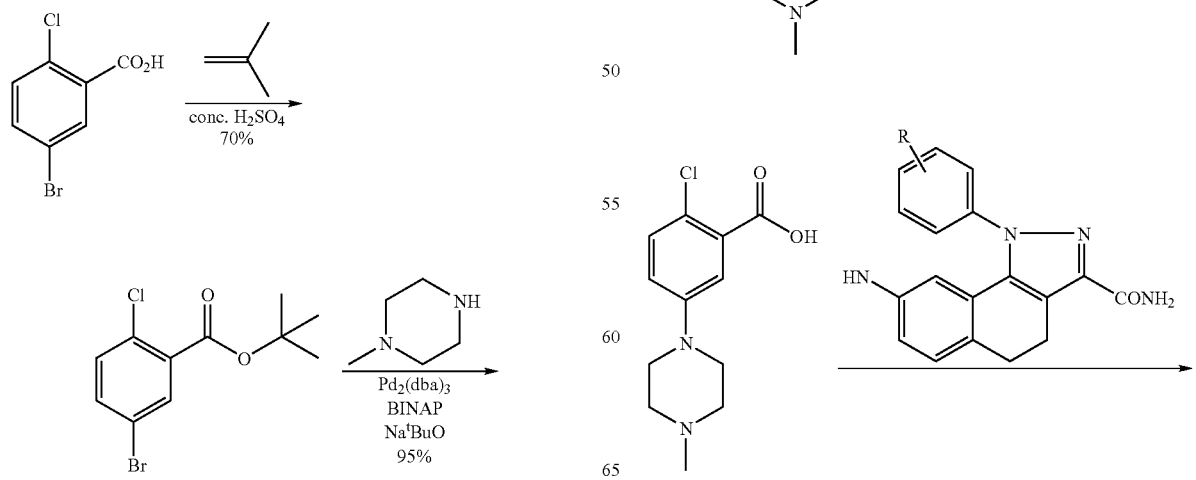

Scheme XVI

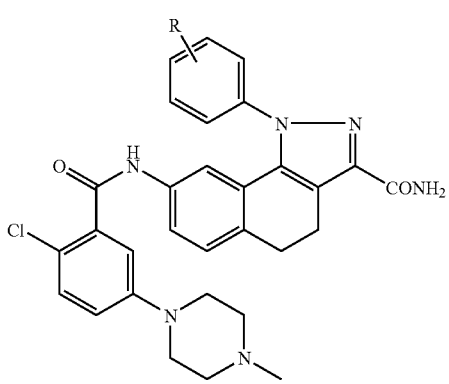

R = 4-F, 4-SO₂Me, 3,4-MDO, etc.

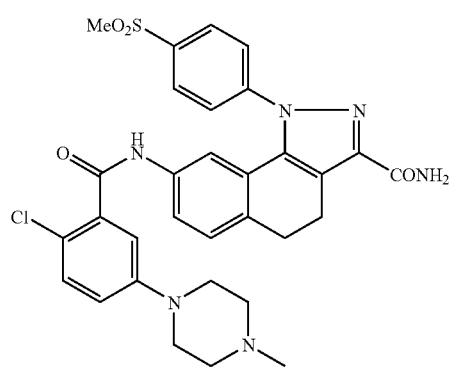

To a mixture of 2-chloro-5-(4-methylpiperazin-1-yl)benzoic acid (0.9 g, 0.0035 mol), the title compound of Example 92 (0.0024 mol) and 1 mL of diisopropylethylamine in 25 mL of DMF was added HATU (1.3 g, 0.0035 mol) in one portion. The reaction mixture was stirred at room temperature for 16 h. Solvent was removed and the residue was purified on preparative HPLC to give the product as a pale white solid (89% yield); mp: 194–195° C.; ¹HNMR (DMSO+TFA-d, 400 MHz) δ: 10.29 (s, 1H), 8.10 (d, J=8.7 Hz, 2H), 7.86 (d, J=8.7 Hz, 2H), 7.64 (s, 1H), 7.43 (dd, J=2.1, 8.2 Hz, 1H), 7.41 (s, 1H), 7.37 (dd, J=2.0, 8.2 Hz, 1H), 7.35 (d, J=8.2 Hz, 1H), 7.08 (dd, J=3.0, 8.9 Hz, 1H), 7.04 (d, J=3.0 Hz, 1H), 3.89 (d, J=12.8 Hz, 2H), 3.51 (d, J=12.8 Hz, 2H), 3.23(s, 3H), 3.11 (m, 2H), 2.95 (m, 4H), 2.86 (m, 2H). The bioactivity in the IKK2 Resin assay for the compound of Example 126 is shown in Table 2.

Examples 127–158 shown in Table 3 were synthesized by the following synthesis scheme were R⁹ is the appropriate aryl, substituted aryl, heteroaryl, substituted heteroaryl, substituted arylalkyl, substituted heteroarylalkyl, or cycloalkyl.

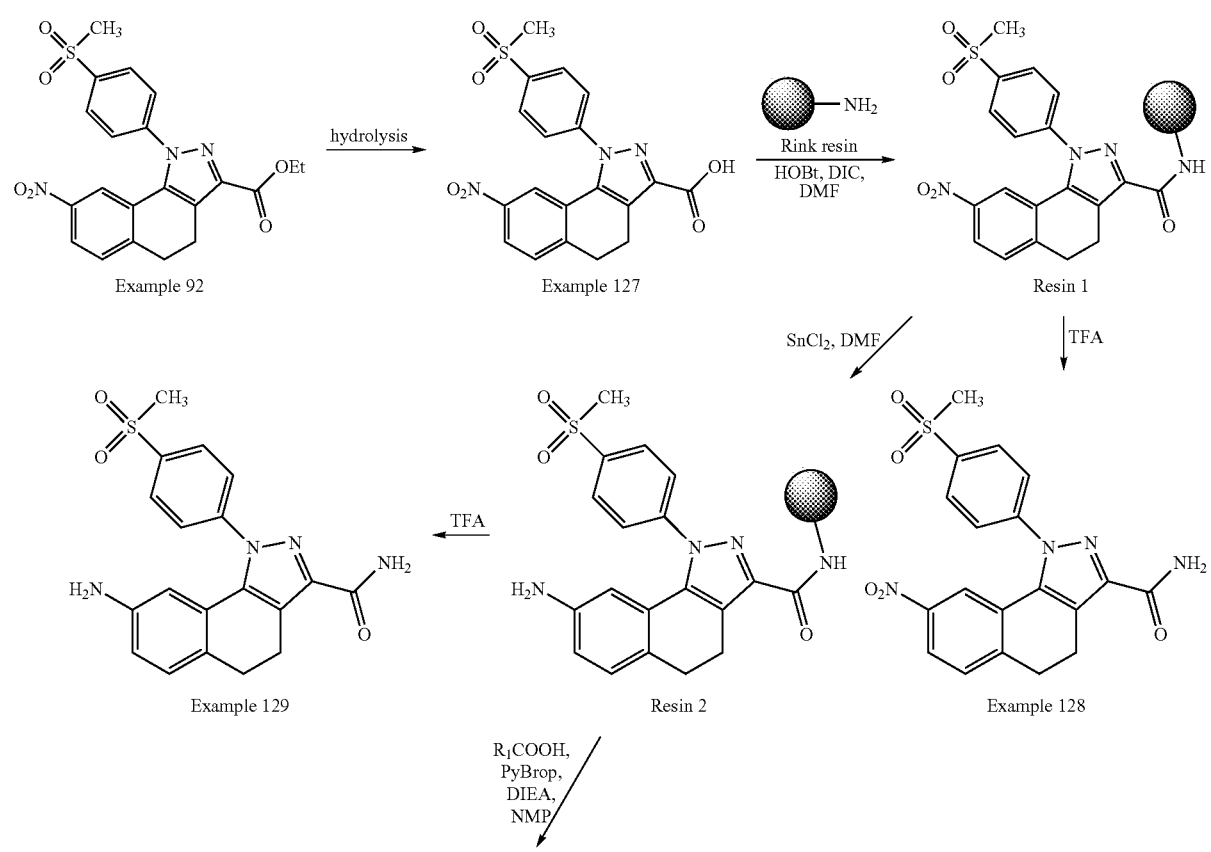

Scheme XVII

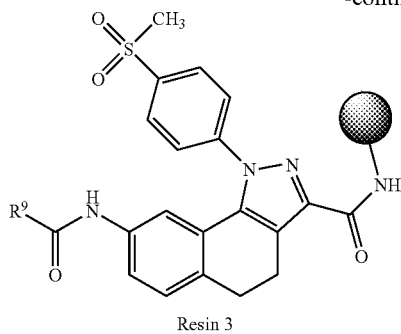

Resin 3

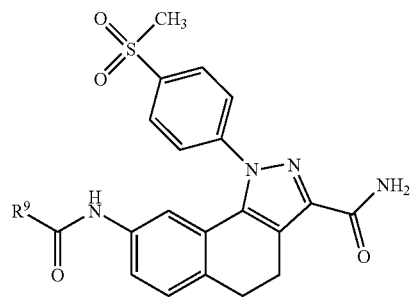

Examples 130–158.

Example 127

1-[4-(methylsulfonyl)phenyl]-8-nitro-4,5-dihydro-1H-benzo[g]indazole-3-carboxylic acid To 5.0 g (11.3 mmol) of Example 92 (ethyl 1-[4-(methylsulfonyl)phenyl]-8-nitro-4,5-dihydro-1H-benzo[g]indazole-3-carboxylate) in 115 mL of THF was added 115 mL of 1N NaOH and the mixture allowed to stir overnight at RT. The solution was acidified with 2N HCl and extracted three times with ethyl acetate. Combined extracts were washed with 10% aq. HCl, brine, dried with $Na_2SO_4$ and concentrated to afford 4.97 g (100%) of a yellow solid: $^1$H NMR (d6-DMSO) 3.00 (m, 2H), 3.11 (m, 2H), 3.31 (s, 3H), 7.39 (d, 1H), 7.67 (d, 1H), 7.90 (d, 2H), 8.07 (dd, 1H), 8.16 (d, 1H); MS (ESI+) 414 (M+1).

Example 128

Resin 1 and 1-[4-(methylsulfonyl)phenyl]-8-nitro-4,5-dihydro-1H-benzo[g]indazole-3-carboxamide Commercially available Rink amide resin (10 g, NovaBiochem #01-64-0013, 100–200 mesh, 0.61 mmol/g) was washed sequentially with dichloromethane (DCM) and dimethylformamide (DMF). The resin was filtered, treated twice with 50% piperidine in DMF for 15 min, and subsequently washed three times each with DMF, DCM, and anhydrous DMF. To the resin was added 4.65 g of Example 127, 1.52 g of HOBt and 1.75 mL of DIC in 35 mL anhydrous DMF. After 3 h at RT, the reagents were removed by filtration and the resin washed three times each with DMF, methanol, and DCM. The resin was used directly in the next step. A small portion (approx. 100 mgs) of resin was cleaved by treatment with 20% TFA in $CH_2Cl_2$ for 30 min. The resin washed twice with $CH_2Cl_2$ and the collected filtrates concentrated in vacuo. The product was purified by silica chromatography to give the title compound as a light yellow solid: $^1$H NMR ($CDCl_3$) 9.03 (s, 2H), 8.20(d, J=8.4 Hz, 2H), 8.10 (dd, J=2 Hz, 8.4 Hz, 1H), 7.79 (d, J=8.4 Hz, 2H), 7.53 (d, J=8.4 Hz, 1H), 7.51 (d, J=2 Hz, 1H), 3.25 (s, 3H), 3.16 (m, 4H); MS(ESI+) 413 (M+1, 100).

Example 129

Resin 2 and 8-amino-1-[4-(methylsulfonyl)phenyl]-4,5-dihydro-1H-benzo[g]indazole-3-carboxamide, trifluoroacetic acid salt To resin 2 (6.0 mmol) was added 50 mL of 2M $SnCl_2$·$2H_2O$ in wet DMF. After agitation of the mixture overnight, the reagents were removed by filtration and the resin washed three times each with DMF, THF, and DCM. The resin was filtered and dried to give 10.96 g of resin 2. A 92.1 mg portion of the resin was treated twice with 20% TFA in $CH_2Cl_2$ and washed three times with $CH_2Cl_2$. The combined filtrates were concentrated in vacuo and resin loading determined by direct cleavage NMR of the title compound: resin loading of 0.46 meq/g; 1H NMR ($CDCl_3$/TFA) 3.14 (brs, 4H), 3.31 (s, 3H), 6.78 (d, 1H, 2.0 Hz), 7.33 (dd, 1H), 7.54 (d, 1H, 8.0 Hz), 7.83 (d, 2H), 8.16 (d, 2H); MS(ESI+) 383 (M+1, 100).

Resin 3

Resin 2 (0.45 mmol/g, 0.200 g, 90 μmol) was washed three times with anhydrous NMP and subsequently treated with 0.45 mmol of carboxylic acid $R^9COOH$ in 0.5 mL of anhydrous NMP, 0.45 mmol of PyBrop in 0.5 mL of anhydrous NMP and 0.9 mmol of DIEA. The resin was shaken at RT under $N_2$ for 2 h. Subsequently, the reagents were removed by filtration, the resins retreated with the appropriate carboxylic acid, PyBrop, and DIEA in the same manner as described above. After agitation of the reaction vessels overnight at RT, the reagents were removed by filtration and the resins washed three times each with NMP, DMF, methanol, and DCM. The products were cleaved from the resins by adding 0.5 mL of 20%. TFA/DCM and agitating the mixture for 15 min. The filtrate was collected and the resin retreated with additional TFA/DCM for 15 min. The resin was washed twice with DCM and the filtrates combined and concentrated in vacuo to afford the final products.

Example 130

8-[(cyclobutylcarbonyl)amino]-1-[4-(methylsulfonyl)phenyl]-4,5-dihydro-1H-benzo[g]indazole-3-carboxamide Using the method described from resin 3, the product was obtained in 57% yield as a light yellow solid: $^1$H NMR ($CDCl_3$/$CD_3OD$). 8.13 (d, J=8.4 Hz, 2H), 7.76(d, J=8.4 Hz, 2H), 7.38 (d, J=1.6 Hz, 1H), 7.24 (d, J=8 Hz, 1H), 6.97 (dd, J=2 Hz, 8 Hz, 1H), 6.88 (s, 1H), 3.23 (s, 3H), 3.10 (m, 2H), 3.02 (m, 1H), 2.95 (m, 2H), 2.16(m, 4H), 1.95 (m, 1H), 1.82 (m, 1H). $^{13}$C NMR($CDCl_3$/$CD_3OD$): 165.0, 144.2, 142.9, 140.4, 137.1, 133.0, 129.3, 129.2, 126.4, 126.0, 123.3, 119.4, 114.8, 114.7, 60.7, 44.8, 40.6, 31.7, 29.6, 25.3, 22.8, 20.1, 18.1, 14.3. High resolution Mass: M+H$^+$=465.1591 (observed), 465.1608 (theoretical).

Example 131

8-[(2-chloro-4,5-dimethoxybenzoyl)amino]-1-[4-(methylsulfonyl)phenyl]-4,5-dihydro-1H-benzo[g]indazole-3-carboxamide Using the method described from resin 3, the product was obtained in 62% yield as a light yellow solid: $^1$H NMR (CDCl$_3$). 8.14(d, J=8.8 Hz, 2H), 8.03(s, 1H), 7.79(d, J=8.8 Hz, 2H), 7.40 (d, 1H), 7.29 (m, 1H), 7.21 (s, 1H), 7.16 (m, 1H), 6.81(s, 1H), 3.89 (s, 3H), 3.88 (s, 3H), 3.14 (m, 2H), 3.13 (s, 3H), 2.99 (m, 2H). $^{13}$C NMR(CDCl$_3$): 171.4, 164.4, 163.7, 151.7, 148.4, 144.3, 143.1, 140.8, 140.2, 136.4, 134.0, 129.6, 129.4, 126.7, 126.4, 126.1, 123.3, 122.4, 119.7, 115.3, 113.2, 113.0, 60.6, 45.0, 29.8, 21.3, 20.2. High resolution Mass: M+H$^+$=581.1277 (observed), 581.1256 (theoretical).

Examples 132–158

The compounds of Examples 132–158 were prepared as previously described for Example 130 using the appropriate aryl, substituted aryl, heteroaryl, substituted heteroaryl, substituted arylalkyl, substituted heteroarylalkyl, or cycloalkyl and are listed in Table 3.

Example 159

8-{[2-chloro-5-(methylsulfonyl)benzoyl]amino}-1-[4-(methylsulfonyl)phenyl]-4,5-dihydro-1H-benzo[g]indazole-3-carboxamide

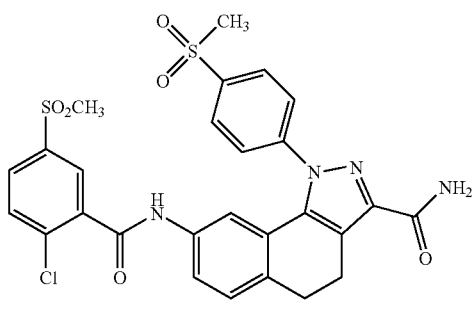

Example 159

To 0.30 g of amino resin 2 (pretreated in DCM for two hrs and washed with dry NMP) was added PyBrop (0.42 g, 0.90 mmol), 2-chloro-5-methylthiobenzoic acid (182 mg, 0.9 mmol), DIEA (314 uL, 1.8 mmol) and dry NMP (2 mL). The resin was shaken for two hrs. The excess reagents were drained, and the resin was washed with DMF (×3), methanol (×3), and DCM (×3), and treated with 20% TFA/DCM mixture containing 1% triisopropylsilane (2×12 min×3 mL). The resin was washed with DMC (2×4 mL). The combined filtrate and washings were evaporated to a solid, which was further dissolved in 10 mL of DCM. To the resulting solution was added MCPBA (440 mg, 77% pure, 1.96 mmol). After 3 h, the reaction was quenched with 30 mL ethylacetate. The organic phase was washed with sat. sodium bicarbonate (×3) and brine (×2), dried over anhydrous magnesium sulfate and concentrated in vacuo. The residue was purified by silica chromatography with 8:2 EtOAc/hexane. The product was isolated as light yellow solid, 37 mg (34%): $^1$H NMR (CDCl$_3$/CD$_3$OD) 8.00(d, J=8.8 Hz, 2H), 7.83 (s, 1H), 7.81 (dd, 1H), 7.68 (d, J=8.4 Hz, 2H), 7.51 (d, J=8.4 Hz, 1H), 7.34 (s, 1H), 7.25–7.17 (m, 2H), 3.02 (s, 3H), 2.98 (s, 3H), 2.96 (m, 2H), 2.88 (m, 2H). LC-MS: 599.0 (M+H$^+$). High resolution Mass: M+NH$_4$$^+$=616.1077 (observed), 616.1086 (theoretical).

Example 160

8-(L-histidylamino)-1-[4-(methylsulfonyl)phenyl]-4,5-dihydro-1H-benzo[g]indazole-3-carboxamide

Scheme XVIII

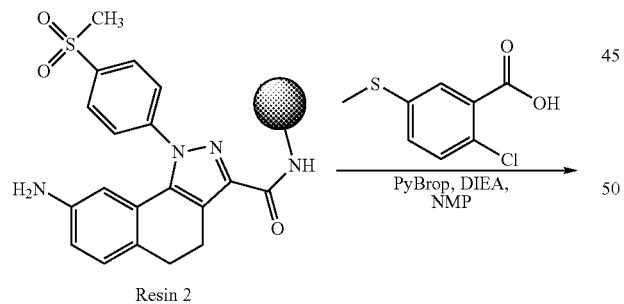

SCHEME XIX

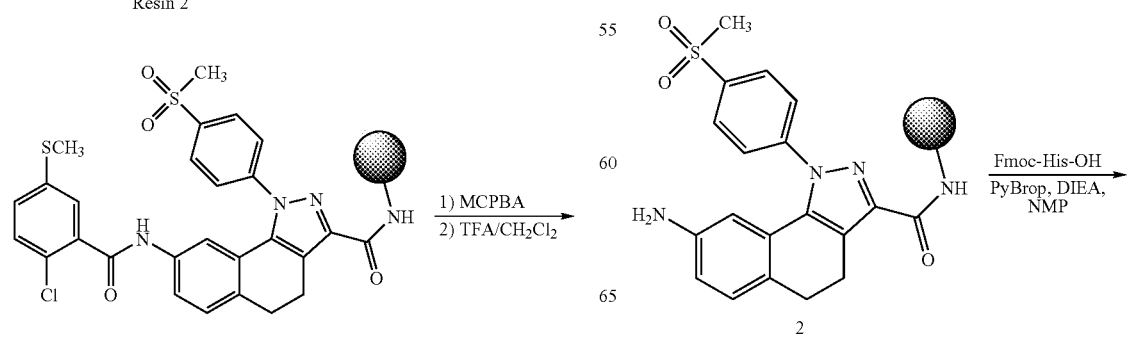

-continued

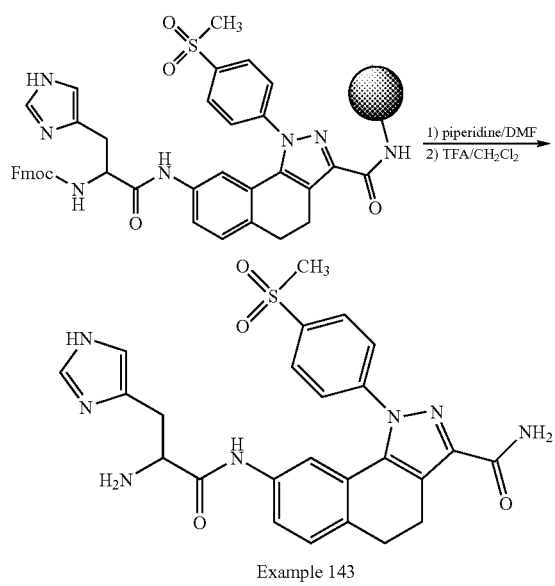

Example 143

Amino resin 3 (0.402 mmols/g, 0.0804 mmols, 0.200 g) was pre-treated in DCM for one hour followed by washing using anhydrous NMP. To this resin added 5.0 equiv. of Fmoc-His-OH (0.402 mmols, 152 mg) followed by addition of PyBroP (NovaBiochem, 0.402 mmols, 187 mg). To this mixture was added 10.0 equiv. of DIEA (0.804 mmols, 140 μl) followed by addition of anhydrous NMP (1 ml). Reaction vessel was capped and agitated under nitrogen for two hours. Reagents were removed by filtration and the resin washed as follows: NMP (×3), DMF (×3), DCM (×3), and anhydrous NMP (×1). Retreated resin as described above and let agitate under nitrogen overnight. Drained vessel and washed as follows: NMP (×3), DMF (×3), MeOH (×3), DCM (×3), and DMF (×1). Deprotected Fmoc group using 50:50 piperidine/DMF (×2, 2 ml) 40 minutes each. Washed resin as follows: DMF (×3), MeOH (×3), and DCM (×3). Let resin air dry for approximately one hour. Resin was then treated with 20:80 TFA/DCM containing 1% triisopropylsilane (×2, 1 ml, 45 minutes). Collected filtrates and washed resin with DCM (×3, 1 ml). Collected all washings and remove volatiles under nitrogen to afford 17.2 mg of an orange solid. MS$^+$+1 ($C_{25}H_{25}N_7O_4S$): 520 (measured).

TABLE 3

| Structure | Formula Weight | Name | IKK Resin IC$_{50}$ | Example |
|---|---|---|---|---|
| 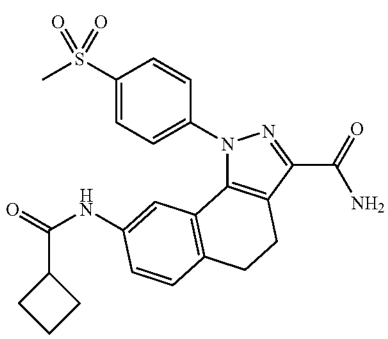 | 464.55 | 8-[(cyclobutylcarbonyl)amino]-1-[4-(methylsulfonyl)phenyl]-4,5-dihydro-1H-benzo[g]indazole-3-carboxamide | 1 ≦ 10 μM | 130 |
| 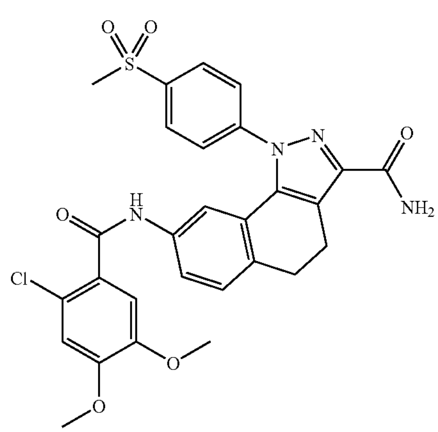 | 581.05 | 8-[(2-chloro-4,5-dimethoxybenzoyl)amino]-1-[4-(methylsulfonyl)phenyl]-4,5-dihydro-1H-benzo[g]indazole-3-carboxamide | ≦1 μM | 131 |

TABLE 3-continued

| Structure | Formula Weight | Name | IKK Resin IC$_{50}$ | Example |
|---|---|---|---|---|
| | 566.00 | 8-[(4-chloro-2-nitrobenzoyl)amino]-1-[4-(methylsulfonyl)phenyl]-4,5-dihydro-1H-benzo[g]indazole-3-carboxamide | ≦1 μM | 132 |
| 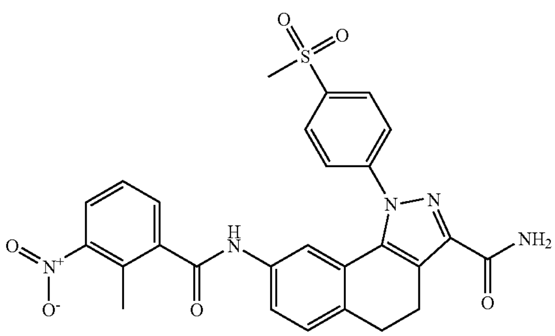 | 545.58 | 8-[(2-methyl-3-nitrobenzoyl)amino]-1-[4-(methylsulfonyl)phenyl]-4,5-dihydro-1H-benzo[g]indazole-3-carboxamide | 1 ≦ 10 μM | 133 |
| 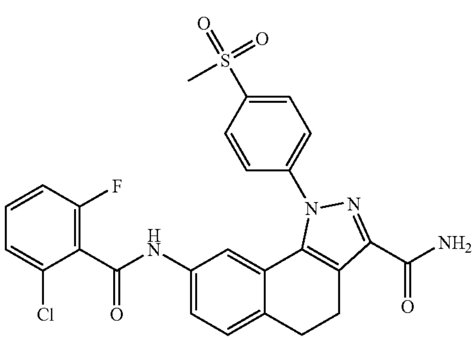 | 538.99 | 8-[(2-chloro-6-fluorobenzoyl)amino]-1-[4-(methylsulfonyl)phenyl]-4,5-dihydro-1H-benzo[g]indazole-3-carboxamide | ≦1 μM | 134 |
| | 566.00 | 8-[(2-chloro-3-nitrobenzoyl)amino]-1-[4-(methylsulfonyl)phenyl]-4,5-dihydro-1H-benzo[g]indazole-3-carboxamide | ≦1 μM | 135 |

TABLE 3-continued

| Structure | Formula Weight | Name | IKK Resin IC$_{50}$ | Example |
|---|---|---|---|---|
| 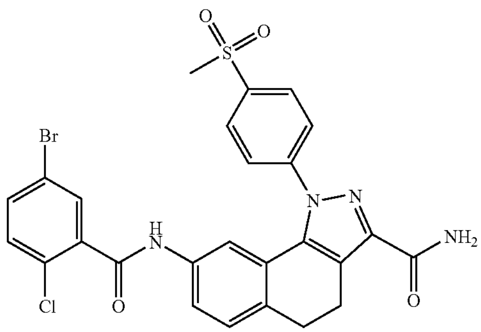 | 599.89 | 8-[(5-bromo-2-chlorobenzoyl)amino]-1-[4-(methylsulfonyl)phenyl]-4,5-dihydro-1H-benzo[g]indazole-3-carboxamide | ≦1 μM | 136 |
| 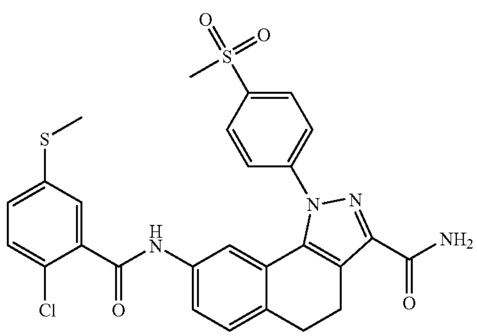 | 567.09 | 8-{[2-chloro-5-(methylthio)benzoyl]amino}-1-[4-(methylsulfonyl)phenyl]-4,5-dihydro-1H-benzo[g]indazole-3-carboxamide | ≦1 μM | 137 |
| 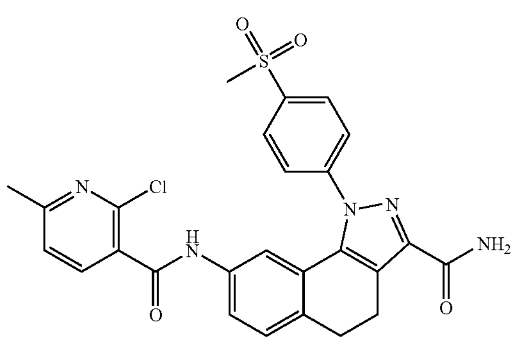 | 536.01 | 8-{[(2-chloro-6-methylpyridin-3-yl)carbonyl]amino}-1-[4-(methylsulfonyl)phenyl]-4,5-dihydro-1H-benzo[g]indazole-3-carboxamide | ≦1 μM | 138 |
| 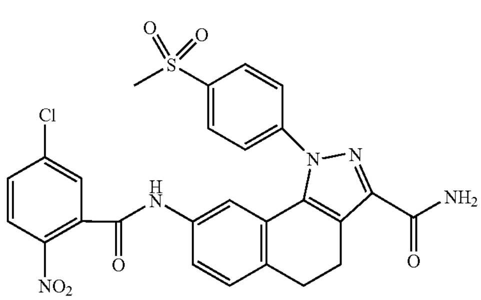 | 566.00 | 8-[(5-chloro-2-nitrobenzoyl)amino]-1-[4-(methylsulfonyl)phenyl]-4,5-dihydro-1H-benzo[g]indazole-3-carboxamide | ≦1 μM | 139 |

TABLE 3-continued

| Structure | Formula Weight | Name | IKK Resin IC$_{50}$ | Example |
|---|---|---|---|---|
| 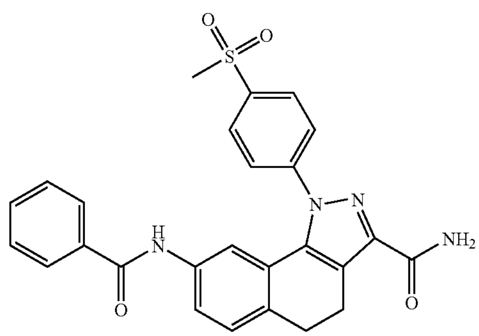 | 486.55 | 8-(benzoylamino)-1-[4-(methylsulfonyl)phenyl]-4,5-dihydro-1H-benzo[g]indazole-3-carboxamide | ≦1 μM | 140 |
| 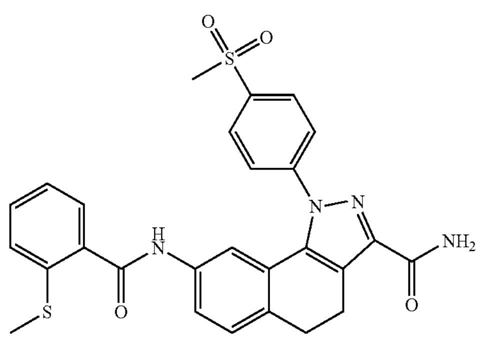 | 532.64 | 1-[4-(methylsulfonyl)phenyl]-8-{[2-(methylthio)benzoyl]amino}-4,5-dihydro-1H-benzo[g]indazole-3-carboxamide | 1 ≦ 10 μM | 142 |
| | 516.58 | 8-](3-methoxybenzoyl)amino]-1-[4-(methylsulfonyl)phenyl]-4,5-dihydro-1H-benzo[g]indazole-3-carboxamide | 1 ≦10 μM | 142 |
| | 516.58 | 8-[(4-methoxybenzoyl)amino]-1-[4-(methylsulfonyl)phenyl]-4,5-dihydro-1H-benzo[g]indazole-3-carboxamide | ≦1 μM | 143 |

TABLE 3-continued

| Structure | Formula Weight | Name | IKK Resin IC$_{50}$ | Example |
|---|---|---|---|---|
| 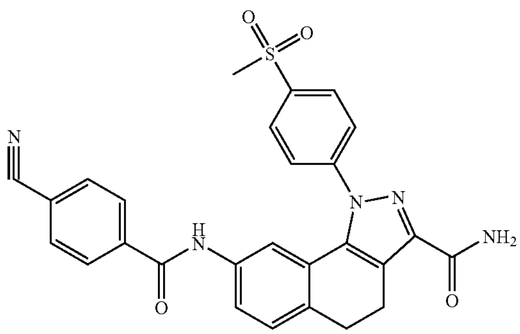 | 511.56 | 8-[(4-cyanobenzoyl)amino]-1-[4-(methylsulfonyl)phenyl]-4,5-dihydro-1H-benzo[g]indazole-3-carboxamide | ≦1 μM | 144 |
| 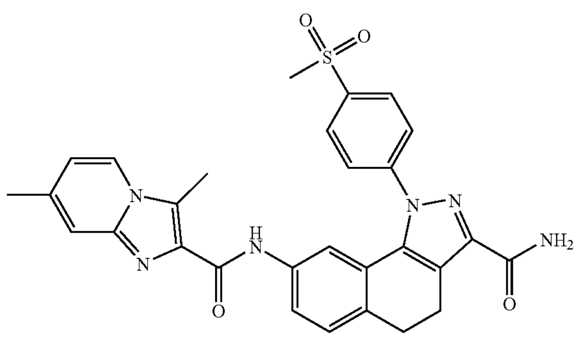 | 554.63 | 8-{[(3,7-dimethylimidazo[1,2-a]pyridin-2-yl)carbonyl]amino}-1-[4-(methylsulfonyl)phenyl]-4,5-dihydro-1H-benzo[g]indazole-3-carboxamide | 1 ≦ 10 μM | 145 |
| 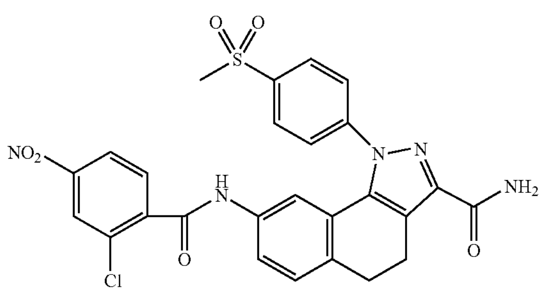 | 566.00 | 8-[(2-chloro-4-nitrobenzoyl)amino]-1-[4-(methylsulfonyl)phenyl]-4,5-dihydro-1H-benzo[g]indazole-3-carboxamide | ≦1 μM | 146 |
| 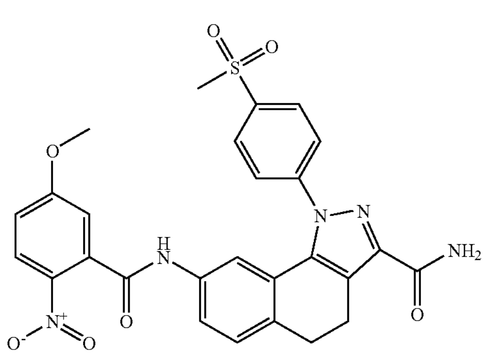 | 561.58 | 8-[(5-methoxy-2-nitrobenzoyl)amino]-1-[4-(methylsulfonyl)phenyl]-4,5-dihydro-1H-benzo[g]indazole-3-carboxamide | ≦1 μM | 147 |

TABLE 3-continued

| Structure | Formula Weight | Name | IKK Resin IC$_{50}$ | Example |
|---|---|---|---|---|
| 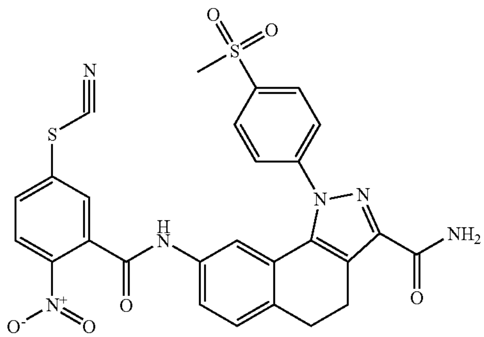 | 588.63 | 3-[({3-(aminocarbonyl)-1-[4-(methylsulfonyl)phenyl]-4,5-dihydro-1H-benzo[g]indazol-8-yl}amino)carbonyl]-4-nitrophenyl thiocyanate | ≦1 μM | 148 |
| 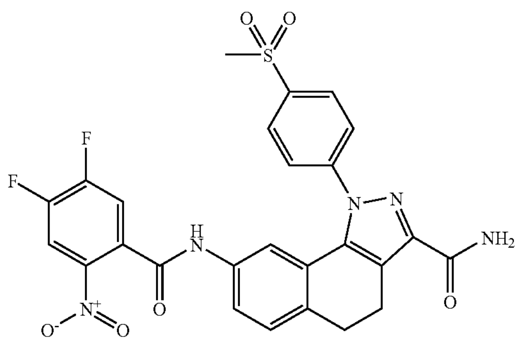 | 567.53 | 8-[(4,5-difluoro-2-nitrobenzoyl)amino]-1-[4-(methylsulfonyl)phenyl]-4,5-dihydro-1H-benzo[g]indazole-3-carboxamide | ≦1 μM | 149 |
| 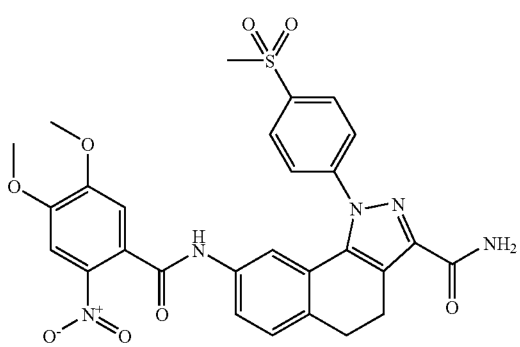 | 591.60 | 8-[(4,5-dimethoxy-2-nitrobenzoyl)amino]-1-[4-(methylsulfonyl)phenyl]-4,5-dihydro-1H-benzo[g]indazole-3-carboxamide | ≦1 μM | 150 |
| 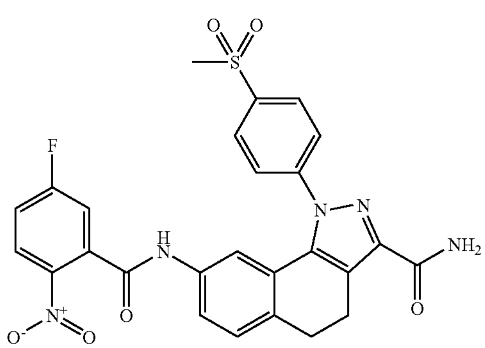 | 549.54 | 8-[(5-fluoro-2-nitrobenzoyl)amino]-1-[4-(methylsulfonyl)phenyl]-4,5-dihydro-1H-benzo[g]indazole-3-carboxamide | ≦1 μM | 151 |

TABLE 3-continued

| Structure | Formula Weight | Name | IKK Resin IC$_{50}$ | Example |
|---|---|---|---|---|
| 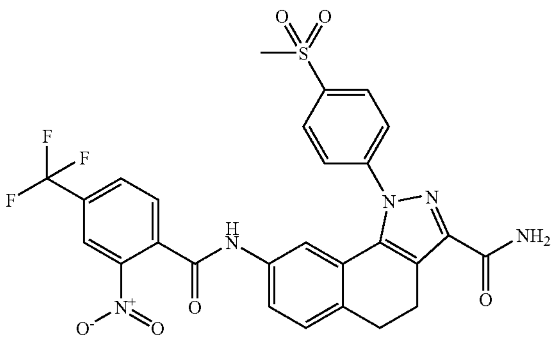 | 599.55 | 1-[4-(methylsulfonyl)phenyl]-8-{[2-nitro-4-(trifluoromethyl)benzoyl]amino}-4,5-dihydro-1H-benzo[g]indazole-3-carboxamide | ≦1 µM | 152 |
| | 545.58 | 8-[(5-methyl-2-nitrobenzoyl)amino]-(methylsulfonyl)phenyl]-4,5-dihydro-1H-benzo[g]indazole-3-carboxamide | ≦1 µM | 153 |
| | 545.58 | 8-[(3-methyl-2-nitrobenzoyl)amino]-1-[4-(methylsulfonyl)phenyl]-4,5-dihydro-1H-benzo[g]indazole-3-carboxamide | 1 ≦ 10 µM | 154 |
| 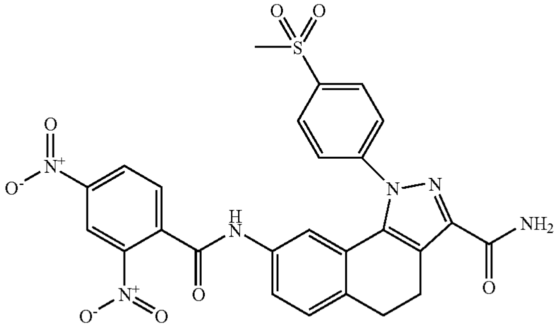 | 576.55 | 8-[(2,4-dinitrobenzoyl)animo]-1-[4-(methylsulfonyl)phenyl]-4,5-dihydro-1H-benzo[g]indazole-3-carboxamide | ≦1 µM | 155 |

TABLE 3-continued

| Structure | Formula Weight | Name | IKK Resin IC$_{50}$ | Example |
|---|---|---|---|---|
| | 500.58 | 8-[(3-methylbenzoyl)amino]-1-[4-(methylsulfonyl)phenyl]-4,5-dihydro-1H-benzo[g]indazole-3-carboxamide | 1 ≦ 10 μM | 156 |
| 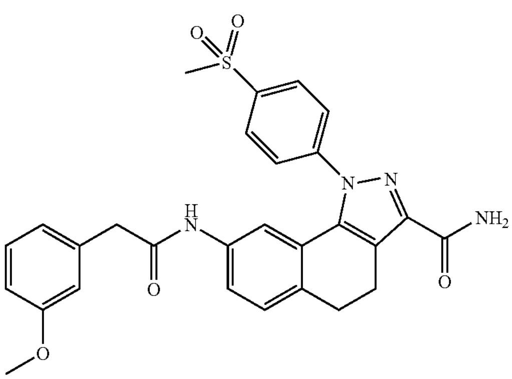 | 530.61 | 8-{[(3-methoxyphenyl)acetyl]amino}-1-[4-(methylsulfonyl)phenyl]-4,5-dihydro-1H-benzo[g]indazole-3-carboxamide | ≦1 μM | 157 |
| | 500.58 | 1-[4-(methylsulfonyl)phenyl]-8-[(phenylacetyl)amino]-4,5-dihydro-1H-benzo[g]indazole-3-carboxamide | 1 ≦ 10 μM | 158 |
| 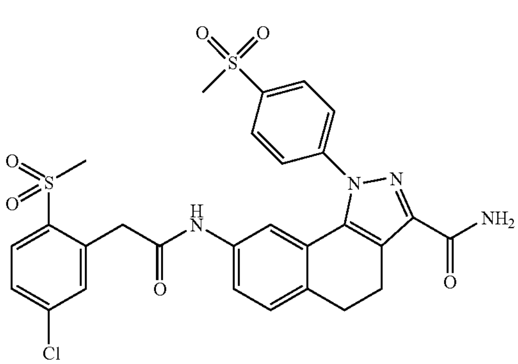 | 599.09 | 8-{[2-chloro-5-(methylsulfonyl)benzoyl]amino}-1-[4-(methylsulfonyl)phenyl]-4,5-dihydro-1H-benzo[g]indazole-3-carboxamide | ≦1 μM | 159 |

TABLE 3-continued

| Structure | Formula Weight | Name | IKK Resin IC$_{50}$ | Example |
|---|---|---|---|---|
| 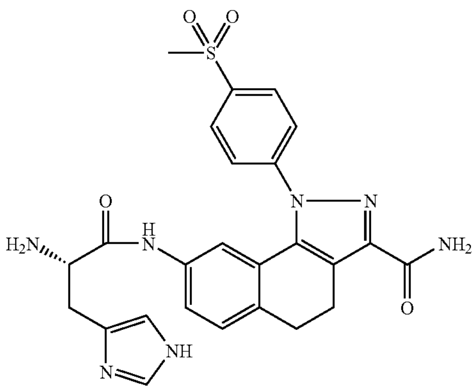 | 519.59 | 8-(L-histidylamino)-1-[4-(methylsulfonyl)phenyl]-4,5-dihydro-1H-benzo[g]indazole-3-carboxamide | 1 ≦ 10 μM | 160 |

Examples 161–206

Examples 161–206 shown in Table 4 were synthesized using the following synthesis procedure similar to Scheme I where $R^9$ is the appropriate aryl, substituted aryl, heteroaryl, substituted heteroaryl, substituted arylalkyl, substituted heteroarylalkyl, or cycloalkyl. The detailed synthesis of 1-(1,3-benzodioxol-5-yl)-8-{[(2-chloropyridin-3-yl)carbonyl]amino}-4,5-dihydro-1H-benzo[g]indazole-3-carboxamide (Example 161) is described below and is illustrative for the compounds of Table 4.

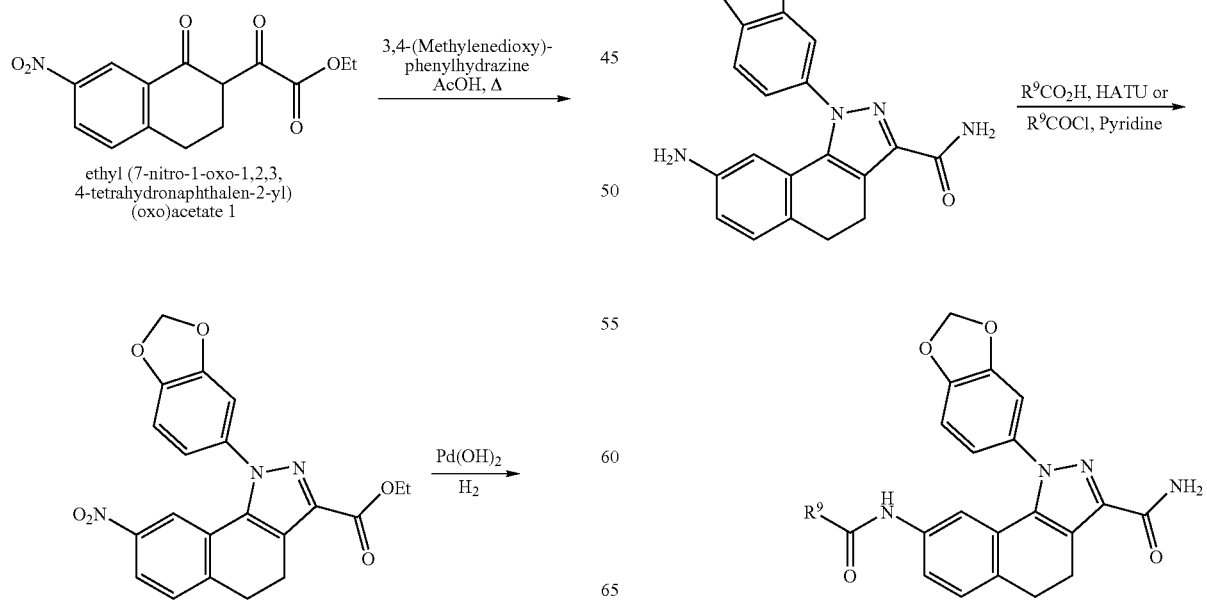

SCHEME XX

Example 161

1-(1,3-benzodioxol-5-yl)-8-{[(2-chloropyridin-3-yl)carbonyl]amino}-4,5-dihydro-1H-benzo[g]indazole-3-carboxamide

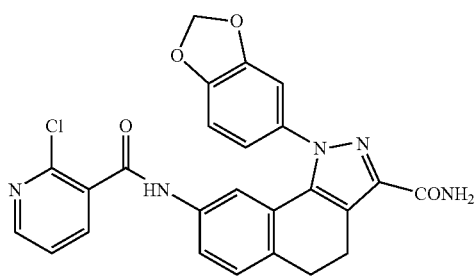

Step 1

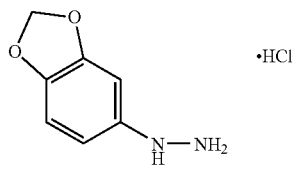

The title compound of step 1 was prepared by the method disclosed by T. Komatsu et al, *Azneim.-Forsch.* (1972) 22(12), 2099–104.

Step 2

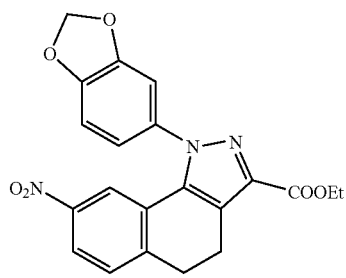

A mixture of 5.00 g (17.2 mmoles) of diketo ester and 3.24 g (17.2 mmoles) of the title product of Step 1 in 100 ml of acetic acid was refluxed with stirring for 3 h, and then cooled. The mixture was concentrated, and the residue triturated with ethyl acetate affording a brown solid which was filtered, washed with ethyl acetate, and dried to give the title compound, 4.79 g. The structure was supported by $^1$H NMR.

Step 3

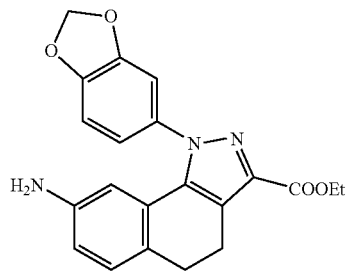

A solution 4.79 g of the title product of Step 2 in acetic acid was treated at room temperature with 5% palladium on carbon under an atmosphere of hydrogen gas at 5 psi. The reaction was followed by LC-MS. When the conversion was complete, the mixture was filtered and concentrated to give the title compound as a brownish oil that was used directly for the next step.

Step 4

8-amino-1-(1,3-benzodioxol-5-yl)-4,5-dihydro-1H-benzo[g]indazole-3-carboxamide

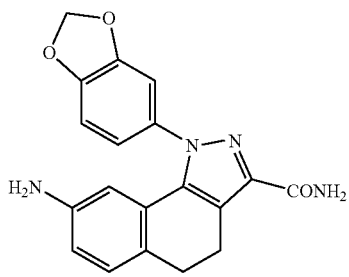

The title product of Step 3 was dissolved in anhydrous ethanol and then an approximately equal volume of liquid ammonia was added. The resulting mixture was sealed in a pressure vessel and then stirred overnight at 100° C. After cooling, the mixture was concentrated. The residue was taken up in dichloromethane-methanol and chromatographed over silica gel using ethyl acetate as eluent to give the title compound, 890 mg, as an oil which crystallized on standing. Anal. for $C_{19}H_{16}N_4O_3 \cdot 0.75H_2O$ (MW 361.87): Calc'd.: C, 63.06; H, 4.46, N, 15.48. Found: C, 63.24; H, 4.70, N, 14.58.

Step 5

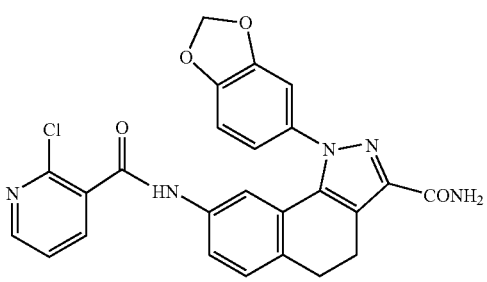

A mixture of the title product of Example 4 (3.6 g, 0.01 mol) and 2-chloronicotinyl chloride (1.8 g, 0.01 mol) in 50 ml of pyridine was stirred at room temperature overnight. Solvent was removed and the residue was triturated with a mixture of acetonitrile and methanol (20:1) to give 2.6 g of the title compound as a light brown solid. The mother liquor was concentrated and purified the same way to give another 0.69 g of product (68% yield); mp: 165–166C. Anal. Calcd. for $C_{25}H_{18}ClN_5O_4 \cdot 0.5H_2O$: C, 60.43; H, 3.85; 14.09. Found: C, 60.27; H, 3.59; N, 14.14.

TABLE 4

| Structure | Mol. Wt. | Compound Name(s) | IKK2 Resin IC50 | Example |
|---|---|---|---|---|
| 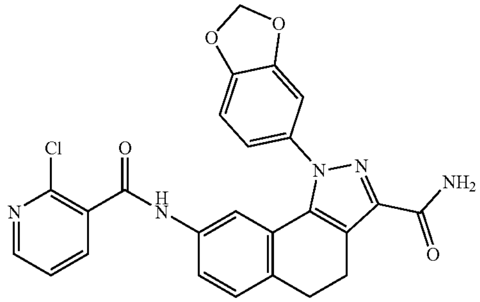 | 487.90 | 1-(1,3-benzodioxol-5-yl)-8-{[(2-chloropyridin-3-yl)carbonyl]amino}-4,5-dihydro-1H-benzo[g]indazole-3-carboxamide | ≦1 µM | 161 |
| 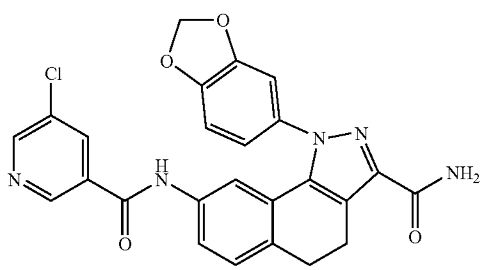 | 522.35 | 1-(1,3-benzodioxol-5-yl)-8-{[(2,5-dichloropyridin-3-yl)carbonyl]amino}-4,5-dihydro-1H-benzo[g]indazole-3-carboxamide | ≦1 µM | 162 |
| 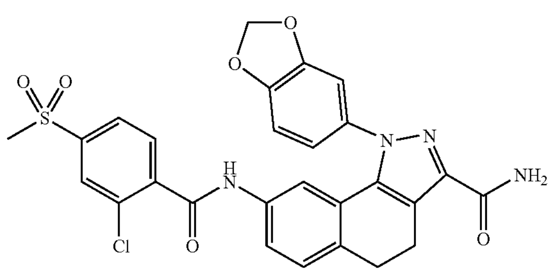 | 565.01 | 1-(1,3-benzodioxol-5-yl)-8-{[2-chloro-4-(methylsulfonyl)benzoyl]amino}-4,5-dihydro-1H-benzo[g]indazole-3-carboxamide | ≦1 µM | 163 |
| 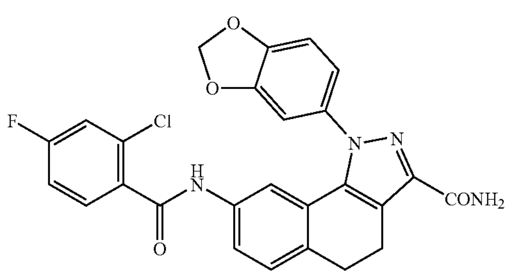 | 504.91 | 1-(1,3-benzodioxol-5-yl)-8-[(2-chloro-4-fluorobenzoyl)amino]-4,5-dihydro-1H-benzo[g]indazole-3-carboxamide | ≦1 µM | 164 |
| 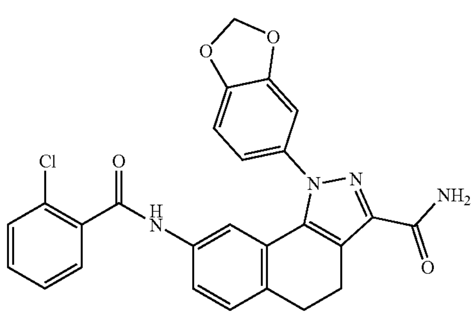 | 486.92 | 1-(1,3-benzodioxol-5-yl)-8-[(2-chlorobenzoyl)amino]-4,5-dihydro-1H-benzo[g]indazole-3-carboxamide | ≦1 µM | 165 |

TABLE 4-continued

| Structure | Mol. Wt. | Compound Name(s) | IKK2 Resin IC50 | Example |
|---|---|---|---|---|
| 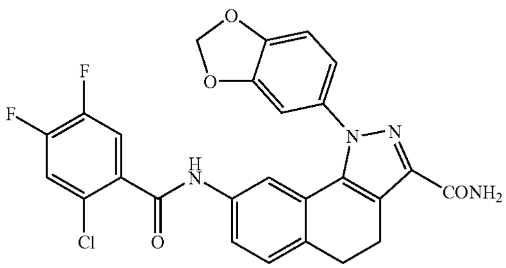 | 522.90 | 1-(1,3-benzodioxol-5-yl)-8-[(2-chloro-4,5-difluorobenzoyl)amino]-4,5-dihydro-1H-benzo[g]indazole-3-carboxamide | $\leq 1$ μM | 166 |
| | 501.93 | 1-(1,3-benzodioxol-5-yl)-8-{[(2-chloro-6-methylpyridin-3-yl)carbonyl]amino}-4,5-dihydro-1H-benzo[g]indazole-3-carboxamide | $\leq 1$ μM | 167 |
| 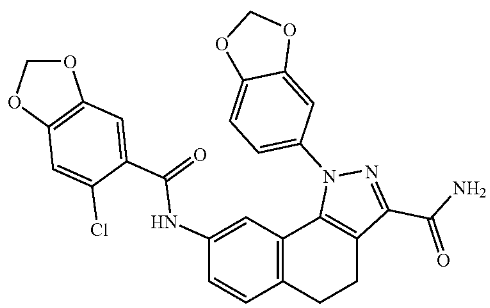 | 530.93 | 1-(1,3-benzodioxol-5-yl)-8-{[(6-chloro-1,3-benzodioxol-5-yl)carbonyl]amino}-4,5-dihydro-1H-benzo[g]indazole-3-carboxamide | $\leq 1$ μM | 168 |
| | 501.93 | 8-[(2-amino-6-chlorobenzoyl)amino]-1-(1,3-benzodioxol-5-yl)-4,5-dihydro-1H-benzo[g]indazole-3-carboxamide | $\leq 1$ μM | 169 |
| 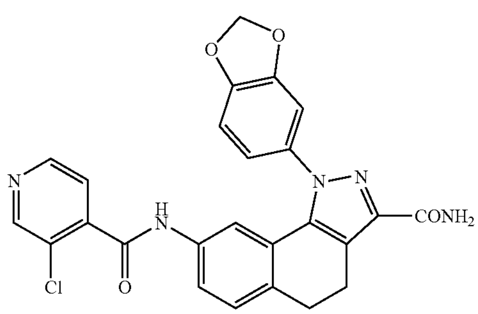 | 487.91 | 1-(1,3-benzodioxol-5-yl)-8-[(3-chloroisonicotinoyl)amino]-4,5-dihydro-1H-benzo[g]indazole-3-carboxamide | $\leq 1$ μM | 170 |

TABLE 4-continued

| Structure | Mol. Wt. | Compound Name(s) | IKK2 Resin IC50 | Example |
|---|---|---|---|---|
| 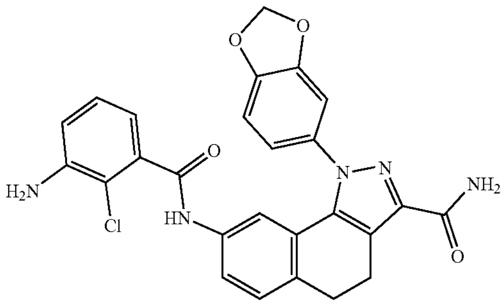 | 538.39 | 8-[(3-amino-2-chlorobenzoyl)amino]-1-(1,3-benzodioxol-5-yl)-4,5-dihydro-1H-benzo[g]indazole-3-carboxamide hydrochloride | ≦1 μM | 171 |
| 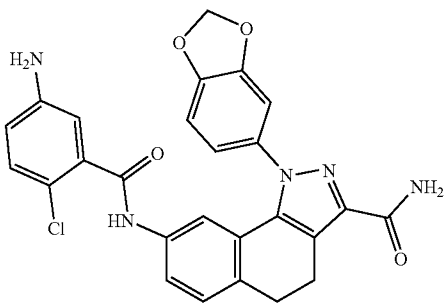 | 501.93 | 8-[(5-amino-2-chlorobenzoyl)amino]-1-(1,3-benzodioxol-5-yl)-4,5-dihydro-1H-benzo[g]indazole-3-carboxamide | ≦1 μM | 172 |
| 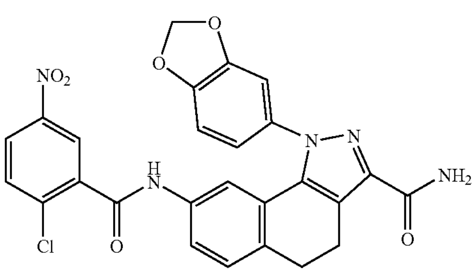 | 531.92 | 1-(1,3-benzodioxol-5-yl)-8-[(2-chloro-5-nitrobenzoyl)amino]-4,5-dihydro-1H-benzo[g]indazole-3-carboxamide | ≦1 μM | 173 |
| 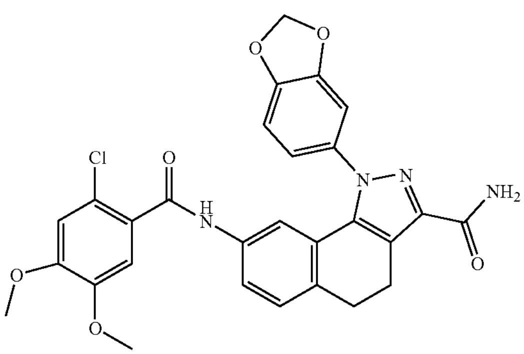 | 546.97 | 1-(1,3-benzodioxol-5-yl)-8-[(2-chloro-4,5-dimethoxybenzoyl)amino]-4,5-dihydro-1H-benzo[g]indazole-3-carboxamide | ≦1 μM | 174 |

TABLE 4-continued

| Structure | Mol. Wt. | Compound Name(s) | IKK2 Resin IC50 | Example |
|---|---|---|---|---|
| 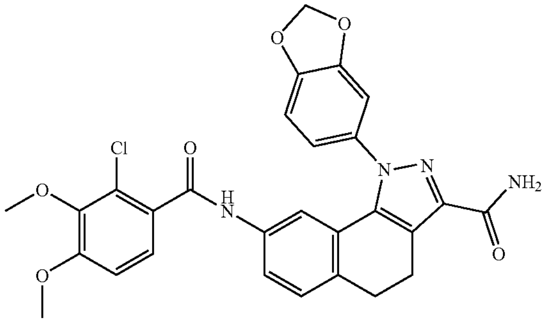 | 546.97 | 1-(1,3-benzodioxol-5-yl)-8-[(2-chloro-3,4-dimethoxybenzoyl)amino]-4,5-dihydro-1H-benzo[g]indazole-3-carboxamide | ≦1 μM | 175 |
| 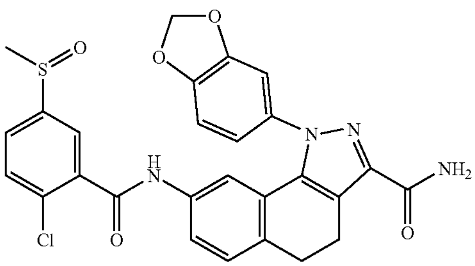 | 549.01 | 1-(1,3-benzodioxol-5-yl)-8-{[2-chloro-5-(methylsulfinyl)benzoyl]amino}-4,5-dihydro-1H-benzo[g]indazole-3-carboxamide | ≦1 μM | 176 |
| 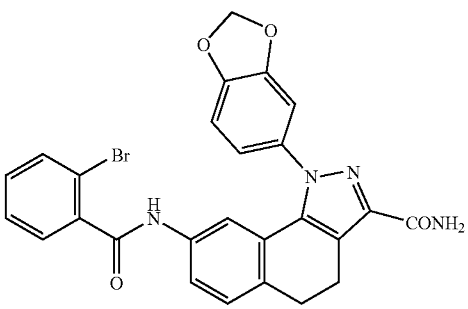 | 531.37 | 1-(1,3-benzodioxol-5-yl)-8-[(2-bromobenzoyl)amino]-4,5-dihydro-1H-benzo[g]indazole-3-carboxamide | ≦1 μM | 177 |
| 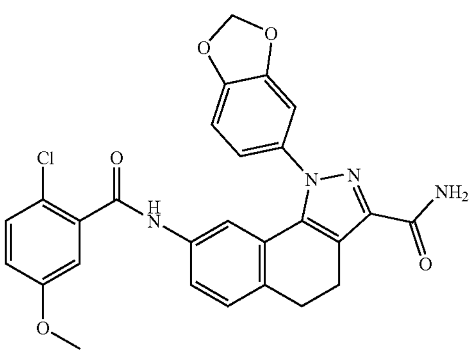 | 516.95 | 1-(1,3-benzodioxol-5-yl)-8-[(2-chloro-5-methoxybenzoyl)amino]-4,5-dihydro-1H-benzo[g]indazole-3-carboxamide | ≦1 μM | 178 |
| 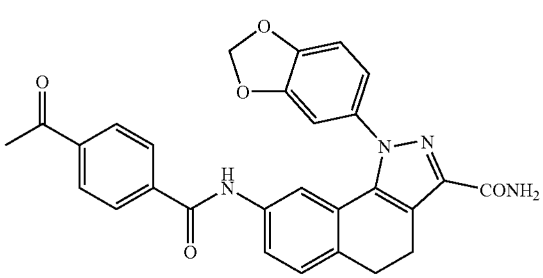 | 494.51 | 8-[(4-acetylbenzoyl)amino]-1-(1,3-benzodioxol-5-yl)-4,5-dihydro-1H-benzo[g]indazole-3-carboxamide | 1 ≦ 10 μM | 179 |

TABLE 4-continued

| Structure | Mol. Wt. | Compound Name(s) | IKK2 Resin IC50 | Example |
|---|---|---|---|---|
| 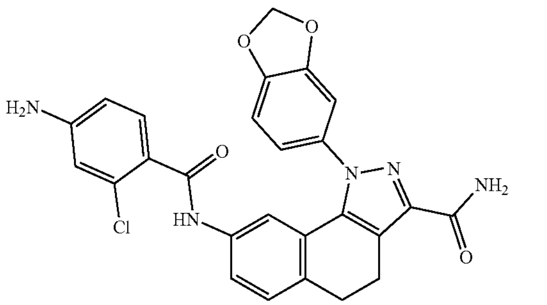 | 501.93 | 8-[(4-amino-2-chlorobenzoyl)amino]-1-(1,3-benzodioxol-5-yl)-4,5-dihydro-1H-benzo[g]indazole-3-carboxamide | ≦1 μM | 180 |
| 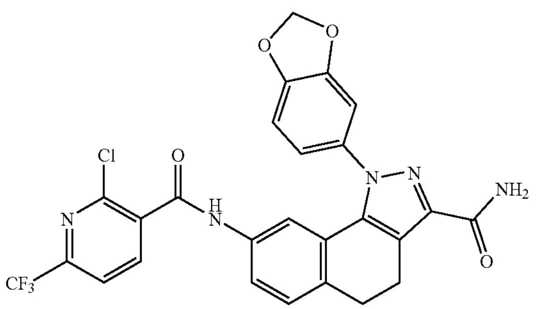 | 555.90 | 1-(1,3-benzodioxol-5-yl)-8-({[2-chloro-6-(trifluoromethyl)pyridin-3-yl]carbonyl}amino)-4,5-dihydro-1H-benzo[g]indazole-3-carboxamide | ≦1 μM | 181 |
| 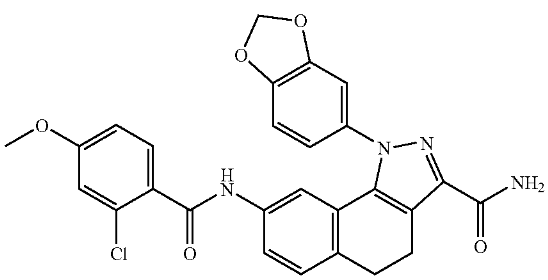 | 516.95 | 1-(1,3-benzodioxol-5-yl)-8-[(2-chloro-4-methoxybenzoyl)amino]-4,5-dihydro-1H-benzo[g]indazole-3-carboxamide | ≦1 μM | 182 |
| 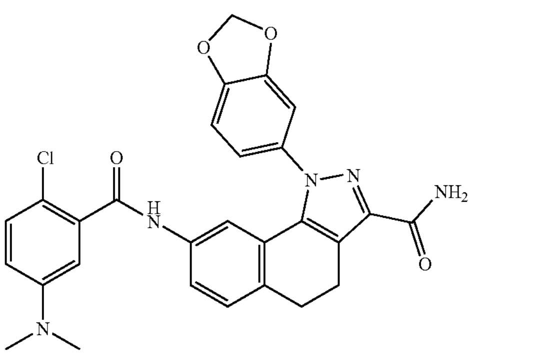 | 529.99 | 1-(1,3-benzodioxol-5-yl)-8-{[2-chloro-5-(dimethylamino)benzoyl]amino}-4,5-dihydro-1H-benzo[g]indazole-3-carboxamide | ≦1 μM | 183 |
| 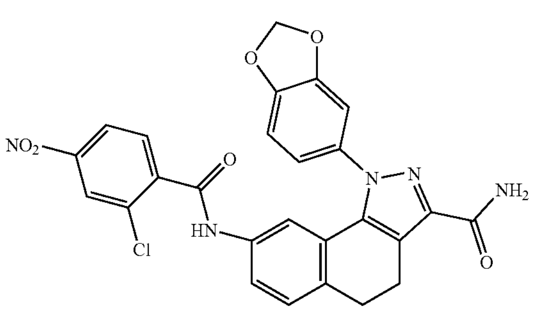 | 531.92 | 1-(1,3-benzodiaxol-5-yl)-8-[(2-chloro-4-nitrobenzoyl)amino]-4,5-dihydro-1H-benzo[g]indazole-3-carboxamide | ≦1 μM | 184 |

TABLE 4-continued

| Structure | Mol. Wt. | Compound Name(s) | IKK2 Resin IC50 | Example |
|---|---|---|---|---|
| 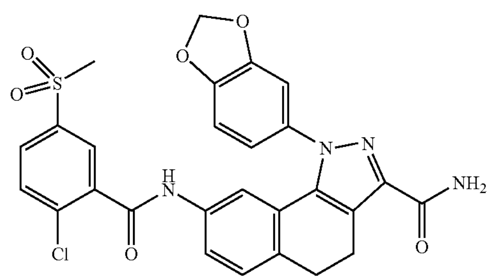 | 565.01 | 1-(1,3-benzodioxol-5-yl)-8-{[2-chloro-5-(methylsulfonyl)benzoyl]amino}-4,5-diliydro-1H-benzo[g]indazole-3-carboxamide | ≦1 μM | 185 |
| 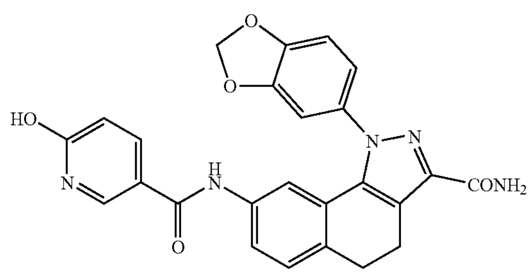 | 469.46 | 1-(1,3-benzodioxol-5-yl)-8-{[(6-hydroxypyridin-3-yl)carbonyl]amino}-4,5-dihydro-1H-benzo[g]indazole-3-carboxamide | ≦1 μM | 186 |
| 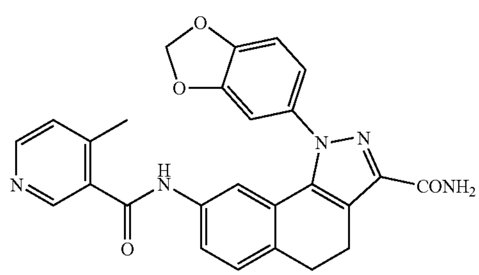 | 467.49 | 1-(1,3-benzodioxol-5-yl)-8-{[(4-methylpyridin-3-yl)carbonyl]amino}-4,5-dihydro-1H-benzo[g]indazole-3-carboxamide | ≦1 μM | 187 |
| 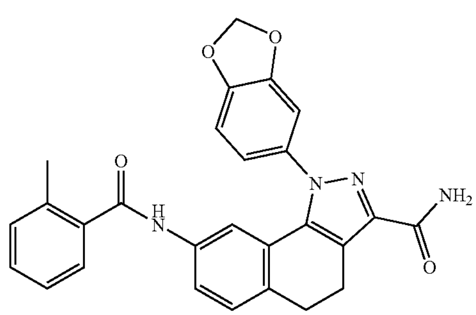 | 466.50 | 1-(1,3-benzodioxol-5-yl)-8-[(2-methylbenzoyl)amino]-4,5-dihydro-1H-benzo[g]indazole-3-carboxamide | 1 ≦ 10 μM | 188 |
| 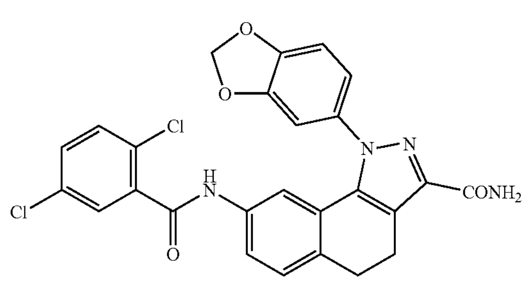 | 521.36 | 1-(1,3-benzodioxol-5-yl)-8-[(2,5-dichlorobenzoyl)amino]-4,5-dihydro-1H-benzo[g]indazole-3-carboxamide | ≦1 μM | 189 |

TABLE 4-continued

| Structure | Mol. Wt. | Compound Name(s) | IKK2 Resin IC50 | Example |
|---|---|---|---|---|
| 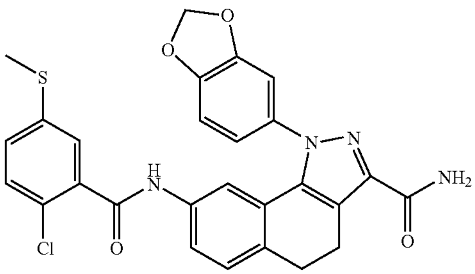 | 533.01 | 1-(1,3-benzodioxol-5-yl)-8-{2-chloro-5-[2-(methylthio)benzoyl]amino}-4,5-dihydro-1H-benzo[g]indazole-3-carboxamide | ≦1 μM | 190 |
| 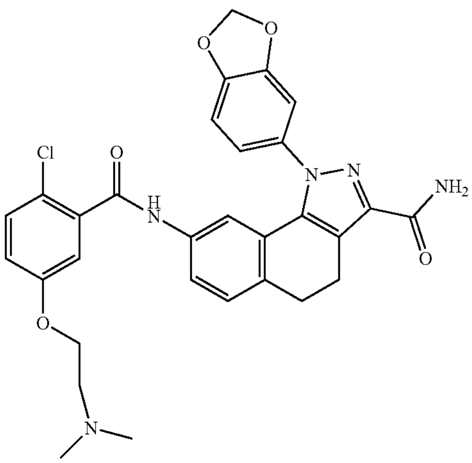 | 574.04 | 1-(1,3-benzodioxol-5-yl)-8-({2-chloro-5-[2-(dimethylamino)ethoxy]benzoyl}amino)-4,5-dihydro-1H-benzo[g]indazole-3-carboxamide | 1 ≦ 10 μM | 191 |
| 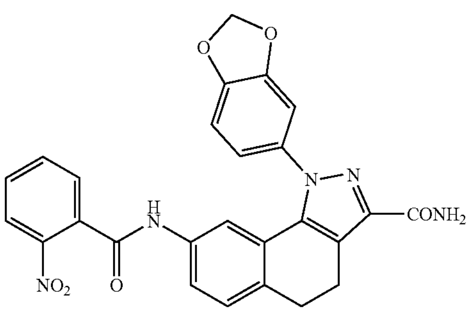 | 497.47 | 1-(1,3-benzodioxol-5-yl)-8-[(2-nitrobenzoyl)amino]-4,5-dihydro-1H-benzo[g]indazole-3-carboxamide | ≦1 μM | 192 |
| 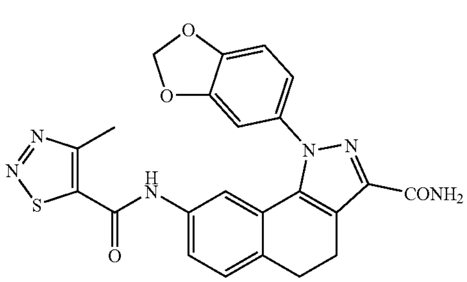 | 474.50 | 1-(1,3-benzodioxol-5-yl)-8-{[(4-methyl-1,2,3-thiadiazol-5-yl)carbonyl]amino}-4,5-dihydro-1H-benzo[g]indazole-3-carboxamide | 1 ≦ 10 μM | 193 |

TABLE 4-continued

| Structure | Mol. Wt. | Compound Name(s) | IKK2 Resin IC50 | Example |
|---|---|---|---|---|
| | 521.36 | 1-(1,3-benzodioxol-5-yl)-8-[(2,3-dichlorobenzoyl)amino]-4,5-dihydro-1H-benzo[g]indazole-3-carboxamide | ≦1 μM | 194 |
| | 521.36 | 1-(1,3-benzodioxol-5-yl)-8-[(2,4-dichlorobenzoyl)amino]-4,5-dihydro-1H-benzo[g]indazole-3-carboxamide | ≦1 μM | 195 |
| 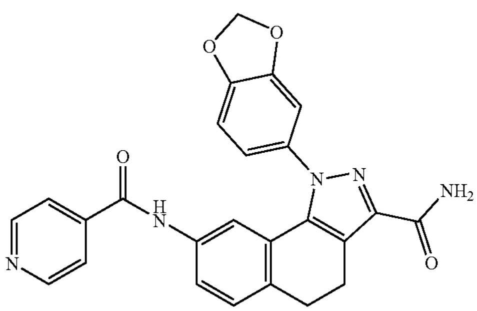 | 453.46 | 1-(1,3-benzodioxol-5-yl)-8-(isonicotinoylamino)-4,5-dihydro-1H-benzo[g]indazole-3-carboxamide | ≦1 μM | 196 |
| 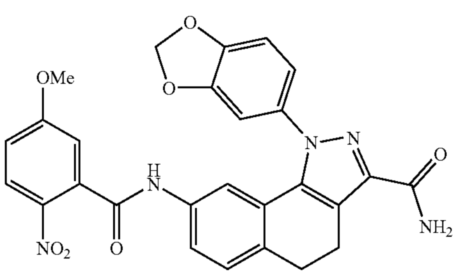 | 527.50 | 1-(1,3-benzodioxol-5-yl)-8-[(5-methoxy-2-nitrobenzoyl)amino]-4,5-dihydro-1H-benzo[g]indazole-3-carboxamide | 1 ≦ 10 μM | 197 |
| 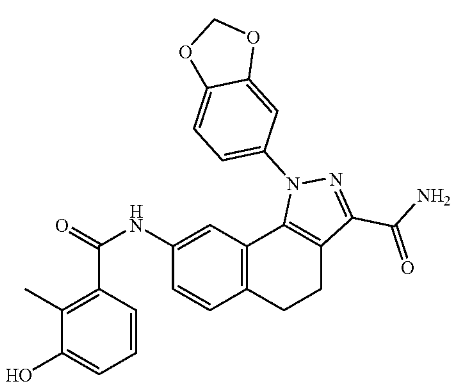 | 482.50 | 1-(1,3-benzodioxol-5-yl)-8-[(3-hydroxy-2-methylbenzoyl)amino]-4,5-dihydro-1H-benzo[g]indazole-3-carboxamide | ≦1 μM | 198 |

TABLE 4-continued

| Structure | Mol. Wt. | Compound Name(s) | IKK2 Resin IC50 | Example |
|---|---|---|---|---|
| 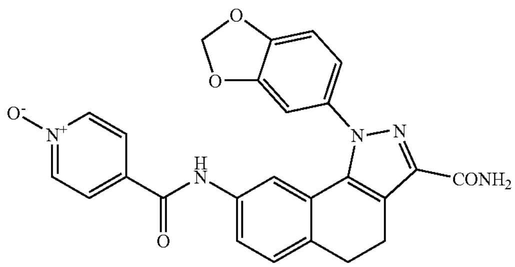 | 469.46 | 1-(1,3-benzodioxol-5-yl)-8-[(1-oxidoisonicotinoyl)amino]-benzo[g]indazole-3-carboxamide | 1 ≦ 10 μM | 199 |
| 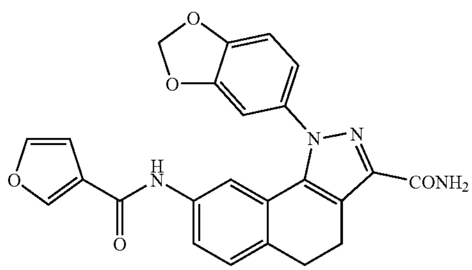 | 442.44 | 1-(1,3-benzodioxol-5-yl)-8-(3-furoylamino)-4,5-dihydro-1H-benzo[g]indazole-3-carboxamide | 1 ≦ 10 μM | 200 |
| 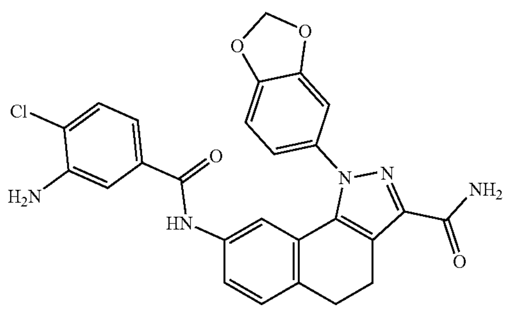 | 501.93 | 8-[(3-amino-4-chlorobenzoyl)amino]-1-(1,3-benzodioxol-5-yl)-4,5-dihydro-1H-benzo[g]indazole-3-carboxamide | 1 ≦ 10 μM | 201 |
| 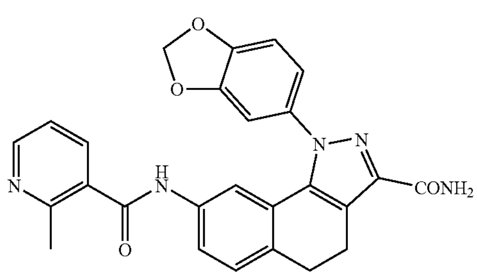 | 467.49 | 1-(1,3-benzodioxol-5-yl)-8-{[(2-methylpyridin-3-yl)carbonyl]amino}-4,5-dihydro-1H-benzo[g]indazole-3-carboxamide | 1 ≦ 10 μM | 202 |
| 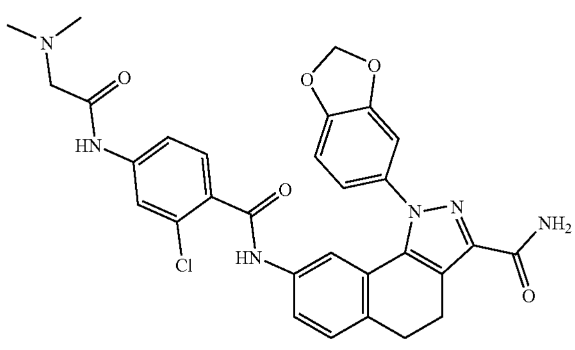 | 587.04 | 1-(1,3-benzodioxol-5-yl)-8-({2-chloro-4-[(N,N-dimethylglycyl)amino]benzoyl}amino)-4,5-dihydro-1H-benzo[g]indazole-3-carboxamide | 1 ≦ 10 μM | 203 |

TABLE 4-continued

| Structure | Mol. Wt. | Compound Name(s) | IKK2 Resin IC50 | Example |
|---|---|---|---|---|
| 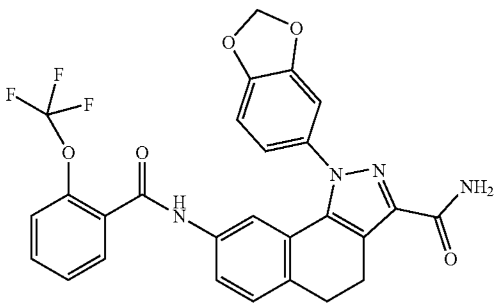 | 536.46 | 1-(1,3-benzodioxol-5-yl)-8-{[2-(trifluoromethoxy)benzoyl]amino}-4,5-dihydro-1H-benzo[g]indazole-3-carboxamide | 1 ≦ 10 μM | 204 |
| 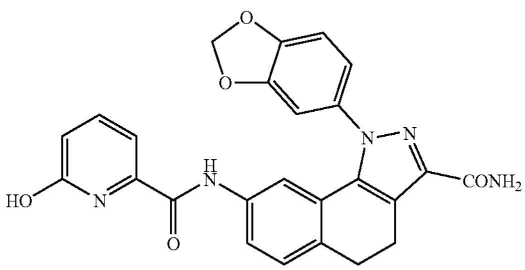 | 469.46 | 1-(1,3-benzodioxol-5-yl)-8-{[(6-hydroxypyridin-2-yl)carbonyl]amino}-4,5-dihydro-1H-benzo[g]indazole-3-carboxamide | 1 ≦ 10 μM | 205 |
| 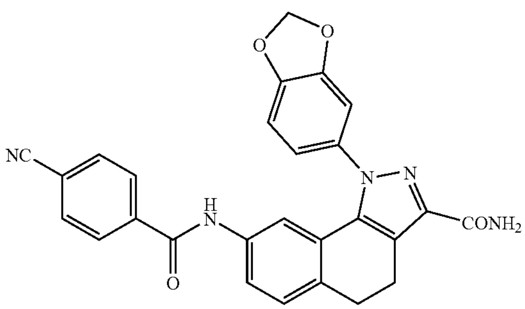 | 477.48 | 1-(1,3-benzodioxol-5-yl)-8-[(4-cyanobenzoyl)amino]-4,5-dihydro-1H-benzo[g]indazole-3-carboxamide | 1 ≦ 10 μM | 206 |

Example 207

1-(1,3-benzodioxol-5-yl)-8-({[2-(methylamino)pyridin-3-yl]carbonyl}amino)-4,5-dihydro-1H-benzo[g]indazole-3-carboxamide

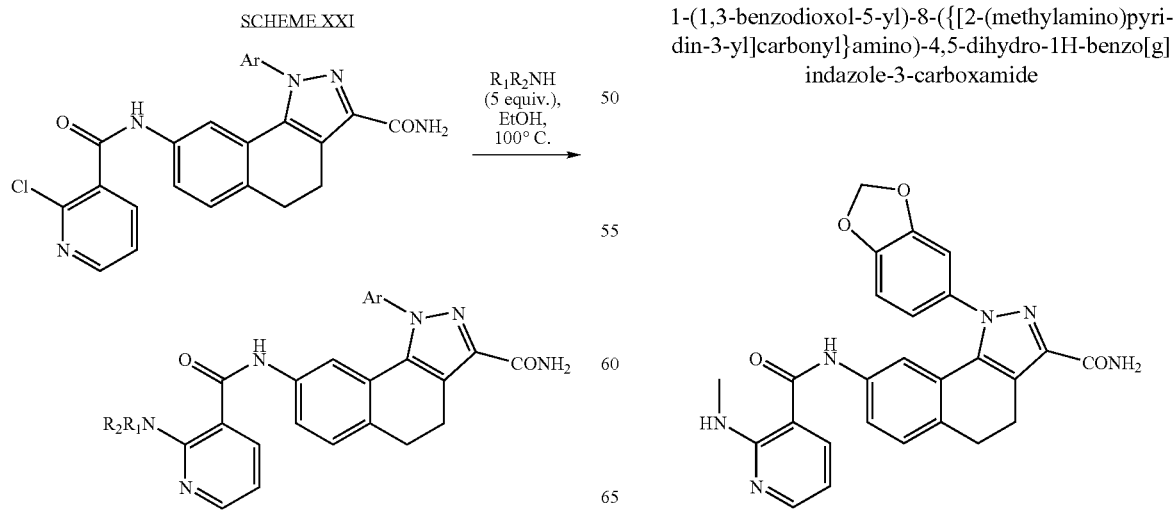

A mixture of the title product of Example 161 (1.4 g, 0.0028 mol) and methylamine (0.014 mol) in 6 mL EtOH was heated in a sealed tube to 100° C. for 48 h. The off-white precipitate that formed in the crude reaction mixture was filtered and washed with EtOH and Et$_2$O to afford 1.05 g of title compound (yield: 75%). Mp: 273–275° C. $^1$H NMR (300 MHz, d$_6$-DMSO): δ 2.88–2.95 (m, 4H+3H), 6.12 (s, 2H) 6.57–6.61 (dd, 1H, J=7.6 Hz, 4.7 Hz), 6.95–6.98 (dd, 1H, J=8 Hz, 2 Hz), 7.07 (d, 1H, J=0.8 Hz), 7.13 (d, 1H, J=2 Hz), 7.25–7.34 (m, 3H), 7.45–7.50 (m, 2H), 7.82–7.83 (m, 1H), 7.91–7.95 (dd, 1H, J=7.6 Hz, 1.7 Hz), 8.18–8.20(dd, 1H, J=4.8 Hz, 1.8 Hz), 10.02 (s, 1H). M+1=483.

Example 208

1-(1,3-benzodioxol-5-yl)-8-[({2-[(2-hydroxyethyl)amino]pyridin-3-yl}carbonyl)amino]-4,5-dihydro-1H-benzo[g]indazole-3-carboxamide

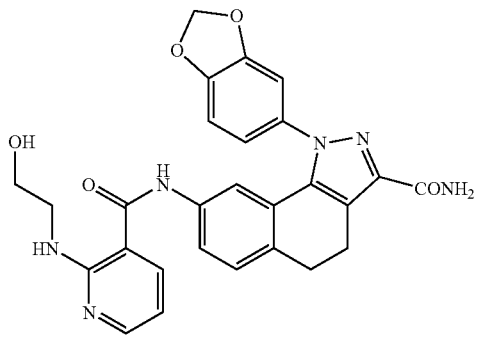

The title compound was synthesized by the same procedure as in Example 207 starting with product of Example 161 (1 g, 0.0020 mol) and ethanolamine (0.626 g, 0.010 mol) in 4 mL of EtOH to afford 0.475 g of title compound (yield: 46%). Mp: 250–253° C. $^1$H NMR (300 MHz, d$_6$-DMSO): δ 2.86–2.93 (m, 4H), 3.43–3.47 (m, 2H), 3.53–3.54 (m, 2H), 4.76 (s, 1H), 6.12 (s, 2H), 6.56–6.59 (dd, 1H, J=7.5 Hz, 4.8 Hz), 6.95–6.97 (dd, 1H, J=8 Hz, 2 Hz), 7.05 (d, 1H, J=8 Hz), 7.11 (d, 1H, J=2 Hz), 7.26–7.37 (m, 4H), 7.51 (s, 1H), 7.89–7.91 (dd, 1H, J=7.6 Hz, 1.5 Hz), 7.97–7.99 (t, 1H, J=5 Hz), 8.14–8.15 (dd, 1H, J=4.7 Hz, 1.6 Hz), 10.02 (s, 1H). Anal. Calcd. for C$_{27}$H$_{24}$N$_6$O$_5$: C, 63.27; H, 4.72; N, 16.40. Found: C, 63.38; H, 4.7; N, 16.34. M+1=513.

Example 209

1-(1,3-benzodioxol-5-yl)-8-[({2-[(4-methoxybenzyl)amino]pyridin-3-yl}carbonyl)amino]-4,5-dihydro-1H-benzo[g]indazole-3-carboxamide

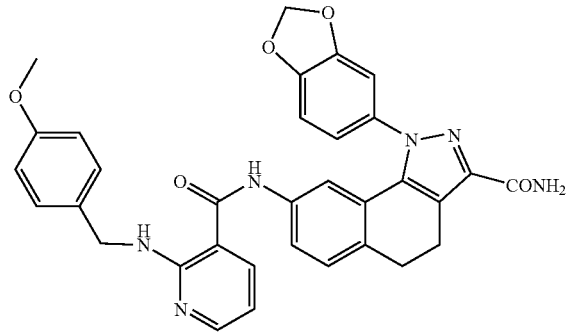

The title compound was synthesized by the same procedure as in Example 207 starting with product of Example 161 (2 g, 0.0040 mol) and p-methoxybenzylamine (2.8 g, 0.020 mol) in 10 mL EtOH to yield 1.96 g of the title compound (yield: 60%). Mp: 181–182° C. $^1$H NMR (300 MHz, d$_6$-DMSO): δ 2.88–2.94 (m, 4H), 3.71 (s, 3H), 4.56 (d, 2H, J=5.6 Hz), 5.98 (s, 2H), 6.60–6.64 (dd, 1H, J=7.5 Hz, 4.7 Hz), 6.88 (d, 2H, J=8.4 Hz), 6.96 (s, 2H), 7.11 (s, 1H), 7.23–7.35 (m, 5H), 7.39 (s, 1H), 7.49 (s, 1H), 7.95 (d, 1H, J=7.45 Hz), 8.17 (d, 1H, J=4.7 Hz), 8.23 (t, 1H, J=5.6 Hz), 10.06 (s, 1H). Anal. Calc. for C$_{33}$H$_{28}$N$_6$O$_5$: C, 67.34; H, 4.79; N, 14.28. Found C, 67.08; H, 4.78; N, 14.19. M+1=589.

Example 210

8-{[(2-aminopyridin-3-yl)carbonyl]amino}-1-(1,3-benzodioxol-5-yl)-4,5-dihydro-1H-benzo[g]indazole-3-carboxamide

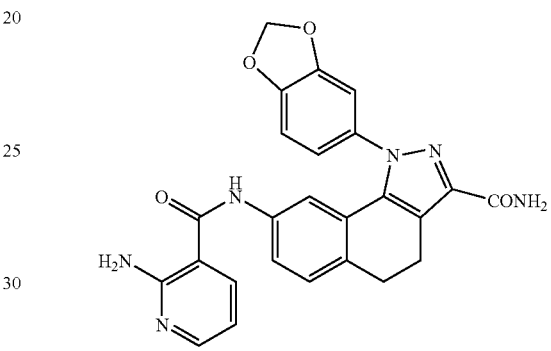

The title compound of Example 209 (1.96 g, 0.0033 mol) was dissolved in 6 mL CH$_2$Cl$_2$ and reacted with 5 mL TFA at room temperature for 36 h. The crude reaction mixture was diluted with CH$_2$Cl$_2$ and basified with a saturated aqueous solution of Na$_2$CO$_3$. The layers were separated and the organic layer was dried over MgSO$_4$. The residue obtained after removal of the solvent under vacuum was triturated with EtOH to afford 0.503 g of title compound (yield: 32%). Mp: 265–267° C. $^1$H NMR (300 MHz, d$_6$-DMSO): δ 2.88–2.95 (m, 4H), 6.12 (s, 2H), 5.58–6.62 (dd, 1H, J=7.6 Hz, 4.7 Hz), 6.97–7.08 (m, 4H), 7.17 (d, 1H, J=1.9 Hz), 7.28 (s, 1H), 7.32 (s, 2H), 7.55 (s, 2H), 7.95–7.98 (dd, 1H, J=7.7 Hz, 1.7 Hz), 8.11–8.13 (dd, 1H, J=4.7 Hz, 1.7 Hz), 9.99 (s, 1H). M+1=469.

SCHEME XXII

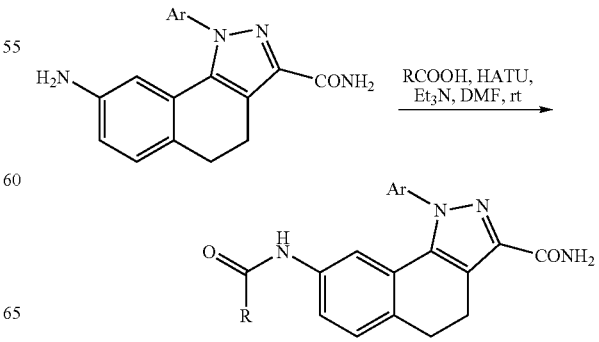

Example 211

1-(1,3-benzodioxol-5-yl)-8-[(2,5-dichloroisonicotinoyl)amino]-4,5-dihydro-1H-benzo[g]indazole-3-carboxamide

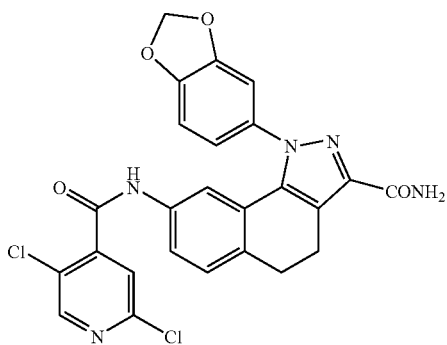

2,5-Dichloroisonicotinic acid (1.65 g, 0.0086 mol), HATU (3.27 g, 0.0086 mol) and finally Et$_3$N (2.32 mL, 0.0166 mol) were added to a solution of the title compound of step 4 of Example 161 (2 g, 0.00574 mol) in 29 mL of DMF. The reaction mixture was stirred at room temperature for 3 h. The completion of the reaction was confirmed by monitoring the disappearance of the title compound of step 4 of Example 161 in LC/MS. The crude reaction mixture was concentrated to about 10 mL of DMF. Upon addition of water to this DMF residue, a white solid was formed. This white solid was triturated in water for 20 min and filtered. The solid was collected, dissolved in THF, and dried with MgSO$_4$. Removal of the solvent afforded a brown solid that was triturated in warm CH$_3$CN (80° C.) to give 2.2 g of the title compound (yield 73%). Mp: 292–293° C. $^1$H NMR (300 MHz, d$_6$-DMSO): δ 2.90–2.92 (m, 4H), 6.09 (s, 2H), 6.94–7.04 (m, 2H), 7.12 (d, 1H, J=2 Hz), 7.26–7.38 (m, 4H), 7.51 (s, 1H), 7.81 (s, 1H), 8.61 (s, 1H), 10.54 (s, 1H). M+1=523.

Example 212

1-(1,3-benzodioxol-5-yl)-8-[(5-chloro-2-morpholin-4-ylisonicotinoyl)amino]-4,5-dihydro-1H-benzo[g]indazole-3-carboxamide

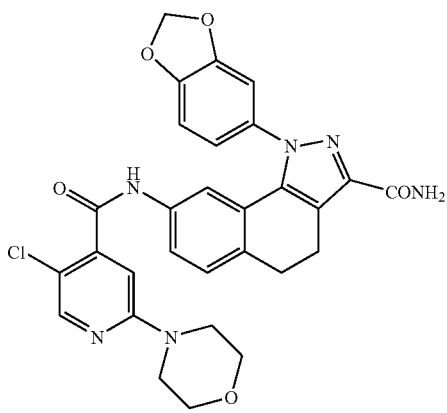

Step 1

5-chloro-2-morpholin-4-ylisonicotinic acid

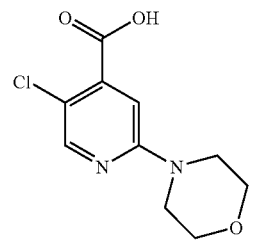

2,5-Dichloroisonicotinic acid, prepared by the method of E. Marzi, A. Bigi, M. Schlosser, *Eur. J. Org. Chem.* 2001, 1371–1376, (1.6 g, 0.0083 mol) and morpholine (10.9 g, 0.125 mol) in 4 mL of N,N-dimethylacetamide were heated at 80° C. for 4 days. The volatiles were removed under vacuum and the resulting yellow solid partitioned between water and Et$_2$O. The aqueous layer was acidified to pH=1.5 using an aqueous solution of HCl and extracted once with Et$_2$O (25 mL) and three times with CH$_2$Cl$_2$ (25 mL). The organic extracts were combined and the solvents removed under vacuum. The resulting yellow solid was crystallized from MeOH to afford the title compound 1.07 g (yield: 34%). $^1$H NMR (300 MHz, d$_6$-DMSO): δ 3.45 (t, 4H, J=4.8 Hz), 3.67 (t, 4H, J=4.8 Hz), 7.06 (s, 1H), 8.21 (s, 1H), 13.79 (s (broad), 1H). $^{13}$C HMR (100 MHz, d$_6$-DMSO): δ 45.6, 66.4, 107.3, 116.1, 141.3, 148.3, 158.5, 166.8. M+1=243.

Step 2

1-(1,3-benzodioxol-5-yl)-8-[(5-chloro-2-morpholin-4-ylisonicotinoyl)amino]-4,5-dihydro-1H-benzo[g]indazole-3-carboxamide

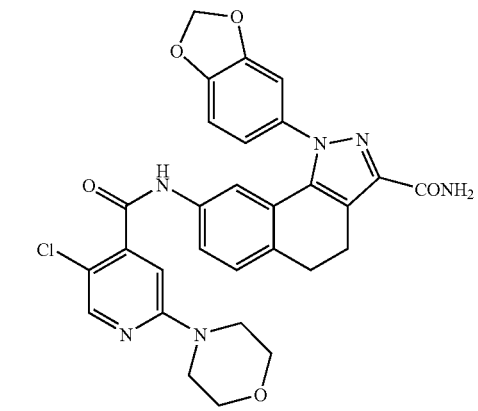

The title compound was synthesized by the same procedure as in Example 211 starting with the title material from step 1 (0.35 g, 0.00144 mol), the title compound of step 4 of Example 161 (0.333 g, 0.00096 mol), HATU (0.54 g, 0.00142 mol) and Et$_3$N (0.39 mL, 0.00279 mol) in DMF (8 mL) to yield 0.487 g of the title compound (yield: 88%). Mp: 269–271° C. $^1$H NMR (300 MHz, d$_6$-DMSO): δ 2.88–2.93 (m, 4H), 3.46 (t, 4H, J=4.6 Hz), 3.66 (t, 4H, J=4.6 Hz), 6.09 (s, 2H), 6.94 (s, 1H), 6.97 (d, 1H, J=2 Hz), 7.02 (d, 1H, J=8.2 Hz), 7.11 (d, 1H, J=1.9 Hz), 7.25 (s, 1H), 7.29–7.32 (m, 2H), 7.39–7.42 (dd, 1H, J=8.2 Hz, 2 Hz), 7.5 (s, 1H), 8.19 (s, 1H), 10.36 (s, 1H). M+1=574.

Example 213

1-(1,3-benzodioxol-5-yl)-8-({[5-chloro-2-(methylthio)pyrimidin-4-yl]carbonyl}amino)-4,5-dihydro-1H-benzo[g]indazole-3-carboxamide

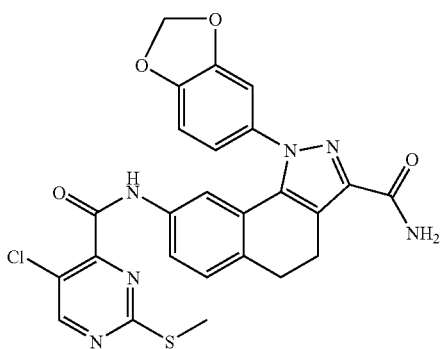

The title compound was synthesized by the same procedure as in Example 211 starting with 5-chloro-2-(methylthio)pyrimidine-4 carboxylic acid (1.76 g, 0.00861 mol), the title compound of step 4 of Example 161 (2 g, 0.00574 mol), HATU (3.27 g, 0.00857 mol), and Et$_3$N (2.32 mL, 0.0166 mol) in DMF (29 mL) to yield 1.3 g of the title compound (yield: 42%). $^1$H NMR (300 MHz, d$_6$-DMSO): δ 2.52 (s, 3H), 2.88–2.93 (m, 4H), 6.08 (s, 2H), 6.94–6.97 (dd, 1H, J=8.2 Hz, 1.9 Hz), 7.01 (d, 1H, J=8.2 Hz), 7.11 (d, 1H, J=1.9 Hz), 7.25–7.33 (m, 3H), 7.38–7.41 (dd, 1H, J=8.2 Hz, 1.9 Hz), 7.5 (s, 1H), 8.88 (s, 1H), 10.59 (s, 1H). M+1=536.

Example 214

1-(1,3-benzodioxol-5-yl)-8-{[5-chloro-2-(4-methylpiperazin-1-yl)isonicotinoyl]amino}-4,5-dihydro-1H-benzo[g]indazole-3-carboxamide

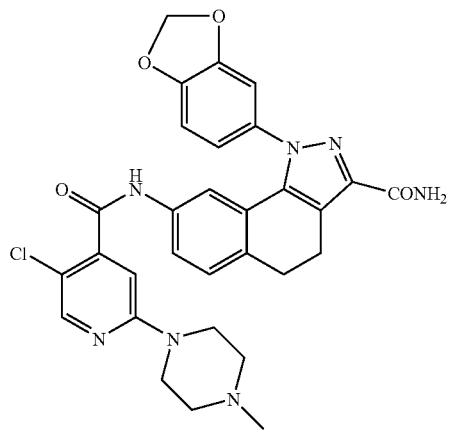

A mixture of the title compound of Example 211 (1.2 g, 0.0023 mol) and N-methylpiperazine (4.6 mL, 0.046 mol) was heated at 100° C. in a sealed tube for 24 h. The completion of the reaction was checked by HPLC. After removal of the volatiles under vacuum, the residue was partitioned between water and CH$_2$Cl$_2$. The organic layer was washed an additional time with water and dried over MgSO$_4$. The crude product mixture was purified by chromatography on silica gel using CH$_2$Cl$_2$/MeOH: 12/1 to 10/2 to give 0.62 g of the title product, yield: 46%. Mp: 305–307° C. $^1$H NMR (400 MHz, d$_6$-DMSO): δ 2.18 (s, 3H), 2.34–2.35 (d, 2H, J=5 Hz), 2.89–2.91 (m, 4H), 3.49 (d, 2H, J=5 Hz), 6.08 (s, 2H), 6.91–7.03 (m, 3H), 7.1 (d, 1H, J=2 Hz), 7.24–7.3 (m, 3H), 7.38–7.41 (dd, 1H, J=8.3 Hz, 2 Hz), 7.49 (s, 1H), 8.13 (s, 1H), 10.33 (s, 1H). M+1=587.

Example 215

1-(1,3-benzodioxol-5-yl)-8-[(5-chloro-2-piperazin-1-ylisonicotinoyl)amino]-4,5-dihydro-1H-benzo[g]indazole-3-carboxamide

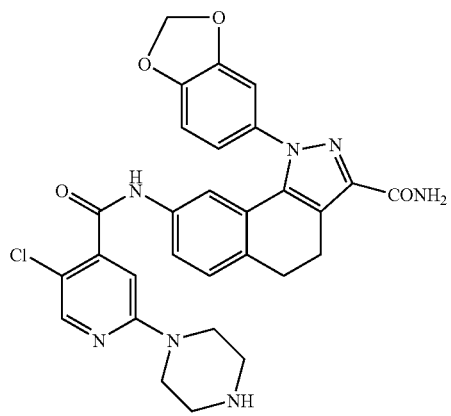

SCHEME XXIII

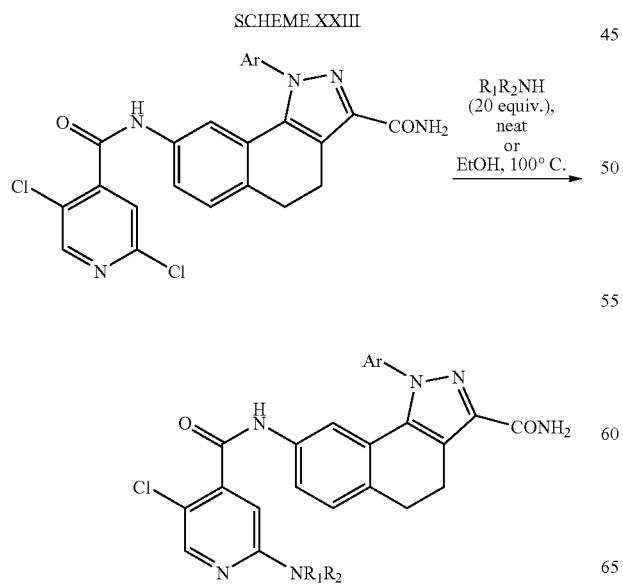

The title compound was synthesized by the same procedure as in Example 214 starting with the title compound of Example 211 (1 g, 0.0018 mol) and piperazine (3 g, 0.036 mol) in EtOH (4 mL). The reaction was run at 95° C. for 24 h. After allowing the reaction mixture to cool down, the volatiles were removed under vacuum. The residue was triturated with H$_2$O and finally with EtOH to yield 0.572 g of the title compound (yield: 55%). $^1$H NMR (300 MHz, d$_6$-DMSO): δ 2.71 (s, broad, 4H), 2.86–3.30 (m, 4H), 3.39 (s, broad, 4H), 6.07 (s, 2H), 6.85 (s, 1H), 6.93–6.95 (dd, 1H, J=8.2 Hz, 1.9 Hz), 7.00 (d, 1H, J=8.2 Hz), 7.09 (d, 1H, J=1.9 Hz), 7.24–7.30 (m, 3H), 7.38–7.41 (dd, 1H, J=8.2 Hz, 1.74 Hz), 7.49 (s, 1H), 8.12 (s, 1H), 10.32 (s, 1H). M+1=573.

Example 216

1-(1,3-benzodioxol-5-yl)-8-{[(3,6-dichloropyridin-2-yl)carbonyl]amino}-4,5-dihydro-1H-benzo[g]indazole-3-carboxamide

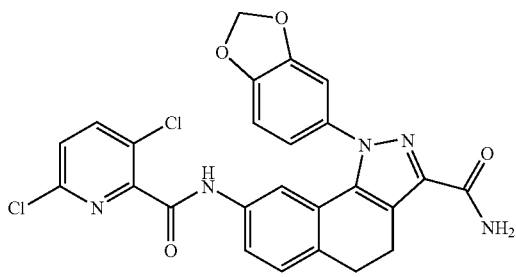

The title compound was synthesized from 1.653 g of 3,6-dichloro-2-pyridine carboxylic acid (CP92740, prepared by the method of E. Marzi, A. Bigi, M. Schlosser, *Eur. J. Org. Chem.* 2001, 1371–1376) and the title compound of step 4 of Example 161 (2.0 g) by the same procedure used for Example 211. The title compound is a brown solid (2.4 g, 80%), m.p. 263–265° C. Its structure was confirmed by $^1$H NMR and LC/MS: $^1$H NMR (d$_6$-DMSO): δ 2.82–3.01 (m, 4H)), 6.11 (s, 2H), 6.97–7.07 (m, 2H), 7.38 d, 1H, J=1 Hz), 7.81 (s, 1H), 7.33–7.42 (m, 3H), 7.52 (s, 1H), 7.51 (d, 1H, J=9 Hz), 8.15 (d, 1H, J=9 Hz), 10.57 (s, 1H). ESI mass spectrum for C$_{25}$H$_{18}$Cl$_2$N$_5$O$_4^+$: 522 (M+1).

Example 217

1-(1,3-benzodioxol-5-yl)-8-({[3-chloro-6-(4-methylpiperazin-1-yl)pyridin-2-yl]carbonyl}amino)-4,5-dihydro-1H-benzo[g]indazole-3-carboxamide

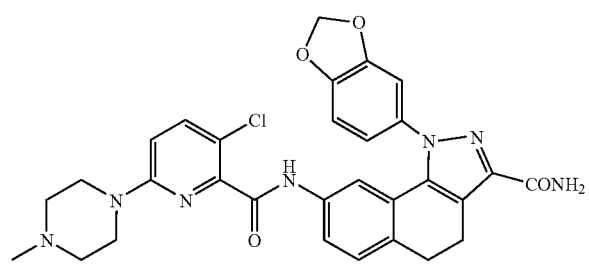

Step 1

Potassium 3-chloro-6-(4-methylpiperazin-1-yl)pyridine-2-carboxylate

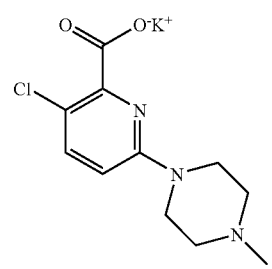

Potassium 3-chloro-6-(4-methylpiperazin-1-yl)pyridine-2-carboxylate was synthesized by the reaction used in Example 250 step 1 starting with 3,6-dichloro-2-pyridine carboxylic acid (0.60 g, 3.125 mmol) N-methylpiperazine (7.2 g, 72 mmol). The reaction was carried out at 95° C. for 3 days. The volatiles were removed under vacuum. The resulting residue was washed with a saturated solution of K$_2$CO$_3$ and with CH$_2$Cl$_2$. Three layers were formed. The middle was separated, dried, and the solvent was removed under reduced pressure giving 0.89 g of Potassium 3-chloro-6-(4-methylpiperazin-1-yl)pyridine-2-carboxylate (96%). Its structure was confirmed by $^1$H NMR and LC/MS: $^1$H NMR (D$_2$O): δ 2.18 (s, 3H), 2.43 (s, broad, 4H), 3.37 (s, broad, 4H), 6.77 (d, 1H, J=9 Hz), 7.58 (d, 1H, J=9 Hz). ESI mass spectrum for C$_{11}$H$_{15}$ClN$_3$O$_2^+$: 256 (M+1) in the presence of TFA.

Step 2

1-(1,3-benzodioxol-5-yl)-8-({[3-chloro-6-(4-methylpiperazin-1-yl)pyridin-2-yl]carbonyl}amino)-4,5-dihydro-1H-benzo[g]indazole-3-carboxamide

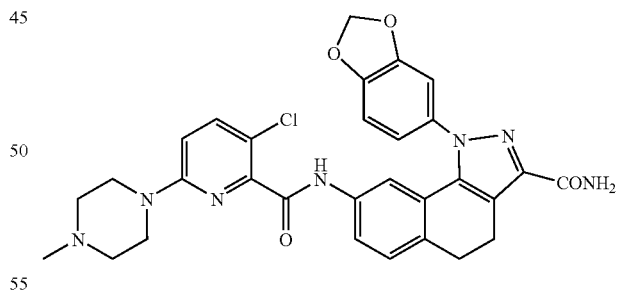

The title compound was synthesized from 0.30 g of 3-chloro-6-(4-methylpiperazin-1-yl)-2-pyridine carboxylic acid, obtained by acidification of its K-salt from step 1, and the title compound of step 4 of Example 161 (0.217 g) by the same procedure used for Example 260. The title compound is a brown solid (0.23 g, 61%), m.p. 264–266° C. (decomposition). Its structure was confirmed by $^1$H NMR and LC/MS: $^1$H NMR (d$_6$-DMSO): δ 2.70 (s, 3H), 2.72–4.30 (m, 12H), 6.02 (s, 2H), 6.92–7.12 (m, 4H), 7.22–7.36 (m, 3H), 7.42–7.53 (m, 2H), 7.77 (d, 1H, J=9 Hz), 10.32 (s, 1H). ESI mass spectrum for C$_{30}$H$_{29}$ClN$_7$O$_4^+$: 586 (M+1).

Example 218

1-(1,3-benzodioxol-5-yl)-8-{[(3-chloro-6-{[2-(dimethylamino)ethyl]thio}pyridin-2-yl)carbonyl]amino}-4,5-dihydro-1H-benzo[g]indazole-3-carboxamide

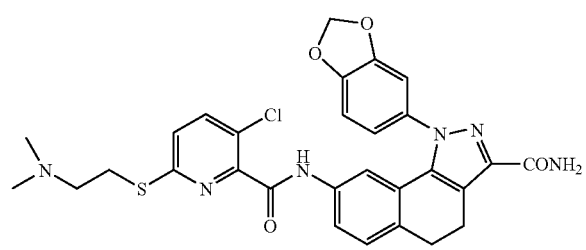

The title compound was synthesized from 0.36 g of the title compound of step 1 of Example 262, and the title compound of step 4 of Example 161 (0.35 g) by the same procedure used for Example 260. The title compound is a white solid (0.51 g, 86%). Its structure was confirmed by $^1$H NMR and LC/MS: $^1$H NMR (d$_6$-DMSO): δ 2.18 (s, 6H), 2.55 (m, 2H), 2.85 (m, 4H), 3.24 (m, 2H), 6.10 (s, 2H), 6.90–7.08 (m, 2H), 7.14 (s, 1H), 7.22–7.35 (m, 2H), 7.36–7.47 (m, 3H), 7.52 (s, 1H), 7.84 (d, 1H, J=9 Hz), 10.40 (s, 1H). ESI mass spectrum for $C_{29}H_{28}ClN_6O_4S^+$: 591 (M+1).

Example 219

1-(1,3-benzodioxol-5-yl)-8-{[(3-chloro-6-morpholin-4-ylpyridin-2-yl)carbonyl]amino}-4,5-dihydro-1H-benzo[g]indazole-3-carboxamide

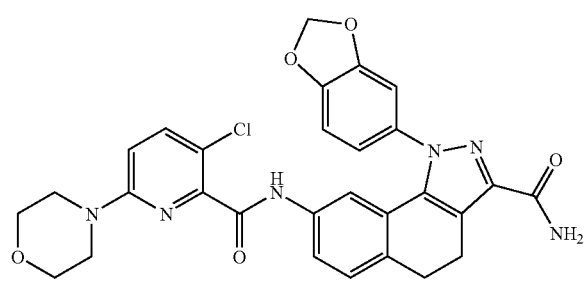

The title compound was synthesized from 0.27 g of morpholine and the title compound of Example 216 (0.522 g) by the same procedure used for Example 207 except that EtOH was replaced by 0.5 ml of DMA. The reaction was carried out at 80° C. for 36 hours. The title compound, isolated by preparative HPLC, is a white solid (0.30 g, 52%), m.p. 260–262° C. (decomposition). Its structure was confirmed by $^1$H NMR and LC/MS: $^1$H NMR (CDCl$_3$) δ 2.96 (m, 2H), 3.15 (m, 2H)), 3.48 (m, 4H), 3.86 (m, 4H), 5.41 (s, 1H), 6.74–6.86 (m, 2H), 6.90–7.04 (m, 2H), 7.16 (d, 1H, J=1 Hz), 7.28–7.35 (m, 2H), 7.54–7.22 (m, 2H), 9.32 (s, 1H). ESI mass spectrum for $C_{29}H_{26}ClN_6O_5^+$: 573 (M+1).

Example 220

1-(1,3-benzodioxol-5-yl)-8-({[3-chloro-6-(methylamino)pyridin-2-yl]carbonyl}amino)-4,5-dihydro-1H-benzo[g]indazole-3-carboxamide

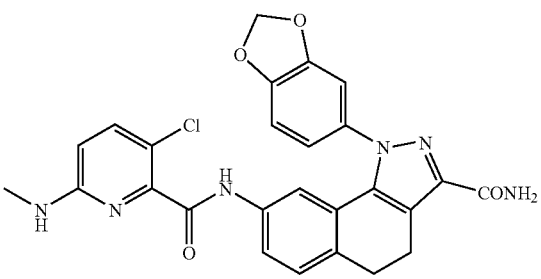

The title compound was synthesized from N-methylamine (6 mL of 33 w % solution in EtOH) and the compound of Example 216 (1.04 g) by the same procedure used for Example 207 except that 1 mL of DMA was added. The reaction was carried out at 82° C. for 5 days. The title compound, isolated by preparative HPLC, is a white solid (0.29 g, 52%), M.p. 269–270° C. (decomposition). Its structure was confirmed by $^1$H NMR and LC/MS: $^1$H NMR (d$_6$-DMSO): δ 2.76 (d, 3H, J=5.5 Hz), 2.84–3.99 (m, 4H), 6.16 (s, 2H), 6.57 (d, 1H, J=9 Hz), 6.91–7.04 (m, 3H), 7.12 (d, 1H, J=1 Hz), 7.22–7.34 (m, 3H), 7.46–7.54 (m, 3H), 10.19 (s, 1H). ESI mass spectrum for $C_{26}H_{22}ClN_6O_4^+$: 517 (M+1).

Example 221

SCHEME XXIV

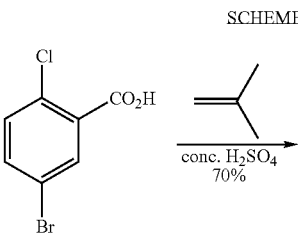

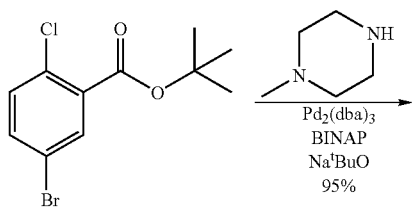

-continued

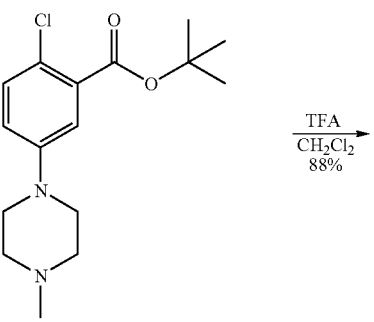

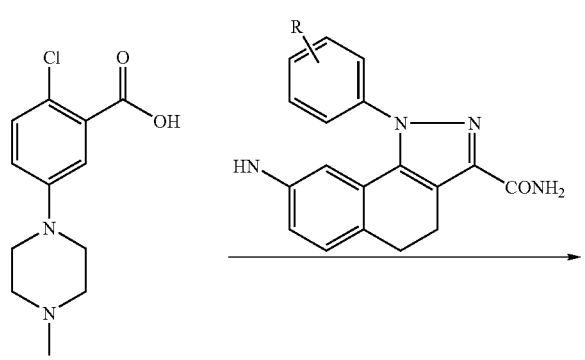

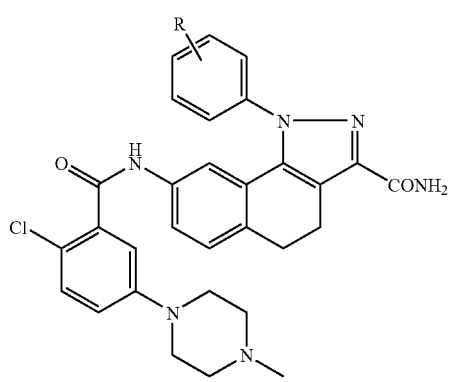

R = 4-F, 4-SO₂Me, 3, 4-MDO, etc.

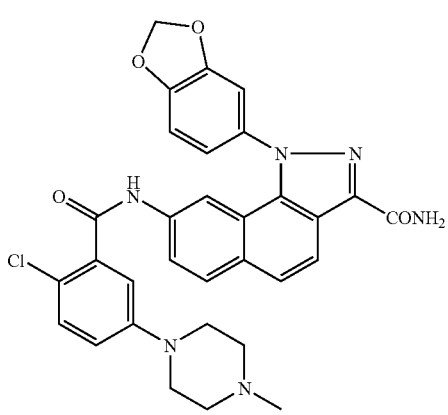

Step 1: A solution of 2-chloro-5-bromobenzoic acid (23.6 g, 0.1 mol), conc. sulfuric acid (5 mL) and condensed isobutene (400 mL) was prepared in a pressure vessel and stirred at room temperature under 12 psi for 2 days. The vessel was opened and the excess isobutene was released. The remaining liquid was treated with sat. NaHCO₃ solution and extracted with methylene chloride. The organic layer was washed with brine, dried over MgSO₄, and filtered. The filtrate was concentrated in vacuum to give 20.5 g of the crude product as brown oil, which was used without further purification (70%).

Step 2: A mixture of tert-butyl 2-chloro-5-bromobenzoate (2.95 g, 0.01 mol), N-methylpiperazine (1.5 g, 0.015 mol), Na'BuO (1.5 g, 0.015 mol), Pd₂(dba)₃ (0.18 g, 0.0002 mol) and BINAP (0.2 g, 0.0003 mol) in toluene was heated at 100° C. under nitrogen for 16 h. The solution was cooled to room temperature and filtered through a pad of Celite®. The filtrate was concentrated and the residue was partitioned between methylene chloride and water. The organic layer was washed with brine, dried over MgSO₄, and filtered. The filtrate was concentrated in vacuum to give 3.0 g of the crude product as a dark brown oil (97%). The NMR and MS were consistent with the proposed structure.

Step 3: To a solution of tert-butyl 2-chloro-5-(4-methylpiperazin-1-yl)benzoate (7.3 g, 0.023 mol) in methylene chloride (150 mL) was added trifluoroacetic acid (62 mL, 0.8 mol) dropwise at 0–5° C. The reaction mixture was stirred overnight while allowing to warm up to room temperature. Solvent and excess TFA was removed and the residue was triturated with ether to give 7.5 g of acid as a light brown solid; $^1$H NMR (DMSO, 400 MHz) δ: 10.11 (s, 1H), 7.39 (d, J=8.9 Hz, 1H), 7.33 (d, J=3.1 Hz, 1H), 7.16 (dd, J=3.1, 8.9 Hz, 1H), 3.90 (d, J=12.2 Hz, 2H), 3.52 (d, J=11.1 Hz, 2H), 3.15 (m, 2H), 2.98 (m, 2H), 2.87 (s, 3H); Anal. Calcd. for $C_{12}H_{15}ClN_2O_2$+1.0 TFA: C, 45.60; H, 4.37; N, 7.60. Found: C, 45.99; H, 4.62; N, 7.21.

Step 4: To a mixture of 2-chloro-5-(4-methylpiperazin-1-yl)benzoic acid (0.9 g, 0.0035 mol), the title compound of step 4 of Example 161 (0.82 g, 0.0024 mol) and 1 mL of diisopropylethylamine in 25 mL of DMF was added HATU (1.3 g, 0.0035 mol) in one portion. The reaction mixture was stirred at room temperature for 16 h. Solvent was removed and the residue was purified on preparative HPLC to give 1.25 g of the product as a pale white solid (89% yield); mp: 185–187° C.; $^1$HNMR (DMSO+TFA-d, 400 MHz) δ: 10.26 (s, 1H), 9.81 (brs, 1H), 7.52 (brs, 1H), 7.44 (dd, J=2.0, 8.1 Hz, 1H), 7.37 (d, J=8.6 Hz, 1H), 7.33 (d, J=2.1 Hz, 1H), 7.31 (d, J=8.4 Hz, 1H), 7.30 (s, 1H), 7.12 (d, J=2.0 Hz, 1H), 7.09 (m, 2H), 7.03 (d, J=8.2 Hz, 1H), 6.98 (dd, J=2.1, 8.2 Hz, 1H), 6.11 (s, 2H), 3.90 (m, 2H), 3.50 (m, 2H), 3.14 (m, 2H), 2.96 (m, 6H), 2.86 (s, 3H).

The bioactivity in the IKK2 Resin assay for the compounds of Examples 207–221 is shown in Table 5.

TABLE 5

| Structure | Mol. Wt. | Compound Name(s) | IKK2 Resin Avg. IC50 (μM) | Example |
|---|---|---|---|---|
| 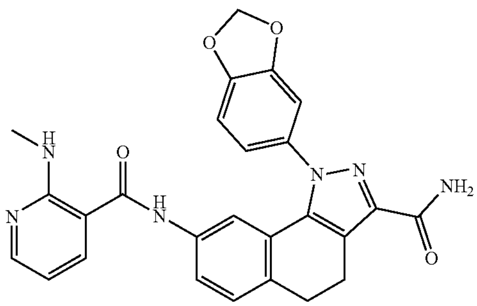 | 482.50 | 1-(1,3-benzodioxol-5-yl)-8-({[2-(methylamino)pyridin-3-yl]carbonyl}amino)-4,5-dihydro-1H-benzo[g]indazole-3-carboxamide | ≦1 μM | 207 |
| 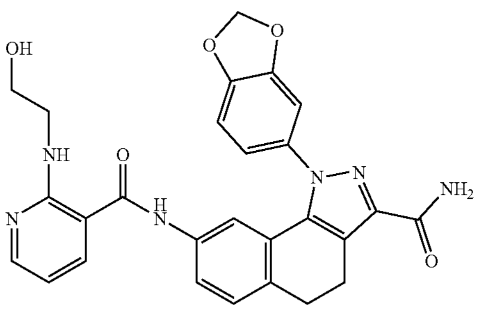 | 512.53 | 1-(1,3-benzodioxol-5-yl)-8-[({2-[(2-hydroxyethyl)amino]pyridin-3-yl}carbonyl)amino]-4,5-dihydro-1H-benzo[g]indazole-3-carboxamide | ≦1 μM | 208 |
| 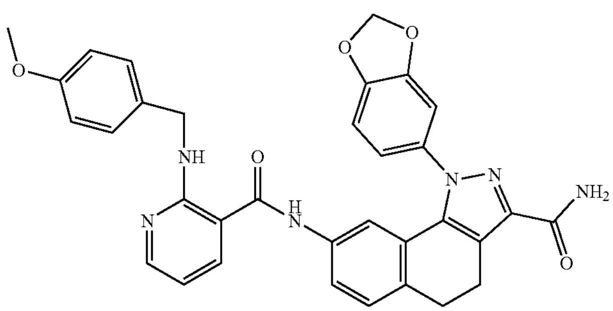 | 588.63 | 1-(1,3-benzodioxol-5-yl)-8-[({2-[(2-methoxybenzyl)amino]pyridin-3-yl}carbonyl)amino]-4,5-dihydro-1H-benzo[g]indazole-3-carboxamide | 10 ≦[100 μM | 209 |
| 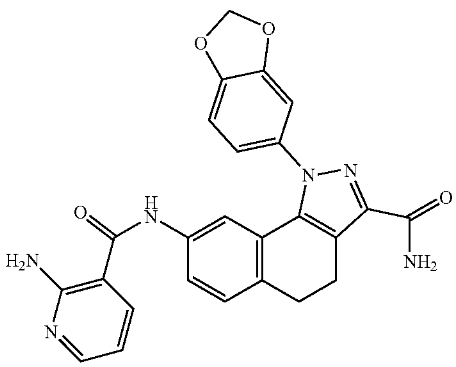 | 468.48 | 8-{[(2-aminopyridin-3-yl)carbonyl]amino}-1-(1,3-benzodioxol-5-yl)-4,5-dihydro-1H-benzo[g]indazole-3-carboxamide | 1 ≦ 10 μM | 210 |

TABLE 5-continued

| Structure | Mol. Wt. | Compound Name(s) | IKK2 Resin Avg. IC50 (μM) | Example |
|---|---|---|---|---|
| 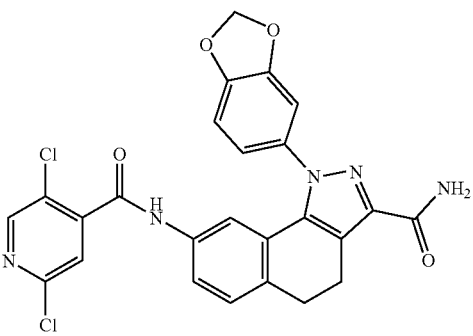 | 522.35 | 1-(1,3-benzodioxol-5-yl)-8-[(2,5-dichloroisonicotinoyl)amino]-4,5-dihydro-1H-benzo[g]indazole-3-carboxamide | ≦1 μM | 211 |
| 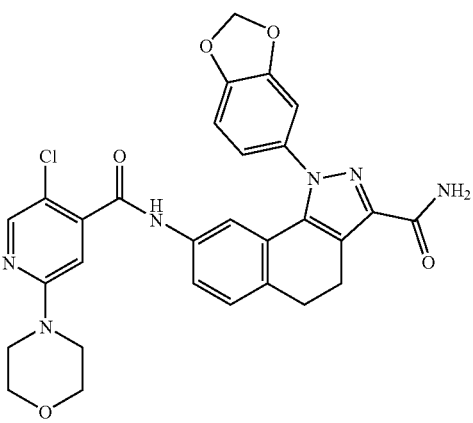 | 573.01 | 1-(1,3-benzodioxol-5-yl)-8-[(5-chloro-2-morpholin-4-ylisonicotinoyl)amino]-4,5-dihydro-1H-benzo[g]indazole-3-carboxamide | ≦1 μM | 212 |
| 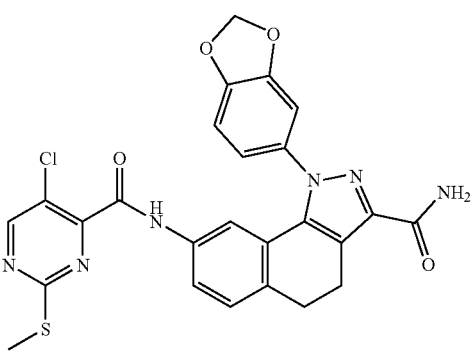 | 534.99 | 1-(1,3-benzodioxol-5-yl)-8-({[5-chloro-2-(methylthio)pyrimidin-4-yl]carbonyl}amino)-4,5-dihydro-1H-benzo[g]indazole-3-carboxamide | ≦1 μM | 213 |

TABLE 5-continued

| Structure | Mol. Wt. | Compound Name(s) | IKK2 Resin Avg. IC50 (μM) | Example |
|---|---|---|---|---|
| | 586.06 | 1-(1,3-benzodioxol-5-yl)-8-{[5-chloro-2-(4-methylpiperazin-1-yl)isonicotinoyl)amino}-4,5-dihydro-1H-benzo[g]indazole-3-carboxamide | ≦1 μM | 214 |
| 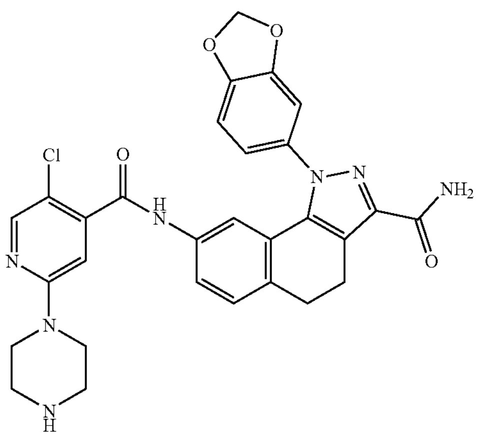 | 572.03 | 1-(1,3-benzodioxol-5-yl)-8-[(5-chloro-2-piperazin-1-ylisonicotinoyl)amino]-4,5-dihydro-1H-benzo[g]indazole-3-carboxamide | ≦1 μM | 215 |
| 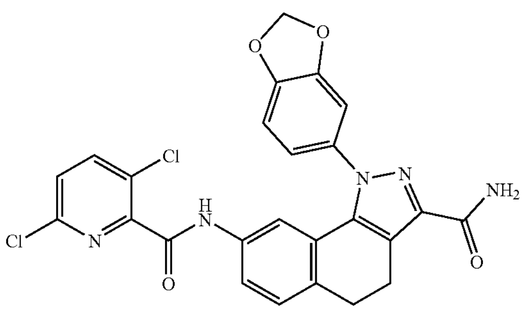 | 522.35 | 1-(1,3-benzodioxol-5-yl)-8-{[(3,6-dichloropyridin-2-yl)carbonyl]amino}-4,5-dihydro-1H-benzo[g]indazole-3-carboxamide | 1 ≦ 10 μM | 216 |
| | 586.06 | 1-(1,3-benzodioxol-5-yl)-8-({[3-chloro-6-(4-methylpiperazin-1-yl)pyridin-2-yl]carbonyl}amino)-4,5-dihydro-1H-benzo[g]indazole-3- | ≦1 μM | 217 |

TABLE 5-continued

| Structure | Mol. Wt. | Compound Name(s) | IKK2 Resin Avg. IC50 (μM) | Example |
|---|---|---|---|---|
| 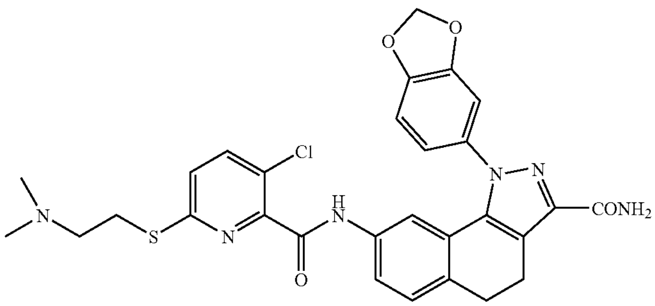 | 591.09 | 1-(1,3-benzodioxol-5-yl)-8-{[(3-chloro-6-{[2-(dimetbylamino)ethyl]thio}pyridin-2-yl)carbonyl]amino}-4,5-dihydro-1H-benzo[g]indazole-3-carboxamide | ≦1 μM | 218 |
| 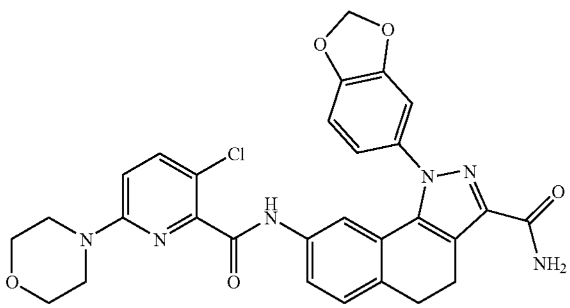 | 573.01 | 1-(1,3-benzodioxol-5-yl)-8-{[(3-chloro-6-morpholin-4-ylpyridin-2-yl)carbonyl]amino}-4,5-dihydro-1H-benzo[g]indazole-3-carboxamide | ≦1 μM | 219 |
| 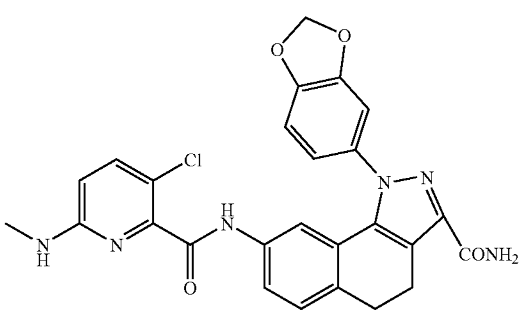 | 516.95 | 1-(1,3-benzodioxol-5-yl)-8-({[3-chloro-6-(methylamino)pyridin-2-yl]carbonyl}amino)-4,5-dihydro-1H-benzo[g]indazole-3-carboxamide | ≦1 μM | 220 |
| 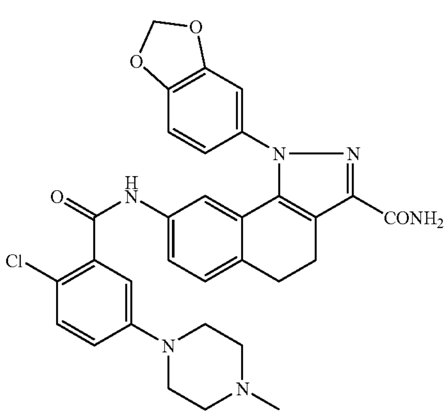 | 585.07 | 1-(1,3-benzodioxol-5-yl)-8-{[2-chloro-5-(4-methylpiperazin-1-yl)benzoyl]amino}-4,5-dihydro-1H-benzo[g]indazole-3-carboxamide | ≦1 [M | 221 |

Examples 222–243

Examples 222–243 shown in Table 6 were synthesized with the corresponding starting compounds using the following synthesis procedure similar to Scheme I where $R^9$ is the appropriate aryl, substituted aryl, heteroaryl, substituted heteroaryl, substituted arylalkyl, substituted heteroarylalkyl, or cycloalkyl.

SCHEME XXV

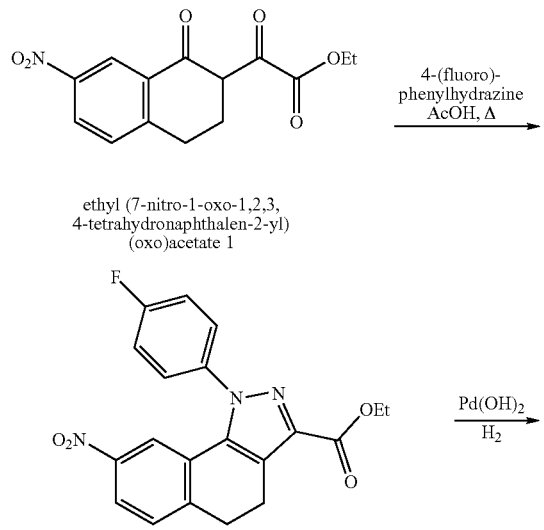

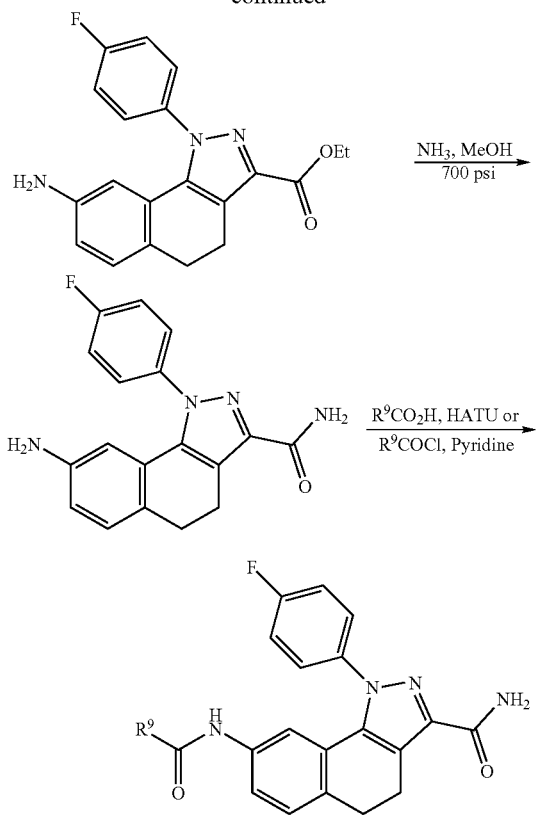

TABLE 6

| Structure | Mol. Wt. | Compound Name(s) | IKK2 Resin IC 50 ( | Example |
|---|---|---|---|---|
| 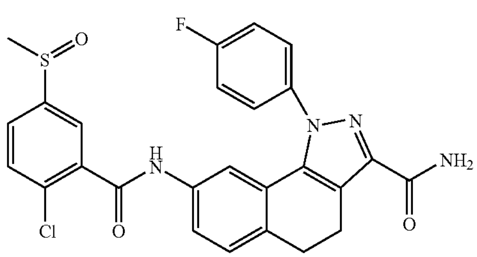 | 522.99 | 8-{[2-chloro-5-(methylsulfinyl)benzoyl]amino}-1-(4-fluorophenyl)-4,5-dihydro-1H-benzo[g]indazole-3-carboxamide | ≦1 μM | 222 |
| 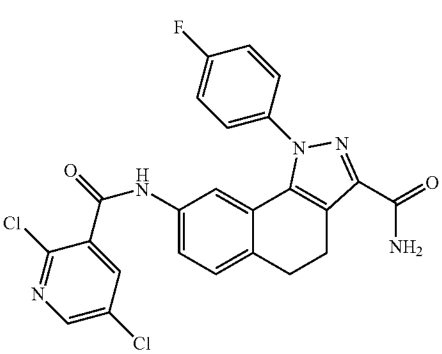 | 496.33 | 8-{[(2,5-dichloropyridin-3-yl)carbonyl]amino}-1-(4-fluorophenyl)-4,5-dihydro-1H-benzo[g]indazole-3-carboxamide | ≦1 μM | 223 |

TABLE 6-continued

| Structure | Mol. Wt. | Compound Name(s) | IKK2 Resin IC 50 ( | Example |
|---|---|---|---|---|
| 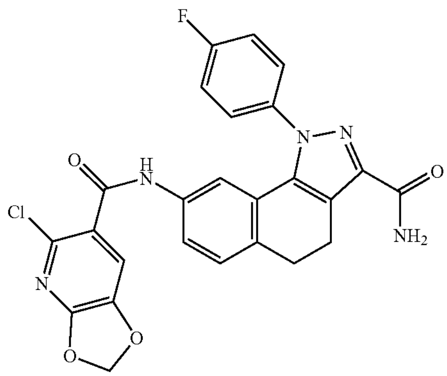 | 504.90 | 8-{[(6-chloro-1,3-benzodioxol-5-yl)carbonyl]amino}-1-(4-fluorophenyl)-4,5-dihydro-1H-benzo[g]indazole-3-carboxamide | ≦1 μM | 224 |
| 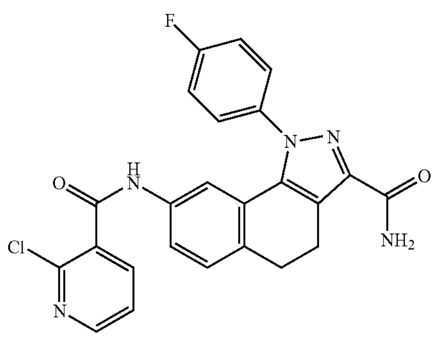 | 461.88 | 8-{[(2-chloropyridin-3-yl)carbonyl]amino}-1-(4-fluorophenyl)-4,5-dihydro-1H-benzo[g]indazole-3-carboxamide | ≦1 μM | 225 |
| 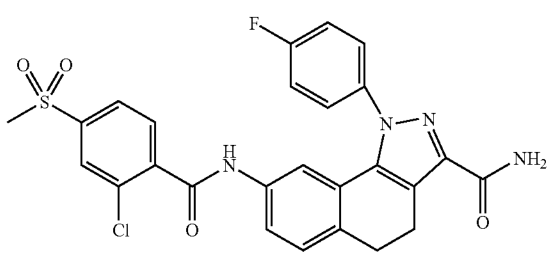 | 538.99 | 8-{[2-chloro-4-(methylsulfonyl)benzoyl]amino}-1-(4-fluorophenyl)-4,5-dihydro-1H-benzo[g]indazole-3-carboxamide | ≦1 μM | 226 |
| 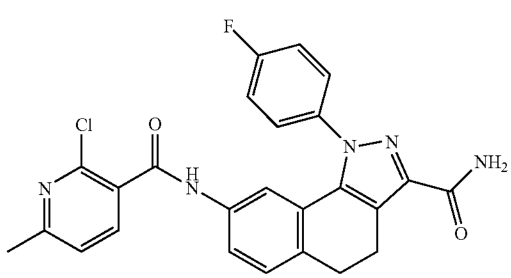 | 475.91 | 8-{[(2-chloro-6-methylpyridin-3-yl)carbonyl]amino}-1-(4-fluorophenyl)-4,5-dihydro-1H-benzo[g]indazole-3-carboxamide | ≦1 μM | 227 |

TABLE 6-continued

| Structure | Mol. Wt. | Compound Name(s) | IKK2 Resin IC 50 ( | Example |
|---|---|---|---|---|
| 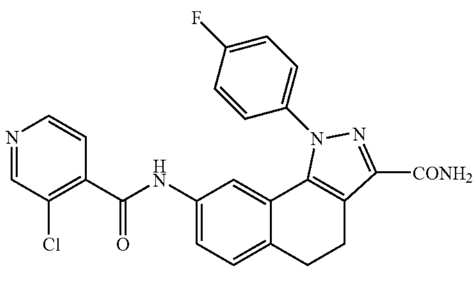 | 498.35 | 8-[(3-chloroisonicotinoyl)amino]-1-(4-fluorophenyl)-4,5-dihydro-1H-benzo[g]indazole-3-carboxamide hydrochloride | ≦1 μM | 228 |
| 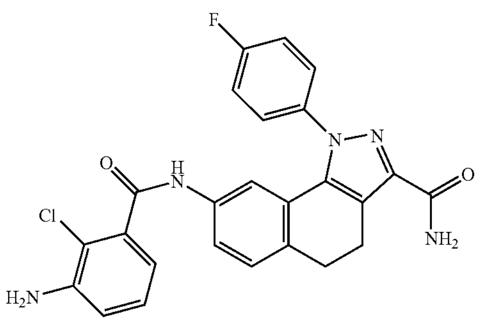 | 475.91 | 8-[(3-amino-2-chlorobenzoyl)amino]-1-(4-fluorophenyl)-4,5-dihydro-1H-benzo[g]indazole-3-carboxamide | ≦1 μM | 229 |
| 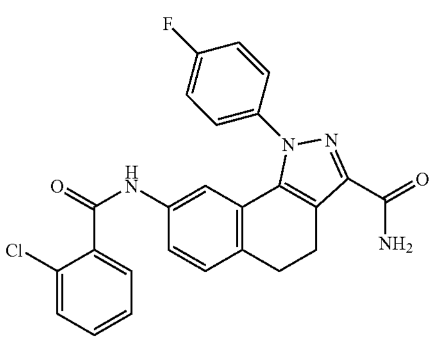 | 460.90 | 8-[(2-chlorobenzoyl)amino]-1-(4-fluorophenyl)-4,5-dihydro-1H-benzo[g]indazole-3-carboxamide | ≦1 μM | 230 |
| 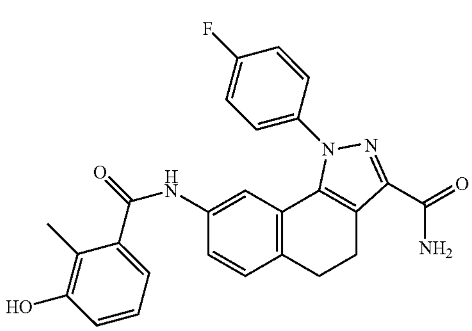 | 456.48 | 1-(4-fluorophenyl)-8-[(3-hydroxy-2-methylbenzoyl)amino]-4,5-dihydro-1H-benzo[g]indazole-3-carboxamide | ≦1 μM | 231 |

TABLE 6-continued

| Structure | Mol. Wt. | Compound Name(s) | IKK2 Resin IC 50 ( | Example |
|---|---|---|---|---|
| 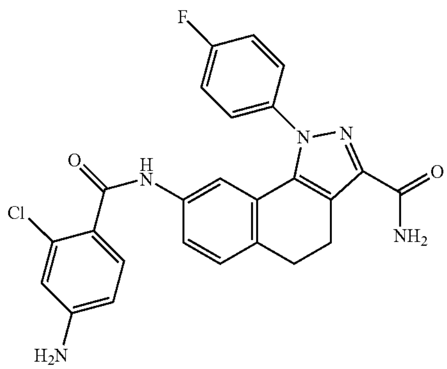 | 475.91 | 8-[(4-amino-2-chlorobenzoyl)amino]-1-(4-fluorophenyl)-4,5-dihydro-1H-benzo[g]indazole-3-carboxamide | ≦1 μM | 232 |
| 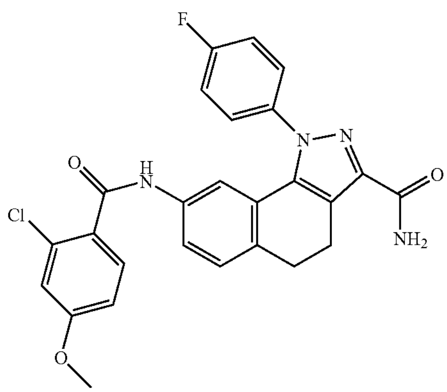 | 490.92 | 8-[(2-chloro-4-methoxybenzoyl)amino]-1-(4-fluorophenyl)-4,5-dihydro-1H-benzo[g]indazole-3-carboxamide | ≦1 μM | 233 |
| 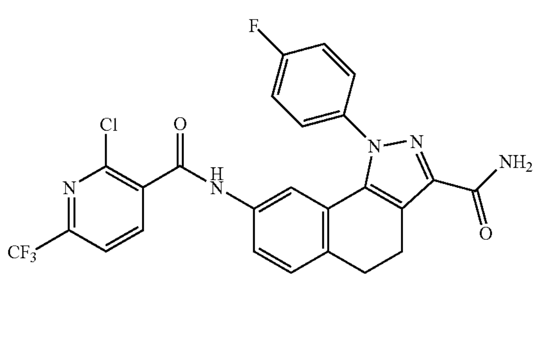 | 529.88 | 8-({[2-chloro-6-(trifluoromethyl)pyridin-3-yl]carbonyl}amino)-1-(4-fluorophenyl)-4,5-dihydro-1H-benzo[g]indazole-3-carboxamide | ≦1 μM | 234 |
| 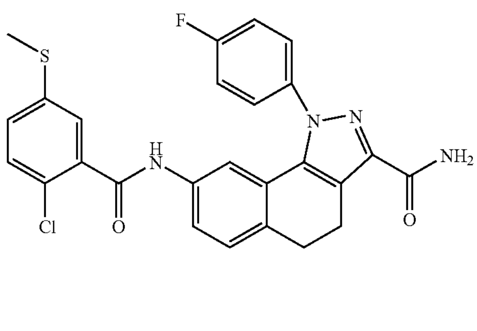 | 506.99 | 8-{[2-chloro-5-(methylthio)benzoyl]amino}-1-(4-fluorophenyl)-4,5-dihydro-1H-benzo[g]indazole-3-carboxamide | ≦1 μM | 235 |

TABLE 6-continued

| Structure | Mol. Wt. | Compound Name(s) | IKK2 Resin IC 50 ( | Example |
|---|---|---|---|---|
| 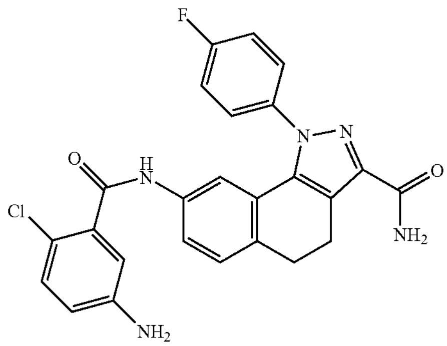 | 475.91 | 8-[(5-amino-2-chlorobenzoyl)amino]-1-(4-fluorophenyl)-4,5-dihydro-1H-benzo[g]indazole-3-carboxamide | ≦1 µM | 236 |
| 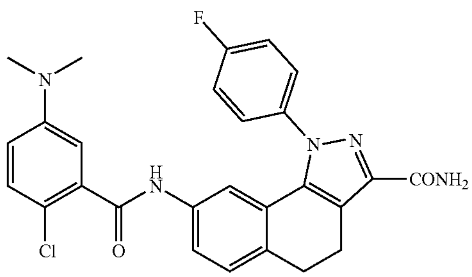 | 503.97 | 8-{[2-chloro-5-(dimethylamino)benzoyl]amino}-1-(4-fluorophenyl)-4,5-dihydro-1H-benzo[g]indazole-3-carboxamide | ≦1 µM | 237 |
| 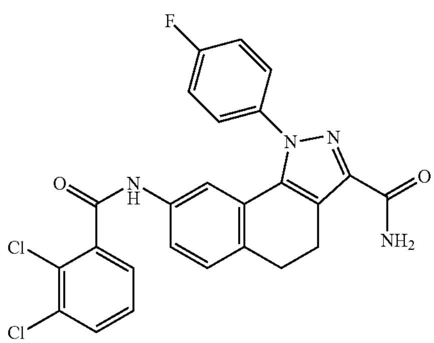 | 495.34 | 8-[(2,3-dichlorobenzoyl)amino]-1-(4-fluorophenyl)-4,5-dihydro-1H benzo[g]indazole-3-carboxamide | ≦1 µM | 238 |
| 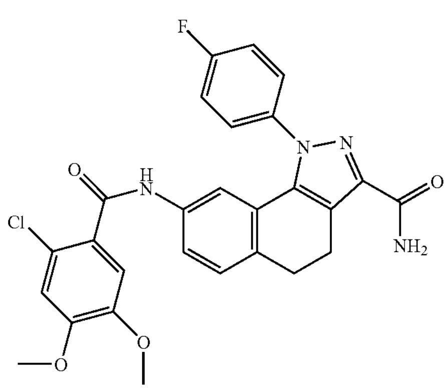 | 520.95 | 8-[(2-chloro-4,5-dimethoxybenzoyl)amino]-1-(4-fluorophenyl)-4,5-dihydro-1H-benzo[g]indazole-3-carboxamide | ≦1 µM | 239 |

TABLE 6-continued

| Structure | Mol. Wt. | Compound Name(s) | IKK2 Resin IC 50 ( | Example |
|---|---|---|---|---|
| 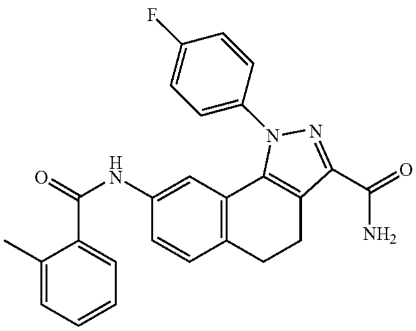 | 440.48 | 1-(4-fluorophenyl)-8-[(2-methylbenzoyl)amino]-4,5-benzo[g]indazole-3-dihydro-1H-carboxamide | ≦1 μM | 240 |
| 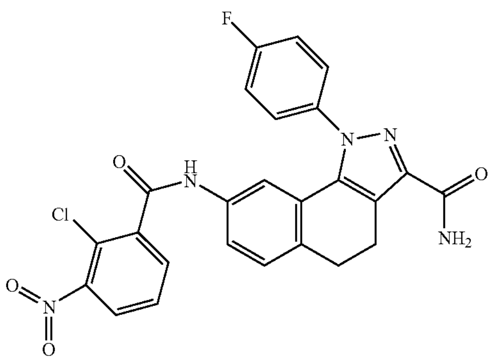 | 505.89 | 8-[(2-chloro-3-nitrobenzoyl)amino]-1-(4-fluorophenyl)-4,5-dihydro-1H-benzo[g]indazole-3-carboxamide | ≦1 μM | 241 |
| 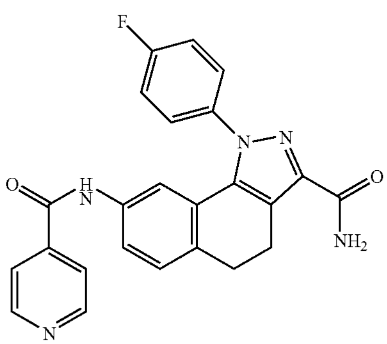 | 400.43 | 1-(4-fluorophenyl)-8-[(methylsulfonyl)amino]-4,5-dihydro-1H-benzo[g]indazole-3-carboxamide | 1 ≦ 10 μM | 242 |
| 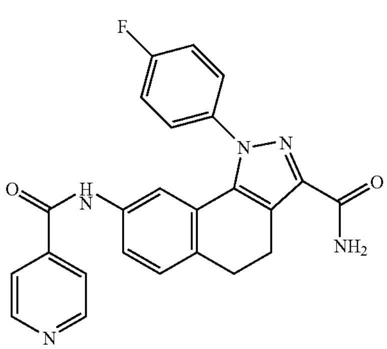 | 427.44 | 1-(4-fluorophenyl)-8-(isonicotinoylamino)-4,5-dihydro-1H-benzo[g]indazole-3-carboxamide | 1 ≦ 10 μM | 243 |

Example 244

8-amino-1-(4-fluorophenyl)-4,5-dihydro-1H-benzo[g]indazole-3-carboxamide

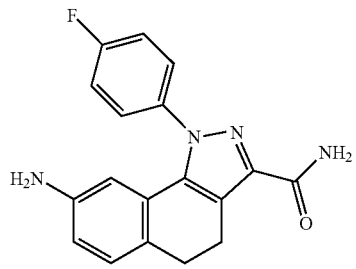

This material was prepared from 4-fluorophenyl hydrazine by the method described for Example 92.

Example 245

1-(4-fluorophenyl)-8-{[(2-piperazin-1-ylpyridin-3-yl)carbonyl]amino}-4,5-dihydro-1H-benzo[g]indazole-3-carboxamide

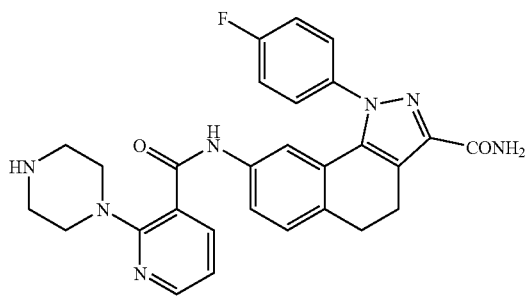

The title compound was synthesized by the same procedure as in Example 207 starting with the title compound of Example 225 (0.81 g, 0.017 mol) and piperazine (3 g, 0.0348 mol) in 4 mL Et OH to afford 0.523 g of title compound (yield: 58%). Mp: 156–157° C. $^1$H NMR (300 MHz, $d_6$-DMSO): δ 2.63 (t, 4H, J=4.5 Hz), 2.86–2.93 (m, 4H), 3.08 (t, 4H, J=4.5 Hz), 6.86–6.90 (dd, 1H, J=7.4 Hz, 4.8 Hz), 7.23 (s, 1H), 7.28 (s, 1H), 7.32 (d, 1H, J=8.3 Hz), 7.40 (t, 2H, J=8.7 Hz), 7.54–7.6 (m, 4H), 7.63–7.66 (dd, 1H, J=7.4 Hz, 1.7 Hz), 8.22–8.25 (dd, 1H, J=4.8 Hz, 1.9 Hz), 10.25 (s, 1H). M+1=512.

Example 246

8-{[(6-chloro-4-methylpyridin-3-yl)carbonyl]amino}-1-(4-fluorophenyl)-4,5-dihydro-1H-benzo[g]indazole-3-carboxamide

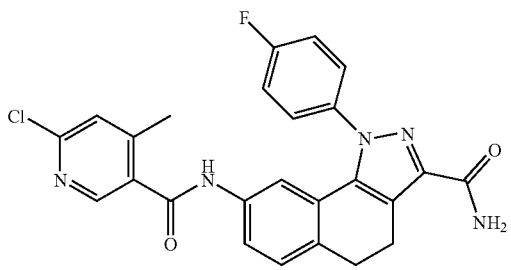

Step 1

6-Hydroxy-4-methyhnicotinic acid

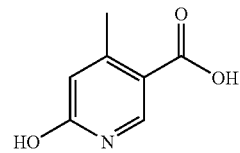

A modification of the procedure of Weglinski and Talik (*Rocz. Chem.* 1977, 51, 2401) was used. Potassium carbonate powder (–325 mesh) was dried under vacuum at 200° C. overnight prior to use. A layer of the dried potassium carbonate (28.56 g, 0.207 mol) was placed in the bottom of a 300-mL Hastelloy-B autoclave followed by a layer of 2-hydroxy-4-methylpyridine (28.51 g, 0.2612 mol) mixed with dried potassium carbonate (28.70 g, 0.208 mol). The vessel was sealed, carefully purged with dry carbon dioxide (5×80 psig), pressurized with dry carbon dioxide to 800 psig, and heated to 130° C. for 18 h. After cooling and careful venting, the product mixture was dissolved in water (560 mL) and added to 132 mL of 6 N HCl with vigorous stirring over about 20 min. The pH of the resulting slurry was 2.43 and potassium carbonate (ca. 0.25 g) was added to pH=2.53. After stirring the slurry for 1 h at 25° C., the precipitate was recovered by vacuum filtration, washed with water (3×35 mL), and dried in vacuo at 100° C. to afford 7.11 g of a tan powder. $^1$H NMR analysis of the tan powder was consistent with a mixture of about 5.6 mol % 2-hydroxy-4-methylpyridine and 94.4 mol % of the desired 2-hydroxy-4-methyl-5-pyridinecarboxylic acid. The yield was estimated to be 17.0% based on the NMR assay of the recovered product. $^1$H NMR (400 MHz, $d_6$-DMSO) δ 2.36 (d, J=1 Hz, 3H), 6.19 (apparent s, 1H), 7.99 (s, 1H), 12.2 (broad s, 2H). $^{13}$C NMR (100 MHz, $d_6$-DMSO) δ 21.6, 109.1, 119.5, 141.1, 151.8, 161.8, 165.8.

Step 2

4-Methyl-6-chloronicotinic acid

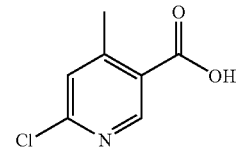

6-Hydroxy-4-methylnicotinic acid (10 g, 65.3 mmol) and phosphorus oxychloride (33 mL) were combined and refluxed for 3 hours. The reaction solution was poured into 300 mL of ice and then 600 mL of water was added. The solution was boiled for 30 minutes before cooling and extracting the product into ether. The solvent was removed and the residue was recrystallized from 900 mL of hot water. Yellow solid, 9.06 g (81% yield). Mp 170–172° C. $^1$H NMR (CD$_3$OD): δ 2.61 (s, 3H), 7.41 (s, 1H), 8.80 (s, 1H). LC-MS, M+1=172.

Step 3

8-{[(6-chloro-4-methylpyridin-3-yl)carbonyl]amino}-1-(4-fluorophenyl)-4,5-dihydro-1H-benzo[g]indazole-3-carboxamide

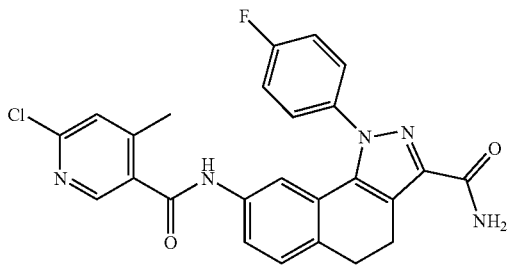

The compound of example 244 (3.872 mmoles), 4-methyl-6-chloronicotinic acid from step 2 (5.828 mmoles), and HATU (5.844 mmoles) were dissolved in 20 mL DMF followed by the addition of 1.9 mL triethylamine. The mixture was stirred at room temperature overnight. The solvent was then stripped and the residue suspended in water, filtered, and washed with water. The solid was recrystallized from acetonitrile, then redissolved in acetonitrile, decolorized with decolorizing carbon, and dried over anhydrous $MgSO_4$. The solvent was then stripped down to a solid. Mp: 280–284° C. $^1$H NMR ($d_6$-DMSO, 400 MHz): δ 2.28 (s, 3H); 2.84–2.98 (m, 4H); 7.25–7.44 (m, 6H); 7.49 (s, 1H); 7.51–7.62 (m, 3H); 8.35 (s, 1H); 10.31 (s, 1H). $^{13}$C NMR (DMSO, 100 MHz): δ 19.13, 20.35, 29.67, 115.01, 117.07, 117.30, 120.08, 121.34, 126.19, 126.60, 128.72, 128.81, 129.58, 132.80, 133.42, 136.81, 136.84, 137.64, 139.71, 143.19, 148.42, 149.96, 151.59, 161.44, 163.88, 164.47, 164.78. M+1=476.

Example 247

1-(4-fluorophenyl)-8-{[(4-methyl-6-morpholin-4-ylpyridin-3-yl)carbonyl]amino}-4,5-dihydro-1H-benzo[g]indazole-3-carboxamide

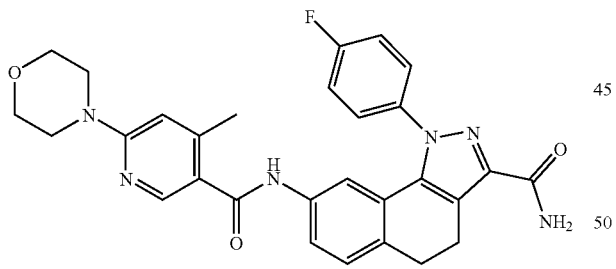

The title compound of Example 246 (1.47 mmoles) and morpholine (23.1 mmoles) were dissolved in 10 mL of N,N-dimethylacetamide. The reaction mixture was then placed under nitrogen and stirred in an oil bath at 100° C. for 27 h. The mixture was partially stripped of solvent then added to water, filtered, and washed with water. The solid was recrystallized from acetonitrile, then dissolved in acetonitrile and dried over anhydrous $MgSO_4$. The solvent was then stripped down to a solid. Mp: 301° C. (decomp.) $^1$H NMR ($d_6$-DMSO, 400 MHz): δ 2.22 (s, 3H); 2.80–2.94 (m, 4H); 3.46 (t, 4H, J=4.8 Hz); 3.62 (t, 4H, J=4.8 Hz); 6.67 (s, 1H); 7.22–7.27 (m, 3H); 7.31–7.38 (m, 2H); 7.42 (dd, 1H, J=1.9 Hz, 8.2 Hz); 7.49–7.57 (m, 3H); 8.11 (s, 1H); 9.92 (s, 1H). $^{13}$C NMR ($d_6$-DMSO, 100 MHz): δ 20.35, 20.38, 29.63, 45.55, 66.54, 108.46, 114.91, 117.02, 117.25, 119.91, 121.23, 122.78, 126.42, 128.64, 128.73, 129.36, 132.60, 136.82, 136.85, 138.38, 139.82, 143.15, 147.70, 148.03, 160.04, 161.39, 163.84, 164.47, 166.18. M+1=527

Example 248

8-[(2,5-dichloroisonicotinoyl)amino]-1-(4-fluorophenyl)-4,5-dihydro-1H-benzo[g]indazole-3-carboxamide

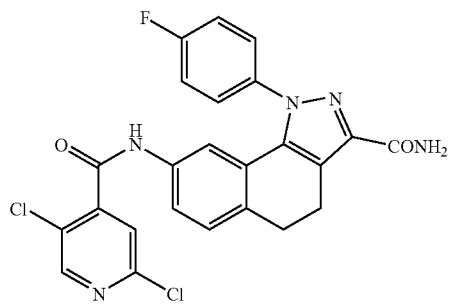

2,5-Dichloroisonicotinic acid (1.65 g, 0.0086 mol), HATU (3.27 g, 0.0086 mol), and $Et_3N$ (2.32 mL, 0.0166 mol) were added to a solution of the title compound of Example 244 (1.85 g, 0.00574 mol) in 29 mL of DMF. The reaction mixture was stirred at room temperature for 3 h. The completion of the reaction was confirmed by monitoring the disappearance of the title compound of Example 246 step 2 in LC/MS. The crude reaction mixture was concentrated to about 10 mL of DMF. Upon addition of water to this DMF residue, a white solid was formed. This white solid was triturated in water for 20 min and filtered. The solid was collected, dissolved in THF, and dried with $MgSO_4$. Removal of the solvent afforded a brown solid that was crystallized from $CH_3CN$ to give 2.1 g of the title compound as white needles (yield 73%). $^1$H NMR (300 MHz, $d_6$-DMSO): 2.86–2.91 (m, 4H), 7.18 (d, 1H, J=1.2 Hz), 7.25 (s, 1H), 7.32–7.36 (m, 4H), 7.52–7.56 (m, 3H), 7.75 (s, 1H), 8.57 (s, 1H), 10.49 (s, 1H). M+1=497.

Example 249

8-[(5-chloro-2-morpholin-4-ylisonicotinoyl)amino]-1-(4-fluorophenyl)-4,5-dihydro-1H-benzo[g]indazole-3-carboxamide

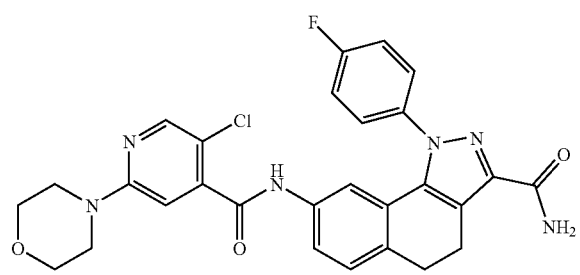

The title compound of Example 244 (0.757 mmoles), 5-chloro-2-morpholin-4-ylisonicotinic acid, (1.38 mmoles), and HATU (1.57 mmoles) were dissolved in 5 mL DMF followed by the addition of 0.4 mL of triethylamine. The mixture was stirred at room temperature for 3 hrs and partially stripped of DMF. The reaction mixture was then added to water, filtered, and washed with water. The solid was dissolved in THF, decolorized with decolorizing carbon, and dried over anhydrous MgSO$_4$. The THF was stripped and the solid triturated in diethyl ether three times, then triturated in ethanol, and twice more with acetonitrile, filtered and dried under vacuum. Mp: 309–313° C. $^1$H NMR (d$_6$-DMSO, 400 MHz): δ 2.80–2.95 (m, 4H); 3.42 (t, 4H, J=5 Hz); 3.62 (t, 4H, J=5 Hz); 6.88 (s, 1H); 7.17–7.21 (m, 1H); 7.23–7.41 (m, 5H); 7.49–7.58 (m, 3H); 8.14 (s, 1H); 10.31 (s, 1H). $^{13}$C NMR (d$_6$-DMSO, 100 MHz): δ 20.34, 29.70, 45.74, 66.50, 106.55, 114.97, 115.87, 117.09, 117.32, 120.05, 121.41, 126.67, 128.64, 128.73, 129.62, 133.47, 136.80, 136.82, 137.48, 139.64, 143.21, 145.28, 147.54, 158.30, 161.39, 163.85, 164.45. M+1=547.

Example 250

8-{[5-chloro-2-(4-methylpiperazin-1-yl)isonicotinoyl]amino}-1-(4-fluorophenyl)-4,5dihydro-1H-benzo[g]indazole-3-carboxamide

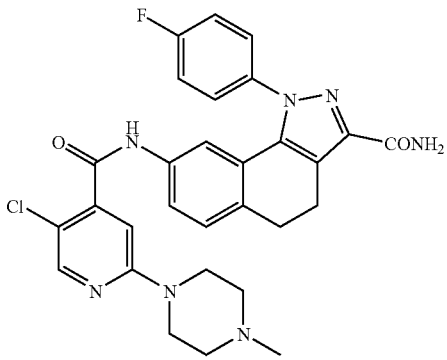

Step 1

5-chloro-2-(4-methylpiperazin-1-yl)isonicotinic acid hydrochloride

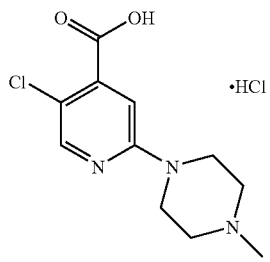

5-chloro-2-(4-methylpiperazin-1-yl)isonicotinic acid hydrochloride was synthesized by the same procedure as for example 212 step 1 starting with 2,5-dichloroisonicotinic acid (3 g, 0.0156 mol) N-methylpiperazine (30.7 g, 0.30 mol) in 10 mL of N,N-dimethylacetamide. The reaction was carried out at 100° C. for 8 days. The volatiles were removed under vacuum. The resulting residue was washed with a saturated solution of K$_2$CO$_3$ and with CH$_2$Cl$_2$. The solvents were removed under vacuum and the resulting residue dissolved in the minimum amount of water, acidified to pH=1 with an aqueous solution of HCl (1N) and washed with CH$_2$Cl$_2$. Upon standing at room temperature, the acidic aqueous layer afforded 2 g (yield: 44%) of title compound. $^1$H NMR (300 MHz, D$_2$O): δ 2.85 (s, 3H), 3.13 (t, 2H, J=12.28 Hz), 3.34 (t, 2H, J=14.3 Hz), 3.56 (d, 2H, J=12.28 Hz), 4.18 (d, 2H, J=14.3 Hz), 7.08 (s, 1H), 8.00 (s, 1H). $^{13}$C NMR (75 MHz, D$_2$O): δ 43.1, 43.4, 52.54, 109.5, 117.6, 142.3, 147.9, 154.4, 169.5.

Step 2

8-{[5-chloro-2-(4-methylpiperazin-1-yl)isonicotinoyl]amino}-1-(4-fluorophenyl)-4,5dihydro-1H-benzo[g]indazole-3-carboxamide

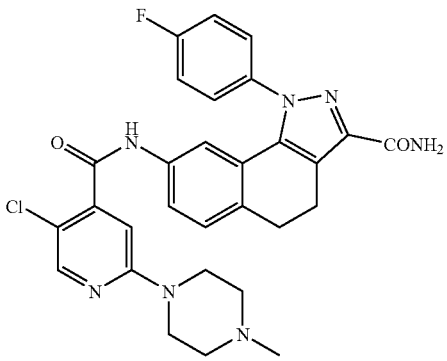

The title compound was synthesized by the same procedure as in Example 211 starting with 5-chloro-2-(N-methylpiperazinyl)isonicotinic acid hydrochloride from step 1)) (0.59 g, 0.00202 mol), the title compound of Example 244 (0.432 g, 0.00134 mol), HATU (0.755 g, 0.00198 mol) and Et$_3$N (1.09 mL, 0.0078 mol) in DMF (8 mL) to yield 0.305 g of the title compound (yield: 40%). $^1$H NMR (300 MHz, d$_6$-DMSO): δ 2.17 (s, 3H), 2.33 (t, 4H, J=4.8 Hz), 2.87–2.93 (m, 4H), 3.47 (t, 4H, J=4.8 Hz), 6.87 (s, 1H), 7.2 (d, 1H, J=1.9 Hz), 7.27 (s, 1H), 7.29–7.41 (m, 5H), 7.53–758 (m, 3H), 8.13 (s, 1H), 10.31 (s, 1H). M+1=561.

Example 251

1-(4-fluorophenyl)-8-{[2-(4-methylpiperazin-1-yl)isonicotinoyl]amino}-4,5-dihydro-1H-benzo[g]indazole-3-carboxamide

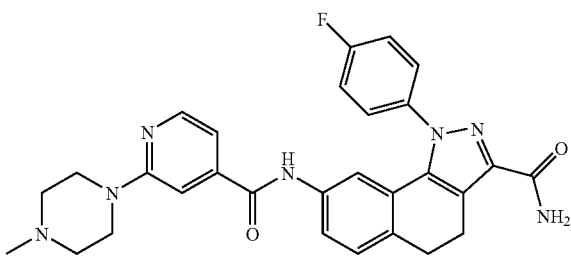

Step 1

8-[(2-chloroisonicotinoyl)amino]-1-(4-fluorophenyl)-4,5-dihydro-1H-benzo[g]indazole-3-carboxamide

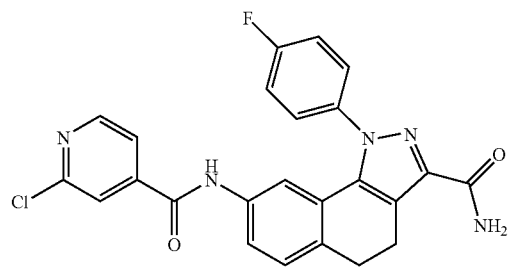

This material was prepared from Example 244 (8-amino-1-(4-fluorophenyl)-4,5-dihydro-1H-benzo[g]indazole-3-carboxamide) and 2-chloroisonicotinic acid by the method described for Example 246 step 3.

Step 2

The material from step 1 (2.17 mmoles) and N-methyl piperazine (32.9 mmoles) were dissolved in 5.0 mL N,N-dimethylacetamide. The reaction mixture was then placed under nitrogen and stirred in an oil bath at 100° C. for 88 h. The mixture was partially stripped of solvent then added to water, filtered, and washed with water. The solid was then dissolved in acetonitrile, decolorized with decolorizing carbon, and dried over anhydrous $MgSO_4$. The solvent was stripped, then the solid residue was recrystallized from acetonitrile. Mp: 277–279° C. $^1H$ NMR (400 MHz, $d_6$-DMSO): δ 2.17 (s, 3H); 2.35 (t, 4H, J=5 Hz); 2.82–2.95 (m, 4H); 3.47 (t, 4H, J=5 Hz); 6.85 (d, 1H, J=5 Hz); 7.01 (s, 1H); 7.21–7.44 (m, 6H); 7.50–7.59 (m, 3H); 8.16 (d, 1H, J=5 Hz); 10.10 (s, 1H). $^{13}C$ NMR (DMSO-$d_6$, 100 MHz): δ 20.32, 29.69, 45.20, 46.46, 55.00, 105.43, 111.23, 115.50, 117.07, 117.30, 120.66, 121.37, 126.54, 128.60, 128.69, 129.48, 133.36, 136.82, 136.85, 137.70, 139.71, 143.19, 144.36, 148.89, 159.88, 161.37, 163.81, 164.44, 165.15. M+1=526.

Example 252

8-{[5-chloro-2-(4-methyl-1,4-diazepan-1-yl)isonicotinoyl]amino}-1-(4-fluorophenyl)-4,5-dihydro-1H-benzo[g]indazole-3-carboxamide

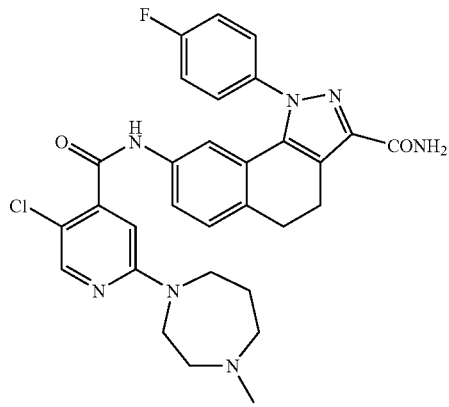

The title compound was synthesized by the same procedure as in Example 214 starting with the title compound of Example 248 (1 g, 0.0020 mol) and 1-methylhomopiperazine (4.6 g, 0.040 mol). The reaction was run at 95° C. for 24 h. After allowing the reaction mixture to cool, the volatiles were removed under vacuum. The residue was triturated with $H_2O$ to yield 0.899 g of the title compound as a tetrahydrate (yield: 71%). $^1H$ NMR (300 MHz, $d_6$-DMSO): δ 1.81–1.83 (m, 2H), 2.21 (s, 3H), 2.41 (t, 2H, J=5.5 Hz), 2.53 (t, 2H, J=4.56 Hz), 2.87–2.93 (m, 4H), 3.53 (t, 2H, J=5.5 Hz), 3.63–3.67 (m, 2H), 6.62 (s, 1H), 7.19 (d, 1H, J=1.9 Hz), 7.27–7.38 (m, 4H), 7.42–7.45 (dd, 1H, J=8.12 Hz, 1.88 Hz), 7.53–7.58 (m, 3H), 8.07 (s, 1H), 10.31 (s, 1H). M+1=575.

Example 253

8-[(5-chloro-2-piperazin-1-ylisonicotinoyl)amino]-1-(4-fluorophenyl)-4,5-dihydro-1H-benzo[g]indazole-3-carboxamide

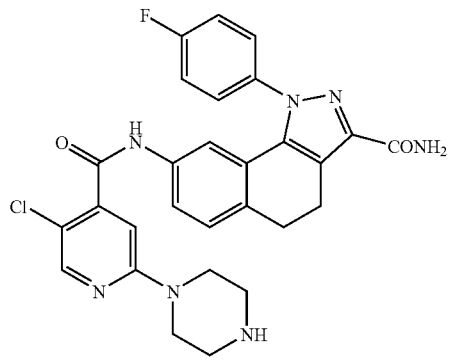

The title compound was synthesized by the same procedure as in Example 214 starting with the title compound of Example 248 (1 g, 0.0020 mol) and piperazine (3.44 g, 0.040 mol) in 5 mL of EtOH. The reaction was run at 100° C. for 24 h. The off-white precipitate that formed in the crude reaction mixture was filtered and washed with EtOH to afford 0.579 g of title compound (yield: 53%). $^1H$ NMR (300 MHz, $d_6$-DMSO): 2.67 (t, 4H, J=4.9 Hz), 2.85–2.90 (m, 4H), 3.36 (t, 4H, J=4.9 Hz), 6.80 (s, 1H), 7.18–7.19 (m, 1H), 7.25 (s, 1H), 7.27–7.35 (m, 3H), 7.37–7.39 (dd, 1H, J=8 Hz, 2 Hz), 7.51–7.55 (m, 3H), 8.09 (s, 1H), 10.28 (s, 1H). M=1=547

Example 254

8-({5-chloro-2-[[2-(dimethylamino)ethyl](methyl)amino]isonicotinoyl}amino)-1-(4-fluorophenyl)-4,5-dihydro-1H-benzo[g]indazole-3-carboxamide

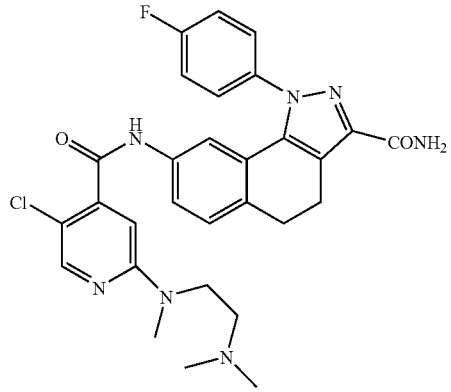

The title compound was synthesized by the same procedure as in Example 214 starting with the title compound of Example 248 (0.8 g, 0.0016 mol) and N,N,N'-trimethylethylene diamine (3.3 g, 0.032 mol). The reaction was run at 100° C. for 24 h. After removal of the volatiles under vacuum, the residue was partitioned between water and $CH_2Cl_2$. The organic layer was washed an additional time with water and dried over $MgSO_4$. The crude product mixture was purified by preparative HPLC to give 0.424 g of the title product, yield: 47%. ¹H NMR (400 MHz, d₆-DMSO): 2.13 (s, 6H), 2.34 (t, 2H, J=6.7 Hz), 2.87–2.95 (m, 4H), 2.96 (s, 3H), 3.59 (t, 2H, J=6.7 Hz), 6.58 (s, 1H), 7.2 (d, 1H, J=2 Hz), 7.27 (s, 1H), 7.29–7.37 (m, 3H), 7.41–7.44 (dd, 1H, J=8 Hz, 2 Hz), 7.53–7.58 (m, 3H), 8.13 (s, 1H), 10.36 (s, 1H). M+1=563.

Example 255

8-{[(3-chloro-6-morpholin-4-ylpyridin-2-yl)carbonyl]amino}-1-(4-fluorophenyl)-4,5-dihydro-1H-benzo[g]indazole-3-carboxamide

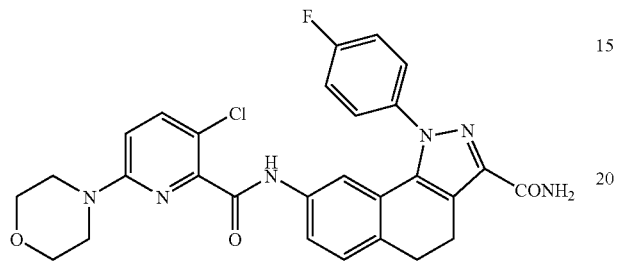

Step 1

3-chloro-6-morpholinyl-2-pyridine carboxylic acid

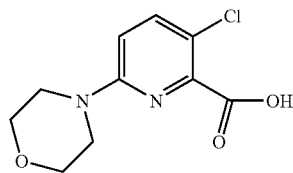

3,6 Dichloropyridine-2-carboxylic acid (0.55 g, 2.86 mmol), morpholine (1.37 g, 15.7 mmol) and N,N dimethylacetamide (1.37 mL) were combined and stirred for 24 h at 80° C. An additional volume of morpholine (1.39 g, 15.7 mmol) was added and heating continued for 40 hours more. After cooling the DMA was removed in the presence of toluene. The residue was dissolved in water and extracted with ether to remove excess morpholine. The aqueous was acidified to pH=2 and the product extracted into ether. Crystallization from water gave a white solid, 369 mg (53% yield). ¹H NMR (CD₃OD): δ 3.52 (t, 4H), 3.78 (t, 4H), 6.97 (d,1H), 7.65 (d, 1H). LC-MS, M+H: 243.

Step 2

8-{[(3-chloro-6-morpholin-4-ylpyridin-2-yl)carbonyl]amino}-1-(4-fluorophenyl)-4,5-dihydro-1H-benzo[g]indazole-3-carboxamide

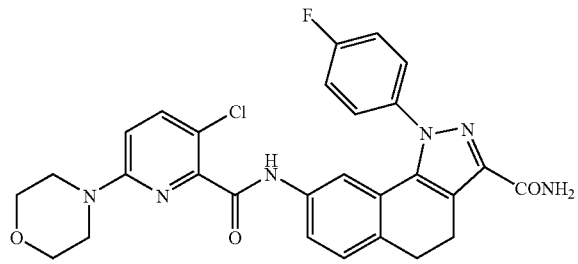

The title compound was synthesized from 0.294 g of 3-chloro-6-morpholinyl-2-pyridine carboxylic acid (from step 1) and (0.258 g) of the title compound of example 244 by the same procedure used for Example 211 except that HATU was replaced by HBTU (BF₄). The title compound is a brown solid (0.37 g, 84%), m.p. 252–254° C. Its structure was confirmed by ¹H NMR and LC/MS: ¹H NMR (CDCl₃): δ 2.95 (m, 2H), 3.12 (m, 2H), 3.48 (m, 4H), 3.88 (m, 4H), 5.39 (s, 1H), 6.65–6.82 (m, 3H), 7.16 7.18–7.23 (m, 3H), 7.43–756 (m, 3H), 7.62 (m, 1H), 9.18 (s, 1H). ESI mass spectrum for $C_{28}H_{25}ClFN_6O_3^+$: 547 (M+1).

Example 256

8-({[3-chloro-6-(4-methylpiperazin-1-yl)pyridin-2-yl]carbonyl}amino)-1-(4-fluorophenyl)-4,5-dihydro-1H-benzo[g]indazole-3-carboxamide

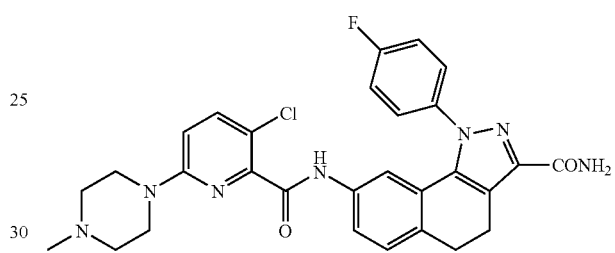

The title compound was synthesized from 0.501 g of 3-chloro-6-piperazinyl-2-pyridine carboxylic acid, obtained by acidification of its K-salt (from step 1 of Example 217), and the title compound of Example 244 (0.37 g) by the same procedure used for Example 217. The title compound is a brown solid (0.56 g, 88%), m.p. 218–220° C. Its structure was confirmed by ¹H NMR and LC/MS: ¹H NMR (d₆-DMSO): δ 2.19 (s, 3H), 2.38 (m, 4H), 2.85 (m, 4H), 3.45 (m, 4H), 6.95 (d, 1H, J=9 Hz), 7.20 (d, 1H, J=2 Hz), 7.26–7.40 (m, 4H), 7.49–7.62 (m, 4H), 7.63 (d, 1H, J=9 Hz), 10.20 (s, 1H). ESI mass spectrum for $C_{29}H_{28}ClFN_7O_2^+$: 560 (M+1).

Example 257

8-{[(3-chloro-6-{[2-(dimethylamino)ethyl]thio}pyridin-2-yl)carbonyl]amino}-1-(4-fluorophenyl)-4,5-dihydro-1H-benzo[g]indazole-3-carboxamide

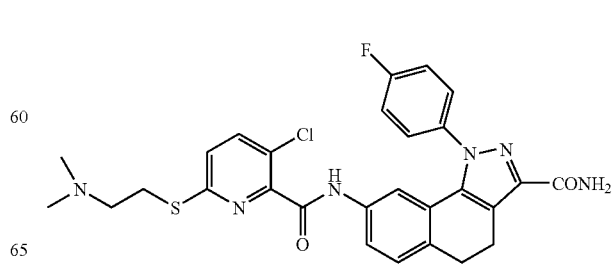

Step 1

2-[(6-carboxy-5-chloropyridin-2-yl)thio]-N,N-dimethylethanaminium chloride

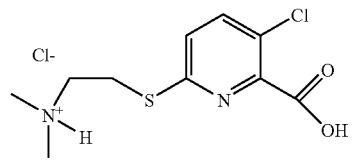

3,6-Dichloropyridine-2-carboxylic acid (1.0 g, 5.23 mmol.), sodium hydroxide (1.64 g, 15.7 mmol.), and anhydrous THF (10 mL) were combined before slowly adding the N,N-dimethylaminoethanethiol (1.9 g, 18.3 mmol). After stirring for several hours under nitrogen, two aliquots of DMF (10 mL each) were added. Several hours later, additional DMF (10 mL) and dimethylaminoethanethiol (1.9 g, 18.3 mmol) were added. The reaction was stirred overnight at room temperature. The solution was diluted with water and extracted three times with methylene chloride. The aqueous was acidified to pH 5 and extracted four times with methylene chloride. The aqueous was acidified to pH 1, the solvent was removed, and the residue was recrystallized from hot water. Yellow solid, 0.786 g (51% yield). $^1$H NMR (300 MHz, CD$_3$OD): δ 2.98 (s, 6H), 3.53 (m, 4H), 7.50 (d, 1H), 7.85 (d, 1H). $^{13}$C NMR (75 MHz, CD$_3$OD): δ 24.4, 42.8, 58.2, 125.7, 128.1, 140.0, 147.3, 158.2, 166.0.

Step 2

8-{[(3-chloro-6-{[2-(dimethylamino)ethyl]thio}pyridin-2-yl)carbonyl]amino}-1-(4-fluorophenyl)-4,5-dihydro-1H-benzo[g]indazole-3-carboxamide

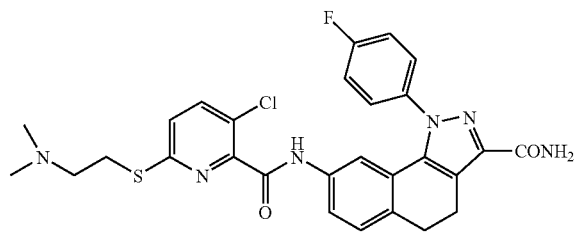

The title compound was synthesized from 0.355 g of the title compound of Step 1 and the title compound of Example 244 (0.32 g) by the same procedure used in Example 255. The title compound is a white solid (0.49 g, 87%). Its structure was confirmed by $^1$H NMR and LC/MS: $^1$H NMR (CD$_3$CN): δ 2.18 (s, 6H), 2.57 (m, 2H), 2.85 (m, 4H), 3.00 (m, 4H), 3.26 (m, 2H), 5.88 (s, 1H), 6.94 (d, 1H), 7.27–7.38 (m, 5H), 7.47–7.62 (m, 3H), 7.69 (d, 1H, J=9 Hz), 9.40 (s, 1H). ESI mass spectrum for C$_{28}$H$_{27}$ClFN$_6$O$_2$S$^+$: 565 (M+1).

Example 258

This compound was synthesized by using the same procedure described for Example 221; mp: 194–195° C.; $^1$HNMR (DMSO+TFA-d, 400 MHz) δ: 10.24 (s, 1H), 9.69 (s, 1H), 7.60 (m, 2H), 7.46 (d, J=4.2 Hz, 1H), 7.38 (m, 4H), 7.10 (dd, J=2.6, 8.9 Hz, 1H), 7.06 (s, 1H), 3.90 (d, J=13.0 Hz, 2H), 3.50 (d, J=12.0 Hz, 2H), 3.12 (m, 2H), 2.95 (m, 4H), 2.91 (s, 3H), 2.86 (s, 2H).

The IKK2 bioactivity for Examples 245–257 is shown in Table 7.

TABLE 7

| Structure | Mol. Wt. | Compound Name(s) | IKK2 Resin IC50 | Example |
|---|---|---|---|---|
| 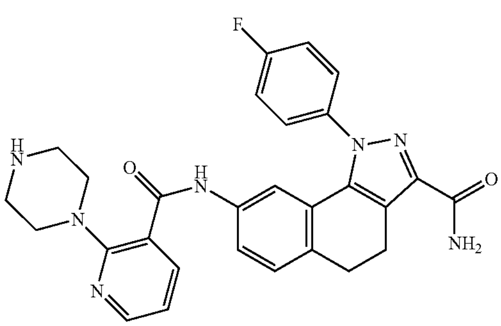 | 511.56 | 1-(4-fluorophenyl)-8-{[(2-piperazin-1-ylpyridin-3-yl)carbonyl]amino}-4,5-dihydro-1H-benzo[g]indazole-3-carboxamide | ≦1 μM | 245 |

TABLE 7-continued

| Structure | Mol. Wt. | Compound Name(s) | IKK2 Resin IC50 | Example |
|---|---|---|---|---|
| 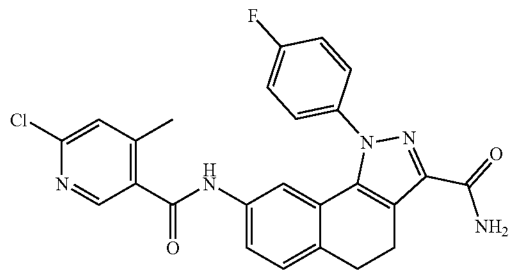 | 475.91 | 8-{[(6-chloro-4-methylpyridin-3-yl)carbonyl]amino}-1-(4-fluorophenyl)-4,5-dihydro-1H-benzo[g]indazole-3-carboxamide | ≦1 μM | 246 |
| 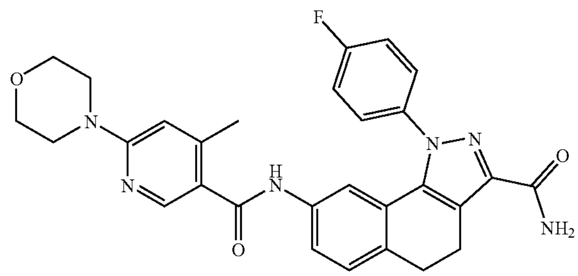 | 526.58 | 1-(4-fluorophenyl)-8-{[(4-methyl-6-morpholin-4-ylpyridin-3-yl)carbonyl]amino}-4,5-dihydro-1H-benzo[g]indazole-3-carboxamide | ≦1 μM | 247 |
| 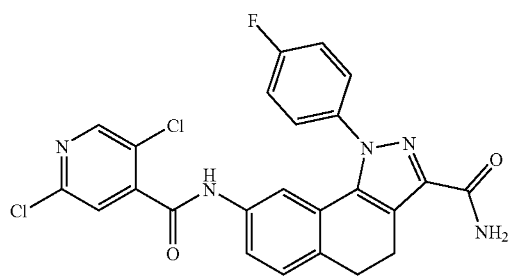 | 496.33 | 8-[(2,5-dichloroisonicotinoyl)amino]-1-(4-fluorophenyl)-4,5-dihydro-1H-benzo[g]indazole-3-carboxamide | ≦1 μM | 248 |
| 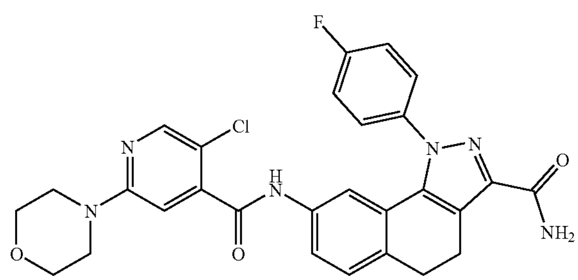 | 546.99 | 8-[(5-chloro-2-morpholin-4-ylisonicotinoyl)amino]-1-(4-fluorophenyl)-4,5-dihydro-1H-benzo[g]indazole-3-carboxamide | ≦1 μM | 249 |
| 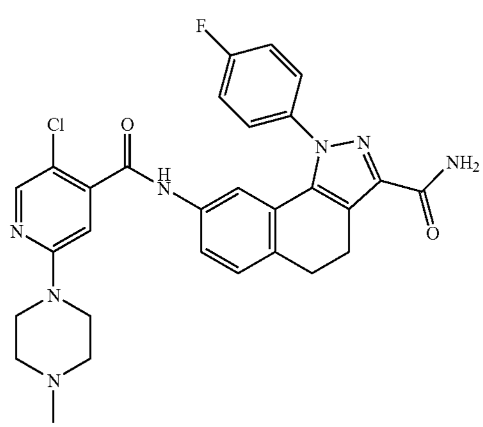 | 560.04 | 8-{[5-chloro-2-(4-methylpiperazin-1-yl)isonicotinoyl]amino}-1-(4-fluorophenyl)-4,5-dihydro-1H-benzo[g]indazole-3-carboxamide | ≦1 μM | 250 |

TABLE 7-continued

| Structure | Mol. Wt. | Compound Name(s) | IKK2 Resin IC50 | Example |
|---|---|---|---|---|
| 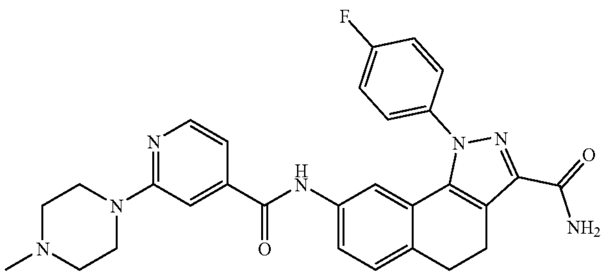 | 525.59 | 1-(4-fluorophenyl)-8-{[2-(4-methylpiperazin-1-yl)isonicotinoyl]amino}-4,5-dihydro-1H-benzo[g]indazole-3-carboxamide | ≦1 μM | 251 |
| 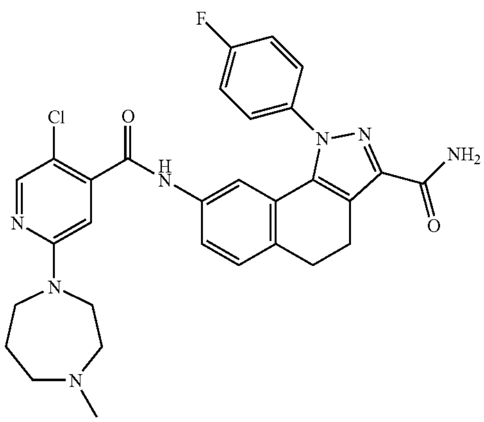 | 574.06 | 8-{[5-chloro-2-(4-methyl-1,4-diazepan-1-yl)isonicotinoyl]amino}-1-(4-fluorophenyl)-4,5-dihydro-1H-benzo[g]indazole-3-carboxamide | ≦1 μM | 252 |
| 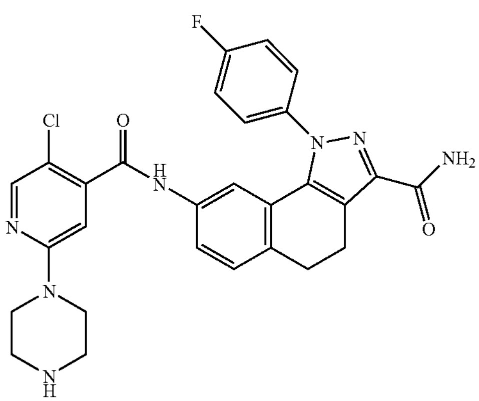 | 546.01 | 8-[(5-chloro-2-piperazin-1-ylisonicotinoyl)amino]-1-(4-fluorophenyl)-4,5-dihydro-1H-benzo[g]indazole-3-carboxamide | ≦1 μM | 253 |
| 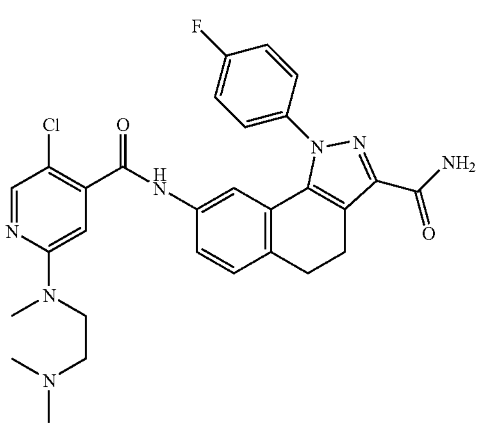 | 562.05 | 8-({5-chloro-2-[[2-(dimethylamino)ethyl](methyl)amino]isonicotinoyl}amino)-1-(4-fluorophenyl)-4,5-dihydro-1H-benzo[g]indazole-3-carboxamide | ≦1 μM | 254 |

TABLE 7-continued

| Structure | Mol. Wt. | Compound Name(s) | IKK2 Resin IC50 | Example |
|---|---|---|---|---|
| 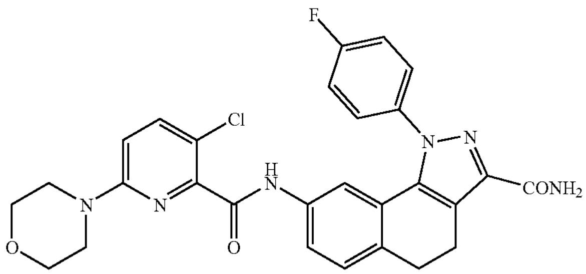 | 546.99 | 8-{[(3-chloro-6-morpholin-4-ylpyridin-2-yl)carbonyl]amino}-1-(4-fluorophenyl)-4,5-dihydro-1H-benzo[g]indazole-3-carboxamide | ≦1 μM | 255 |
| 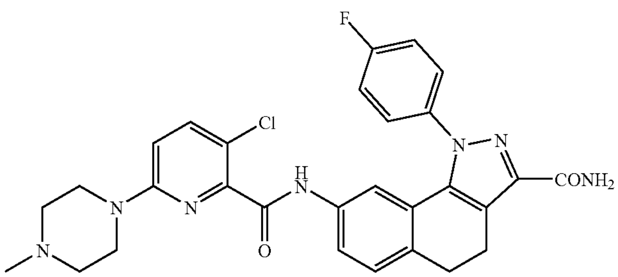 | 560.04 | 8-({[3-chloro-6-(4-methylpiperazin-1-yl)pyridin-2-yl]carbonyl}amino)-1-(4-fluorophenyl)-4,5-dihydro-1H-benzo[g]indazole-3-carboxamide | ≦1 μM | 256 |
| 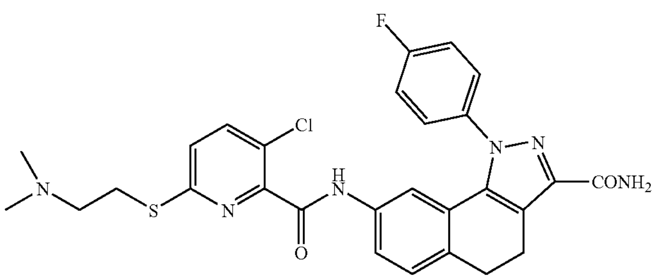 | 565.07 | 8-{[(3-chloro-6-{[2-(dimethylamino)ethyl]thio}pyridin-2-yl)carbonyl]amino}-1-(4-fluorophenyl)-4,5-dihydro-1H-benzo[g]indazole-3-carboxamide | ≦1 μM | 257 |
| 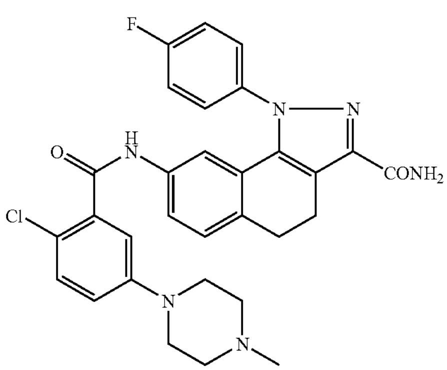 | 559.05 | 8-{[2-chloro-5-(4-methylpiperazin-1-yl)benzoyl]amino}-1-(4-fluorophenyl)-4,5-dihydro-1H-benzo[g]indazole-3-carboxamide | ≦1 μM | 258 |

Examples 259–263

Examples 259–263 were synthesized with the corresponding starting compounds using the following synthesis procedures similar to scheme I where $R^9$ is the appropriate aryl, substituted aryl, heteroaryl, substituted heteroaryl, substituted arylalkyl, substituted heteroarylalkyl, or cycloalkyl.

SCHEME XXVI

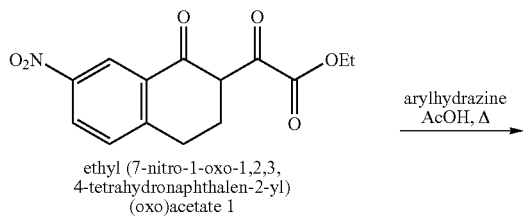
ethyl (7-nitro-1-oxo-1,2,3,4-tetrahydronaphthalen-2-yl)(oxo)acetate 1

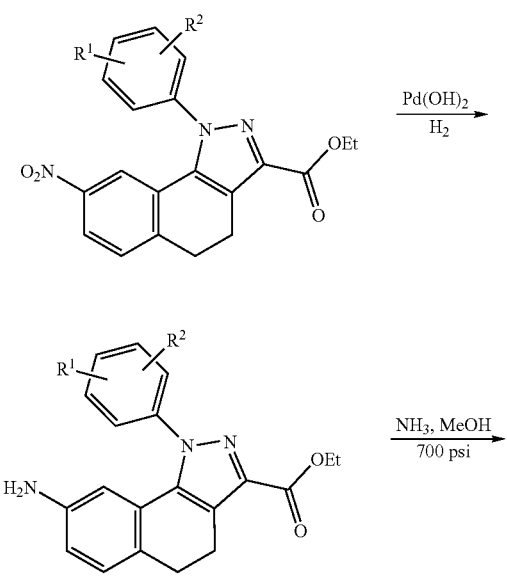

SCHEME XXVII

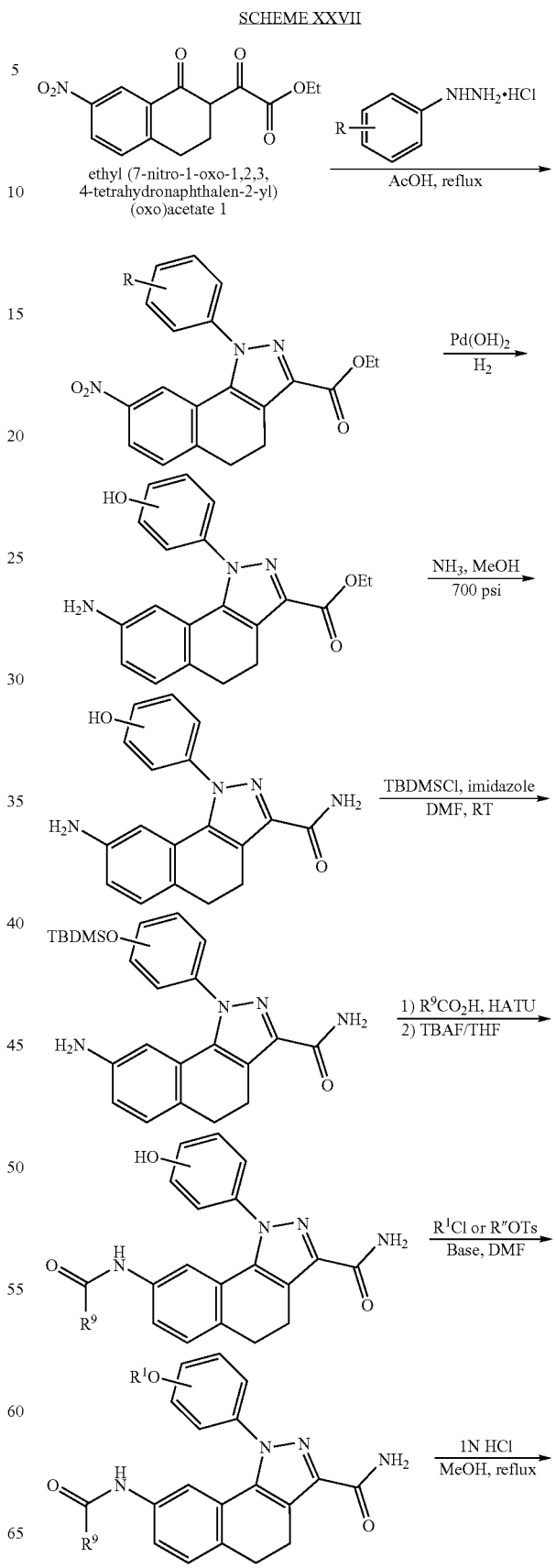

-continued

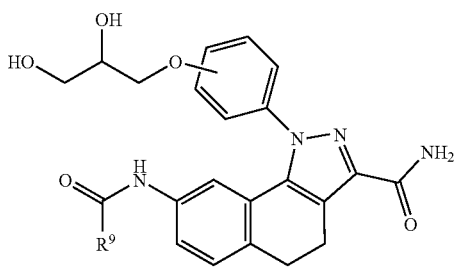

R = 3- or 4-benzyloxyl

Example 259

1-[4-(benzyloxy)phenyl]-8-[(2-chlorobenzoyl)amino]-4,5-dihydro-1H-benzo[g]indazole-3-carboxamide

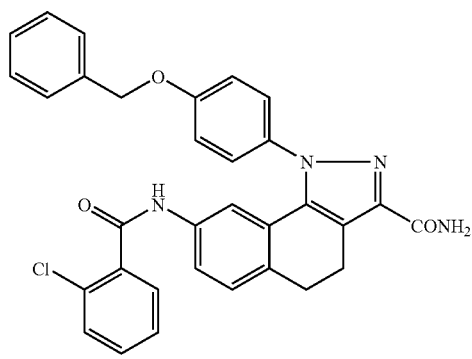

Step 1: A mixture of 4-benzyloxylphenylhydrazine hydrochloride (6.42 g, 0.03 mol) and ethyl (7-nitro-1-oxo-1,2,3,4-tetrahydronaphthalen-2-yl)(oxo)acetate 1 (9.2 g, 0.03 mol) in 200 mL of acetic acid was refluxed for 16 h, then cooled to room temperature. The precipitate was collected by filtration and air-dried to give 8.5 g of product as a light green solid (60% yield); $^1$HNMR (DMSO, 400 MHz) δ: 8.07 (dd, 1H), 7.66 (d, 1H), 7.35–7.53 (m, 8H), 7.24 (dd, 2H), 5.26 (s, 2H), 4.32 (q, 2H), 3.11 (m, 2H), 3.30 (m, 2H), 1.32 (t, 3H).

Step 2: A mixture of the product from step 1 (15.0 g, 0.032 mol) and tin chloride (21.6 g, 0.096 mol) in 400 mL of ethanol was heated at reflux overnight. Another two equivalent of tin chloride was added and stirred for 6 h. The reaction mixture was cooled to room temperature and the precipitate was filtered and washed with ether to give 13.5 g of the amine as a light yellow solid (96% yield); $^1$HNMR (DMSO, 400 MHz) δ: 8.07 (dd, 1H), 7.66 (d, 1H), 7.35–7.53 (m, 8H), 7.24 (dd, 2H), 5.26 (s, 2H), 4.32 (q, 2H), 3.11 (m, 2H), 3.30 (m, 2H), 1.32 (t, 3H).

Step 3: A sealed reaction vessel containing the product from step 2 (6.2 g, 0.014 mol) and 40 mL of liquid ammonia in 200 mL of absolute alcohol was heated at 120° C. and 600 psi for 24 h. After cooling, solvent was removed and the residue was purified by chromatography on silica gel (ethyl acetate/hexane, 6:4) to give 4.0 g of product as a pale yellow solid (70% yield); $^1$HNMR (CDCl$_3$, 400 MHz) δ: 7.35–7.47 (m, 7H), 7.07 (m, 3H), 6.81 (s, 1H), 6.50 (dd, 1H), 6.07 (d, 1H), 5.49 (s, 1H), 5.15 (s, 2H), 3.37 (s, 2H), 3.08 (m, 2H), 2.86 (m, 2H).

Step 4: To a solution of the product from step 3 (7.08 g, 0.017 mol) in 100 mL of pyridine was added 2-chlorobenzoyl chloride (3.4 g, 0.019 mol) in one portion and the reaction mixture was stirred at room temperature overnight. Solvent was removed and the residue was stirred with water. The precipitate was collected by filtration and air-dried to give 7.5 g of product as a white solid (80% yield); $^1$HNMR (DMSO, 400 MHz) δ: 10.29 (s, 1H), 7.15–7.51 (m, 18H), 5.16 (s, 2H), 2.90 (m, 4H); Anal. Calcd. for C$_{32}$H$_{25}$ClN$_4$O$_3$: C, 70.01; H, 4.59; N, 10.20. Found: C, 69.62; H, 4.44; N, 10.24.

Example 260

1-[4-(benzyloxy)phenyl]-8-{[(2-chloropyridin-3-yl)carbonyl]amino}-4,5-dihydro-1H-benzo[g]indazole-3-carboxamide

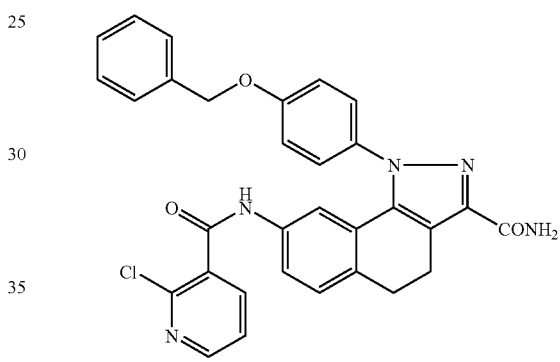

This compound was synthesized by following the same procedure as Example 259 except using 2-chloronicotinyl chloride in step 4; $^1$HNMR (DMSO, 400 MHz) δ: 10.42 (s, 1H), 8.50 (d, 1H), 7.96 (d, 1H), 7.16–7.54 (m, 15H), 5.16 (s, 2H), 2.93 (m, 4H); Anal. Calcd. for C$_{31}$H$_{24}$ClN$_5$O$_3$: C, 67.70; H, 4.40; N, 12.73. Found: C, 66.75; H, 4.17; N, 12.41.

Example 261

8-[(2-chlorobenzoyl)amino]-1-(4-hydroxyphenyl)-4,5-dihydro-1H-benzo[g]indazole-3-carboxamide

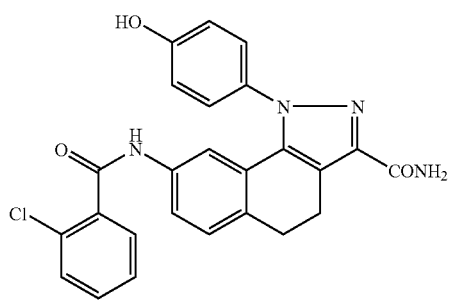

The final product from Example 259 (7.5 g, 0.014 mol) was dissolved of TFA (120 mL) and the dark brown solution was stirred at room temperature for 84 h. Solvent was removed and the residue was taken up with 200 mL of water. The solid was collected and air-dried to give 6.5 g of product as a pale white solid (83% yield); $^1$HNMR (DMSO, 400 MHz) δ: 10.29 (s, 1H), 9.84 (s, 1H), 7.24–7.51 (m, 11H), 6.87 (d, 2H), 2.90 (m, 4H); Anal. Calcd. for $C_{25}H_{19}ClN_4O_3$+1.0 $H_2O$: C, 62.96; H, 4.44; N, 11.75. Found: C, 62.92; H, 4.28; N, 11.76.

Example 262

8-[(2-chlorobenzoyl)amino]-1-(3-hydroxyphenyl)-4,5-dihydro-1H-benzo[g]indazole-3-carboxamide

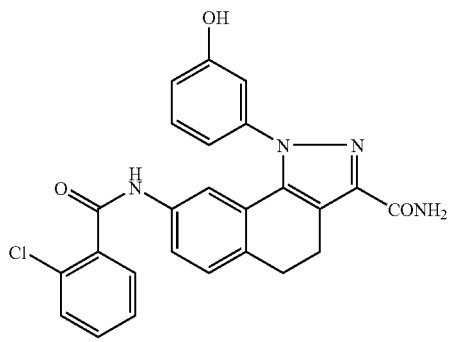

This compound was synthesized by following the same procedure as Example 261 except using 3-benzyloxyphenylhydrazine hydrochloride in step 1; $^1$HNMR (DMSO, 400 MHz) δ: 10.31 (s, 1H), 7.27–7.54 (m, 10H), 6.89 (m, 3H), 2.92 (m, 4H); Anal. Calcd. for $C_{25}H_{19}ClN_4O_3$+0.5 $H_2O$: C, 64.17; H, 4.31; N, 11.97. Found: C, 64.29; H, 4.36; N, 11.63.

Example 263

8-{[(2-chloropyridin-3-yl)carbonyl]amino}-1-(4-hydroxyphenyl)-4,5-dihydro-1H-benzo[g]indazole-3-carboxamide

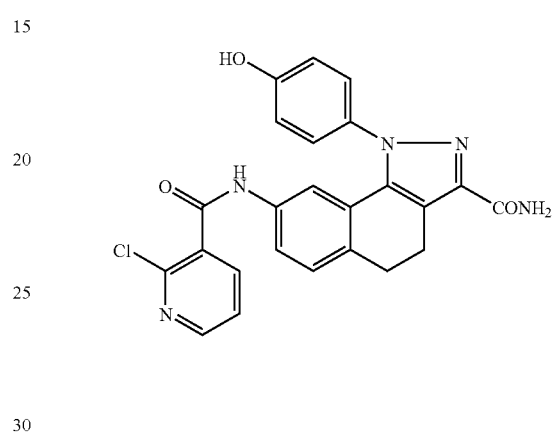

This compound was synthesized by following the same procedure as Example 261 except using 2-chloronicotinyl chloride in step 4; $^1$HNMR (DMSO, 400 MHz) δ: 10.31 (s, 1H), 7.27–7.54 (m, 10H), 6.89 (m, 3H), 2.92 (m, 4H); Anal. Calcd. for $C_{24}H_{18}ClN_5O_3$: C, 62.68; H, 3.95; N, 15.23. Found: C, 62.03; H, 3.89; N, 14.83.

The bioactivity in the IKK2 resin assay of Examples 259–263 is shown Table 8.

TABLE 8

| Compound No., Structure | Mol. Wt. | Compound Name(s) | IKK2 Resin IC50 | MS (M + H) | Example |
|---|---|---|---|---|---|
| | 549.03 | 1-[4-(benzyloxy)phenyl]-8-[(2-chlorobenzoyl)amino]-4,5-dihydro-1H-benzo[g]indazole-3-carboxamide | >10μM | 550 | 259 |

TABLE 8-continued

| Compound No., Structure | Mol. Wt. | Compound Name(s) | IKK2 Resin IC50 | MS (M + H) | Example |
|---|---|---|---|---|---|
| | 550.02 | 1-[4-(benzyloxy)phenyl]-8-{[(2-chloropyridin-3-yl)carbonyl]amino}-4,5-dihydro-1H-benzo[g]indazole-3-carboxamide | 1 ≦ 10 μM | 551 | 260 |
| | 458.91 | 8-[(2-chlorobenzoyl)amino]-1-(4-hydroxyphenyl)-4,5-dihydro-1H-benzo[g]indazole-3-carboxamide | ≦1μM | 459 | 261 |
| | 458.90 | 8-[(2-chlorobenzoyl)amino]-1-(3-hydroxyphenyl)-4,5-dihydro-1H-benzo[g]indazole-3-carboxamide | ≦1μM | 459 | 262 |
| | 459.89 | 8-{[(2-chloropyridin-3-yl)carbonyl]amino}-1-(4-hydroxyphenyl)-4,5-dihydro-1H-benzo[g]indazole-3-carboxamide | ≦1μM | 460 | 263 |

Example 264

8-[(2-chlorobenzoyl)amino]-1-[4-(2-morpholin-4-ylethoxy)phenyl]-4,5-dihydro-1H-benzo[g]indazole-3-carboxamide

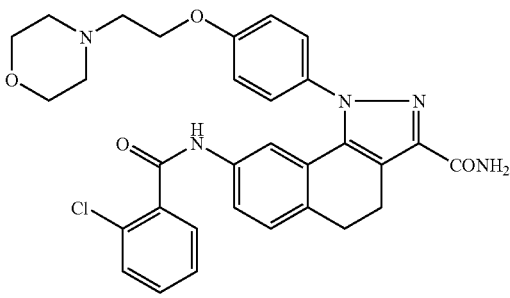

To a suspension of the product from Example 261 (0.6 g, 0.001 mol) and cesium carbonate in 10 mL of DMF was added 4-(2-chloroethyl)morpholine hydrochloride (0.19 g, 0.001 mol) in one portion. The reaction mixture was stirred at room temperature overnight. After the removal of solvent, the residue was partitioned between water and ethyl acetate. The organic layer was washed with brine, dried over magnesium sulfate, and concentrated. This crude was purified by HPLC to give 0.15 of product as a light yellow (26% yield); $^1$HNMR (DMSO, 400 MHz) δ: 11.49 (brs, 1H), 10.33 (s, 1H), 7.14–7.54 (m, 10H), 4.53 (s, 2H), 3.82 (m, 2H), 3.58 (m, 8H), 3.08 (m, 2H), 2.93 (m, 4H); Anal. Calcd. for $C_{31}H_{30}ClN_5O_4$ 1.0 $H_2O$ 1.0 HCl: C, 59.43; H, 5.31; N, 11.18. Found: C, 59.58; H, 5.26; N, 10.92.

Example 265

8-[(2-chlorobenzoyl)amino]-1-{4-[(2,2-dimethyl-1,3-dioxolan-4-yl)methoxy]phenyl}-4,5-dihydro-1H-benzo[g]indazole-3-carboxamide

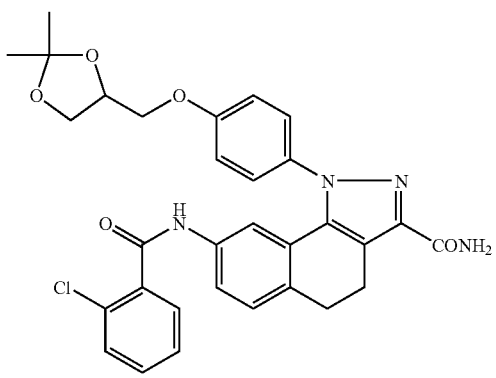

This compound was synthesized by following the same procedure as Example 264 except using 2,2-dimethyl-1,3-dioxolan-4-ylmethyl p-toluenesulfonate (78% yield); $^1$HNMR (CDCl$_3$, 400 MHz) δ: 7.69 (d, 1H), 7.59 (m, 2H), 7.44 (d, 2H), 7.30–7.40 (m, 3H), 7.05 (d, 2H), 6.83 (d, 2H), 4.52 (m, 1H), 4.13 (m, 2H), 4.02 (m, 2H), 3.93 (m, 2H), 3.14 (m, 2H), 2.98 (m, 2H), 1.46 (s, 3H), 1.26 (s, 3H); Anal. Calcd. for $C_{31}H_{29}ClN_4O_5$: C, 64.98; H, 5.10; N, 9.78. Found: C, 64.56; H, 4.97; N, 9.68.

Example 266

8-[(2-chlorobenzoyl)amino]-1-[4-(2,3-dihydroxypropoxy)phenyl]-4,5-dihydro-1H-benzo[g]indazole-3-carboxamide

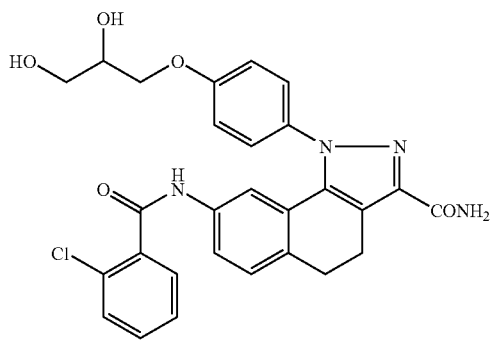

To a suspension of the product from Example 265 (0.36 g, 0.00063 mol) in methanol was added 1N HCl and the mixture was heated at reflux for 16 h. Solvent was removed and the crude was recrystallized from water and methanol to give 0.24 g of the desired product as a white solid (72%); $^1$H NMR (DMSO, 400 MHz) δ: 10.30 (s, 1H), 7.36–7.57 (m, 6H), 7.33 (d, 1H), 7.28 (brs, 1H), 7.18 (d, 1H), 7.09 (d, 2H), 4.98 (d, 1H), 4.68 (t, 1H), 4.10 (q, 1H), 4.05 (dd, 1H), 3.92 (dd, 1H), 3.83 (m, 1H), 3.45 (t, 1H), 3.16 (d, 2H), 2.94 (m, 4H); Anal. Calcd. for $C_{28}H_{25}ClN_4O_5$: C, 63.10; H, 4.73; N, 10.51. Found: C, 62.81; H, 4.45; N, 10.16.

The compounds of Examples 267–275 were synthesized as described in Example 264 using the appropriate aryl, substituted aryl, heteroaryl, substituted heteroaryl, substituted arylalkyl, substituted heteroarylalkyl, or cycloalkyl.

The bioactivity in the IKK2 Resin assay for the compounds of Examples 264–275 is shown in Table 9.

TABLE 9

| Compound No., Structure | Mol. Wt. | Compound Name(s) | IKK2 Resin IC50 | MS (M + H) | Example |
|---|---|---|---|---|---|
| | 572.07 | 8-[(2-chlorobenzoyl) amino]-1-[4-(2-morpholin-4-ylethoxy)phenyl]-4,5-dihydro-1H-benzo[g]indazole-3-carboxamide | ≦1 μM | 573 | 264 |
| | 573.05 | 8-[(2-chlorobenzoyl) amino]-1-{4-[(2,2-dimethyl-1,3-dioxolan-4-yl)methoxy]phenyl}-4,5-dihydro-1H-benzo[g]indazole-3-carboxamide | ≦1 μM | 574 | 265 |
| | 532.99 | 8-[(2-chlorobenzoyl) amino]-1-[4-(2,3-dihydroxypropoxy)phenyl]-4,5-dihydro-1H-benzo[g]indazole-3-carboxamide | ≦1 μM | 533 | 266 |
| | 533.98 | 8-[(3-chloroisonicotinoyl) amino}-1-[4-(2,3-dihydroxypropoxy)phenyl]-4,5-dihydro-1H-benzo[g]indazole-3-carboxamide | ≦1 μM | 534 | 267 |

TABLE 9-continued

| Compound No., Structure | Mol. Wt. | Compound Name(s) | IKK2 Resin IC50 | MS (M + H) | Example |
| --- | --- | --- | --- | --- | --- |
|  | 611.08 | 8-{[2-chloro-4-(methylsulfonyl)benzoyl]amino}-1-[4-(2,3-dihydroxypropoxy)phenyl]-4,5-dihydro-1H-benzo[g]indazole-3-carboxamide | ≦1 μM | 612 | 268 |
|  | 548.00 | 8-[(5-amino-2-chlorobenzoyl)amino]-[4-(2,3-dihydroxypropoxy)phenyl[-4,5-dihydro-1H-benzo[g]indazole-3-carboxamide | ≦1 μM | 548 | 269 |
|  | 533.98 | 8-{[(2-chloropyridin-3-yl)carbonyl]amino}-1-[4-(2,3-dihydroxypropoxy)phenyl]-4,5-dihydro-1H-benzo[g]indazole-3-carboxamide | ≦1 μM | 534 | 270 |
|  | 530.03 | 8-[(2-chlorobenzoyl)amino]-1-{4-[2-(dimethylanimo)ethoxy]phenyl}-4,5-dihydro-1H-benzo[g]indazole-3-carboxamide | 1 ≦ 10 μM | 530 | 271 |

TABLE 9-continued

| Compound No., Structure | Mol. Wt. | Compound Name(s) | IKK2 Resin IC50 | MS (M + H) | Example |
|---|---|---|---|---|---|
| | 544.06 | 8-[(2-chlorobenzoyl)amino]-1-{4-[3-(dimethylamino)propoxy]phenyl}-4,5-dihydro-1H-benzo[g]indazole-3-carboxamide | 1 ≦ 10 μM | 544 | 272 |
| | 651.14 | 8-{[2-chloro-4-(methylsulfonyl)benzoyl]amino}-1-{4-[(2,2-dimethyl-1,3-dioxalan-4-yl)methoxy]phenyl}-4,5-dihydro-1H-benzo[g]indazole-3-carboxamide | 1 ≦ 10 μM | 651 | 273 |
| | 574.04 | 8-{[(2-chloropyridin-3-yl)carbonyl]amino}-1-{4-[(2,2-dimethyl-1,3-dioxolan-4-yl)methoxy]phenyl}-4,5-dihydro-1H-benzo[g]indazole-3-carboxamide | 1 ≦ 10 μM | 574 | 274 |
| | 574.04 | 8-[(3-chloroisonicotinoyl)amino]-1-{3-[(2,2-dimethyl-1,3-dioxolan-4-yl)methoxy]phenyl}-4,5-dihydro-1H-benzo[g]indazole-3-carboxamide | 1 ≦ 10 μM | 574 | 275 |

Example 276

8-[(2-chlorobenzoyl)amino]-1-(4-cyanophenyl)-4,5-dihydro-1H-benzo[g]indazole-3-carboxamide

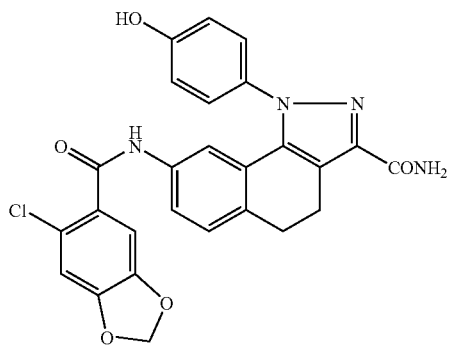

Step 1: The product (45.0 g, 0.096 mol) from step 1 of Example 261 was hydrogenated in 400 mL of acetic with Pd(OH)$_2$/C as catalyst for 17 h under 15 psi in a Parr shaker. After the removal of solvent, the residue was triturated with a mixture of methanol and ether (1:2) to give 23.0 g of the desired product as a white solid (68% yield); $^1$HNMR (DMSO, 400 MHz) δ: 10.06 (s, 1H), 7.27 (d, 2H), 6.98 (d, 1H), 6.92 (d, 2H), 6.43 (dd, 1H), 6.02 (d, 1H), 4.82 (brs, 2H), 4.29 (q, 2H), 2.75 (m, 2H), 1.30 (t, 3H).

Step 2: A sealed reaction vessel containing the product from step 1 (25.0 g, 0.072 mol) and 40 mL of liquid ammonia in 250 mL of absolute alcohol was heated at 120° C. and 600 psi for 30 h. After cooling, the precipitate was collected by filtration to give 16.7 g of product as a pale yellow solid (73% yield); $^1$HNMR (CDCl$_3$, 400 MHz) δ: 7.44 (s, 1H), 7.27 (d, 2H), 7.20 (s, 1H), 6.97 (d, 1H), 6.91 (d, 2H), 6.40 (d, 1H), 6.03 (s, 1H), 4.77 (brs, 2H), 2.85 (m, 2H), 2.72 (m, 2H).

Step 3: To a solution of the product form step 1 (5.25 g, 0.016 mol) and TBDMSCl (3.0 g, 0.02 mol) in 100 mL of DMF was added imidazole (2.72 g, 0.04 mol) in one portion. The reaction mixture was stirred at room temperature for 36 h. Solvent was removed and the residue was partitioned between water and ethyl acetate. The organic layer was washed with brine, dried over magnesium sulfate, and concentrated. This crude was purified by chromatography on silica gel (ethyl acetate/hexane, 1:1) to give 4.0 g of product as a white solid (57% yield). The NMR was consistent with the proposed structure.

Step 4: To a mixture of the product from step 3 (1.05 g, 0.0024 mol) and 2-chloro-4,5-methylenedioxanylbenzoic cid (0.73 g, 0.0036 mol) in 25 mL of DMF was added 1 mL of diisopropylethylamine, followed by the addition of HATU (1.37 g, 0.0036 mol). The reaction was stirred at room temperature for 16 h and concentrated. The residue was partitioned between water and ethyl acetate and the organic phase was concentrated. This crude was then dissolved in 20 mL of THF and treated with 10 eq of TBAF for 1 h at RT. After the removal of solvent, the residue was partitioned between water and ethyl acetate. The organic layer was washed with brine, dried over magnesium sulfate, and filtered. The filtrate was concentrated and triturated with a mixture of acetonitrile to give 1.04 g of desired product as an off-white solid (86% yield); $^1$HNMR (DMSO, 400 MHz) δ: 10.17 (s, 1H), 9.85 (s, 1H), 7.47 (m, 2H), 7.27 (m, 5H), 7.14 (s, 1H), 7.04 (s, 1H), 6.88 (d, 2H), 6.12 (s, 2H), 2.92 (m, 4H).

Example 277

8-{[(6-chloro-1,3-benzodioxol-5-yl)carbonyl]amino}-1-(3-hydroxyphenyl)-4,5-dihydro-1H-benzo[g]indazole-3-carboxamide

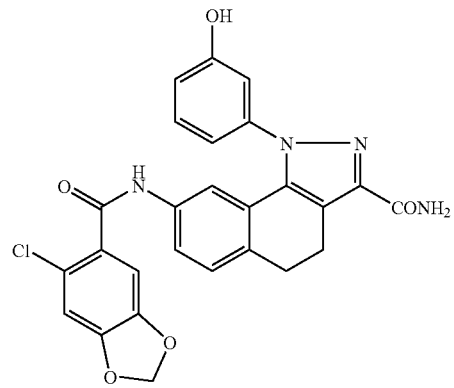

This compound was synthesized by following the same procedure as Example 276 except using 3-benzyloxyphenyhydrazine hydrochloride in step 1; $^1$HNMR (DMSO, 400 MHz) δ: 10.19 (s, 1H), 9.86 (s, 1H), 7.51 (m, 2H), 7.31 (m, 3H), 7.24 (d, 1H), 7.14 (s, 1H), 7.04 (s, 1H), 6.88 (m, 3H), 6.12 (s, 2H), 2.91 (m, 4H); Anal. Calcd. for C$_{26}$H$_{19}$ClN$_4$O$_5$: C, 62.10; H, 3.81; N, 11.14. Found: C, 61.52; H, 3.53; N, 11.11.

Example 278

8-[(2-chloro-5-nitrobenzoyl)amino]-1-(4-hydroxyphenyl)-4,5-dihydro-1H-benzo[g]indazole-3-carboxamide

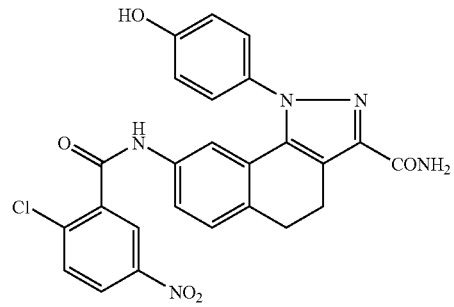

This compound was synthesized by following the same procedure as Example 276 except using 2-chloro-5-nitrobenzoic acid in step 4; Anal. Calcd. for $C_{25}H_{18}ClN_5O_5 1.5H_2O$: C, 56.56; H, 3.99; N, 13.19. Found: C, 56.89; H, 4.45; N, 12.81.

Example 279

8-{[2-chloro-5-(methylsulfinyl)benzoyl]amino}-1-(4-hydroxyphenyl)-4,5-dihydro-1H-benzo[g]indazole-3-carboxamide

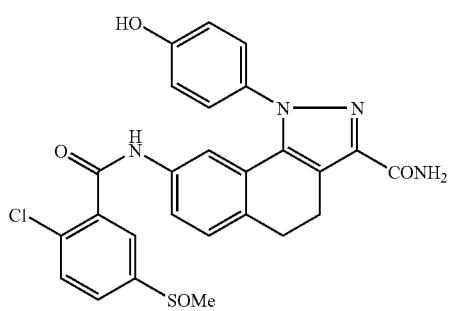

This compound was synthesized by following the same procedure as Example 276 except using 2-chloro-5-(methylthio)benzoic acid in step 4 and then oxidized to the desired product with mCPBA; $^1$HNMR (DMSO, 400 MHz) δ: 10.43 (s, 1H), 9.85 (s, 1H), 7.26–7.79 (m, 10H), 6.88 (d, J=8.5 Hz, 2H), 2.92 (m, 4H), 2.80 (s, 3H); Anal. Calcd. for $C_{26}H_{21}ClN_4O_4S$: C, 59.94; H, 4.06; N, 10.75; S, 6.15. Found: C, 59.48; H, 4.09; N, 10.54; S, 6.18.

Example 280

8-[(5-amino-2-chlorobenzoyl)amino]-1-(4-hydroxyphenyl)-4,5-dihydro-1H-benzo[g]indazole-3-carboxamide

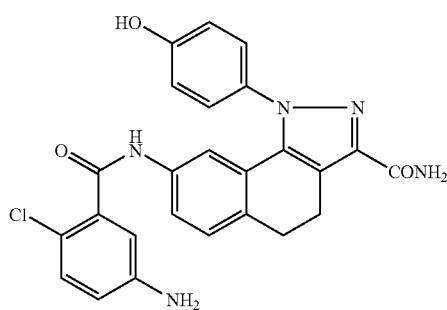

This compound was synthesized by following the same procedure as Example 276 except using 5-[(tert-butoxycarbonyl)amino]-2-chlorobenzoic acid in step 4 and then deprotected with 4N HCl in dioxane; $^1$HNMR (DMSO, 400 MHz) δ: 10.19 (s, 1H), 9.84 (s, 1H), 7.49 (d, 1H), 7.46 (d, 1H), 7.28–7.31 (m, 5H), 7.12 (d, 1H), 6.88 (d, 2H), 6.64 (m, 2H), 2.90 (m, 4H), 2.80; Anal. Calcd. for $C_{25}H_{20}ClN_5O_3$ 3.0 $H_2O$: C, 56.87; H, 4.96; N, 13.26. Found: C, 56.18; H, 5.10; N, 13.09.

The compounds of Examples 281–287 listed in the Table 10 were prepared according to the procedure of Example 276 using the appropriate acylating agent.

The bioactivity in the IKK2 Resin assay for the compounds of Examples 276–287 is shown in Table 10.

TABLE 10

| Compound No., Structure Mol. | Mol. Wt. | Compound Name(s) | IKK2 Resin IC50 | MS (M + H) | Example |
|---|---|---|---|---|---|
| 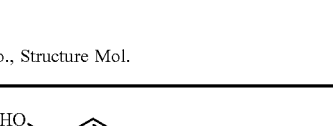 | 502.91 | 8-{[(6-chloro-1,3-benzodioxol-5-yl)carbonyl]amino}-1-(4-hydxoxyphenyl)-4,5-dihydro-1H-benzo[g]indazole-3-carboxamide | ≦1 μM | 503 | 276 |

TABLE 10-continued

| Compound No., Structure Mol. | Mol. Wt. | Compound Name(s) | IKK2 Resin IC50 | MS (M + H) | Example |
|---|---|---|---|---|---|
| | 502.92 | 8-{[(6-chloro-1,3-benzodioxol-5-yl)carbonyl]amino}-1-(3-hydroxyphenyl)-4,5-dihydro-1H-benzo[g]indazole-3-carboxamide | ≦1 μM | 503 | 277 |
| | 503.91 | 8-[(2-chloro-5-nitrobenzoyl)amino]-1-(4-hydroxyphenyl)-4,5-dihydro-1H-benzo[g]indazole-3-carboxamide | ≦1 μM | 504 | 278 |
| | 521.00 | 8-{[2-chloro-5-(methylsulfinyl)benzoyl]amino}-1-(4-hydroxyphenyl)-4,5-dihydro-1H-benzo[g]indazole-3-carboxamide | ≦1 μM | 521 | 279 |
| | 473.92 | 8-[(5-amino-chlorobenzoyl)amino]-1-(4-hydroxyphenyl)-4,5-dihydro-1H-benzo[g]indazole-3-carboxamide | ≦1 μM | 474 | 280 |

TABLE 10-continued

| Compound No., Structure Mol. | Mol. Wt. | Compound Name(s) | IKK2 Resin IC50 | MS (M + H) | Example |
|---|---|---|---|---|---|
| | 459.90 | 8-[(3-chloroisonicotnoyl)amino]-1-(3-hydroxyphenyl)-4,5-dihydro-1H-benzo[g]indazole-3-carboxamide | ≦1 μM | 460 | 281 |
| | 510.38 | 8-[(5-amino-2-chlorobenzoyl)amino]-1-(3-hydroxyphenyl)-4,5-dihydro-1H-benzo[g]indazole-3-carboxamide hydrochloride | ≦1 μM | 511 | 282 |
| | 488.94 | 8-[(2-chloro-4-methoxybenzoyl)amino]-1-(3-hydroxyphenyl)-4,5-dihydro-1H-benzo[g]indazole-3-carboxamide | ≦1 μM | 489 | 283 |
| | 459.90 | 8-{[(2-chloropyridin-3-yl)carbonyl]amino}-1-(3-hydroxyphenyl)-4,5-dihydro-1H-benzo[g]indazole-3-carboxamide | ≦1 μM | 460 | 284 |

TABLE 10-continued

| Compound No., Structure Mol. | Mol. Wt. | Compound Name(s) | IKK2 Resin IC50 | MS (M + H) | Example |
|---|---|---|---|---|---|
| | 398.44 | 1-(3-hydroxyphenyl)-8-[(methylsulfonyl)amino]-4,5-dihydro-1H-benzo[g]indazole-3-carboxamide | 1 ≦ 10 μM | 399 | 285 |
| | 518.96 | 8-[(2-chloro-3,4-dimethoxybenzoyl)amino]-1-(3-hydroxyphenyl)-4,5-dihydro-1H-benzo[g]indazole-3-carboxamide | ≦1 μM | 519 | 286 |
| | 473.92 | 8-{[(2-chloro-4-methylpyridin-3-yl)carbonyl]amino}-1-(3-hydroxyphenyl)-4,5-dihydro-1H-benzo[g]indazole-3-carboxamide | ≦1 μM | 474 | 287 |

Example 288

8-{[(2-chloropyridin-3-yl)carbonyl]amino}-1-(4-morpholin-4-ylphenyl)-4,5-dihydro-1H-benzo[g]indazole-3-carboxamide

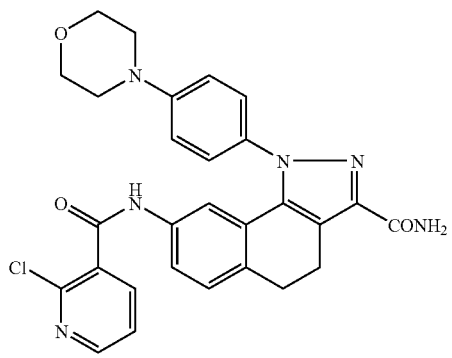

This compound was synthesized in an analogous manner to Example 3 by substituting 4-morpholinylphenylhydrazine hydrochloride and 2-chloronicotinyl chloride.; $^1$HNMR (DMSO, 400 MHz) δ: 10.39 (s, 1H), 8.50 (d, 1H), 7.94 (d, 1H), 7.05–7.53 (m, 10H), 3.74 (m, 4H), 3.18 (m, 4H), 2.92 (m, 4H); Anal. Calcd. for $C_{28}H_{25}ClN_6O_3$: C, 63.57; H, 4.76; N, 15.89. Found: C, 63.19; H, 4.61; N, 15.48. IKK-2 resin $IC_{50}$ 1≦10 μM.

Example 289

8-[(2-chlorobenzoyl)amino]-1-{4-[(1E)-3-hydroxy-3-methylbut-1-enyl]phenyl}-4,5-dihydro-1H-benzo[g]indazole-3-carboxamide

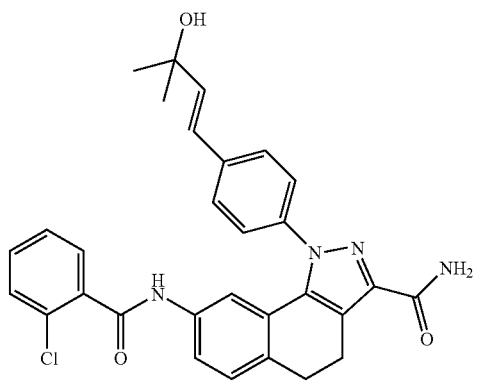

A 50 mL round bottomed flask with a magnetic stir bar was charged with 1-(4-bromophenyl)-8-[(2-chlorobenzoyl)amino]-4,5-dihydro-1H-benzo[g]indazole-3-carboxamide (987 mg, 1.89 mmol), palladium (II) acetate (44 mg, 0.19 mmol), 1,1'-biphenyl-2-yl[di(tert-butyl)]phosphine (254 mg, 0.822 mmol), and dimethylformamide (20 mL). The resulting solution was sparged with argon for 10 minutes. To the solution was added 2-methyl-3-buten-2-ol (823 mg, 6.07 mmol) and triethylamine (614 mg, 6.07 mmol). The solution was sparged with argon for an additional 2 minutes. The flask was sealed with a rubber septum and heated to 100° C. in an oil bath for 90 minutes. The reaction was allowed to cool to room temperature and water was added. The resulting precipitate was collected and purified by silica gel chromatography (100% hexane to 100% ethyl acetate). The pure fractions were combined, concentrated to dryness, triturated with diethyl ether, and dried under vacuum to give 215 mg of 8-[(2-chlorobenzoyl)amino]-1-{4-[(1E)-3-hydroxy-3-methylbut-1-enyl]phenyl}-4,5-dihydro-1H-benzo[g]indazole-3-carboxamide (0.408 mmol, 21% yield) as a solid. $^1$H NMR (400 MHz, DMSO-$d_6$) δ 1.29 (s, 6H), 2.88–2.98 (m, 4H), 4.76 (s, 1H), 6.48 (d, 1H), 6.58 (d, 1H), 7.23 (d, 1H), 7.30–7.50 (m, 8H), 7.53–7.59 (m, 3H), 10.28 (s, 1H); MS (ESI+) for $C_{30}H_{27}ClN_4O_3$ m/z 527 (M+H)$^+$.

The compounds of Example 290–308 listed in the Table 11 were prepared according to the procedure of Example 289 using the appropriate alkene.

The bioactivity in the IKK2 Resin assay for the compounds of Examples 289–308 is shown in Table 11.

TABLE 11

| Compound No., Structure | Mol. Wt. | Compound Name | IKK2 Resin IC50 | MS (M + H) | Example |
|---|---|---|---|---|---|
| (structure) | 527.03 | 8-[(2-chlorobenzoyl)amino]-1-{4-[(1E)-3-hydroxy-3-methylbut-1-enyl]phenyl}-4,5-dihydro-1H-benzo[g]indazole-3-carboxamide | ≦1 μM | 527 | 289 |
| (structure) | 541.01 | ethyl(2E)-3-(4-{3-(aminocarbonyl)-8-[(2-chlorobenzoyl)amino]-4,5-dihydro-1H-benzo[g]indazol-1-yl}phenyl)prop-2-enoate | 1 ≦ 10 μM | 541 | 290 |

TABLE 11-continued

| Compound No., Structure | Mol. Wt. | Compound Name | IKK2 Resin IC50 | MS (M + H) | Example |
|---|---|---|---|---|---|
| | 512.96 | (2E)-3-(4-{3-(aminocarbonyl)-8-[(2-chlorobenzoyl)amino]-4,5-dihydro-1H-benzo[g]indazol-1-yl}phenyl)prop-2-enoic acid | ≦1 μM | 513 | 291 |
| | 511.97 | 1-{4-[(1E)-3-amino-3-oxoprop-1-enyl]phenyl}-8-[(2-chlorobenzoyl)amino]-4,5-dihydro-1H-benzo[g]indazole-3-carboxamide | ≦1 μM | 512 | 292 |
| | 535.01 | 8-[(2-chlorobenzoyl)amino]-1-{4-[(E)-2-(1H-imidazol-1-yl)ethenyl]phenyl}-4,5-dihydro-1H-benzo[g]indazole-3-carboxamide | ≦1 μM | 535 | 293 |
| | 539.00 | 8-[(2-chlorobenzoyl)amino]-1-{4-[(E)-(2-oxodihydrofuran-3(2H)-ylidene)methyl]phenyl}-4,5-dihydro-1H-benzo[g]indazole-3-carboxamide | 1 ≦ 10 μM | 539 | 294 |

TABLE 11-continued

| Compound No., Structure | Mol. Wt. | Compound Name | IKK2 Resin IC50 | MS (M + H) | Example |
|---|---|---|---|---|---|
| | 513.00 | 8-[(2-chlorobenzoyl)amino]-1-{4-[(1E)-3-hydroxybut-1-enyl]phenyl}-4,5-dihydro-1H-benzo[g]indazole-3-carboxamide | ≦1 μM | 513 | 295 |
| | 513.00 | 8-[(2-chlorobenzoyl)amino]-1-[4-(3-oxobutyl)phenyl]-4,5-dihydro-1H-benzo[g]indazole-3-carboxamide | ≦1 μM | 513 | 296 |
| | 547.04 | 8-[(2-chlorobenzoyl)amino]-1-{4-[(E)-2-(methylsulfonyl)ethenyl]phenyl}-4,5-dihydro-1H-benzo[g]indazole-3-carboxamide | ≦1 μM | 547 | 297 |

TABLE 11-continued

| Compound No., Structure | Mol. Wt. | Compound Name | IKK2 Resin IC50 | MS (M + H) | Example |
|---|---|---|---|---|---|
| | 513.00 | 8-[(2-chlorobenzoyl)amino]-1-{4-[(1E)-4-hydroxybut-1-enyl]phenyl}-4,5-dihydro-1H-benzo[g]indazole-3-carboxamide | ≦1 μM | 513 | 298 |
| | 529.00 | 8-[(2-chlorobenzoyl)amino]-1-[4-(4-hydroxy-3-oxobutyl)phenyl]-4,5-dihydro-1H-benzo[g]indazole-3-carboxamide | ≦1 μM | 529 | 299 |
| | 499.96 | 8-{[(2-chloropyridin-3-yl)carbonyl]amino}-1-{4-[(1Z)-3-hydroxyprop-1-enyl]phenyl}-4,5-dihydro-1H-benzo[g]indazole-3-carboxamide | ≦1 μM | 500 | 300 |

TABLE 11-continued

| Compound No., Structure | Mol. Wt. | Compound Name | IKK2 Resin IC50 | MS (M + H) | Example |
|---|---|---|---|---|---|
| 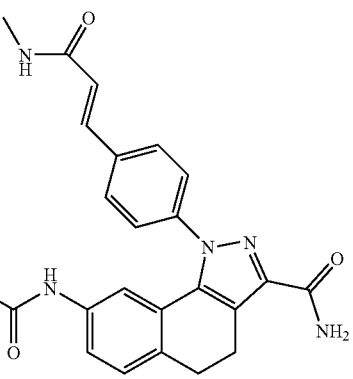 | 526.99 | 8-{[(2-chloropyridin-3-yl)carbonyl]amino}-1-{4-[(1E)-3-(methylamino)-3-oxoprop-1-enyl]phenyl}-4,5-dihydro-1H-benzo[g]indazole-3-carboxamide | ≦1 µM | 527 | 301 |
| 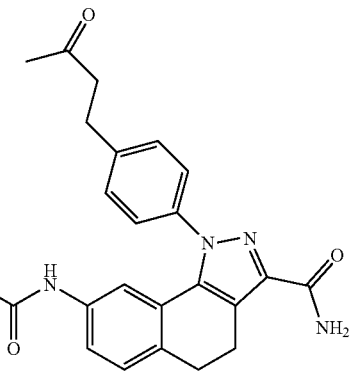 | 513.99 | 8-{[(2-chloropyridin-3-yl)carbonyl]amino}-1-[4-(3-oxobutyl)phenyl]-4,5-dihydro-1H-benzo[g]indazole-3-carboxamide | ≦1 µM | 514 | 302 |
| 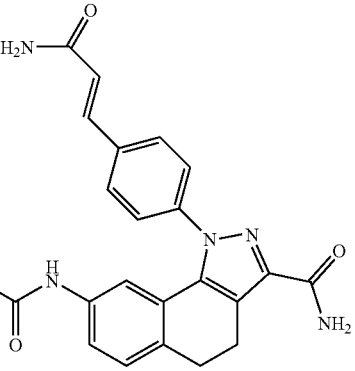 | 512.96 | 1-{4-[(1E)-3-amino-3-oxoprop-1-enyl]phenyl}-8-{[(2-chloropyridin-3-yl)carbonyl]amino}-4,5-dihydro-1H-benzo[g]indazole-3-carboxamide | ≦1 M | 513 | 303 |
| 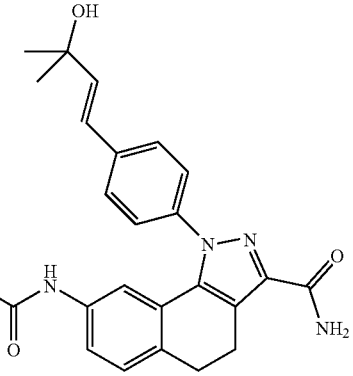 | 528.01 | 8-{[(2-chloropyridin-3-yl)carbonyl]amino}-1-{4-[(1E)-3-hydroxy-3-methylbut-1-enyl]phenyl}-4,5-dihydro-1H-benzo[g]indazole-3-carboxamide | 1 ≦ 10 µM | 528 | 304 |

| Compound No., Structure | Mol. Wt. | Compound Name | IKK2 Resin IC50 | MS (M + H) | Example |
|---|---|---|---|---|---|
| | 541.01 | 8-{[(2-chloropyridin-3-yl)carbonyl]amino}-1-{4-[(1E)-3-(dimethylamino)-3-oxoprop-1-enyl]phenyl}-4,5-dihydro-1H-benzo[g]indazole-3-carboxamide | 1 ≦ 10 μM | 541 | 305 |
| | 452.54 | 8-[(methylsulfonyl)amino]-1-[4-(3-oxobutyl)phenyl]-4,5-dihydro-1H-benzo[g]indazole-3-carboxamide | 1 ≦ 10 μM | 453 | 306 |
| | 465.54 | 1-{4-[(1E)-3-(methylamino)-3-oxoprop-1-enyl]phenyl}-8-[(methylsulfonyl)amino]-4,5-dihydro-1H-benzo[g]indazole-3-carboxamide | ≦1 μM | 566 | 307 |
| | 562.50 | 8-[(2-chlorobenzoyl)amino]-1-{4-[(1E)-3-(dimethylamino)prop-1-enyl]phenyl}-4,5-diliydro-1H-benzo[g]indazole-3-carboxamide hydrochloride | 1 ≦ 10 μM | 526 | 308 |

Example 309

8-[(2-chlorobenzoyl)amino]-1-(4-{(1E)-3-[(2-methoxyethyl)amino]-3-oxoprop-1-enyl}phenyl)-4,5-dihydro-1H-benzo[g]indazole-3-carboxamide

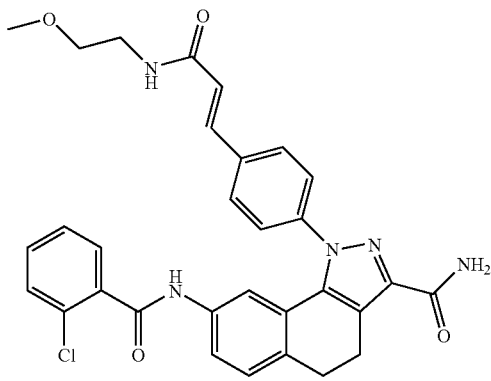

To a 50 mL syringe barrel equipped with a fritted disk was added 2.02 g of PS-MB-CHO (Argonaut Technologies, 1.46 mmol/g loading). The resin was washed with N,N-dimethylformamide. To the resin was added a solution of sodium triacetoxyborohydride (3.20 g, 15.1 mmol) dissolved in trimethylorthoformate (1.5 mL), acetic acid (1.5 mL), and N,N-dimethylformamide (12 mL). 2-Methoxyethylamine (1.11 g, 14.8 mmol) was added to the mixture. The mixture was allowed to shake on an orbital shaker for 16 hrs. The solution was drained from the resin and washed with a solution of 8 parts N,N-dimethylfromamide to 1 part trimethylorthoformate to 1 part acetic acid. The resin was then washed with N,N-dimethylformamide, 1 part N,N-dimethylformamide to 1 part triethylamine, N,N-dimethylformamide, dichloromethane, and diethyl ether. The resin was dried under vacuum.

To a 4 mL peptide flask was added 100 mg of the resin. A solution of HBTU (127 mg, 0.336 mmol), 1-hydroxybenzotriazole (52 mg, 0.38 mmol), triethylamine (34 mg, 0.34 mmol), and (2E)-3-(4-{3-(aminocarbonyl)-8-[(2-chlorobenzoyl)amino]-4,5-dihydro-1H-benzo[g]indazol-1-yl}phenyl)prop-2-enoic acid (172 mg, 0.335 mmol) in 2 mL of N,N-dimethylformamide was added to the resin. The peptide flask was agitated on an orbital shaker for 16 hrs, after which the solution was drained and the resin was washed with DMF, dichloromethane, and diethyl ether. The resin was dried under vacuum.

The resin was suspended in 2 mL of 90% aqueous trifluoroacetic acid and agitated for 30 minutes. The solution was filtered. The resin was washed 10 with 2 mL of 90% aqueous trifluoroacetic acid, with the wash being collected. The TFA solutions were combined, diluted to 15 mL with water, and concentrated to dryness. The resulting oil was triturated with methanol to yield the title compound. MS (ESI+) for $C_{31}H_{28}ClN_5O_4$ m/z 570.2 (M+H)$^+$.

The compounds of Examples 310–315 listed in the Table 12 were prepared according to the procedure of Example 309 using the appropriate amine.

The bioactivity in the IKK2 Resin assay for the compounds of Examples 309–315 is shown in Table 12.

TABLE 12

| Compound No., Structure | Mol. Wt. | Compound Name(s) | IKK2 Resin IC50 | MS (M + H) | Example |
|---|---|---|---|---|---|
| | 570.0 | 8-[(2-chlorobenzoyl)amino]-1-(4-{(1E)-3-[(2-methoxyethyl)amino]-3-oxoprop-1-enyl}phenyl)-4,5-dihydro-1H-benzo[g]indazole-3-carboxamide | ≦1 μM | 570 | 309 |
| | 592.1 | 8-[(2-chlorobenzoyl)amino]-1-(4-{(1E)-3-[(2-furylmethyl)amino]-3-oxoprop-1-enyl}phenyl)-4,5-dihydro-1H-benzo[g]indazole-3-carboxamide | ≦1 μM | 592 | 310 |

TABLE 12-continued

| Compound No., Structure | Mol. Wt. | Compound Name(s) | IKK2 Resin IC50 | MS (M + H) | Example |
|---|---|---|---|---|---|
| | 526.0 | 8-[(2-chlorobenzoyl)amino]-1-{4-[(1E)-3-(methylamino)-3-oxoprop-1-enyl]phenyl}-4,5-dihydro-1H-benzo[g]indazole-3-carboxamide | ≦1 μM | 526 | 311 |
| | 540.0 | 8-[(2-chlorobenzoyl)amino]-1-{4-[(1E)-3-(ethylamino)-3-oxoprop-1-enyl]phenyl)-4,5-dihydro-1H-benzo[g]indazole-3-carboxamide e | ≦1 μM | 540 | 312 |
| | 602.1 | 1-{4-[(1E)-3-(benzylamino)-3-oxoprop-1-enyl]phenyl}-8-[(2-chlorobenzoyl)amino]-4,5-dihydro-1H-benzo[g]indazole-3-carboxamide | 1 ≦ 10 μM | 602 | 313 |

TABLE 12-continued

| Compound No., Structure | Mol. Wt. | Compound Name(s) | IKK2 Resin IC50 | MS (M + H) | Example |
|---|---|---|---|---|---|
| (structure) | 387.44 | 8-amino-1-{4-[(1E)-3-(methylamino)-3-oxoprop-1-enyl]phenyl}-4,5-dihydro-1H-benzo[g]indazole-3-carboxamide | 1 ≦ 10 μM | 388 | 314 |
| (structure) | 479.56 | 1-{4-[(1E)-3-(dimethylamino)-3-oxoprop-1-enyl]phenyl}-8-[(methylsulfonyl)amino]-4,5-dihydro-1H-benzo[g]indazole-3-carboxamide | 1 ≦ 10 μM | 480 | 315 |

Example 316

8-{[(2-chloropyridin-3-yl)carbonyl]amino}-1-[4-(3-hydroxypropyl)phenyl]-4,5-dihydro-1H-benzo[g]indazole-3-carboxamide

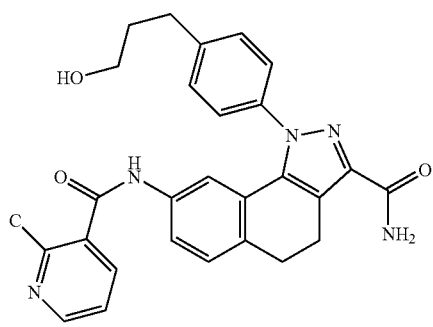

Using standard hydrogenation conditions 8-{[(2-chloropyridin-3-yl)carbonyl]amino}-1-{4-[(1Z)-3-hydroxyprop-1-enyl]phenyl}-4,5-dihydro-1H-benzo[g]indazole-3-carboxamide was converted to 8-{[(2-chloropyridin-3-yl)carbonyl]amino}-1-[4-(3-hydroxypropyl)phenyl]-4,5-dihydro-1H-benzo[g]indazole-3-carboxamide. MS (ESI+) for m/z 502 (M+H)⁺. IKK-2 resin IC$_{50}$≦1 μM.

Example 317

8-[(2-chlorobenzoyl)amino]-1-[4-(3-furyl)phenyl]-4,5-dihydro-1H-benzo[g]indazole-3-carboxamide

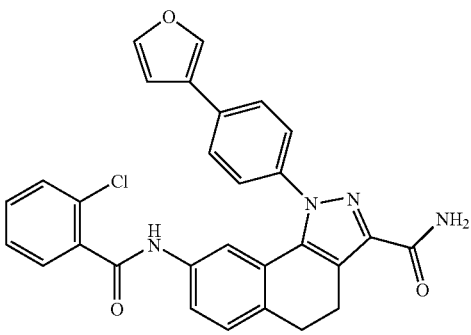

Step 1: A suspension of ethyl 1-(4-bromophenyl)-8-nitro-4,5-dihydro-1H-benzo[g]indazole-3-carboxylate (4.4 g) in THF (80 mL) was treated with 1 N aq. NaOH (80 mL) and stirred vigorously overnight. The reaction mixture was diluted with ethyl acetate and acidified to pH=2 with 1 N aq. HCl. The organic layer was separated and the aqueous fraction extracted with EtOAc (3×). Combined extracts were washed with brine, dried over Na$_2$SO$_4$, filtered and concentrated in vacuo to afford 4.0 g (97%) of 1-(4-bromophenyl)-8-nitro-4,5-dihydro-1H-benzo[g]indazole-3-carboxylic acid as a solid: MS(ESI+) 414 [M+H]$^+$. $^1$H NMR (400 MHz, d$^6$ DMSO) δ 8.07 (dd, 1H), 7.83 (d, 2H), 7.66 (d, 1H), 7.56 (d, 2H), 7.42 (d, 1H), 3.10 (m, 2H), 2.99 (m, 2H).

Step 2: A suspension of Rink amide resin (5.3 g, 2.5 mmol, 0.47 meq/g, NovaBiochem), in 30% piperidine/DMF was prepared in a solid phase reactor equipped with an overhead stirrer. The mixture was stirred for 15 min, filtered, and treated a second time with 30% piperidine/DMF for 15 min. The solvent was removed by filtration and the resin washed with DMF (3×), MeOH (3×), and DCM (4×). A solution of 1-(4-bromophenyl)-8-nitro-4,5-dihydro-1H-benzo[g]indazole-3-carboxylic acid (2.07 g) in 1:1 DCM/DMF (10 mL) was prepared and added to the resin, followed by 1M HOBt in DMF (5 mL) and 1M DIC in DMF (5 mL). The resin was stirred at RT. After stirring for 16 h, the resin was washed with DMF (3×), MeOH (3×), DCM (4×), and filter to afford loaded resin. Resin loading was determined by direct cleavage $^1$H NMR: 0.569 mmol/g. Evaporated direct cleavage NMR sample from the resin gave an oil: MS(ESI+) 413 [M+H]$^+$. $^1$H NMR (400 MHz, 10% TFA/CDCl$_3$): δ 8.10 (dd, 1H), 7.76 (d, 2H), 7.63 (d, 1H), 7.53 (d, 1H), 7.41 (d, 2H), 3.16 (m, 4H).

Step 3: In a solid phase reactor equipped with an overhead stirrer to a suspension of resin from step 2 (7.8 g, 4.43 mmol) in NMP (15 mL) was added 2M SnCl$_2$ in NMP (15 mL). The mixture was stirred for 1 h, filtered, and retreated with 2M SnCl$_2$ in NMP (15 mL). After stirring overnight the resin was filtered, washed with DMF (3×), MeOH (3×), DCM (4×), filtered, and air dried to afford the intermediate amine resin. Determined resin loading by direct cleavage $^1$H NMR: 0.414 mmol/g. In a solid phase reactor equipped with an overhead stirrer was prepared a suspension of 0.4 g of the amine resin in NMP.

Step 4: The resin was allowed to stir for 5 min and subsequently treated with a solution of 2-chlorobenzoic acid (126 mg) in NMP (1 mL). The mixture was treated with HATU (307 mg), DIEA (0.28 mL) and stirred for 1 h. The resultant resin was filtered, subjected to a second treatment of 2-chlorobenzoic acid, HATU and DIEA in NMP, and allowed to stir. After stirring overnight, the resin was filtered, washed with DMF (3×), MeOH (3×), and DCM (4×). The resin was filtered and air dried to afford resin. Determined resin loading by direct cleavage $^1$H NMR: 0.702 mmol/g.

Step 5: To a reaction vessel was added resin from step 4 (0.20 g, 0.09 mmol) in a suspension of toluene/EtOH (2:1). The vessels were purged with argon for 5 min and subsequently treated with Pd(PPh$_3$)$_4$ (41.6 mg, 0.036 mmol), an 3-furylboronic acid (0.2 mmol), and 2M Na$_2$CO$_3$ (200 µL, 0.4 mmol). The vessels were heated to 100° C. and allowed to agitate for 30 h. Each vessel was quenched with 25% NH$_4$OH for 30 min, filtered and washed three times each with DMF, MeOH, MeOH:H20 (1:1), 0.2N HCl, MeOH:H20 (1:1), MeOH and DCM. The resins were allowed to dry and cleaved with 10% TFA/DCM (2 mL) for 30 min. The resins were washed twice with 0.5 mL DCM and the combined filtrates concentrated to afford the desired final product.

The compounds of Examples 318–323 listed in the Table 13 were prepared according to the procedure of Example 317 using the appropriate boronic acid in step 5.

The bioactivity in the IKK2 Resin assay for the compounds of Examples 316–323 is shown in Table 13.

TABLE 13

| Compound No., Structure | Mol. Wt. | Compound Name | IKK2 Resin IC50 | MS (M + H) | Example |
| --- | --- | --- | --- | --- | --- |
| | 501.96 | 8-{[(2-chloropyridin-3-yl)carbonyl]amino}-1-[4-(3-hydroxypropyl)phenyl]-4,5-dihydro-1H-benzo[g]indazole-3-carboxamide | ≦1 µM | 502 | 316 |
| | 508.97 | 8-[(2-chlorobenzoyl)amino]-1-[4-(3-furyl)phenyl]-4,5-dihydro-1H-benzo[g]indazole-3-carboxamide | 1 ≦ 10 µM | 509 | 317 |

TABLE 13-continued

| Compound No., Structure | Mol. Wt. | Compound Name | IKK2 Resin IC50 | MS (M + H) | Example |
|---|---|---|---|---|---|
| | 520.00 | 8-[(2-chlorobenzoyl)amino]-1-(4-pyridin-3-ylphenyl)-4,5-dihydro-1H-benzo[g]indazole-3-carboxamide | 1 ≦ 10 μM | 520 | 318 |
| | 549.03 | 8-[(2-chlorobenzoyl)amino]-1-[3'-(hydroxymethyl)-1,1'-biphenyl-4-yl]-4,5-dihydro-1H-benzo[g]indazole-3-carboxamide | 1 ≦ 10 μM | 549 | 319 |
| | 534.02 | 1-(3'-amino-1,1'-biphenyl-4-yl)-8-[(2-chlorobenzoyl)amino]-4,5-dihydro-1H-benzo[g]indazole-3-carboxamide | 1 ≦ 10 μM | 534 | 320 |
| | 563.02 | 4'-{3-(aminocarbonyl)-8-[(2-chlorobenzoyl)amino]-4,5-dihydro-1H-benzo[g]indazol-1-yl}-1,1'-biphenyl-3-carboxylic acid | 1 ≦ 10 μM | 563 | 321 |

TABLE 13-continued

| Compound No., Structure | Mol. Wt. | Compound Name | IKK2 Resin IC50 | MS (M + H) | Example |
|---|---|---|---|---|---|
| 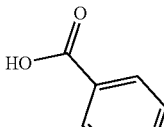 | 563.02 | 4'-{3-(aminocarbonyl)-8-[(2-chlorobenzoyl)amino]-4,5-dihydro-1H-benzo[g]indazol-1-yl}-1,1'-biphenyl-4-carboxylic acid | 1 ≦ 10 μM | 563 | 322 |
| 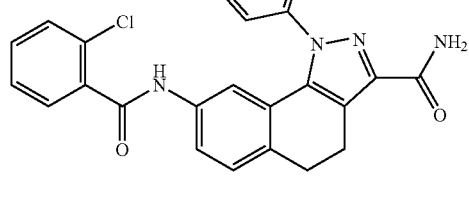 | 579.06 | 8-[(2-chlorobenzoyl)amino]-1-(3',4'-dimethoxy-1,1'-biphenyl-4-yl)-4,5-dihydro-1H-benzo[g]indazole-3-carboxamide | 1 ≦ 10 μM | 579 | 323 |

The compounds of Examples 324–366 in Table 14 were prepared in a manner analogous to Example 3 using the appropriate hydrazine and acylating or sulfonating agent. The bioactivity in the IKK2 Resin assay for the compounds of Examples 324–366 is shown in Table 14.

TABLE 14

| Compound No., Structure | Mol. Wt. | Compound Name(s) | IKK2 Resin IC50 | MS (M + H) | Example |
|---|---|---|---|---|---|
| 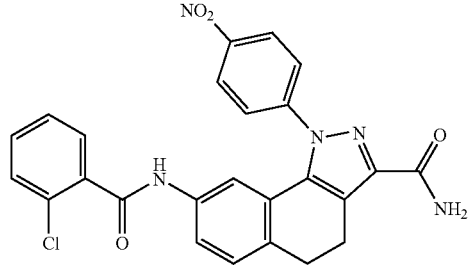 | 487.91 | 8-[(2-chlorobenzoyl)amino]-1-(4-nitrophenyl)-4,5-dihydro-1H-benzo[g]indazole-3-carboxamide | ≦1 μM | 488 | 324 |

TABLE 14-continued

| Compound No., Structure | Mol. Wt. | Compound Name(s) | IKK2 Resin IC50 | MS (M + H) | Example |
|---|---|---|---|---|---|
| | 487.91 | 8-[(2-chlorobenzoyl)amino]-1-(3-nitrophenyl)-4,5-dihydro-1H-benzo[g]indazole-3-carboxamide | 1 ≦ 10 μM | 488 | 325 |
| | 511.80 | 8-[(2-chlorobenzoyl)amino]-1-(3,4-dichlorophenyl)-4,5-dihydro-1H-benzo[g]indazole-3-carboxamide | 1 ≦ 10 μM | 512 | 326 |
| | 443.90 | 8-[(2-chlorobenzoyl)amino]-1-pyridin-3-yl-4,5-dihydro-1H-benzo[g]indazole-3-carboxamide | 1 ≦ 10 μM | 444 | 327 |
| | 442.91 | 8-[(2-chlorobenzoyl)amino]-1-phenyl-4,5-dihydro-1H-benzo[g]indazole-3-carboxamide | ≦1 μM | 443 | 328 |
| | 486.92 | 4-{3-(aminocarbonyl)-8-[(2-chlorobenzoyl)amino]-4,5-dihydro-1H-benzo[g]indazol-1-yl}benzoic acid | 1 ≦ 10 μM | 487 | 329 |

TABLE 14-continued

| Compound No., Structure | Mol. Wt. | Compound Name(s) | IKK2 Resin IC50 | MS (M + H) | Example |
|---|---|---|---|---|---|
| | 382.44 | 8-[(methylsulfonyl)amino]-1-phenyl-4,5-dihydro-1H-benzo[g]indazole-3-carboxamide | 1 ≦ 10 μM | 383 | 330 |
| | 443.90 | 8-[(3-chloroisonicotinoyl)amino]-1-phenyl-4,5-dihydro-1H-benzo[g]indazole-3-carboxamide | ≦1 μM | 444 | 331 |
| | 477.35 | 8-[(2-chlorobenzoyl)amino]-1-(4-chlorophenyl)-4,5-dihydro-1H-benzo[g]indazole-3-carboxamide | ≦1 μM | 478 | 332 |
| | 526.91 | 8-[(2-chlorobenzoyl)amino]-1[4-(trifluoromethoxy)phenyl]-4,5-dihydro-1H-benzo[g]indazole-3-carboxamide | 1 ≦ 10 μM | 527 | 333 |
| | 477.35 | 8-[(2-chlorobenzoyl)amino]-1-(3-chlorophenyl)-4,5-dihydro-1H-benzo[g]indazole-3-carboxamide | ≦1 μM | 478 | 334 |

TABLE 14-continued

| Compound No., Structure | Mol. Wt. | Compound Name(s) | IKK2 Resin IC50 | MS (M + H) | Example |
|---|---|---|---|---|---|
| | 456.94 | 8-[(2-chlorobenzoyl)amino]-1-(4-methylphenyl)-4,5-dihydro-1H-benzo[g]indazole-3-carboxamide | ≦1 μM | 457 | 335 |
| | 456.94 | 8-[(2-chlorobenzoyl)animo]-1-(3-methylphenyl)-4,5-dihydro-1H-benzo[g]indazole-3-carboxamide | ≦1 μM | 457 | 3336 |
| | 484.99 | 8-[(2-chlorobenzoyl)amino]-1-(4-isopropylphenyl)-4,5-dihydro-1H-benzo[g]indazole-3-carboxamide | 1 ≦ 10 μM | 485 | 337 |
| | 443.89 | 8-[(2-chlorobenzoyl)amino]-1-pyridin-4-yl-4,5-dihydro-1H-benzo[g]indazole-3-carboxamide | ≦1 μM | 444 | 338 |

TABLE 14-continued

| Compound No., Structure | Mol. Wt. | Compound Name(s) | IKK2 Resin IC50 | MS (M + H) | Example |
|---|---|---|---|---|---|
| | 460.89 | 8-[(2-chlorobenzoyl)amino]-1-(3-fluorophenyl)-4,5-dihydro-1H-benzo[g]indazole-3-carboxamide | ≦1 μM | 461 | 339 |
| | 372.35 | 8-amino-1-[4-(trifluoromethyl)phenyl]-4,5-dihydro-1H-benzo[g]indazole-3-carboxamide | 1 ≦ 10 μM | 373 | 340 |
| | 460.89 | 8-[(2-chlorobenzoyl)amino]-1-(2-fluorophenyl)-4,5-dihydro-1H-benzo[g]indazole-3-carboxamide | ≦1 μM | 461 | 341 |
| | 462.43 | 8-[(2,3-difluorobenzoyl)amino]-1-(3-fluorophenyl)-4,5-dihydro-1H-benzo[g]indazole-3-carboxamide | 1 ≦ 10 μM | 463 | 342 |

TABLE 14-continued

| Compound No., Structure | Mol. Wt. | Compound Name(s) | IKK2 Resin IC50 | MS (M + H) | Example |
|---|---|---|---|---|---|
| *(structure)* | 498.51 | 3-({[3-(aminocarbonyl)-1-(3-fluorophenyl)-4,5-dihydro-1H-benzo[g]indazol-8-yl]amino}carbonyl)-2-methylphenyl acetate | 1 ≦ 10 μM | 499 | 343 |
| *(structure)* | 495.34 | 8-[(2,3-dichlorobenzoyl)amino]-1-(3-fluorophenyl)-4,5-dihydro-1H-benzo[g]indazole-3-carboxamide | 1 ≦ 10 μM | 496 | 344 |
| *(structure)* | 461.88 | 8-{[(2-chloropyridin-3-yl)carbonyl]amino}-1-(3-fluorophenyl)-4,5-dihydro-1H-benzo[g]indazole-3-carboxamide | ≦1 μM | 462 | 345 |
| *(structure)* | 478.88 | 8-[(2-chlorobenzoyl)amino]-1-(3,5-difluorophenyl)-4,5-dihydro-1H-benzo[g]indazole-3-carboxamide | ≦1 μM | 479 | 346 |

TABLE 14-continued

| Compound No., Structure | Mol. Wt. | Compound Name(s) | IKK2 Resin IC50 | MS (M + H) | Example |
|---|---|---|---|---|---|
| | 479.87 | 8-{[(2-chloropyridin-3-yl)carbonyl]amino}-1-(3,5-difluorophenyl)-4,5-dihydro-1H-benzo[g]indazole-3-carboxamide | ≦1 μM | 480 | 347 |
| | 513.33 | 8-[(2,3-dichlorobenzoyl)amino]-1-(3,5-difluorophenyl)-4,5-dihydro-1H-benzo[g]indazole-3-carboxamide | 1 ≦ 10 μM | 513 | 348 |
| | 510.91 | 8-[(2-chlorobenzoyl)amino]-1-[4-(trifluoromethyl)phenyl]-4,5-dihydro-1H-benzo[g]indazole-3-carboxamide | 1 ≦ 10 μM | 511 | 349 |
| | 521.81 | 1-(4-bromophenyl)-8-[(2-chlorobenzoyl)amino]-4,5-dihydro-1H-benzo[g]indazole-3-carboxamide | ≦1 μM | 521 | 350 |

TABLE 14-continued

| Compound No., Structure | Mol. Wt. | Compound Name(s) | IKK2 Resin IC50 | MS (M + H) | Example |
|---|---|---|---|---|---|
| | 501.39 | 1-(4-bromophenyl)-8-[(2-methylbenzoyl)amino]-4,5-dihydro-1H-benzo[g]indazole-3-carboxamide | ≦1 μM | 502 | 351 |
| | 383.25 | 8-amino-1-(4-bromophenyl)-4,5-dihydro-1H-benzo[g]indazole-3-carboxamide | 1 ≦ 10 μM | 383 | 352 |
| | 478.89 | 8-[(2-chlorobenzoyl)amino]-1-(2,4-difluorophenyl)-4,5-dihydro-1H-benzo[g]indazole-3-carboxamide | ≦1 μM | 479 | 353 |
| | 479.87 | 8-[(3-chloroisonicotinoyl)amino]-1-(3,4-difluorophenyl)-4,5-dihydro-1H-benzo[g]indazole-3-carboxamide | ≦1 μM | 480 | 354 |
| | 479.87 | 8-[(3-chloroisonicotinoyl)amino]-1-(3,5-difluorophenyl)-4,5-dihydro-1H-benzo[g]indazole-3-carboxamide | ≦1 μM | 480 | 355 |

TABLE 14-continued

| Compound No., Structure | Mol. Wt. | Compound Name(s) | IKK2 Resin IC50 | MS (M + H) | Example |
|---|---|---|---|---|---|
| | 495.34 | 8-[(2-chlorobenzoyl)amino]-1-(3-chloro-4-fluorophenyl)-4,5-dihydro-1H-benzo[g]indazole-3-carboxamide | ≦1 μM | 495 | 356 |
| | 436.42 | 8-amino-1-{4-[(trifluoromethyl)sulfonyl]phenyl}-4,5-dihydro-1H-benzo[g]indazole-3-carboxamide | 1 ≦ 10 μM | 437 | 357 |
| | 612.42 | 8-[(3-chloroisonicotinoyl)amino]-1-{4-[(trifluoromethyl)sulfonyl]phenyl}-4,5-dihydro-1H-benzo[g]indazole-3-carboxamide hydrochloride | ≦1 μM | 576 | 358 |
| | 575.96 | 8-{[(2-chloropyridin-3-yl)carbonyl]amino}-1-{4-[(trifluoromethyl)sulfonyl]phenyl}-4,5-dihydro-1H-benzo[g]indazole-3-carboxamide | ≦1 μM | 576 | 359 |
| | 478.34 | 1-(4-chlorophenyl)-8-{[(4-chloropyridin-3-yl)carbonyl]amino}-4,5-dihydro-1H-benzo[g]indazole-3-carboxamide | ≦1 μM | 478 | 360 |

TABLE 14-continued

| Compound No., Structure | Mol. Wt. | Compound Name(s) | IKK2 Resin IC50 | MS (M + H) | Example |
|---|---|---|---|---|---|
| | 472.94 | 8-[(2-chlorobenzoyl)amino]-1-{3-methoxyphenyl)-4,5-dihydro-1H-benzo[g]indazole-3-carboxamide | 1 ≦ 10 μM | 473 | 361 |
| | 478.88 | 8-[(3-chloro-2-fluorobenzoyl)amino]-1-(3-fluorophenyl)-4,5-dihydro-1H-benzo[g]indazole-3-carboxamide | 1 ≦ 10 μM | 479 | 362 |
| | 478.88 | 8-[(2-chlorobenzoyl)amino]-1-(3,4-difluorophenyl)-4,5-dihydro-1H-benzo[g]indazole-3-carboxamide | ≦1 μM | 479 | 363 |
| | 479.87 | 8-{[(2-chloropyridin-3-yl)carbonyl]amino}-1-(3,4-difluorophenyl)-4,5-dihydro-1H-benzo[g]indazole-3-carboxamide | ≦1 μM | 480 | 364 |

TABLE 14-continued

| Compound No., Structure | Mol. Wt. | Compound Name(s) | IKK2 Resin IC50 | MS (M + H) | Example |
|---|---|---|---|---|---|
|  | 513.33 | 8-[(2,3-dichlorobenzoyl)amino]-1-(3,4-difluorophenyl)-4,5-dihydro-1H-benzo[g]indazole-3-carboxamide | 1 ≦ 10 μM | 513 | 365 |
|  | 479.88 | 8-{[(2-chloropyridin-3-yl)carbonyl]amino}-1-(2,4-difluorophenyl)-4,5-dihydro-1H-benzo[g]indazole-3-carboxamide | ≦1 μM | 480 | 366 |

Example 367

8-[(2-chlorobenzoyl)amino]-1-[5-(methylsulfonyl)pyridin-2-yl]-4,5-dihydro-1H-benzo[g]indazole-3-carboxamide

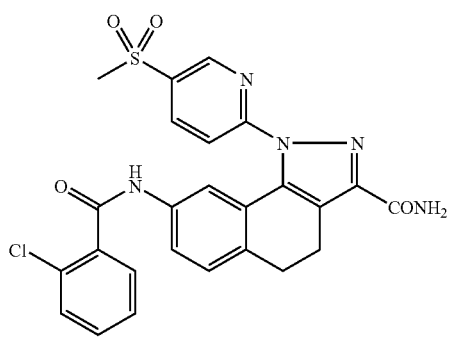

Step 1

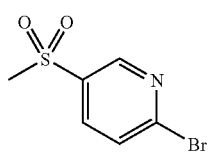

To a suspension of 2,5-dibromopyridine (12.0 g, 0.05 mol) in ether was added ⁿBuLi (32 mL of 1.6 N in hexane, 0.05 mol) at −78° C. dropwise. The purple suspension was stirred for 1 hour and then treated with dimethyl disulfide. The reaction mixture was kept at this temperature for 1 h and ½ h at 0° C. The reaction was quenched with a mixture of concentrated HCl and ether. The organic phase was washed with brine, dried over MgSO₄, and filtered. The filtrate was concentrated to give 10.3 g of crude as brown oil, which was used without purification. To a solution of this crude (10.0 g, 0.05 mol) in methanol (200 mL) was added a solution of OXONE® in 300 mL of water. The reaction was stirred at room temperature for 72 h. Solvent was removed and the residue was basified with 50% NaOH solution. The precipitate was collected by filtration, air-dried to give 8.2 g of product as a white crystal (72% yield over two step). NMR spectrum was consistent with the proposed structure.

Step 2

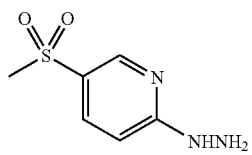

A mixture of the product from step 1 (8.0 g, 0.034 mol) and hydrazine (2.3 g, 0.068 mol) in 100 mL of ethanol was heated at reflux for 2 h. cooled to room temperature, and the solid was collected by filtration, washed with sat. NaHCO₃, water, air-dried to give 4.0 g of crude as a pale white solid (63% yield); NMR spectrum was consistent with the proposed structure.

Step 3

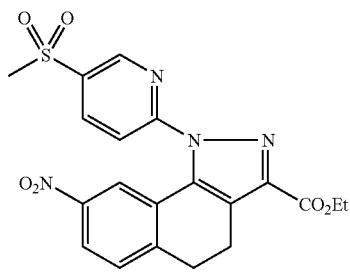

A mixture of the product from step 2 (1.4 g, 0.007 mol) and ethyl (7-nitro-1-oxo-1,2,3,4-tetrahydronaphthalen-2-yl)(oxo)acetate (2.03 g, 0.007 mol) in 75 mL of acetic acid was heated at reflux under nitrogen for 3 h. The solvent was removed and the residue was treated with a mixture of methanol/ethyl acetate/ether to give 1.67 g of the product as a yellow solid (54% yield); $^1$HNMR (DMSO, 400 MHz) δ: 8.98 (dd, 1H), 8.68 (dd, 1H), 8.21 (d, 1H), 8.13 (dd, 1H), 7.95 (d, 1H), 7.68 (d, 1H), 4.37 (q, 2H), 3.42 (s, 3H), 3.11 (m, 2H), 3.00 (m, 2H), 1.35 (t, 3H); Anal. Calcd. for $C_{20}H_{18}N_4O_6S$: C, 54.29; H, 4.10; N, 12.66; S, 7.23. Found: C, 53.71; H, 4.41; N, 12.56; S, 7.14.

Step 4

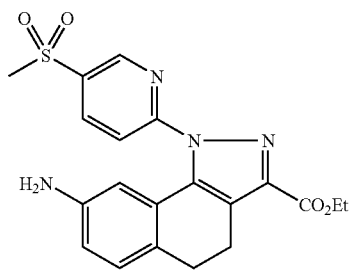

The product from step 3 (1.6 g, 0.0036 mol) was hydrogenated in a Parr shaker with 20% Pd(OH)$_2$/C in acetic acid for 2 h at 5 psi. After the removal of solvent, the residue was triturated with a mixture of methanol and ether to give 1.0 g of the product as a white solid (67% yield): $^1$HNMR (DMSO, 400 MHz) δ: 9.01 (dd, 1H), 8.62 (dd, 1H), 8.07 (dd, 1H), 7.01 (d, 1H), 6.46 (dd, 1H), 6.12 (d, 1H), 4.90 (brs, 2H), 4.33 (q, 2H), 3.42 (s, 3H), 2.87 (m, 2H), 2.78 (m, 2H), 1.33 (t, 3H); Anal. Calcd. for $C_{20}H_{20}N_4O_4S$: C, 58.24; H, 4.89; N, 13.58; S, 7.77. Found: C, 57.70; H, 4.68; N, 13.43; S, 7.60.

Step 5

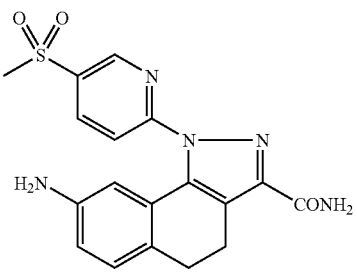

To a suspension of the product from step 4 (0.95 g, 0.0023 mol) in 25 mL of methanol was added liquid ammonia through a dry-ice condenser. The solution was sealed with a septum and stirred at room temperature for 48 h. Solvent was removed and the solid was triturated with methanol to give 0.68 g of product as a yellow solid (77% yield): $^1$HNMR (CDCl$_3$, 400 MHz) δ: 8.99 (d, 1H), 8.63 (ddd, 1H), 8.10 (d, 1H), 7.66 (s, 1H), 7.43 (s, 1H), 7.00 (d, 1H), 6.45 (d, 1H), 6.22 (s, 1H), 4.89 (s, 2H), 3.41 (s, 3H), 2.86 (m, 2H), 2.74 (m, 2H); Anal. Calcd. for $C_{18}H_{17}N_5O_3S$: C, 56.39; H, 4.47; N, 18.27; S, 8.36. Found: C, 55.48; H, 4.29; N, 17.84; S, 8.19.

Step 6

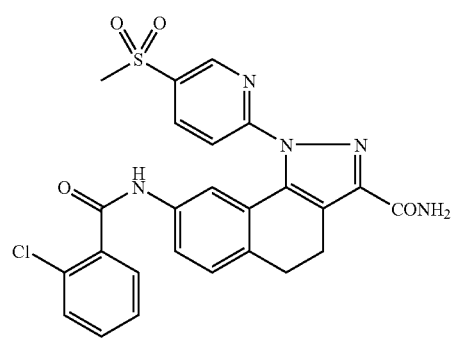

To a suspension of the product from step 5 (0.62 g, 0.0016 mol) in 10 mL of pyridine was added 2-chlorobenzoyl chloride (0.29 g, 0.0016 mol) in one portion and the reaction mixture was stirred at room temperature overnight. Solvent was removed and the residue was partitioned between ethyl acetate and water. The organic phase was washed with brine, dried over MgSO4, and filtered. The filtrate was concentrated and purified by chromatography on silica gel (ethyl acetate) to give 0.6 g of the product as a yellow solid (72% yield); $^1$HNMR (DMSO, 400 MHz) δ: 10.36 (s, 1H), 9.00 (d, 1H), 8.62 (dd, 1H), 8.15 (d, 1H), 7.74 (s, 1H), 7.39–7.54 (m, 7H), 7.34 (d, 1H), 3.32 (s, 3H), 2.93 (m, 4H); Anal. Calcd. for $C_{25}H_{20}ClN_5O_4S$: C, 57.53; H, 3.86; N, 13.42; S, 6.14. Found: C, 56.69; H, 4.37; N, 12.82; S, 5.86. IKK-2 resin IC$_{50}$ ≦ 1 μM.

Example 368

8-[(2-chlorobenzoyl)amino]-1-[6-(methylsulfonyl)pyridin-3-yl]-4,5-dihydro-1H-benzo[g]indazole-3-carboxamide

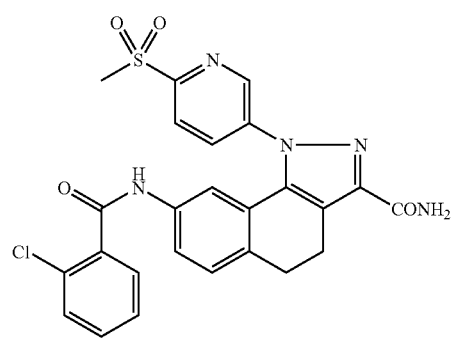

Step 1

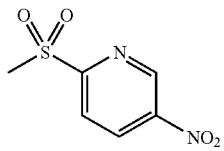

Steps 3–6

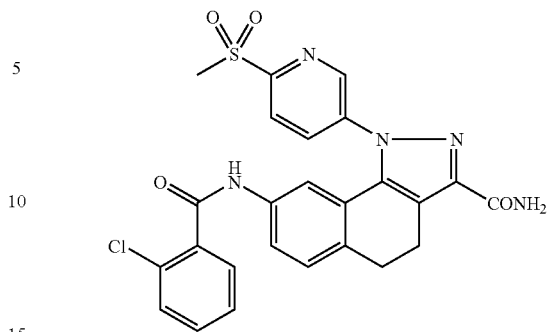

A mixture of 2-chloro-5-nitropyridine (20.5 g, 0.13 mol) and sodium thiomethoxide (10.9 g, 0.16 mol) in DMS was heated at 100° C. under nitrogen for 3 h. Cooled to room temperature and water was added. The precipitate was collected, air-dried to give 14.5 g of product as a brown solid. To a solution of this solid (16.5 g, 0.097 mol) in 100 mL of acetone was added 170 mL of 2N sulfuric acid solution. Then a solution of $KMnO_4$ (20.0 g, 0.126 mol) in 375 mL of water was added dropwise to the above suspension. The reaction mixture was stirred at RT overnight and then it was filtered. The solid was stirred with 400 mL of hot ethanol, then cooled and filtered. The filtrate was concentrated to half volume and the precipitate was collected and air-dried to give 12.5 g of the desired product as a pale yellow solid, which was used without further purification. The NMR and MS were consistent with the proposed structure.

The title compound was synthesized by using the same procedure from step 3 to step 6 for Example 367 except using the above hydrazine; $^1$H NMR (DMSO, 400 MHz) 10.38 (s,1H), 9.08 (s, 1H), 1H), 8.41 (d, 1H), 8.25 (d, 1H), 7.71 (s, 1H), 7.35–7.53 (m, 8H), 3.28 (s, 3H), 2.96 (m, 4H); Anal. Calcd. for $C_{25}H_{20}ClN_5O_4S$: C, 57.53; H, 3.86; N, 13.42; S, 6.14. Found: C, 56.62; H, 4.09; N, 13.09; S, 5.99. IKK-2 resin $IC_{50} \leq 1$ μM.

Example 369

8-[(2-chlorobenzoyl)amino]-1-(4-cyanophenyl)-4,5-dihydro-1H-benzo[g]indazole-3-carboxamide Step 2

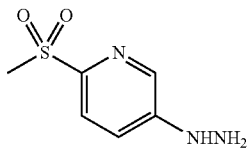

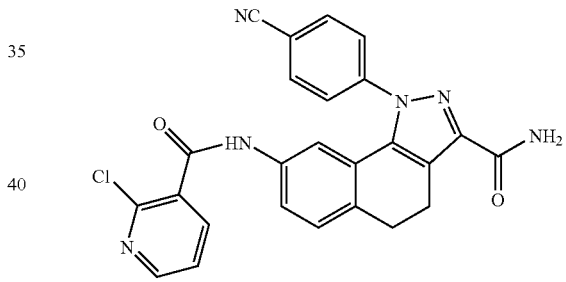

A mixture of the product from step 1 (12.3 g, 0.061 mol), iron (6.5 g, 0.11 mol) and 1 mL of acetic acid in 250 mL of water was heated at reflux for 4 h. Cooled to room temperature, 400 mL of sat. $NaHCO_3$ solution was added and extracted with ethyl acetate. The organic layer was washed with brine, dried over $MgSO_4$, and concentrated to give 3.5 g of crude as a dark brown solid. To a solution of this crude in conc. HCl at −10° C. was added a solution of $NaNO_2$ dropwise. The mixture was stirred at this temperature for 2 h and then a solution tin chloride in conc. HCl was added slowly to keep the temperature under −5° C. The reaction was stirred overnight while allowing to warm up to RT. NaOH solution was added to adjust pH to 9 and filtered through a pad of Celite®. The aqueous phase was extracted with THF and the organic layer was washed with brine, dried over MgSO4, and concentrated. The crude was triturated with methanol to give the hydrazine as a yellow solid. The NMR and MS were consistent with the proposed structure.

1-(4-Bromophenyl)-8-[(2-chlorobenzoyl)amino]-4,5-dihydro-1H-benzo[g]indazole-3-carboxamide (5.2 g) and $Zn(CN)_2$ (0.9 g) were dissolved in 100 ml DMF under $N_2$. Then $Pd(Ph_3P)_4$ (1.38 g) was added. The reaction mixture was heated up to 100° C. under $N_2$ for 12 hours. After the reaction is completed by HPLC, the solvent was evaporated, and the residue was suspended in ethyl acetate and water. After filtration, and washing with water and ethyl acetate, the filtrate of the organic layer was separated and dried with $Na_2SO_4$. After filtration and evaporation of solvent, the residue was triturated with ether. Solid obtained was filtered and washed with ether, then dried under vacuum. The desired compound (3.4 g) was obtained and characterized by $^1$H NMR, LC-MS (468, M+1), and CHN analysis. IKK-2 resin $IC_{50} \leq 1$ μM.

The compounds of Examples 370–380 in the Table 15 were prepared by the reduction and/or acylation or sulfonation from either Example 324 or Example 325 using standard conditions. The bioactivity in the IKK2 Resin assay for the compounds of Examples 370–380 is shown in Table 15.

TABLE 15

| Compound No., Structure | Mol Wt. | Compound Name(s) | IKK2 Resin IC50 | MS (M + H) | Example |
|---|---|---|---|---|---|
| | 457.92 | 1-(4-aminophenyl)-8-[(2-chlorobenzoyl)amino]-4,5-dihydro-1H-benzo[g]indazole-3-carboxamide | ≦1 μM | 458 | 370 |
| | 499.96 | 1-[4-(acetylamino)phenyl]-8-[(2-chlorobenzoyl)amino]-4,5-dihydro-1H-benzo[g]indazole-3-carboxamide | ≦1 μM | 500 | 371 |
| | 536.01 | 8-[(2-chlorobenzoyl)amino]-1-{4-[(methylsulfonyl)amino]phenyl}-4,5-dihydro-1H-benzo[g]indazole-3-carboxamide | ≦1 μM | 536 | 372 |
| | 562.03 | 1-[4-(benzoylamino)phenyl]-8-[(2-chlorobenzoyl)amino]-4,5-dihydro-1H-benzo[g]indazole-3-carboxamide | 1 ≦ 10 μM | 562 | 373 |
| | 529.99 | 8-[(2-chlorobenzoyl)amino]-1-{4-[(methoxyacetyl)amino]phenyl}-4,5-dihydro-1H-benzo[g]indazole-3-carboxamide | ≦1 μM | 530 | 374 |

TABLE 15-continued

| Compound No., Structure | Mol Wt. | Compound Name(s) | IKK2 Resin IC50 | MS (M + H) | Example |
|---|---|---|---|---|---|
| 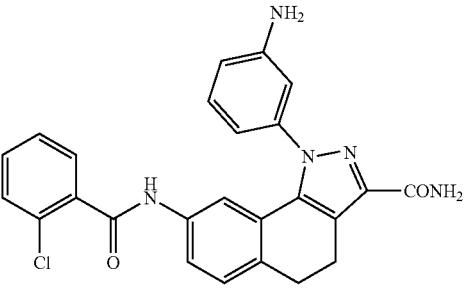 | 457.92 | 1-(3-aminophenyl)-8-[(2-chlorobenzoyl)amino]-4,5-dihydro-1H-benzo[g]indazole-3-carboxamide | ≦1 μM | 458 | 375 |
| 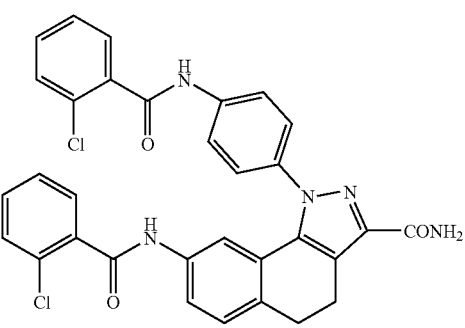 | 596.48 | 8-[(2-chlorobenzoyl)amino]-1-{4-[(2-chlorobenzoyl)amino]phenyl}-4,5-dihydro-1H-benzo[g]indazole-3-carboxamide | 1 ≦ 10 μM | 596 | 376 |
| 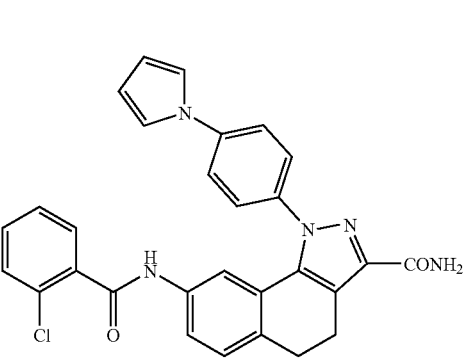 | 507.98 | 8-[(2-chlorobenzoyl)amino]-1-[4-(1H-pyrrol-1-yl)phenyl]-4,5-dihydro-1H-benzo[g]indazole-3-carboxamide | 1 ≦ 10 μM | 508 | 377 |
| 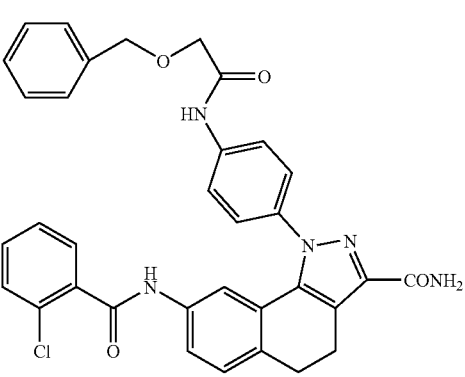 | 606.09 | 1-(4-{[(benzyloxy)acetyl]amino}phenyl)-8-[(2-chlorobenzoyl)amino]-4,5-dihydro-1H-benzo[g]indazole-3-carboxamide | 1 ≦ 10 μM | 606 | 378 |

TABLE 15-continued

| Compound No., Structure | Mol Wt. | Compound Name(s) | IKK2 Resin IC50 | MS (M + H) | Example |
| --- | --- | --- | --- | --- | --- |
| | 657.18 | 8-[(2-chlorobenzoyl)amino]-1-{4-[(5-{[(2,2-dimethylpropanoyl)oxy]amino}pentanoyl)amino]phenyl}-4,5-dihydro-1H-benzo[g]indazole-3-carboxamide | 1 ≦ 10 μM | 657 | 379 |
| | 593.52 | 8-[(2-chlorobenzoyl)amino]-1-[4-({[2-(dimethylamino)ethyl]amino}carbonyl)phenyl]-4,5-dihydro-1H-benzo[g]indazole-3-carboxamide hydrochloride | 1 ≦ 10 μM | 557 | 380 |

Example 381

1-(6-aminopyridin-3-yl)-8-[(3-chloroisonicotinoyl)amino]-4,5-dihydro-1H-benzo[g]indazole-3-carboxamide

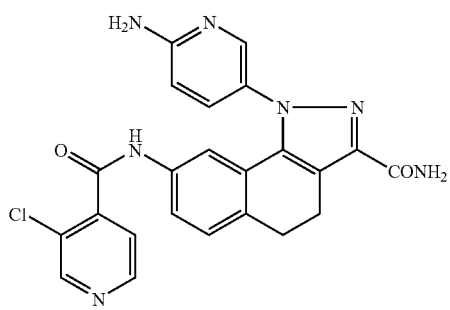

Step 1: A 100 mL 3-neck flask was charged with (in order) CuI (300 mg, 1.6 mmol), 1,10-phenanthroline (350 mg, 1.94 mmol) and 25 mL DMF. A dark cherry red solution resulted. To this solution was added (in order) 2-Chloro-5-iodopyridine (2.0 g, 8.4 mmol), t-butyl carbamate (1.33 g, 10.1 mmol), 25 mL DMF and $Cs_2CO_3$ (4.75 g, 14.6 mmol). To the flask was attached a reflux condenser with a nitrogen inlet, a thermometer and a glass stopper. With stirring the slurry was heated to 70° C. for 3 h. The reaction was allowed to cool to room temperature. The crude reaction mixture was poured into 200 mL water giving a rust colored solid. The product was extracted from this aqueous slurry using 2×200 mL diethyl ether. The ether layers were extracted with 200 mL water, dried over $MgSO_4$, filtered, and then concentrated giving a dark oil. The oil was chromatographed on silica gel (25 g) using 20% EtOAc/80% hexane giving 0.9 g (3.7 mmol, 44%) of product (light yellow oil which slowly solidified). NMR and MS were consistent with the proposed structure.

Step 2: To a mixture of the product from step 1 (6.35 g, 0.023 mol) and ethyl (7-nitro-1-oxo-1,2,3,4-tetrahydronaphthalen-2-yl)(oxo)acetate (6.6 g, 0.023 mol) in 200 mL of ethanol was added 10 mL of 1N HCl and the reaction mixture was heated at reflux under nitrogen for 6 h. After the solution was cooled, the precipitate was collected by filtration and air-dried to give 7.5 g of the product as a yellow crystal (83% yield); $^1$HNMR (DMSO, 400 MHz) δ: 8.76

(dd, 1H), 8.22 (dd, 1H), 8.12 (dd, 1H), 7.85 (dd, 1H), 7.71 (d, 1H), 7.44 (d, 1H), 4.35 (q, 2H), 3.14 (m, 2H), 3.03 (m, 2H), 1.33 (t, 3H); Anal. Calcd. for $C_{19}H_{15}ClN_4O_4$: C, 57.22; H, 3.79; N, 14.05; Cl, 8.89. Found: C, 57.03; H, 3.95; N, 13.71; Cl, 9.04.

Step 3: The product from step 2 (7.5 g, 0.019 mol) was hydrogenated in a Parr shaker with 5% Pt/C in acetic acid for 2 h at 5 psi. After the removal of solvent, the residue was triturated with a mixture of methanol and ether to give 6.5 g of the product as a pale yellow solid (94% yield): $^1$HNMR (DMSO, 400 MHz) δ: 8.64(dd, 1H), 8.09 (dd, 1H), 7.75 (dd, 1H), 7.02 (d, 1H), 6.45 (dd, 1H), 6.03 (d, 1H), 4.99 (brs, 2H), 4.31 (q, 2H), 2.88 (m, 2H), 2.78 (m, 2H), 1.31 (t, 3H); Anal. Calcd. for $C_{19}H_{17}ClN_4O_2$: C, 61.88; H, 4.65; N, 15.19; Cl, 9.61. Found: C, 60.97; H, 5.06; N, 14.65; Cl, 9.50.

Step 4: To a mixture of the product from step 3 (0.96 g, 0.0026 mol) and 3-chloroisonicotinic cid (0.65 g, 0.004 mol) in 25 mL of DMF was added 1 mL of diisopropylethylamine, followed by the addition of HATU (1.50 g, 0.004 mol). The reaction was stirred at room temperature for 16 h and concentrated. The residue was triturated with methanol and acetonitrile to give 1.08 g of product as a pale yellow solid (82% yield); $^1$HNMR (DMSO, 400 MHz) δ: 10.56 (s, 1H), 8.76 (s, 1H), 8.69 (d, 1H), 8.63 (d, 1H), 8.14 (dd, 1H), 7.76 (d, 1H), 7.56 (d, 1H), 7.53 (dd, 1H), 7.40 (d, 1H), 7.26 (d, 1H), 4.32 (q, 2H), 2.97 (s, 4H), 1.31 (t, 3H).

Step 5: A sealed reaction vessel containing the product from step 4 (0.8 g, 0.0016 mol) and 10 mL of liquid ammonia in 50 mL of absolute alcohol was heated at 120° C. and 600 psi for 24 h. After cooling, solvent was removed and the residue was triturated with a mixture of methanol and acetonitrile to give 0.38 g of product as a pale yellow solid (52% yield); $^1$HNMR (DMSO, 400 MHz) δ: 10.57 (s, 1H), 8.75 (s, 1H), 8.63 (d, 1H), 8.02 (d, 1H), 7.47–7.56 (m, 3H), 7.35 (d, (d, 1H), 7.27 (s, 1H), 6.54 (d, 1H), 6.36 (s, 2H), 2.92 (m, 4H); Anal. Calcd. for $C_{23}H_{18}ClN_7O_2$: C, 60.07; H, 3.95; N, 21.32. Found: C, 59.26; H, 3.99; N, 20.85.

Example 382

8-[(3-chloroisonicotinoyl)amino]-1-thien-2-yl-4,5-dihydro-1H-benzo[g]indazole-3-carboxamide

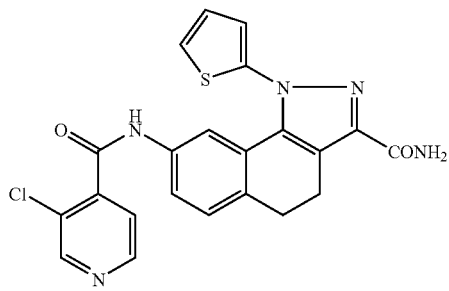

Step 1: To a mixture of tert-butyl 1-thien-2-ylhydrazin-ecarboxylate (3.9 g, 0.016 mol, synthesized by using the same method as the previous example) and ethyl (7-nitro-1-oxo-1,2,3,4-tetrahydronaphthalen-2-yl)(oxo)acetate (4.6 g, 0.016 mol) in 100 mL of ethanol was added 5 mL of 1N HCl and the reaction mixture was heated at reflux under nitrogen for 6 h. After the solution was cooled, the precipitate was collected by filtration and air-dried to give 2.6 g of the product as a brown solid (44% yield). This solid was refluxed with 3 eq of tin chloride in ethanol under nitrogen for 3 h. Solvent was removed and the residue was partitioned between THF and sat. NaHCO$_3$ solution. Organic layer was washed with brine, dried over MgSO$_4$, and concentrated to give 1.4 g of crude as a yellow solid, used without further purification. The MS and NMR were consistent with the proposed structure.

Step 2: A sealed reaction vessel containing the crude product from step 1 (1.3 g, 0.004 mol) and 10 mL of liquid ammonia in 50 mL of absolute alcohol was heated at 120° C. and 600 psi for 24 h. After cooling, solvent was removed and the residue was triturated with a mixture of methanol and acetonitrile to give 1.0 g of product as a pale yellow solid. To a mixture of this solid (0.56 g, 0.0018 mol) and 3-chloroisonicotinic cid (0.39 g, 0.0027 mol) in 20 mL of DMF was added 1 mL of diisopropylethylamine, followed by the addition of HATU.(1.03 g, 0.0027 mol). The reaction was stirred at room temperature for 16 h and concentrated. The residue was triturated with methanol and water to give 0.31 g of product as pale yellow solid (38% yield); $^1$HNMR (DMSO, 400 MHz) δ: 10.55 (s, 1H), 8.75 (s, 1H), 8.62 (d, 1H), 7.67 (d, 1H), 7.62 (s, 1H), 7.55 (d, 1H), 7.44 (s, 3H), 7.42 (s, 1H), 7.35 (m, 3H), 7.12 (m, 1H), 2.93 (m, 4H); Anal. Calcd. for $C_{22}H_{16}ClN_5O_2S$: C, 58.73; H, 3.58; N, 15.57. Found: C, 58.26; H, 3.62; N, 15.48.

Example 383

8-[(3-chloroisonicotinoyl)amino]-1-thien-3-yl-4,5-dihydro-1H-benzo[g]indazole-3-carboxamide

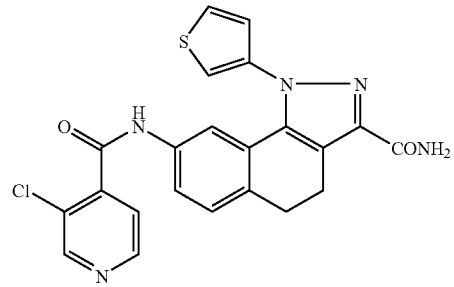

This compound was synthesized by using the same method as previously described in Example 381. $^1$HNMR (DMSO, 400 MHz) δ: 10.54 (s, 1H), 8.75 (s, 1H), 8.62 (d, 1H), 7.85 (dd, 1H), 7.75 (dd, 1H), 7.58 (s, 1H), 7.54 (d, 1H), 7.38 (m, 3H), 7.31 (s, 1H), 7.28 (dd, 1H), 2.92 (m, 4H); Anal. Calcd. for $C_{22}H_{16}ClN_5O_2S$: C, 58.73; H, 3.58; N, 15.57. Found: C, 58.65; H, 3.77; N, 15.59.

Example 384

1-(4-amino-3,5-difluorophenyl)-8-[(3-chloroisonico-tinoyl)amino]-4,5-dihydro-1H-benzo[g]indazole-3-carboxamide

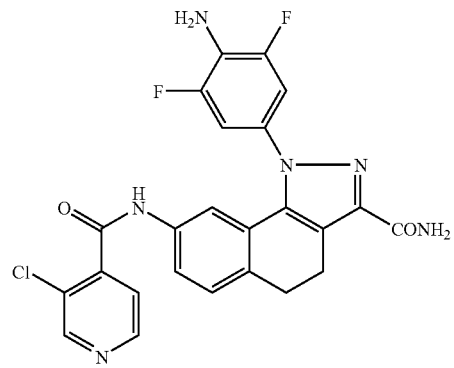

Step 1: 1-Bromo-3,4,5 trifluorobenzene (5 g, 24 mmol) was added to a slurry of Pd(OAc)$_2$ (0.269 g, 5 mol %), bisdiphenylphosphino-ferrocene (1.0 g, 7 mol %) in anhydrous toluene (50 mL) at rt. Benzophenone hydrazone (4.9 g) was added, stirred for 5 min following by addition of dried cesium acetate (9.33 g) and toluene (40 mL). The flask was removed from a glove box and heated to 86° C. for 72 hours. The reaction was monitored by disappearance of bromotrifluourobenzene by LC (210 nm) or $^{19}$F NMR. The reaction mixture was cooled down to room temperature and filtered through a sintered glass funnel. The solvent was removed under the vacuum. The orange solid residue was re-dispersed in ether (15 mL) and hexane (150 mL) and heated up to 58° C., stirred for 20 min. The hot solution was quickly filtered, solid discarded and the solution was allowed to cool to room temperature, stirred for 30 min, then 1 hour at 4° C. The formed slurry was filtered, washed with cold hexane (2×25 mL). Crystals were dried in air then in the vacuum at 80° C. for 1 hour to give 5 g of diphenylmethanone (3,4,5-trifluorophenyl)hydrazone (64% yield) as a yellowish solid.

Step 2: The product from step 1 (1.9 g) and ethyl (7-nitro-1-oxo-1,2,3,4-tetrahydronaphthalen-2-yl)(oxo)acetate (1.66 g) were dispersed in 1M HCl in ethanol (125 mL), heated to reflux, and stirred until the starting material disappeared (overnight). The solution was cooled down to 4° C. and stirred for 2 hrs. The cold slurry was filtered, solid washed with anhydrous ethanol (2×25 mL), dried on air and in the vacuum oven at 70° C. for 1 hour to give 1.4 g of 8-nitro-1-(3,4,5-trifluorophenyl)-4,5-dihydro-1H-benzo[g]indazole-3-carboxamide as a brown powder (58% yield).

Step 3: The product from step 2 (1.17 g, 0.0028 mol) was hydrogenated in a Parr shaker with 5% Pt/C in acetic acid for 4 h at 5 psi. After the removal of solvent, the residue was triturated with a mixture of methanol and ether to give 1.0 g of the product as a pale yellow solid. A sealed reaction vessel containing this solid and 10 mL of liquid ammonia in 50 mL of absolute alcohol was heated at 120° C. and 600 psi for 24 h. After cooling, solvent was removed and the residue was triturated with a mixture of methanol and acetonitrile to give 0.8 g of 8-amino-1-(4-amino-3,5-difluorophenyl)-4,5-dihydro-1H-benzo[g]indazole-3-carboxamide as a pale yellow solid (80% yield over two steps); NMR spectrum, was consistent with the proposed structure.

Step 4: To a mixture of the product from step 3 (0.75 g, 0.0021 mol) and 3-chloroisonicotinic cid (0.33 g, 0.0023 mol) in 20 mL of DMF was added 1 mL of diisopropylethylamine, followed by the addition of HATU (0.9 g, 0.0023 mol). The reaction was stirred at room temperature for 16 h and concentrated. The crude was purified by reverse phase HPLC to give 0.15 g of 1-(4-amino-3,5-difluorophenyl)-8-[(3-chloroisonicotinoyl)amino]-4,5-dihydro-1H-benzo[g]indazole-3-carboxamide as a pale white solid (15% yield); $^1$HNMR (DMSO, 400 MHz) δ: 10.56 (s, 1H), 8.76 (s, 1H), 8.63 (d, 1H), 8.56 (s, 1H), 7.54 (d, 1H), 7.49 (dd, 1H), 7.35 (m, 2H), 7.31 (s, 1H), 6.71 (m, 2H), 5.88 (s, 2H), 2.92 (m, 4H); Anal. Calcd. for $C_{24}H_{17}FClN_6O_2$+0.5$H_2O$: C, 57.21; H, 3.60; N, 16.68. Found: C, 56.91; H, 3.70; N, 16.64.

Example 385

1-(4-amino-2,5-difluorophenyl)-8-[(3-chloroisonicotinoyl)amino]-4,5-dihydro-1H-benzo[g]indazole-3-carboxamide

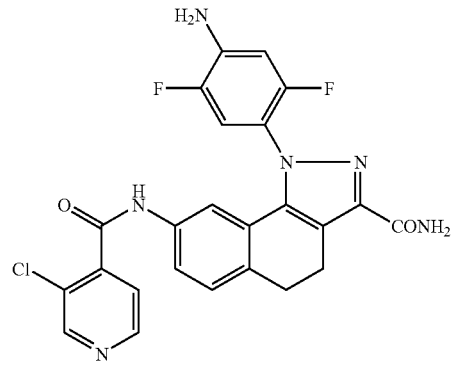

This compound was synthesized by using the same method as Example 384; mp: 289–290° C.; $^1$HNMR (DMSO, 400 MHz) δ: 10.55 (s, 1H), 8.75 (s, 1H), 8.63 (d, 1H), 7.57 (d, 1H), 7.55 (s, 1H), 7.39 (m, 4H), 7.29 (s, 1H), 6.70 (m, 1H), 5.90 (brs, 2H), 2.89(s, 4H); Anal. Calcd. for $C_{24}H_{17}FClN_6O_2$: C, 58.25; H, 3.46; N, 16.98. Found: C, 57.65; H, 3.73; N, 16.82.

Additional analytical data is presented in Table 16 for the compounds of Examples 381–385.

TABLE 14

| Compound No., Structure | Mol. Wt. | Compound Name(s) | IKK2 Resin IC50 | MS (M + H) | Example |
|---|---|---|---|---|---|
|  | 459.90 | 1-(6-aminopyridin-3-yl)-8-[(3-chloroisonicotinoyl)amino]-4,5-dihydro-1H-benzo[g]indazole-3-carboxamide | ≦1 μM | 460 | 381 |

TABLE 14-continued

| Compound No., Structure | Mol. Wt. | Compound Name(s) | IKK2 Resin IC50 | MS (M + H) | Example |
|---|---|---|---|---|---|
| | 449.92 | 8-[(3-chloroisonicotinoyl)amino]-1-thien-2-yl-4,5-dihydro-1H-benzo[g]indazole-3-carboxamide | ≦1 μM | 450 | 382 |
| | 449.92 | 8-[(3-chloroisonicotinoyl)amino]-1-thien-3-yl-4,5-dihydro-1H-benzo[g]indazole-3-carboxamide | ≦1 μM | 450 | 383 |
| | 494.89 | 1-(4-amino-3,5-difluorophenyl)-8-[(3-chloroisonicotinoyl)amino]-4,5-dihydro-1H-benzo[g]indazole-3-carboxamide | ≦1 μM | 495 | 384 |
| | 494.89 | 1-(4-amino-2,5-difluorophenyl)-8-[(3-chloroisonicotinoyl)amino]-4,5-dihydro-1H-benzo[g]indazole-3-carboxamide | ≦1 μM | 495 | 385 |

Example 386

8-{[(2-chloropyridin-3-yl)carbonyl]amino}-1-[4-(3-hydroxyprop-1-ynyl)phenyl]-4,5-dihydro-1H-benzo[g]indazole-3-carboxamide

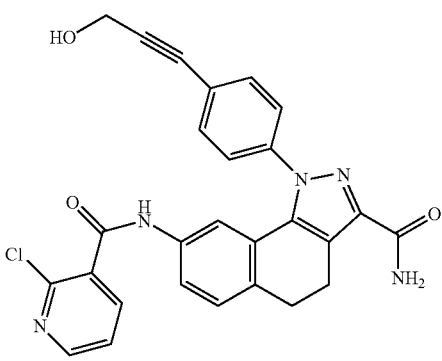

The following scheme was used for the synthesis of the title compound of Example 386.

SCHEME XXVIII

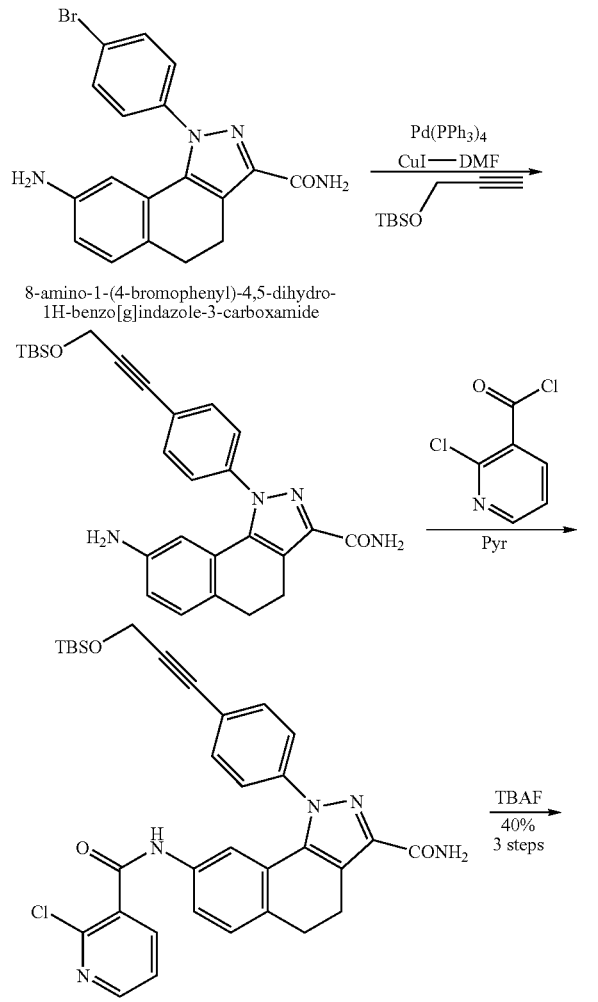

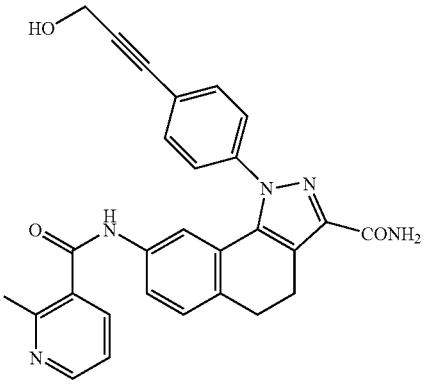

Example 386

A stirred solution of 8-amino-1-(4-bromophenyl)-4,5-dihydro-1H-benzo[g]indazole-3-carboxamide (2.30 g, 6 mmol) and tert-butyldimethyl-(2-propynl-oxy)silane (1.12 g, 6.6 mmol) in DMF-triethylamine (6 mL—6 mL) was added CuI (114 mg, 0.6 mmol) and tetrakis(triphenylphosphine) palladium (346 mg, 0.3 mmol) and the resulted mixture was heated at 100° C. for 14 h before cooled to rt. The mixture was filtered through silica gel pad, washed with EtOAc, and concentrated. The crude material was taken into pyridine (20 mL), treated 2-chloronicotinyl chloride (1.23 g, 7 mmol) at RT for 14 h. Tetrabutylammonium fluoride (25 mL of 1M THF solution, 25 mmol) was added at RT and stirred overnight. Aqueous ammonium chloride was added, the mixture extracted with EtOAc (5×30 mL). The organic portions were combined, dried over MgSO$_4$, filtered, and separated by silica gel column (EtOAc). This gave 8-{[(2-chloropyridin-3-yl)carbonyl]amino}-1-[4-(3-hydroxyprop-1-ynyl)phenyl]-4,5-dihydro-1H-benzo[g]indazole-3-carboxamide as a pale yellow solid (1.19 g, 40% over 3 steps). $^1$H NMR was consistent with its structure.

Example 387

8-{[(2-chloropyridin-3-yl)carbonyl]amino}-1-[4-(5-hydroxypent-1-ynyl)phenyl]-4,5-dihydro-1H-benzo[g]indazole-3-carboxamide

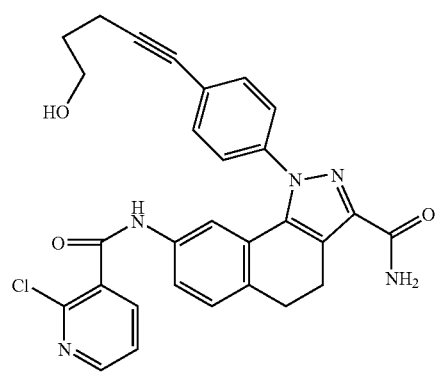

Example 388

8-{[(2-chloropyridin-3-yl)carbonyl]amino}-1-(4-ethynylphenyl)-4,5-dihydro-1H-benzo[g]indazole-3-carboxamide

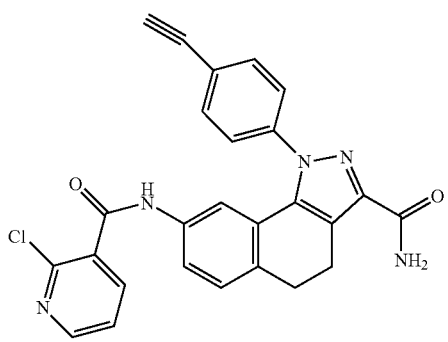

A stirred solution of 8-amino-1-(4-bromophenyl)-4,5-dihydro-1H-benzo[g]indazole-3-carboxamide (5.74 g, 15 mmol) and tert-butyldimethylsilylacetylene (2.31 g, 16.5 mmol) in DMF-triethylamine (20 mL-10 mL) was added CuI (285 mg, 1.5 mmol) and tetrakis(triphenylphosphine)palladium (870 mg, 0.75 mmol) and the resulted mixture was heated at 100° C. for 14 h before cooled to rt. The mixture was filtered through silica gel pad, washed with EtOAc, and concentrated. The crude material was taken into pyridine (30 mL), treated with 2-chloronicotinyl chloride (2.90 g, 16.5 mmol) at RT for 14 h. Tetrabutylammonium fluoride (25 mL of 1M THF solution, 25 mmol) was added at RT and stirred overnight. Aqueous ammonium chloride was added, the mixture extracted with EtOAc (5×30 mL). The organic portions were combined, dried over MgSO$_4$, filtered, and separated by silica gel column (EtOAc). This gave product as a pale yellow solid (3.5 g, 49% over 3 steps). $^1$H NMR was consistent with its structure. CNH calculated for $C_{26}H_{18}N_5O_2Cl(H_2O)_{1.3}$: C(63.5%), H(4.2%), N(14.3%); found: C(63.6%), H(4.0%), N(14.3%).

Example 389

8-{[(2-chloropyridin-3-yl)carbonyl]amino}-1-(4-vinylphenyl)-4,5-dihydro-1H-benzo[g]indazole-3-carboxamide

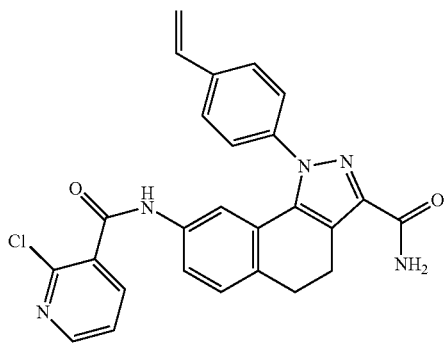

A solution of 8-{[(2-chloropyridin-3-yl)carbonyl]amino}-1-(4-ethynylphenyl)-4,5-dihydro-1H-benzo[g]indazole-3-carboxamide (557 mg, 1.19 mmol) in DMF-DMSO (20 mL-1 mL) was treated at RT with H$_2$ (5 psi) and Pd—CaSO$_4$ (5%, 100 mg) for 12 min. The mixture was filtered through celite pad, concentrated and added water. The solid product was collected via filtration, washed with water and ether, and dried to give product (262 mg, 47%). $^1$H NMR was consistent with its structure.

Example 390

1-(4-acetylphenyl)-8-{[(2-chloropyridin-3-yl)carbonyl]amino}-4,5-dihydro-1H-benzo[g]indazole-3-carboxamide

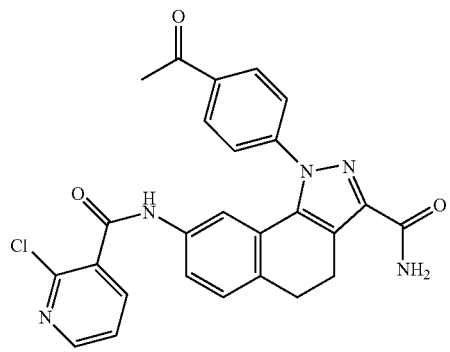

A mixture of 8-{[(2-chloropyridin-3-yl)carbonyl]amino}-1-(4-ethynylphenyl)-4,5-dihydro-1H-benzo[g]indazole-3-carboxamide (442 mg, 1.2 mmol), water (65 mg, 3.6 mmol), and triflic acid (270 mg, 1.8 mmol) in dioxane (10 mL) was heated to 100° C. for 18 h. The mixture was cooled to RT, aqueous NaHCO$_3$ was added, and filtered. The product was washed with water and ether, and dried. This gave product (293 mg, 67%). $^1$H NMR was consistent with its structure.

Example 391

8-{[(2-chloropyridin-3-yl)carbonyl]amino}-1-[4-(1-hydroxyethyl)phenyl]-4,5-dihydro-1H-benzo[g]indazole-3-carboxamide

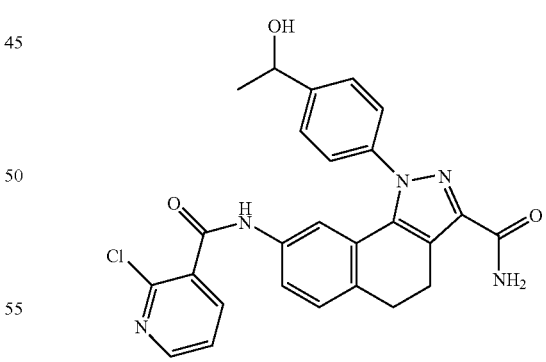

A mixture of 1-(4-acetylphenyl)-8-{[(2-chloropyridin-3-yl)carbonyl]amino}-4,5-dihydro-1H-benzo[g]indazole-3-carboxamide (200 mg, 0.41 mmol) in MeOH (3 mL) and water (0.3 mL) was added NaBH$_4$ (10 mg, 0.25 mmol) at RT and stirred for 14 h. The mixture was separated on silica gel column (EtOAc) to give product (100 mg, 50%). $^1$H NMR was consistent with its structure.

Additional analytical data for the compounds of Examples 386–391 is presented in Table 17

TABLE 17

| Compound No., Structure | Mol. Wt. | Compound Name(s) | IKK2 Resin IC50 | MS (M + H) | Example |
|---|---|---|---|---|---|
| | 497.94 | 8-{[(2-chloropyridin-3-yl)carbonyl]amino}-1-[4-(3-hydroxyprop-1-ynyl)phenyl]-4,5-dihydro-1H-benzo[g]indazole-3-carboxamide | ≦1 μM | 498 | 386 |
| | 525.99 | 8-{[(2-chloropyridin-3-yl)carbonyl]amino}-1-[4-(5-hydroxypent-1-ynyl)phenyl]-4,5-dihydro-1H-benzo[g]indazole-3-carboxamide | ≦1 μM | 526 | 387 |
| | 467.91 | 8-{[(2-chloropyridin-3-yl)carbonyl]amino}-1-(4-ethynylphenyl)-4,5-dihydro-1H-benzo[g]indazole-3-carboxamide | 1 ≦ 10 μM | 468 | 388 |
| | 469.93 | 8-{[(2-chloropyridin-3-yl)carbonyl]amino}-1-(4-vinylphenyl)-4,5-dihydro-1H-benzo[g]indazole-3-carboxamide | ≦1 μM | 470 | 389 |

TABLE 17-continued

| Compound No., Structure | Mol. Wt. | Compound Name(s) | IKK2 Resin IC50 | MS (M + H) | Example |
|---|---|---|---|---|---|
| 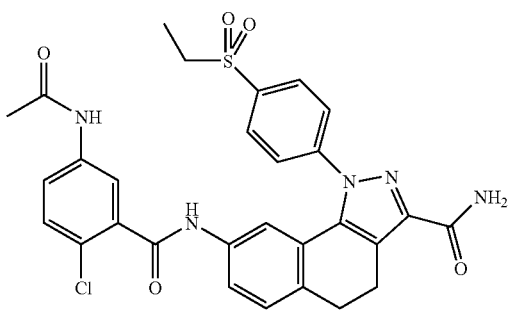 | 485.93 | 1-(4-acetylphenyl)-8-{[(2-chloropyridin-3-yl)carbonyl]amino}-4,5-dihydro-1H-benzo[g]indazole-3-carboxamide | 1 ≦ 10 μM | 486 | 390 |
| 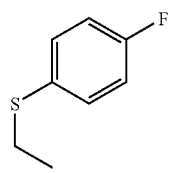 | 487.95 | 8-{[(2-chloropyridin-3-yl)carbonyl]amino}-1-[4-(1-hydroxyethyl)phenyl]-4,5-dihydro-1H-benzo[g]indazole-3-carboxamide | ≦1 μM | 488 | 391 |

Example 392

8-{[5-(acetylamino)-2-chlorobenzoyl]amino}-1-[4-(ethylsulfonyl)phenyl]-4,5-dihydro-1H-benzo[g]indazole-3-carboxamide Step 1

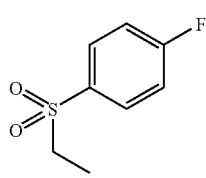

To a stirring solution of NaOH (11.26 g, 281.6 mmol) in water (500 mL) was added dropwise a solution of 4-fluorothiophenol (25 mL, 234.6 mmol) in methanol (50 mL). After 15 minutes ethyl bromide (14.4 mL, 281.6 mmol) was added. After 6 hours more NaOH (1 g) was added and the reaction mixture was extracted with ether (3×300 mL). The combined organic extracts were treated with brine followed by MgSO$_4$ then concentrated down to give 1-(ethylthio)-4-fluorobenzene (29 g, 80%) as a slightly yellow colored liquid.

Step 2

To a solution of the crude product of step 1 in CH$_2$Cl$_2$ (500 mL) was added m-CPBA (82 g of 77% max powder, 368 mmol) portion-wise with vigorous stirring. After 5 hours the reaction mixture was concentrated down and ethyl acetate (750 mL) was added. The organic phase was then washed with 4% aqueous NaOH (2×100 mL), water (100 mL), then brine (75 mL), and finally dried over MgSO$_4$. The solution was concentrated down to yield a white solid (17.9 g) that was carried onto the next step without purification.

Step 3

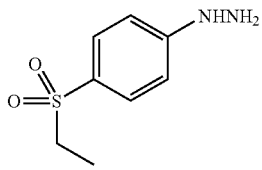

The crude product of step 2 was dissolved in ethanol (200 mL) and hydrazine (24 mL, 758 mmol) was added. The reaction mixture was heated to reflux for 6 hours then left at room temperature overnight. The ethanol was concentrated down to a smaller volume then water was added. A white precipitate formed and was collected (12.87 g, 68%). The desired compound (1-[4-(ethylsulfonyl)phenyl]hydrazine) was used in the next step without purification.

Step 4

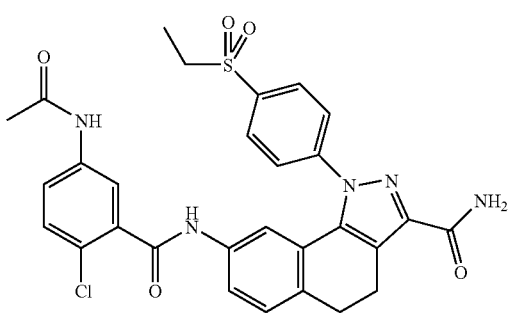

The title compound was prepared in a manner analogous to Example 3 using 1-[4-(ethylsulfonyl)phenyl]hydrazine and the appropriate acylating agent. The desired product crystallizes out of the reaction media in 81% yield. Anal. Calcd for $C_{29}H_{26}ClN_5O_5S$ (MW=591.13): C, 58.83; H, 4.43; N, 11.83. Found: C, 58.69; H, 4.46; N, 12.16.

Example 393

8-[(2-chlorobenzoyl)amino]-1-[4-(isopropylsulfonyl)phenyl]-4,5-dihydro-1H-benzo[g]indazole-3-carboxamide

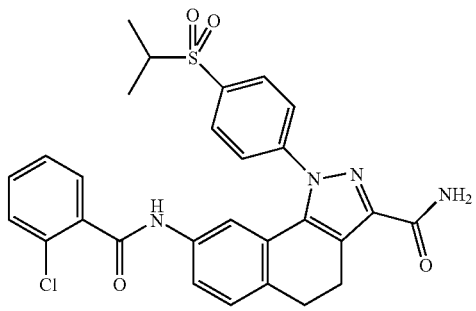

Step 1

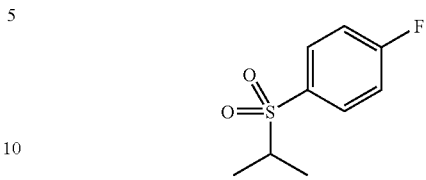

To a 250 mL round-bottomed flask was placed KH (35 wt % in mineral oil) (1.64 g, 14.35 mmol). The solid was washed with hexane (2×10 mL) under nitrogen. THF (50 mL) was added and the suspension was cooled to 0° C. Iodomethane (0.89 mL, 14.35 mmol) followed by a solution of 4-fluorophenylmethylsulfone (1.25 g, 7.17 mmol) in THF (10 mL) was added. The reaction mixture was stirred at 0° C. for 1 hour then allowed to warm to room temperature overnight. A mixture of ethyl and isopropyl sulfone was observed, so LiHMDS (7.2 mL, 14.35 mmol) and iodomethane (0.45 mL, 14.35 mmol) were added. After 2.5 hours water was added to the reaction mixture and the aqueous phase was extracted with ether (3×150 mL). The combined organic extracts were treated with brine and dried over MgSO$_4$. The ether solution was concentrated down to give the desired compound as a yellow solid. The crude material was used in the nest step without further purification.

Step 2

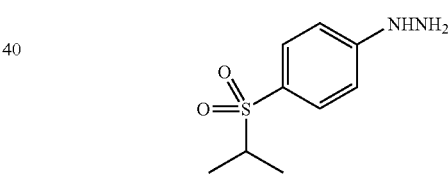

The product of step 1 (640 mg, 3.15 mmol) was dissolved in absolute ethanol (12 mL), the system was flushed with N$_2$ and hydrazine (404 mg, 12.6 mmol) was added and the reaction refluxed overnight. HPLC showed 78% product and 21% starting material. To drive the reaction to completion 2 equivalents of additional hydrazine was added and reaction was refluxed for additional 5 hours, at this time HPLC indicated 95% product. The reaction mixture was concentrated and the residue was stirred with water. A white solid, 390 mg (58%) was isolated. HPLC indicated 86% product and 14% starting material. The aqueous phase was extracted with ethyl acetate (3×50 mL). The organic phase was dried over MgSO$_4$, and concentrated to yield 258 mg (38%) of 1-[4-(isopropylsulfonyl)phenyl]hydrazine with 99% purity. MH$^+$=215. The 390 mg was re-dissolved in 10 mL ethanol and treated once more with additional hydrazine to obtain additional product with the desired purity.

Step 3

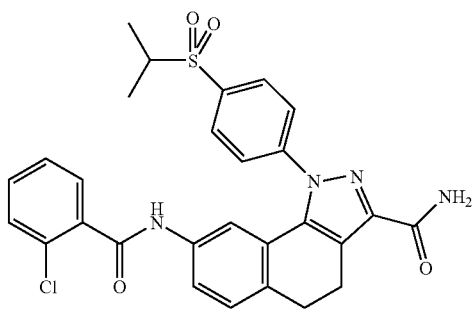

The title compound was prepared in a manner analogous to Example 3 using 1-[4-(isopropylsulfonyl)phenyl]hydrazine and the appropriate acylating agent. The desired compound was recovered in 86% yield. HPLC indicated the compound had 94% purity. Anal. Calcd for $C_{28}H_{25}ClN_4O_4S+0.1H_2O$ (MW=550.05): C, 61.05; H, 4.61; N, 10.17. Found: C, 60.67; H, 4.44; N, 10.14.

Example 394

1-{4-[(3-aminopropyl)sulfonyl]phenyl}-8-{[(2-chloropyridin-3-yl)carbonyl]amino}-4,5-dihydro-1H-benzo[g]indazole-3-carboxamide hydrochloride

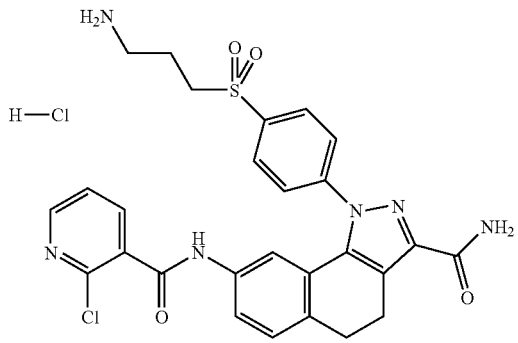

Step 1

Commercially available 3-bromopropylamino hydrogen bromide (10 g, 45.7 mmol) was suspended in $CH_2Cl_2$ (125 mL). Triethylamine (10 mL, 98 mmol) was added followed by $(Boc)_2O$ (11 g, 50 mmol) as a solid. After stirring overnight at room temperature the reaction mixture was diluted with $CH_2Cl_2$ (100 mL). The organic phase was washed with 1M HCl (100 mL), sat. aq. NaHCO$_3$ (50 mL), and brine (50 mL) then dried over MgSO$_4$. Evaporation under reduced pressure yielded the desired compound as a slightly yellow liquid (10.55 g, 97%) and no purification was necessary.

Step 2

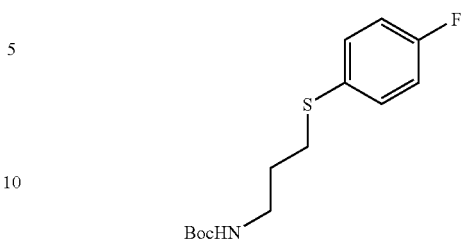

To a stirring solution of NaOH (624 mg, 15.6 mmol) in water (20 mL) was added drop-wise a solution of 4-fluorobenzenethiol (2 g, 15.6 mmol) in methanol (5 mL) at room temperature. After 30 minutes a solution of the product of step 2 (3.71 g, 15.6 mmol) in methanol (5 mL) was added drop-wise and the reaction mixture was allowed to stir at room temperature overnight. Ether (450 mL) was added and the aqueous layer separated. The organic phase was then washed successively with 1N NaOH (75 mL), conc. aq. NH$_4$Cl (75 mL), and brine (50 mL). The solution was dried over MgSO$_4$ and concentrated down to give the desired compound as a colorless liquid (3.2 g, 72%). The compound was used in the next step without further purification.

Step 3

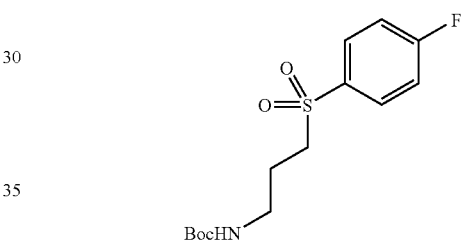

To a stirring solution of the product of step 2 (3.2 g, 11.2 mmol) in $CH_2Cl_2$ (150 mL) was added m-CPBA (77% max powder) (9.56 g, mmol) portion-wise at room temperature. The reaction was left overnight then it was concentrated down and ethyl acetate (750 mL) was added. The organic phase was then washed with 4% aqueous NaOH (2×100 mL), water (100 mL), then brine (75 mL), and finally dried over MgSO$_4$. The solution was concentrated down to yield a white solid that was carried onto the next step without purification.

Step 4

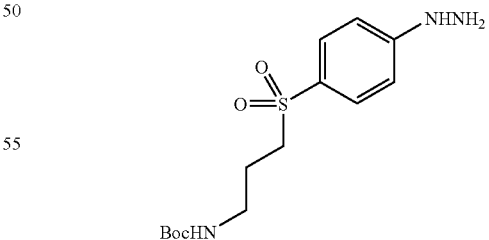

All of the crude material from step 3 was dissolved in ethanol (30 mL) and hydrazine (2.4 mL, 75 mmol) was added. The reaction mixture was refluxed overnight then concentrated down to a volume of 5 mL and added to water. The resulting precipitate was collected to yield tert-butyl 3-[(4-hydrazinophenyl)sulfonyl]propylcarbamate as a white solid (1.88 g, 51%). The compound was used in the next step without further purification.

Step 5

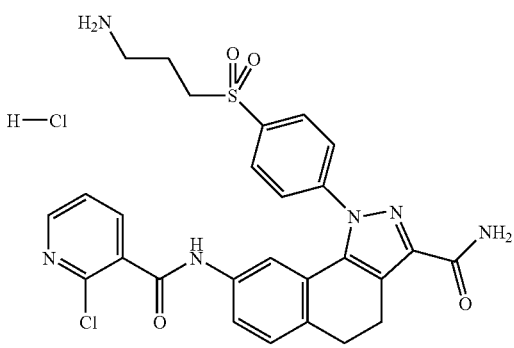

The title compound was prepared in a manner analogous to Example 3 using tert-butyl 3-[(4-hydrazinophenyl)sulfonyl]propylcarbamate and the appropriate acylating agent. The title compound was isolated as a tan colored HCl salt following standard Boc deprotection using 4N HCl in dioxane.

The compounds of Examples 395–409 in Table 18 were prepared in a manner analogous to Examples 392, 393, and 394 using the appropriate hydrazine and acylating agent.

The bioactivity in the IKK2 Resin assay for the compounds of Examples 392–409 is shown in Table 18.

TABLE 18

| Compound No., Structure | Mol. Wt. | Compound Name | IKK2 Resin IC50 | MS (M + H) | Example |
|---|---|---|---|---|---|
|  | 592.08 | 8-{[5-(acetylamino)-2-chlorobenzoyl]amino}-1-[4-(ethylsulfonyl)phenyl]-4,5-dihydro-1H-benzo[g]indazole-3-carboxamide | ≦1 μM | 592 | 392 |
|  | 550.05 | 8-[(2-chlorobenzoyl)amino]-1-[4-(isopropylsulfonyl)phenyl]-4,5-dihydro-1H-benzo[g]indazole-3-carboxamide | ≦1 μM | 550 | 393 |
|  | 601.52 | 1-{4-[(3-aminopropyl)sulfonyl]phenyl}-8-{[(2-chloropyridin-3-yl)carbonyl]amino}-4,5-dihydro-1H-benzo[g]indazole-3-carboxamide hydrochloride | 1 ≦ 10 μM | 565 | 394 |
|  | 535.03 | 8-[(2-chlorobenzoyl)amino]-1-[4-(ethylsulfonyl)phenyl]-4,5-dihydro-1H-benzo[g]indazole-3-carboxamide | ≦1 μM | 535 | 395 |

TABLE 18-continued

| Compound No., Structure | Mol. Wt. | Compound Name | IKK2 Resin IC50 | MS (M + H) | Example |
|---|---|---|---|---|---|
| | 536.01 | 8-{[(2-chloropyridin-3-yl)carbonyl]amino}-1-[4-(ethylsulfonyl)phenyl]-4,5-dihydro-1H-benzo[g]indazole-3-carboxamide | ≦1 μM | 536 | 396 |
| | 650.16 | tert-butyl 3-[({3-(aminocarbonyl)-1-[4-(ethylsulfonyl)phenyl]-4,5-dihydro-1H-benzo[g]indazol-8-yl}amino)carbonyl]-4-chlorophenylcarbamate | ≦1 μM | 650 | 397 |
| | 550.04 | 8-[(5-amino-2-chlorobenzoyl)amino]-1-[4-(ethylsulfonyl)phenyl]-4,5-dihydro-1H-benzo[g]indazole-3-carboxamide | ≦1 μM | 550 | 398 |
| | 474.56 | 1-[4-(ethylsulfonyl)phenyl]-8-[(metbylsulfonyl)amino]-4,5-dihydro-1H-benzo[g]indazole-3-carboxamide | 1 ≦ 10 μM | 475 | 399 |
| | 549.05 | 8-[(2-chlorobenzoyl)amino]-1-[4-(propylsulfonyl)phenyl]-4,5-dihydro-1H-benzo[g]indazole-3-carboxamide | ≦1 μM | 549 | 400 |

TABLE 18-continued

| Compound No., Structure | Mol. Wt. | Compound Name | IKK2 Resin IC50 | MS (M + H) | Example |
|---|---|---|---|---|---|
| | 550.04 | 8-{[(2-chloropyridin-3-yl)carbonyl]amino}-1-[4-(propylsulfonyl)phenyl]-4,5-dihydro-1H-benzo[g]indazole-3-carboxamide | 1 ≦ 10 μM | 550 | 401 |
| | 678.09 | 8-[(5-amino-2-chlorobenzoyl)amino]-1-[4-(propylsulfonyl)phenyl]-4,5-dihydro-1H-benzo[g]indazole-3-carboxamide trifluoroacetate | ≦1 μM | 678 | 402 |
| | 488.59 | 8-[(methylsulfonyl)amino]-1-[4-(propylsulfonyl)phenyl]-4,5-dihydro-1H-benzo[g]indazole-3-carboxamide | 1 ≦ 10 μM | 489 | 403 |
| | 600.53 | 1-{4-[(3-aminopropyl)sulfonyl]phenyl}-8-[(2-chlorobenzoyl)amino]-4,5-dihydro-1H-benzo[g]indazole-3-carboxamide hydrochloride | ≦1 μM | 564 | 404 |
| | 563.08 | 1-[4-(butylsulfonyl)phenyl]-8-[(2-chlorobenzoyl)amino]-4,5-dihydro-1H-benzo[g]indazole-3-carboxamide | 1 ≦ 10 μM | 563 | 405 |

TABLE 18-continued

| Compound No., Structure | Mol. Wt. | Compound Name | IKK2 Resin IC50 | MS (M + H) | Example |
|---|---|---|---|---|---|
| | 396.47 | 8-amino-1-[4-(ethylsulfonyl)phenyl]-4,5-dihydro-1H-benzo[g]indazole-3-carboxamide | 1 ≦ 10 μM | 397 | 406 |
| | 410.50 | 8-amino-1-[4-(propylsulfonyl)phenyl]-4,5-dihydro-1H-benzo[g]indazole-3-carboxamide | 1 ≦ 10 μM | 411 | 407 |
| | 664.19 | tert-butyl 3-[({3-(animocarbonyl)-1-[4-(propylsulfonyl)phenyl]-4,5-dihydro-1H-benzo[g]indazol-8-yl}amino)carbonyl]-4-chlorophenylcarbamate | 1 ≦ 10 μM | 664 | 408 |
| | 561.06 | 8-[(2-chlorobenzoyl)amino]-1-{4-[(cyclopropylmethyl)sulfonyl]phenyl}-4,5-dihydro-1H-benzo[g]indazole-3-carboxamide | 1 ≦ 10 μM | 561 | 409 |

Example 410

8-[(2-chlorobenzoyl)amino]-1-[4-(methylthio)phenyl]-4,5-dihydro-1H-benzo[g]indazole-3-carboxamide

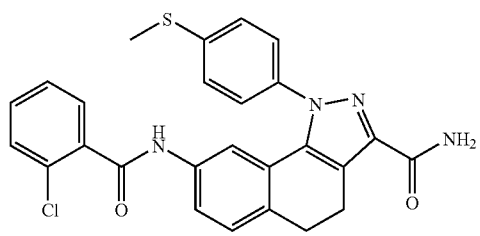

Step 1

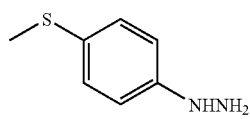

4-Methylthiol-aniline (10.0 g; 7.2 mmoles) was suspended in 6N HCl (50 mL). The solution was cooled to 0° C. and sodium nitrite (5.26 g; 7.6 mmoles) dissolved in water (20 mL) was added dropwise keeping the temperature at 0° C. When the addition is complete, the reaction mixture is homogeneous and has changed from a dark brown to an orange color. After letting this stir for an hour, $SnCl_2 \cdot 2H_2O$ (42.5 g; 18.8 mmoles) dissolved in conc. HCl (35 mL) was added to the cold solution over a period of 15 minutes. The reaction was allowed to stir for 2 hours allowing the temperature to reach room temperature. The white solid was filtered of and suspended in ice water (300 mL). 50% NaOH solution was added till reaction mixture becomes basic (pH 12). Any undissolved solid was filtered off and the aqueous phase was extracted with ethyl ether (3×300 mL). The organic phase was dried over $MgSO_4$ and concentrated to a yellow solid (7.8 g; 71% yield) HPLC indicated that product is 64% pure and has M+1=155 (other impurity was starting material); $^1$H NMR ($CDCl_3$) δ 2.44 (s, 3H), 6.78 (m, 2H), 7.23 (m, 2H).

Step 2

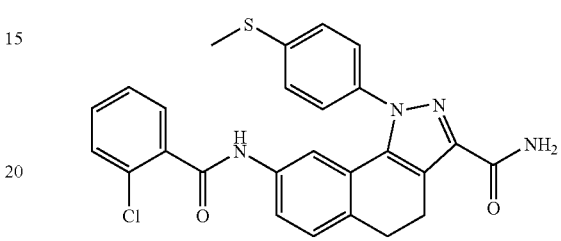

The title compound was prepared in a manner analogous to Example 3 using 1-[4-methylsulfonyl)phenyl]hydrazine and the appropriate acylating agent.

The compounds of Examples 411–414 in Table 19 were prepared in a manner analogous to Examples 410 using the appropriate acylating agent.

The bioactivity in the IKK2 Resin assay for the compounds of Examples 410–414 is shown in Table 19.

TABLE 19

| Compound No., Structure | Mol. Wt. | Compound Name | IKK2 Resin IC50 | MS (M + H) | Example |
|---|---|---|---|---|---|
|  | 489.00 | 8-[(2-chlorobenzoyl)amino]-1-[4-(methylthio)phenyl]-4,5-dihydro-1H-benzo[g]indazole-3-carboxamide | 1 ≦ 10 μM | 489 | 410 |
|  | 428.54 | 8-[(methylsulfonyl)amino]-1-[4-(methylthio)phenyl]-4,5-dihydro-1H-benzo[g]indazole-3-carboxamide | ≦1 μM | 429 | 411 |
|  | 526.45 | 8-[(3-chloroisonicotinoyl)amino]-1-[4-(methylthio)phenyl]-4,5-dihydro-1H-benzo[g]indazole-3-carboxamide hydrochloride | ≦1 μM | 490 | 412 |

TABLE 19-continued

| Compound No., Structure | Mol. Wt. | Compound Name | IKK2 Resin IC50 | MS (M + H) | Example |
|---|---|---|---|---|---|
| | 533.01 | 8-{[(6-chloro-1,3-benzodioxol-5-yl)carbonyl]amino}-1-[4-(methylthio)phenyl]-4,5-dihydro-1H-benzo[g]indazole-3-carboxamide | ≦1 μM | 533 | 413 |
| | 540.48 | 8-[(5-amino-2-chlorobenzoyl)amino]-1-[4-(methylthio)phenyl]-4,5-dihydro-1H-benzo[g]indazole-3-carboxamide hydrochloride | ≦1 μM | 504 | 414 |

The compounds of Examples 415–420 in Table 20 were prepared by oxidation with m-CPBA with the appropriate sulfide.

The bioactivity in the IKK2 Resin assay for the compounds of Examples 415–420 is shown in Table 20.

TABLE 20

| Compound No., Structure | Mol. Wt. | Compound Name(s) | IKK2 Resin IC50 | MS (M + H) | Example |
|---|---|---|---|---|---|
| | 444.54 | 1-[4-(methylsulfinyl)phenyl]-8-[(methylsulfonyl)amino]-4,5-dihydro-1H-benzo[g]indazole-3-carboxamide | 1 ≦ 10 μM | 445 | 415 |
| | 542.45 | 8-[(3-chloroisonicotinoyl)amino]-1-[4-(methylsulfinyl)phenyl]-4,5-dihydro-1H-benzo[g]indazole-3-carboxamide hydrochloride | ≦1 μM | 543 | 416 |

TABLE 20-continued

| Compound No., Structure | Mol. Wt. | Compound Name(s) | IKK2 Resin IC50 | MS (M + H) | Example |
|---|---|---|---|---|---|
| | 549.01 | 8-{[(6-chloro-1,3-benzodioxol-5-yl)carbonyl]amino}-1-[4-(methylsulfinyl)phenyl]-4,5-dihydro-1H-benzo[g]indazole-3-carboxamide | ≦1 μM | 550 | 417 |
| | 556.48 | 8-[(5-amino-2-chlorobenzoyl)amino]-1-[4-(methylsulfinyl)phenyl]-4,5-dihydro-1H-benzo[g]indazole-3-carboxamide hydrochloride | ≦1 μM | 557 | 418 |
| | 505.00 | 8-[(2-chlorobenzoyl)amino]-1-[4-(methylsulfinyl)phenyl]-4,5-dihydro-1H-benzo[g]indazole-3-carboxamide | ≦1 μM | 505 | 419 |
| | 505.99 | 8-{[(2-chloropyridin-3-yl)carbonyl]amino}-1-[4-(methylsulfinyl)phenyl]-4,5-dihydro-1H-benzo[g]indazole-3-carboxamide | ≦1 μM | 506 | 420 |

Example 421

1-{4-[(allylamino)sulfonyl]phenyl}-8-[(2-chlorobenzoyl)amino]-4,5-dihydro-1H-benzo[g]indazole-3-carboxamide

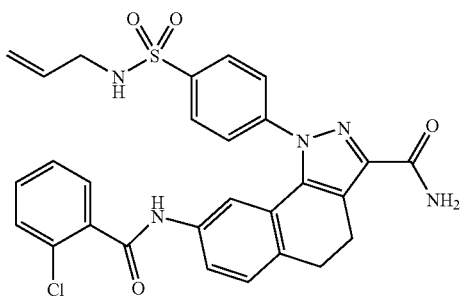

Step 1

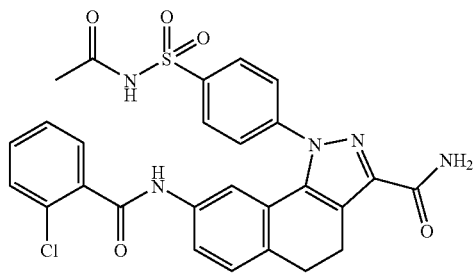

To a stirring solution of 1-[4-(aminosulfonyl)phenyl]-8-[(2-chlorobenzoyl)amino]-4,5-dihydro-1H-benzo[g]indazole-3-carboxamide (2967 mg, 5.7 mmol) in THF (120 mL) was added DMAP (348 mg, 2.8 mmol), then tri-ethyl amine (0.95 mL, 6.8 mmol), followed by acetic anhydride (1.62 mL, 17.1 mmol). The reaction mixture was stirred at room temperature for overnight and then concentrated. To the residue was added 5% aq. NaHCO$_3$ (100 mL). All compounds were dissolved. The aq. Layer was washed with EA (100 mL×2), CH$_2$Cl$_2$ (100 mL). The aq. layer was separated. To the aq. Layer was added 1N HCl to pH=6. A white precipitate was formed. It was filtered and washed with ether to give a white solid. The solid was dried under reduced pressure at 45° C. to give 1-{4-[(acetylamino)sulfonyl]phenyl}-8-[(2-chlorobenzoyl)amino]-4,5-dihydro-1H-benzo[g]indazole-3-carboxamide (2255.4 mg, 70%).

Step 2

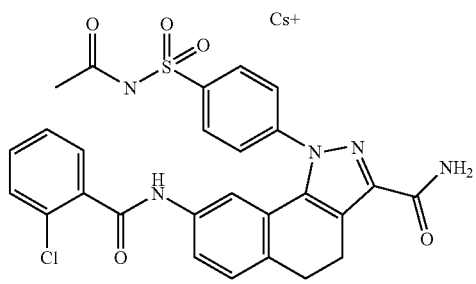

To a stirring solution of 1-{4-[(acetylamino)sulfonyl]phenyl}-8-[(2-chlorobenzoyl)amino]-4,5-dihydro-1H-benzo[g]indazole-3-carboxamide (563 mg, 1 mmol) in H$_2$O (5 mL) was added cesium carbonate (163 mg, 0.5 mmol). The suspension was stirred at room temperature for overnight. All compounds were dissolved. It was dried to give the Cs$^+$ salt (650 mg, 93%).

Step 3

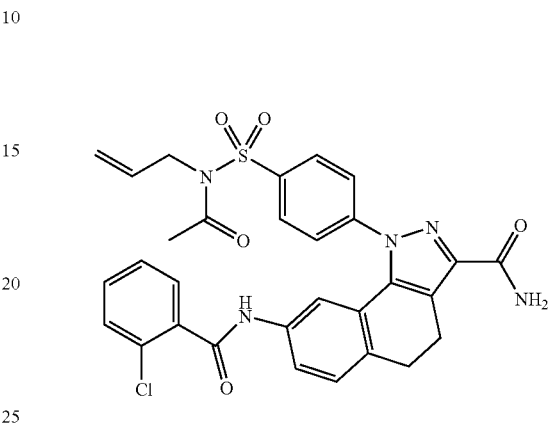

To a stirring solution of the Cs$^+$ salt of 1-{4-[(acetylamino)sulfonyl]phenyl}-8-[(2-chlorobenzoyl)amino]-4,5-dihydro-1H-benzo[g]indazole-3-carboxamide (637 mg, 0.92 mmol) in DMF (8 mL) was added a solution of allyl bromide (111 mg, 0.92 mmol). The solution was stirred at room temperature for over the weekend and concentrated. To the mixture was added MeOH—H$_2$O (2:1). A precipitate was formed. It was filtered to give a yellow solid of 1-(4-[acetyl(allyl)amino]sulfonyl}phenyl)-8-[(2-chlorobenzoyl)amino]-4,5-dihydro-1H-benzo[g]indazole-3-carboxamide (360 mg, 65%.)

Step 4

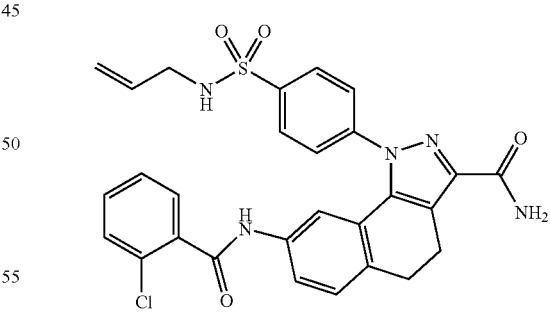

A solid of 1-(4-{[acetyl(allyl)amino]sulfonyl}phenyl)-8-[(2-chlorobenzoyl)amino]-4,5-dihydro-1H-benzo[g]indazole-3-carboxamide (360 mg, 0.6 mmol) was dissolved in 0.5 N solution of NaOH in EtOH (10 mL) and stirred at room temperature for overnight. The mixture was concentrated. It was purified by HPLC to give the desired compound (210 mg, 62%.) IKK-2 resin IC$_{50}$≦1 μM.

Example 422

8-[(2-chlorobenzoyl)amino]-1-{4-[(methylamino)sulfonyl]phenyl}-4,5-dihydro-1H-benzo[g]indazole-3-carboxamide

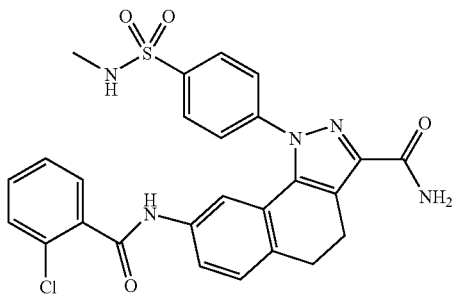

Step 1

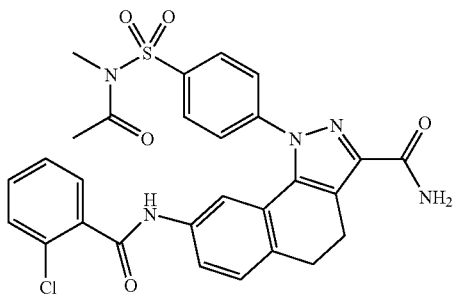

To a stirring solution of 1-{4-[(acetylamino)sulfonyl]phenyl}-8-[(2-chlorobenzoyl)amino]-4,5-dihydro-1H-benzo[g]indazole-3-carboxamide (563 mg, 1 mmol) in DMF (20 mL) was added NaH₂ (40 mg, 1 mmol). The mixture was stirred at room temperature for 1 h. To the mixture was added a solution of Iodomethane (170.3 mg, 1.2 mmol) in DMF (1 mL). The solution was stirred at room temperature for 4 h and concentrated. It was purified by HPLC to give a solid of the desired compound 1-(4-{[acetyl(methyl)amino]sulfonyl}phenyl)-8-[(2-chlorobenzoyl)amino]-4,5-dihydro-1H-benzo[g]indazole-3-carboxamide (155 mg, 27%.)

Step 2

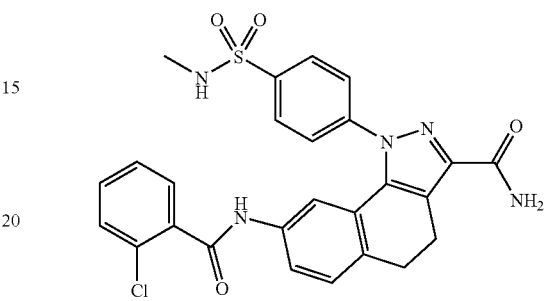

A solid of 1-(4-{[acetyl(methyl)amino]sulfonyl}phenyl)-8-[(2-chlorobenzoyl)amino]-4,5-dihydro-1H-benzo[g]indazole-3-carboxamide was dissolved in 0.5 N solution of NaOH in EtOH (3 mL) and stirred at room temperature for 2 h. A suspension was formed. It was filtered and washed to give the desired compound (29 mg, 53%.) IKK-2 resin $IC_{50} \leq 1\ \mu M$.

The compounds of Examples 423–433 in Table 21 were prepared in a manner analogous to Example 46 using the appropriate alkylating agent and when appropriate acylating or sulfonating agent.

TABLE 21

| Compound No., Structure | Mol. Wt. | Compound Name | IKK2 Resin IC50 | MS (M + H) | Example |
|---|---|---|---|---|---|
|  | 435.51 | 8-amino-1-[4-(2,5-dihydro-1H-pyrrol-1-ylsulfonyl)phenyl]-4,5-dihydro-1H-benzo[g]indazole-3-carboxamide | $1 \leq 10\ \mu M$ | 436 | 423 |
|  | 453.52 | 8-amino-1-[4-(morpholin-4-ylsulfonyl)phenyl]-4,5-dihydro-1H-benzo[g]indazole-3-carboxamide | $1 \leq 10\ \mu M$ | 454 | 424 |

TABLE 21-continued

| Compound No., Structure | Mol. Wt. | Compound Name | IKK2 Resin IC50 | MS (M + H) | Example |
|---|---|---|---|---|---|
| | 459.53 | 8-amino-1-{4-[(diprop-2-ynylamino)sulfonyl]phenyl}-4,5-dihydro-1H-benzo[g]indazole-3-carboxamide | ≦1 μM | 460 | 425 |
| | 489.58 | 1-{4-[(dimethylamino)sulfonyl]phenyl}-8-[(methylsulfonyl)amino]-4,5-dihydro-1H-benzo[g]indazole-3-carboxamide | ≦1 μM | 490 | 426 |
| | 550.04 | 8-[(2-chlorobenzoyl)amino]-1-{4-[(dimethylamino)sulfonyl]phenyl}-4,5-dihydro-1H-benzo[g]indazole-3-carboxamide | ≦1 μM | 550 | 427 |
| | 593.11 | 8-[(2-chlorobenzoyl)amino]-1-[4-({[2-(dimethylamino)ethyl]amino}sulfonyl)phenyl]-4,5-dihydro-1H-benzo[g]indazole-3-carboxamide | ≦1 μM | 594 | 428 |

TABLE 21-continued

| Compound No., Structure | Mol. Wt. | Compound Name | IKK2 Resin IC50 | MS (M + H) | Example |
|---|---|---|---|---|---|
| | 550.04 | 8-[(3-chlorobenzoyl)amino]-1-{4-[(dimethylamino)sulfonoyl]phenyl}-4,5-dihydro-1H-benzo[g]indazole-3-carboxamide | 1 ≦ 10 μM | 550 | 429 |
| | 453.52 | 8-(acetylamino)-1-{4-[(dimethylamino)sulfonyl]phenyl}-4,5-dihydro-1H-benzo[g]indazole-3-carboxamide | 1 ≦ 10 μM | 454 | 430 |
| | 541.65 | 1-{4-[(diallylamino)sulfonyl]phenyl}-8-[(methylsulfonyl)amino]-4,5-dihydro-1H-benzo[g]indazole-3-carboxamide | 1 ≦ 10 M | 542 | 431 |
| | 598.08 | 8-[(2-chlorobenzoyl)amino]-1-{4-[(diprop-2-ynylamino)sulfonyl]phenyl}-4,5-dihydro-1H-benzo[g]indazole-3-carboxamide | 1 ≦ 10 μM | 598 | 432 |

TABLE 21-continued
| Compound No., Structure | Mol. Wt. | Compound Name | IKK2 Resin IC50 | MS (M + H) | Example |
|---|---|---|---|---|---|
| [structure] | 454.56 | 8-amino-1-[4-({[2-(dimethylamino)ethyl]amino}sulfonyl)phenyl]-4,5-dihydro-1H-benzo[g]indazole-3-carboxamide | 1 ≦ 10 µM | 455 | 433 |
The following scheme was used for the synthesis of Examples 434
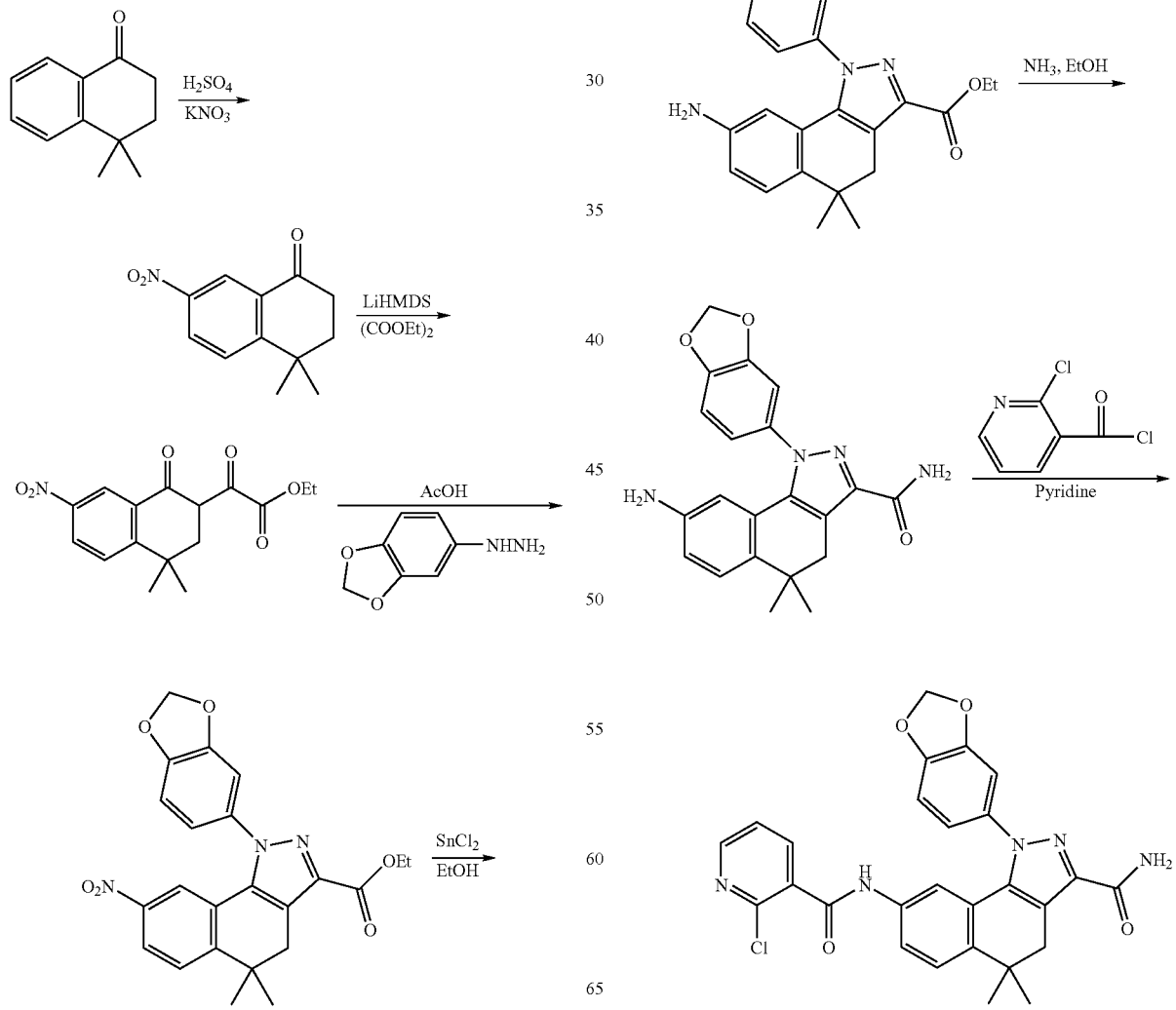
SCHEME XVIV

Example 434

1-(1,3-benzodioxol-5-yl)-8-{[(2-chloropyridin-3-yl)carbonyl]amino}-5,5-dimethyl-4,5-dihydro-1H-benzo[g]indazole-3-carboxamide Step 1

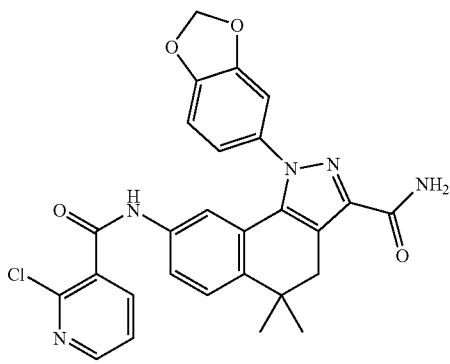

4,4-dimethyl-tetralone (6 g) was suspended in 120 ml conc. H$_2$SO$_4$ at 0° C., then KNO$_3$(3.8 g)/H$_2$SO$_4$ (15 ml) solution was added drop wise at 0° C. The reaction mixture was stirred at 0° C. for three hours until the starting material was gone, then poured into about 100 g of ice. After cooling down, the mixture was filtered, and the solid obtained was washed with water, hexane, and then dried under vacuum. 5.6 g of desired product was obtained. It was used as it was without further purification. They structure was proved by LC-MS(220, M+1), HPLC, $^1$HNMR.

Step 2

The title compound of Step 1 (5.6 g) was dissolved in 100 ml THF, then (COOEt)$_2$ (5.6 g) was added. The mixture was cooled down to −40° C., and then, LiHMDS/1M THF solution (40 ml) was added slowly. The reaction mixture was warmed up to r. t. slowly, then stirred overnight, and then neutralized with 2N aq. HCl. The mixture was extracted with EA (3×200 ml). The EA solution was dried over NaSO$_4$. After filtration and evaporation of solvent, the residue was purified by HPLC (50% CH$_3$CN to 90% CH$_3$CN in 30 minutes). 1.3 g of desired product was obtained. The structure was proved by LC-MS(320, M+1) and HPLC.

Step 3

The title compound of step 2 (1.3 g) and 3,4-methylenedioxyphenylhydrazine hydrochloride (0.85 g) were suspended in 100 ml of HOAc. The mixture was heated up to reflux for 3 hours, and then the solvent was evaporated, and the residue was purified by HPLC (50% CH$_3$CN/H$_2$O to 90% CH$_3$CN/H$_2$O in 30 minutes). 0.65 g of desired product was obtained and characterized by LC-MS(436, M+1), $^1$HNMR, HPLC analysis.

Step 4

The title compound of step 3 (0.65 g) was suspended in 100 ml of EtOH, and then SnCl$_2$ (1.2 g) were added. The reaction mixture was refluxed overnight. Then the solvent was evaporated, and residue was dissolved in 15 ml CH$_3$CN and filtered. The solution was purified by HPLC (40% CH$_3$CN/H$_2$O to 90% CH$_3$CN/H$_2$O in 30 minutes). 0.25 g of desired product was obtained and characterized by HPLC and LC-MS(406, M+1).

Step 5

The title compound of step 4 (0.25 g) was dissolved in EtOH and liquid ammonia, and heated up to 100° C. under 600 PSI for 36 hours. After releasing pressure and evaporating solvent, the residue is purified by HPLC (5% CH$_3$CN/H$_2$O to 60% CH$_3$CN/H$_2$O in 30 minutes). 200 mg of desired product was obtained, and characterized by LC-MS(376, M+1) and HPLC analysis.

Step 6

The title compound of step 5 (90 mg) was dissolved in pyridine (5 ml), then 2-chloro-nictinoyl chloride (52 mg) were added. The reaction mixture was stirred overnight, and then solvent was evaporated. The residue was purified by HPLC (30% CH$_3$CN/H$_2$O to 90% CH$_3$CN/H$_2$O in 30 minutes) 49 mg of desired compound 1-(1,3-benzodioxol-5-yl)-8-{[(2-chloropyridin-3-yl)carbonyl]amino}-5,5-dimethyl-4,5-dihydro-1H-benzo[g]indazole-3-carboxamide

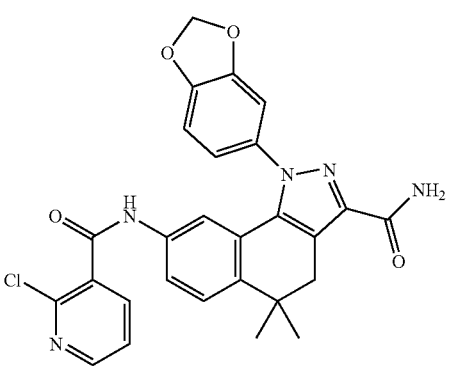

The resulting compound was obtained and analyzed by $^1$HNMR, LC-MS(516, M+1), HPLC and CHN analysis.

Example 435

1-(1,3-benzodioxol-5-yl)-8-[(3-chloroisonicotinoyl)amino]-5,5-dimethyl-4,5-dihydro-1H-benzo[g]indazole-3-carboxamide

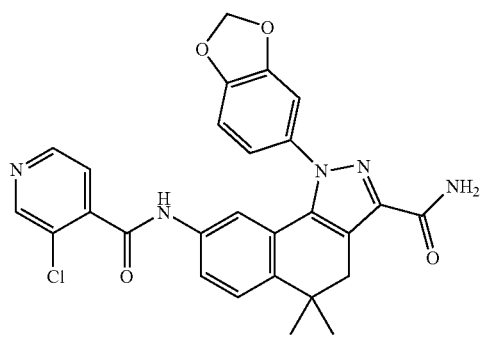

The tile compound of Example 332 (90 mg) was dissolved in 5 ml DMF, then 2-chloroisonicotinic acid (100 mg), HATU (150 mg) and diiospropylethylamine (0.5 ml) were added. The reaction mixture was stirred at r. t. for two days. After the reaction was complete, solvent was evaporated, and the residue was purified by HPLC (30% CH$_3$CN/H$_2$O to 90% CH$_3$CN/H$_2$O in 30 minutes). 100 mg of product was obtained and characterized by $^1$HNMR, LC-MS (516, M+1), HPLC, CHN analysis.

The compounds of Examples 436–443 in Table 22 were prepared in a manner analogous to Examples 434 and 435

The bioactivity in the IKK2 Resin assay for the compounds of Examples 434–443 is shown in Table 22.

TABLE 22

| Compound No., Structure | Mol. Wt. | Compound Name | IKK2 Resin IC50 | MS (M + H) | Example |
|---|---|---|---|---|---|
| | 515.96 | 1-(1,3-benzodioxol-5-yl)-8-{[(2-chloropyridin-3-yl)carbonyl]amino}-5,5-dimethyl-4,5-dihydro-1H-benzo[g]indazole-3-carboxamide | ≦1 μM | 516 | 434 |
| | 515.96 | 1-(1,3-benzodioxol-5-yl)-8-[(3-chloroisonicotinoyl)amino]-5,5-dimethyl-4,5-dihydro-1H-benzo[g]indazole-3-carboxamide | ≦1 μM | 552 | 435 |
| | 475.91 | 8-[(3-chloroisonicotinoyl)amino]-1-(4-fluorophenyl)-5-methyl-4,5-dihydro-1H-benzo[g]indazole-3-carboxamide | ≦1 μM | 476 | 436 |
| | 475.91 | 8-{[(2-chloropyridin-3-yl)carbonyl]amino}-1-(4-fluorophenyl)-5-methyl-4,5-dihydro-1H-benzo[g]indazole-3-carboxamide | ≦1 μM | 476 | 437 |

TABLE 22-continued

| Compound No., Structure | Mol. Wt. | Compound Name | IKK2 Resin IC50 | MS (M + H) | Example |
|---|---|---|---|---|---|
| | 354.36 | 8-amino-1-(2,4-difluorophenyl)-5-methyl-4,5-dihydro-1H-benzo[g]indazole-3-carboxamide | nd | 355 | 438 |
| | 351.39 | 8-amino-1-(4-amino-2-fluorophenyl)-5-methyl-4,5-dihydro-1H-benzo[g]indazole-3-carboxamide | nd | 352 | 439 |
| | 493.90 | 8-[(3-chloroisonicotinoyl)amino]-1-(2,4-difluorophenyl)-5-methyl-4,5-dihydro-1H-benzo[g]indazole-3-carboxamide | ≦1 μM | 494 | 440 |
| | 573.08 | 8-{[2-chloro-5-(4-methylpiperazin-1-yl)benzoyl]amino}-1-(4-fluorophenyl)-5-methyl-4,5-dihydro-1H-benzo[g]indazole-3-carboxamide | ≦1 μM | 574 | 441 |

TABLE 22-continued

| Compound No., Structure | Mol. Wt. | Compound Name | IKK2 Resin IC50 | MS (M + H) | Example |
|---|---|---|---|---|---|
|  | 490.93 | 1-(4-amino-2-fluorophenyl)-8-[(3-chloroisonicotinoyl)amino]-5-methyl-4,5-dihydro-1H-benzo[g]indazole-3-carboxamide | ≤1 μM | 491 | 442 |
|  | 493.90 | 8-{[(2-chloropyridin-3-yl)carbonyl]amino}-1-(2,4-difluorophenyl)-5-methyl-4,5-dihydro-1H-benzo[g]indazole-3-carboxamide | nd | 494 | 443 | nd = not determined

Example 444

1-(1,3-benzodioxol-5-yl)-8-[(N-isopropylglycyl)amino]-4,5-dihydro-1H-benzo[g]indazole-3-carboxamide

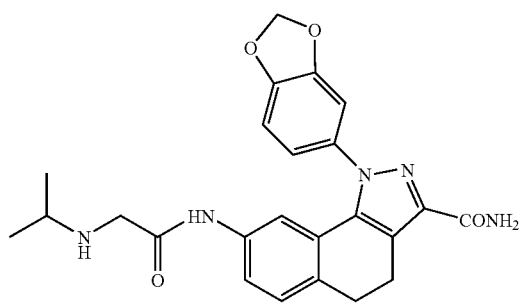

Step 1

To a solution of 8-amino-1-(1,3-benzodioxol-5-yl)-4,5-dihydro-1H-benzo[g]indazole-3-carboxamide (1.00 g, 2.87 mmol) in DMA (5.0 mL) was added chloroacetyl chloride (0.27 mL, 3.44 mmol) and triethylamine (0.48 mL, 3.44 mmol) and the mixture was stirred at RT overnight. The reaction mixture was triturated with distilled water (3×40 mL) and the solid product precipitated out once the water was added. The mixture was filtered and the solid was dried under the vacuum oven overnight to give 8-[(chloroacetyl)amino]-1-(4-fluorophenyl)-4,5-dihydro-1H-benzo[g]indazole-3-carboxamide. MS (ESI+) for $C_{21}H_{17}ClN_4O_4$ m/z 425 (M+H)$^+$.

Step 2

To a solution of product from step 1 (0.10 g, 0.24 mmol) dissolved in DMA (2.0 mL) was added isopropyl amine (3.0 eq) followed by the PS-DIEA resin (2.0 eq). The mixture was stirred and heated at 100° C. overnight. The reaction mixture was cooled to RT and the solution was filtered. The filtrate was then evaporated under a stream of nitrogen overnight. The sample was purified on the SPE silica column. The clean fractions were combined and concentrated to give the title material. $^1$H NMR (CD$_3$OD) δ 7.38 (dd, 1H), 7.28 (d, 1H), 7.18 (d, 1H), 7.0 (t, 1H), 6.96 (d, 2H), 6.12 (s, 2H), 3.29 (s, 2H), 3.04 (m, 2H), 2.95 (m, 2H), 2.79 (m, 1H), 1.08 (d, 6H); MS (ESI+) for $C_{24}H_{25}N_5O_4$ m/z 448 (M+H)$^+$.

The compounds of Examples 445–452 listed in the table below where prepared according to the procedure of Example 444 using the appropriately substituted aniline and appropriate amine.

The bioactivity in the IKK2 Resin assay for the compounds of Examples 444–452 is shown in Table 23

TABLE 23

| Compound No., Structure | Mol. Wt. | Compound Name(s) | IKK2 Resin IC50 | LCMS (M + H) | Example |
|---|---|---|---|---|---|
| | 447.50 | 1-(1,3-benzodioxol-5-yl)-8-[(N-isopropylglycyl)amino]-4,5-dihydro-1H-benzo[g]indazole-3-carboxamide | ≦1 μM | 448 | 444 |
| | 495.97 | 1-(1,3-benzodioxol-5-yl)-8-[(N-cyclobutylglycyl)amino]-4,5-dihydro-1H-benzo[g]indazole-3-carboxamide hydrochloride | ≦1 μM | 460 | 445 |
| | 495.97 | 1-(1,3-benzodioxol-5-yl)-8-[(pyrrolidin-1-ylacetyl)amino]-4,5-dihydro-1H-benzo[g]indazole-3-carboxamide hydrochloride | 1 ≦ 10 μM | 460 | 446 |
| | 524.02 | 1-(1,3-benzodioxol-5-yl)-8-[(N-cyclohexylglycyl)amino]-4,5-dihydro-1H-benzo[g]indazole-3-carboxamide hydrochloride | 1 ≦ 10 μM | 488 | 447 |
| | 455.91 | 1-(1,3-benzodioxol-5-yl)-8-[(N-methylglycyl)amino]-4,5-dihydro-1H-benzo[g]indazole-3-carboxamide hydrochloride | 1 ≦ 10 μM | 420 | 448 |

TABLE 23-continued

| Compound No., Structure | Mol. Wt. | Compound Name(s) | IKK2 Resin IC50 | LCMS (M + H) | Example |
|---|---|---|---|---|---|
| 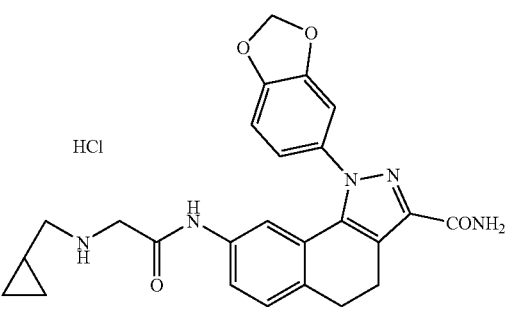 | 495.97 | 1-(1,3-benzodioxol-5-yl)-8-{[N-(cyclopropylmethyl)glycyl]amino}-4,5-dihydro-1H-benzo[g]indazole-3-carboxamide hydrochloride | $1 \leq 10\ \mu M$ | 460 | 449 |
| 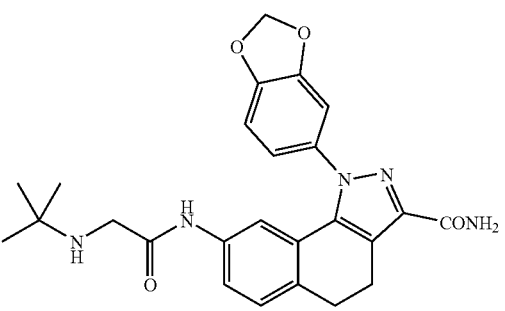 | 461.53 | 1-(1,3-benzodioxol-5-yl)-8-{[N-(tert-butyl)glycyl]amino}-4,5-dihydro-1H-benzo[g]indazole-3-carboxamide | $\leq 1\ \mu M$ | 462 | 450 |
| 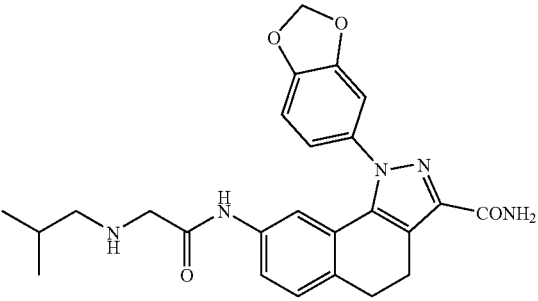 | 461.53 | 1-(1,3-benzodioxol-5-yl)-8-[(N-isobutylglycyl)amino]-4,5-dihydro-1H-benzo[g]indazole-3-carboxamide | $\leq 1\ \mu M$ | 462 | 451 |
| 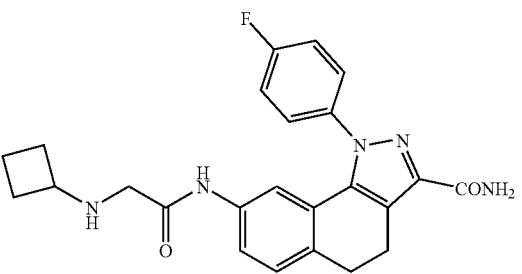 | 433.49 | 8-[(N-cyclobutylglycyl)amino]-1-(4-fluorophenyl)-4,5-dihydro-1H-benzo[g]indazole-3-carboxamide | $\leq 1\ \mu M$ | 434 | 452 |

BIOLOGICAL EVALUATION

Materials

SAM²™96 Biotin capture plates were from Promega. Anti-FLAG affinity resin, FLAG-peptide, NP-40 (Nonidet P-40), BSA, ATP, ADP, AMP, LPS (*E. coli* serotype 0111: B4), and dithiothreitol were obtained from Sigma Chemicals. Antibodies specific for NEMO (IKKγ) (FL-419), IKK1 (H-744), IKK2 (H-470) and IκBα (C-21) were purchased from Santa Cruz Biotechnology. Ni-NTA resin was purchased from Qiagen. Peptides were purchased from American Peptide Company. Protease inhibitor cocktail tablets were from Boehringer Mannheim. Sephacryl S-300 column was from Pharmacia LKB Biotechnology. Centriprep-10 concentrators with a molecular weight cutoff of 10 kDa and membranes with molecular weight cut-off of 30 kDa were obtained from Amicon. [γ-$^{33}$P] ATP (2500 Ci/mmol) and [γ-$^{32}$P] ATP (6000 Ci/mmol) were purchased from Amersham. The other reagents used were of the highest grade commercially available.

Cloning and Expression cDNAs of human IKK1 and IKK2 were amplified by reverse transcriptase-polymerase chain reaction from human placental RNA (Clonetech). hIKK1 was subcloned into pFastBac HTa (Life Technologies) and expressed as N-terminal $His_6$-tagged fusion protein. The hIKK2 cDNA was amplified using a reverse oligonucleotide primer which incorporated the peptide sequence for a FLAG-epitope tag at the C-terminus of the IKK2 coding region (DYKD-DDDKD). The hIKK2:FLAG cDNA was subcloned into the baculovirus vector pFastBac. The rhIKK2 (S177S, E177E) mutant was constructed in the same vector used for wild type rhIKK2 using a QuikChange™ mutagenesis kit (Stratagene). Viral stocks of each construct were used to infect insect cells grown in 40 L suspension culture. The cells were lysed at a time that maximal expression and rhIKK activity were demonstrated. Cell lysates were stored at −80° C. until purification of the recombinant proteins was undertaken as described below.

Enzyme Isolation

All purification procedures were carried out at 4° C. unless otherwise noted. Buffers used are: buffer A: 20 mM Tris-HCl, pH 7.6, containing 50 mM NaCl, 20 mM NaF, 20 mM β-Glycerophosphate, 500 uM sodiumortho-vanadate, 2.5 mM metabisulfite, 5 mM benzamidine, 1 mM EDTA, 0.5 mM EGTA, 10% glycerol, 1 mM DTT, 1× Complete™ protease inhibitors; buffer B: same as buffer A, except 150 mM NaCl, and buffer C: same as buffer A, except 500 mM NaCl.

Isolation of rhIKK1 Homodimer

Cells from an 8-liter fermentation of baculovirus-expressed IKK1 tagged with His peptide were centrifuged and the cell pellet (MOI 0.1, I=72 hr) was re-suspended in 100 ml of buffer C. The cells were microfluidized and centrifuged at 100,000×g for 45 min. The supernatant was collected, imidazole added to the final concentration of 10 mM and incubated with 25 ml of Ni-NTA resin for 2 hrs. The suspension was poured into a 25 ml column and washed with 250 ml of buffer C and then with 125 ml of 50 mM imidazole in buffer C. rhIKK1 homodimer was eluted using 300 mM imidazole in buffer C. BSA and NP-40 were added to the enzyme fractions to the final concentration of 0.1%. The enzyme was dialyzed against buffer B, aliquoted and stored at −80° C.

Isolation of rhIKK2 Homodimer

A 10-liter culture of baculovirus-expressing IKK2 tagged with FLAG peptide was centrifuged and the cell pellet (MOI=0.1 and I=72 hrs) was re-suspended in buffer A. These cells were microfluidized, and centrifuged at 100,000×g for 45 min. Supernatant was passed over a G-25 column equilibrated with Buffer A. Protein peak was collected and incubated with anti-FLAG affinity resin on a rotator overnight in buffer B. The resin was washed in batch with 10–15 bed volumes of buffer C. Washed resin was poured into a column and rhIKK2 homodimer was eluted using 5 bed volumes of buffer B containing FLAG peptide. 5 mM DTT, 0.1% NP-40 and BSA (concentrated to 0.1% in final amount) was added to the eluted enzyme before concentrating in using an Amicon membrane with a molecular weight cut-off of 30 kDa. Enzyme was aliquoted and stored at −80° C.

Isolation of rhIKK1/IKK2 Heterodimer

The heterodimer enzyme was produced by coinfection in a baculovirus system (FLAG IKK2/IKK1 His; MOI=0.1 and I=72 hrs). Infected cells were centrifuged and the cell pellet (10.0 g) was suspended in 50 ml of buffer A. The protein suspension was microfluidized and centrifuged at 100,000×g for 45 min. Imidazole was added to the supernatant to a final concentration of 10 mM. The protein was allowed to bind 25 ml of Ni-NTA resin by mixing for 2 hrs. The protein-resin slurry was poured into a 25 ml column and washed with 250 ml of buffer A containing 10 mM imidazole followed by 125 ml of buffer A containing 50 mM imidazole. Buffer A, containing 300 mM imidazole, was then used to elute the protein. A 75 ml pool was collected and NP-40 was added to a final concentration of 0.1%. The protein solution was then dialyzed against buffer B. The dialyzed heterodimer enzyme was then allowed to bind to 25 ml of anti-FLAG M2 agarose affinity gel overnight with constant mixing. The protein-resin slurry was then centrifuged for 5 min at 2,000 rpm. The supernatant was collected and the resin re-suspended in 100 ml of buffer C containing 0.1% NP-40. The resin was washed with 375 ml of buffer C containing 0.1% NP-40. The protein-resin was poured into a 25 ml column and the enzyme eluted using buffer B containing FLAG peptide. Enzyme fractions (100 ml) were collected and concentrated to 20 ml using an Amicon membrane with molecular weight cut-off of 30 kDa. Bovine serum albumin was added to the concentrated enzyme to final concentration of 0.1%. The enzyme was then aliquoted and stored at −80° C.

Cell Culture

The wild type (wt) human pre-B cell line, 70Z/3, and its mutant, 1.3E2, were generously provided by Dr. Carol Sibley. Wt 70Z/3 and 1.3E2 cells were grown in RPMI 1640 (Gibco) supplemented with 7% defined bovine serum (Hyclone) and 50 μM 2-mercaptoethanol. Human monocytic leukemia THP-1 cells, obtained from ATCC, were cultured in RPMI 1640 supplemented with 10% defined bovine serum, 10 mM HEPES, 1.0 mM sodium pyruvate and 50 μM 2-mercaptoethanol. For experiments, cells were plated in 6 well plates at $1×10^6$ cells/ml in fresh media. Pre-B cells were stimulated by the addition of 10 μg/ml LPS for varying lengths of time ranging from 0–4 hr. THP-1 cells were stimulated by the addition of 1 μg/ml LPS for 45 minutes. Cells were pelleted, washed with cold 50 mM sodium phosphate buffer, pH 7.4 containing 0.15 M NaCl and lysed at 4° C. in 20 mM Hepes buffer, pH 7.6 containing 50 mM NaCl, 1 mM EDTA, 1 mM EGTA, 1 mM sodium ortho-vanadate, 10 mM O-glycerophosphate, 1 mM NaF, 1 mM PMSF, 1 mM DTT and 0.5% NP40 (lysis buffer). The cytosolic fractions obtained following centrifugation at 10,000×g were stored at −80° C. until used.

Immunoprecipitation and Western Blotting

SF9 cells paste containing rhIKKs were centrifuged (100,000×g, 10 min) to remove debris. rhIKKs were immunoprecipitated (100 μg of cell paste) from the cell supernatant using 3 μg of anti-NEMO antibody (FL-419), followed by coupling to protein A sepharose beads. rhIKKs were also immunoprecipitated from affinity chromatography purified protein preparations (1 μg) using anti-FLAG, anti-His or anti-NEMO antibodies (1–4 μg) followed by protein A sepharose coupling. The native, human IKK complex was immunoprecipitated from THP-1 cell homogenates (300 μg/condition) using the anti-NEMO antibody. Immune complexes were pelleted and washed 3 times with 1 ml cold lysis buffer. Immunoprecipitated rhIKKs were chromatographed by SDS-PAGE (8% Tris-glycine) and transferred to nitrocellulose membranes (Novex) and detected by chemiluminescence (SuperSignal) using specific anti-IKK antibodies (IKK2H-470, IKK1H-744). Native IKK2, IκBα, and NEMO proteins from cytosolic lysates (20–80 μg) were separated by SDS-PAGE and visualized by chemiluminescence using specific antibodies.

Phosphatase Treatment

Immunoprecipitated rhIKKs were washed 2 times in 50 mM Tris-HCl, pH 8.2 containing 0.1 mM EDTA, 1 mM DTT, 1 mM PMSF and 2 mM MnCl₂ and resuspended in 50 μl. Phosphatase (λPPase, 1000 U) was pre-diluted in the same buffer and added to the IKK samples. Following an incubation at room temperature for 30 minutes with intermittent mixing, cold lysis buffer was added to the tubes to stop the reaction. After several washes, 10% of the beads were removed for Western analysis, and the remaining material was pelleted and resuspended in 100 μl of the buffer used for the in vitro kinase assay.

IKKα SAM Enzyme Assay

IKKα kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu), a SAM²™96 Biotin capture plate and a vacuum system. The standard reaction mixture contained 5 M biotinylated IκBα peptide, 1 μM [γ-$^{33}$P] ATP (about 1×10⁵ cpm), 1 mM DTT, 50 mM KCl, 2 mM MgCl₂, 2 mM MnCl₂, 10 mM NaF, 25 mM Hepes buffer, pH. 7.6 and enzyme solution (1–10 μl) in a final volume of 50 μl. After incubation at 25° C. for 30 min, 25 μl of the reaction mixture was withdrawn and added to a SAM²™96 Biotin capture 96-well plate. Each well was then washed successively with 800 μl 2 M NaCl, 1.2 ml of NaCl containing 1% H₃PO₄, 400 μl H₂O, and 200 μl 95% ethanol. The plate was allowed to dry in a hood at 25° C. for 1 hr and then 25 μl of scintillation fluid (Microscint 20) was added to each well. Incorporation of [γ-$^{33}$P] ATP was measured using a Top-Count NXT (Packard). Under each assay condition, the degree of phosphorylation of IκBα peptide substrate was linear with time and concentration for all purified enzymes. Results from the biotinylated peptide assay were confirmed by SDS-PAGE analysis of kinase reaction utilizing a GST-IκBα$_{1-54}$ and [γ-$^{32}$P] ATP. The resulting radiolabeled substrate was quantitated by Phosphoimager (Molecular Dynamics). An ion exchange resin assay was also employed using [γ-$^{33}$P] ATP and GST-IκBα$_{1-54}$ fusion protein as the substrates. Each assay system yielded consistent results in regard to $K_m$ and specific activities for each of the purified kinase isoforms. One unit of enzyme activity was defined as the amount required to catalyze the transfer of 1 nmole of phosphate from ATP to IκBα peptide per min. Specific activity was expressed as units per mg of protein. For experiments related to $K_m$ determination of purified enzymes, various concentrations of ATP or IκBα peptide were used in the assay at either a fixed IκBα or ATP concentration. For IκBα peptide $K_m$, assays were carried out with 0.1 μg of enzyme, 5 μM ATP and IκBα peptide from 0.5 to 20 μM. For ATP $K_m$, assays were carried out with 0.1 μg of enzyme, 100 IκBα peptide and ATP from 0.1 to 10 μM. For $K_m$ determination of rhIKK1 homodimer, due to its low activity and higher $K_m$ for IκBα peptide, rhIKK1 homodimer (0.3 μg) was assayed with 125 μM IκBα peptide and a 5-fold higher specific activity of ATP (from 0.1 to 10 μM) for ATP $K_m$ experiments and a 5-fold higher specific activity of 5 μM ATP and IκBα peptide (from 5 to 200 μM) for IκBα peptide $K_m$ experiments.

IKKβ Resin Enzyme Assay

IKKβ kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 μM biotinylated IκBα peptide, 0.1 μCi/reaction [γ-$^{33}$P] ATP (Amersham) (about 1×10⁵ cpm), 1 μM ATP (Sigma), 1 mM DTT (Sigma), 2 mM MgCl₂ (Sigma), 2 mM MnCl₂ (Sigma), 10 mM NaF (Sigma), 25 mM Hepes (Sigma) buffer, pH 7.6 and 20 μl enzyme solution and 10 ul inhibitor in a final volume of 50 μl. After incubation at 25° C. for 30 min, 150 μl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 μl of scintillation fluid (Microscint 40) (Packard) was added to each well. Incorporation of [γ-$^{33}$P] ATP was measured using a Top-Count NXT (Packard).

IKK Heterodimer Resin Enzyme Assay

IKK heterodimer kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 μM biotinylated IκBα peptide, 0.1 μCi/reaction [γ-$^{33}$P] ATP (Amersham) (about 1×10⁵ cpm), 1 μM ATP (Sigma), 1 mM DTT (Sigma), 2 mM MgCl₂ (Sigma), 2 mM MnCl₂ (Sigma), 10 mM NaF (Sigma), 25 mM Hepes (Sigma) buffer, pH 7.6 and 20 μl enzyme solution and 10 μl inhibitor in a final volume of 50 μl. After incubation at 25° C. for 30 min, 150 μl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 μl of scintillation fluid (Microscint 40) (Packard) was added to each well. Incorporation of [γ-$^{33}$P] ATP was measured using a Top-Count NXT (Packard).

What is claimed is:

1. A method of treating inflammation in a subject, said method comprising administering to the subject having or susceptible to such inflammation a therapeutically-effective amount of a compound of of formula II

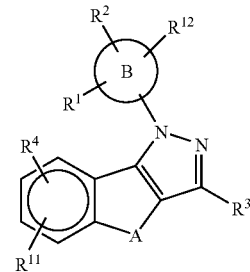

wherein

A is $(CH_2)_m$: wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 to 4;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, NO₂, OR⁵, OCOOR⁵, CO₂R⁷, CON(R⁶) R⁷, COR⁶, SR⁶, SOR⁶, SO₂R⁶, NR⁶R⁷, NR⁶COR⁷, NR⁶CONHR⁷, NR⁶SO₂R⁷, NR⁶SO₂NHR⁷, and SO₂N (R⁶)R⁷ wherein R⁶ and R⁷ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO^2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$ with the proviso that when $R^3$ is $NH_2$ or $NHCH_3$, then $R^1$, $R^2$, $R^4$, $R^{11}$, and $R^{12}$ are not hydrido;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, carriers, prodrugs, or pharmaceutically acceptable salts thereof.

2. The method of claim 1 for use in the treatment of inflammation.

3. The method of claim 1 for use in the treatment of an inflammation-associated disorder.

4. The method of claim 3 wherein the inflammation-associated disorder is arthritis.

5. The method of claim 3 wherein the inflammation-associated disorder is pain.

6. The method of claim 3 wherein the inflammation-associated disorder is fever.

7. The method of claim 1 wherein said compound is a compound of formula II

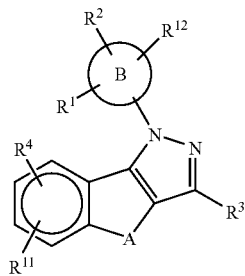

wherein

A is $(CH_2)_m$; wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 to 4;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is hydrido;

$R^3$ is selected from the group consisting of: substituted or unsubstituted amidine, alkylamino, aminoalkyl, $CONHR^7$, $NH_2$, $NHCOR^6$, and $CH_2NHCOR^6$ with the proviso that when $R^3$ is $NH_2$ or $NHCH_3$, then $R^1$, $R^2$, $R^4$, $R^{11}$, and $R^{12}$ are not hydrido;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N ,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, carriers, prodrugs, or pharmaceutically acceptable salts thereof.

8. The method of claim 1 wherein said compound is a compound of formula II

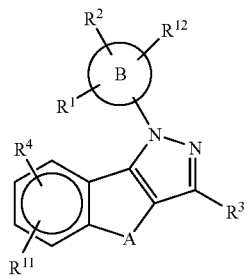

wherein

A is $(CH_2)_m$; wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 to 4;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6SOR^6$, $SO_2R^6$, $NR^6R^7$, $NR^6COR^7$, $NR^6CONHR^7$, $NR^6SO_2R^7$, $NR^6SO_2NHR^7$, and $SO^2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONNHR^7$, $NR^6SO_2R^7$, $NR^6SO_2NHR^7$, and $SO^2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$ with the proviso that when $R^3$ is $NH_2$ or $NHCH_3$, then $R^1$, $R^2$, $R^4$, $R^{11}$, and $R^{12}$ are not hydrido;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is hydrido;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, carriers, prodrugs, or pharmaceutically acceptable salts thereof.

9. The method of claim 1 wherein said compound is a compound of formula II

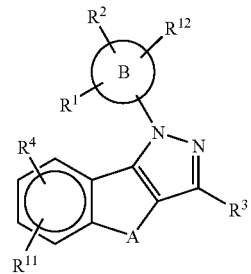

wherein

A is $(CH_2)_m$; wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 to 4;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is hydrido;

$R^3$ is selected from the group consisting of: substituted or unsubstituted amidine, alkylamino, aminoalkyl, $CONHR^7$, $NH_2$, $NHCOR^6$, and $CH_2NHCOR^6$ with the proviso that when $R^3$ is $NH_2$ or $NHCH_3$, then $R^1$, $R^2$, $R^4$, $R^{11}$, and $R^{12}$ are not hydrido;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and NR⁶ wherein said aryl, heterocyclic, heteroaryl, or alkenyl are optionally substituted with R⁹;

R⁵ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR¹⁴, N(R¹⁴)R¹⁴', and glycols;

R⁶ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R⁷ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R⁸ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁸' is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁹ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R¹⁰ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹⁰' is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹¹ is hydrido;

R¹² is hydrido;

R¹³ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR¹⁴, N(R¹⁴) R¹⁴', and glycols;

R¹⁴ is independently selected from the group consisting of hydrido, and lower alkyl; and R¹⁴' is independently selected from the group consisting of hydrido, and lower alkyl;

with the proviso that when R¹ is sulfamyl, then R⁴ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R⁴ is sulfamyl, then R¹ is not sulfamyl, halogen, alkyl, alkoxy, hydroxyl and haloalkyl;

or tautomers, carriers, prodrugs, or pharmaceutically acceptable salts thereof.

10. The method of claim 1 wherein said compound is a compound of formula II

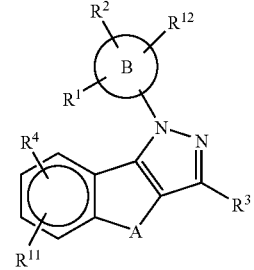

wherein

A is (CH₂)$_m$; wherein each CH² may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 or 2;

B is a 5 or 6 membered heteroaryl, aryl, saturated or unsaturated heterocyclic wherein said aryl, heteroaryl, or heterocyclic are optionally substituted with R¹, R², and R¹²;

R¹ is selected from the group consisting of: hydrido, halogen, alkyl, aryl, heteroaryl, alkenyl, alkynyl, haloalkyl, CN, NO₂, OR⁵, OCOOR⁵, CO₂R⁷, CON(R⁶) R⁷, COR⁶, SR⁶, SOR⁶, SO₂R⁶, NR⁶R⁷, NR⁶COR⁷, NR⁶CONHR⁷, NR⁶SO₂R⁷, NR⁶SO₂NHR⁷, and SO²N (R⁶)R⁷ wherein R⁶ and R⁷ may be taken together to form a 3–7 membered carbocyclic ring having 1 to 3 substituted or unsubstituted heteroatoms selected from the group consisting of: S, SO, SO₂, O, and NR⁶; wherein said alkenyl, alkynyl, alkyl, aryl, heteroaryl or OR⁵ are optional substituted with, hydrido, halogen, alkyl, hydroxyalkyl, aryl, heteroaryl, haloalkyl, COCF₃, CN, NO₂, OR⁵, OCOOR⁵, CO₂R⁷, CON(R⁶) R⁷, COR⁶, SR⁶, SOR⁶, SO₂R⁶, NR⁶R⁷, NR⁶COR⁷, NR⁶CONHR⁷, NR⁶SO₂R⁷, NR⁶SO₂NHR⁷, and SO²N (R⁶)R⁷ wherein R⁶ and R⁷ may be taken together to form a 3–7 membered carbocyclic ring having 1 to 3 substituted or unsubstituted heteroatoms selected from the group consisting of: S, SO, SO$_2$, O, and NR$^6$;

R$^2$ is selected from the group consisting of: halogen, hydrido, hydroxyalkyl, alkyl, OR$^6$, CN, NO$_2$, SR$^6$, NHR$^6$, CON(R$^6$)R$^7$, NHCONHR$^6$, CO$_2$H, and haloalkyl;

R$^1$ and R$^2$ may be taken together to form a 5 to 7 membered saturated or unsaturated carbocyclic ring optionally containing 0 to 3 heteroatoms selected from the group consisting of N, O, or S, and wherein said ring is optionally substituted with R$^1$;

R$^3$ is selected from the group consisting of: substituted or unsubstituted amidine, alkylamino, aminoalkyl, CONHR$^7$, NH$_2$, NHCOR$^6$, and CH$_2$NHCOR$^6$ with the proviso that when R$^3$ is NH$_2$ or NHCH$_3$, then R$^1$, R$^2$, R$^4$, R$^{11}$, and R$^{12}$ are not hydrido;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$)NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

R$^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R$^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{11}$ is selected from the group consisting of: hydrido, halogen, haloalkyl, CN, CO$_2$R$^5$, lower alkyl, lower alkenyl, lower alkynyl, alkoxy, and CONH$_2$;

R$^{12}$ is selected from the group consisting of: hydrido, halogen, alkyl, and alkoxy;

R$^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^{14}$ is independently selected from the group consisting of hydrido, and lower alkyl; and R$^{14'}$ is independently selected from the group consisting of hydrido, and lower alkyl;

with the proviso that when R$^1$ is sulfamyl, then R$^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R$^4$ is sulfamyl, then R$^1$ is not sulfamyl, halogen, alkyl, alkoxy, hydroxyl and haloalkyl;

or tautomers, carriers, prodrugs, or pharmaceutically acceptable salts thereof.

11. The method of claim 10 wherein

A is (CH$_2$)$_m$; wherein each CH$_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;

m is 1 or 2;

B is a 6 membered heteroaryl, aryl, saturated or unsaturated heterocyclic wherein said aryl, heteroaryl, or heterocyclic are optionally substituted with R$^1$, R$^2$, and R$^{12}$;

R¹ is selected from the group consisting of: hydrido, halogen, alkyl, aryl, heteroaryl, alkenyl, alkynyl, haloalkyl, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$^2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$; wherein said alkenyl, alkynyl, alkyl, aryl, heteroaryl or OR$^5$ are optional substituted with, hydrido, halogen, alkyl, hydroxyalkyl, aryl, heteroaryl, haloalkyl, COCF$_3$, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$^2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$;

R$^2$ is hydrido;

R$^3$ is CONH$^2$;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$^2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

R$^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R$^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{11}$ is selected from the group consisting of: hydrido, halogen, haloalkyl, CN, CO$_2$R$^5$, lower alkyl, lower alkenyl, lower alkynyl, alkoxy, and CONH$^2$;

R$^{12}$ is hydrido;

R$^{13}$ is selected the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^{14}$ is independently selected from the group consisting of hydrido, and lower alkyl; and R14' is independently selected from the group consisting of hydrido, and lower alkyl;

with the proviso that when R$^1$ is sulfamyl, then R$^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R$^4$ is sulfamyl, then R$^1$ is not sulfamyl, halogen, alkyl, alkoxy, hydroxyl and haloalkyl;

or tautomers, carriers, prodrugs, or pharmaceutically acceptable salts thereof.

12. The method of claim 10 wherein

A is (CH$_2$)$_2$;

B is a 5 or 6 membered heteroaryl, aryl, saturated or unsaturated heterocyclic wherein said aryl, heteroaryl, or heterocyclic are optionally substituted with R$^1$, R$^2$, and R$^2$;

R$^1$ is SO$_2$R$^6$ or SO$_2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$;

R$^2$ is hydrido;

R$^3$ is CONH$_2$;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$ R$^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R$^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{11}$ is hydrido;

R$^{12}$ is hydrido;

R$^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR$^{14}$, N(R$^{14}$)R$^{14'}$, and glycols;

R$^{14}$ is independently selected from the group consisting of hydrido, and lower alkyl; and R$^{14'}$ is independently selected from the group consisting of hydrido, and lower alkyl;

with the proviso that when R$^1$ is sulfamyl, then R$^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R$^4$ is sulfamyl, then R$^1$ is not sulfamyl, halogen, alkyl, alkoxy, hydroxyl and haloalkyl;

or tautomers, carriers, prodrugs, or pharmaceutically acceptable salts thereof.

13. The method of claim 10 wherein said compound is a compound of the formula

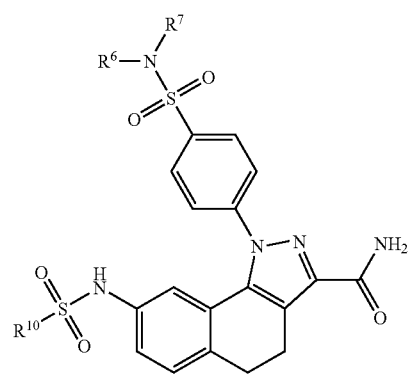

wherein

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; and $R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, or tautomers, carriers, prodrugs, or pharmaceutically acceptable salts thereof.

14. The method of claim 10 wherein said compound is a compound of the formula

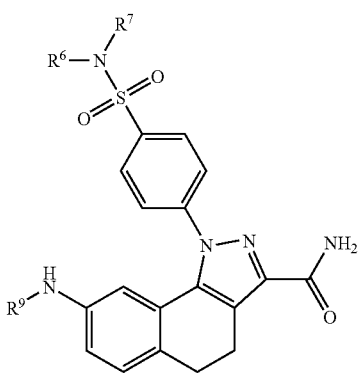

$R^6$ is independently selected from the group consisting of: hydrido, awl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; and $R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylam inoalkyloxy, and heterocyclic optionally substituted with alkyl, alkylamino, aminoalkyl, hydroxyalkyl, and alkylaminoalkyl;

or tautomers, carriers, prodrugs, or pharmaceutically acceptable salts thereof.

15. The method of claim 10 wherein said compound is a compound of the formula

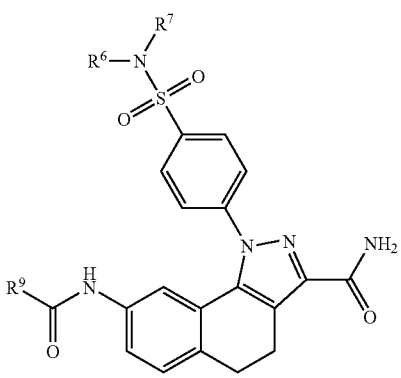

wherein $R^6$ is independently selected from the group consisting of: hydrido, awl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; and $R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

or tautomers, carriers, prodrugs, or pharmaceutically acceptable salts thereof.

16. The method of claim 10 wherein said compound is selected from the group consisting of:

1-[4-(aminosulfonyl)phenyl]-8-{[(trifluoromethyl)sulfonyl]amino}-4,5-dihydro-1H-benzo[g]indazole-3-carboxamide, 1-[4-(aminosulfonyl)phenyl]-8-[(ethylsulfonyl)amino]-4,5-dihydro-1H-benzo[g]indazole-3-carboxamide, 1-[4-(aminosulfonyl)phenyl]-8-{[(2,2,2-trifluoroethyl)sulfonyl]amino}-4,5-dihydro-1H-benzo[g]indazole-3-carboxamide, 1-[4-(aminosulfonyl)phenyl]-8-[(propylsulfonyl)amino]-4,5-dihydro-1H-benzo[g]indazole-3-carboxamide, 1-[4-(aminosulfonyl)phenyl]-8-[(isopropylsulfonyl)amino]-4,5-dihydro-1H-benzo[g]indazole-3-carboxamide, 1-[4-(aminosulfonyl)phenyl]-8-[(butylsulfonyl)amino]-4,5-dihydro-1H-benzo[g]indazole-3-carboxamide, 1-[4-(aminosulfonyl)phenyl]-8-[(benzylsulfonyl)amino]-4,5-dihydro-1H-benzo[g]indazole-3-carboxamide, 1-[4-(aminosulfonyl)phenyl]-8-[(1-naphthylsulfonyl)amino]-4,5-dihydro-1H-benzo[g]indazole-3-carboxamide, 1-[4-(aminosulfonyl)phenyl]-8-({[5-(dimethylamino)-1-naphthyl]sulfonyl}amino)-4,5-dihydro-1H-benzo[g]indazole-3-carboxamide, 1-[4-(aminosulfonyl)phenyl]-8-[(isoquinolin-5-ylsulfonyl)amino]-4,5-dihydro-1H-benzo[g]indazole-3-carboxamide, 1-[4-(aminosulfonyl)phenyl]-8-[(quinolin-7-ylsulfonyl)amino]-4,5-dihydro-1H-benzo[g]indazole-3-carboxamide, 1-[4-(aminosulfonyl)phenyl]-8-[(2,1,3-benzoxadiazol-4-ylsulfonyl)amino]-4,5-dihydro-1H-benzo[g]indazole-3-carboxamide, 1-[4-(aminosulfonyl)phenyl]-8-[(1,1'-biphenyl-4-ylsulfonyl)amino]-4,5-dihydro-1H-benzo[g]indazole-3-carboxamide, 1-[4-(aminosulfonyl)phenyl]-8-{[(5-pyridin-2-ylthien-2-yl)sulfonyl]amino}-4,5-dihydro-1H-benzo[g]indazole-3-carboxamide, 1-[4-(aminosulfonyl)phenyl]-8-{[(1-methyl-1H-imidazol-4-yl)sulfonyl]amino}-4,5-dihydro-1H-benzo[g]indazole-3-carboxamide, 1-[4-(aminosulfonyl)phenyl]-8-{[(1,2-dimethyl-1H-imidazol-4-yl)sulfonyl]amino}-4,5-dihydro-1H-benzo[g]indazole-3-carboxamide, 8-({[2-(acetylamino)-4-methyl-1,3-thiazol-5-yl]sulfonyl}amino)-1-[4-(aminosulfonyl)phenyl]-4,5-dihydro-1H-benzo[g]indazole-3-carboxamide, 1-[4-(aminosulfonyl)phenyl]-8-{[(4-methylphenyl)sulfonyl]amino}-4,5-dihydro-1H-benzo[g]indazole-3-carboxamide, 1-[4-(aminosulfonyl)phenyl]-8-{[(4-methoxyphenyl)sulfonyl]amino}-4,5-dihydro-1H-benzo[g]indazole-3-carboxamide, 1-[4-(aminosulfonyl)phenyl]-8-{[(4-fluorophenyl)sulfonyl]amino}-4,5-dihydro-1H-benzo[g]indazole-3-carboxamide, 1-[4-(aminosulfonyl)phenyl]-8-{[(4-chlorophenyl)sulfonyl]amino}-4,5-dihydro-1H-benzo[g]indazole-3-carboxamide, 1-[4-(aminosulfonyl)phenyl]-8-{[(4-bromophenyl)sulfonyl]amino}-4,5-dihydro-1H-benzo[g]indazole-3-carboxamide, 1-[4-(aminosulfonyl)phenyl]-8-({[3-(trifluoromethyl)phenyl]sulfonyl}amino)-4,5-dihydro-1H-benzo[g]indazole-3-carboxamide, 1-[4-(aminosulfonyl)phenyl]-8-{[(3,4-dichlorophenyl)sulfonyl]amino}-4,5-dihydro-1H-benzo[g]indazole-3-carboxamide, 1-[4-(aminosulfonyl)phenyl]-8-{[(2,5-dichlorophenyl)sulfonyl]amino}-4,5-dihydro-1H-benzo[g]indazole-3-carboxamide, 1-[4-(aminosulfonyl)phenyl]-8-{[(2,4-dichlorophenyl)sulfonyl]amino}-4,5-dihydro-1H-benzo[g]indazole-3-carboxamide, 1-[4-(aminosulfonyl)phenyl]-8-{[(2,4-difluorophenyl)sulfonyl]amino}-4,5-dihydro-1H-benzo[g]indazole-3-carboxamide, 1-[4-(aminosulfonyl)phenyl]-8-{[(3,4-difluorophenyl)sulfonyl]amino}-4,5-dihydro-1H-benzo[g]indazole-3-carboxamide, 1-[4-(aminosulfonyl)phenyl]-8-{[(4-bromo-2-fluorophenyl)sulfonyl]amino}-4,5-dihydro-1H-benzo[g]indazole-3-carboxamide, 1-[4-(aminosulfonyl)phenyl]-8-{[(3,4-dimethoxyphenyl)sulfonyl]amino}-4,5-dihydro-1H-benzo[g]indazole-3-carboxamide, 1-[4-(aminosulfonyl)phenyl]-8-({[3,5-bis(trifluoromethyl)phenyl]sulfonyl}amino)-4,5-dihydro-1H-benzo[g]indazole-3-carboxamide, 1-[4-(aminosulfonyl)phenyl]-8-{[(2,4,5-trichlorophenyl)sulfonyl]amino}-4,5-dihydro-1H-benzo[g]indazole-3-carboxamide, 1-[4-(aminosulfonyl)phenyl]-8-(propionylamino)-4,5-dihydro-1H-benzo[g]indazole-3-carboxamide, 1-[4-(aminosulfonyl)phenyl]-8-(benzoylamino)-4,5-dihydro-1H-benzo[g]indazole-3-carboxamide, 1-[4-(aminosulfonyl)phenyl]-8-{[(ethylamino)carbonyl]amino}-4,5-dihydro-1H-benzo[g]indazole-3-carboxamide, 1-[4-(aminosulfonyl)phenyl]-8-[(anilinocarbonyl)amino]-4,5-dihydro-1H-benzo[g]indazole-3-carboxamide, 1-[4-(aminosulfonyl)phenyl]-8-(benzylamino)-4,5-dihydro-1H-benzo[g]indazole-3-carboxamide, 1-[4-(aminosulfonyl)phenyl]-8-[(4-methylbenzyl)amino]-4,5-dihydro-1H-benzo[g]indazole-3-carboxamide, 1-[4-(aminosulfonyl)phenyl]-8-[(4-methoxybenzyl)amino]-4,5-dihydro-1H-benzo[g]indazole-3-carboxamide, 1-[4-(aminosulfonyl)phenyl]-8-[(4-chlorobenzyl)amino]-4,5-dihydro-1H-benzo[g]indazole-3-carboxamide, 1-[4-(aminosulfonyl)phenyl]-8-(isobutylamino)-4,5-dihydro-1H-benzo[g]indazole-3-carboxamide, 8-amino-1-{4-[(dimethylamino)sulfonyl]phenyl}-4,5-dihydro-1H-benzo[g]indazole-3-carboxamide, 8-amino-1-{4-[(diallylamino)sulfonyl]phenyl}-4,5-dihydro-1H-benzo[g]indazole-3-carboxamide, 8-(L-alanylamino)-1-[4-(aminosulfonyl)phenyl]-4,5-dihydro-1H-benzo[g]indazole-3-carboxamide, 8-(D-alanylamino)-1-[4-(aminosulfonyl)phenyl]-4,5-dihydro-1H-benzo[g]indazole-3-carboxamide, 1-[4-(aminosulfonyl)phenyl]-8-(pentanoylamino)-4,5-dihydro-1H-benzo[g]indazole-3-carboxamide, 1-[4-(aminosulfonyl)phenyl]-8-[(cyclohexylcarbonyl)amino]-4,5-dihydro-1H-benzo[g]indazole-3-carboxamide, 1-[4-(aminosulfonyl)phenyl]-8-[(cyclopentylcarbonyl)amino]-4,5-dihydro-1H-benzo[g]indazole-3-carboxamide, 1-[4-(aminosuifonyl)phenyl]-8-[(cyclobutylcarbonyi) amino]-4,5dihydro-1H-benzo[g]indazole-3-carboxamide,
1-[4-(aminosulfonyl)phenyl]-8-[(cyclopropylcarbonyl) amino]-4,5-dihydro-1H-benzo[g]indazole-3-carboxamide,
1-[4-(aminosulfonyl)phenyl]-8-(butyrylamino)-4,5-dihydro-1H-benzo[g]indazole-3-carboxamide,
1-[4-(aminosulfonyl)phenyl]-8-[(phenylacetyl)amino]-4,5-dihydro-1H-benzo[g]indazole-3-carboxamide,
1-[4-(aminosulfonyl)phenyl]-8-[(methoxyacetyl)aminol-4,5-dihydro-1H-benzo[g]indazole-3-carboxamide,
1-[4-(aminosulfonyl)phenyl]-8-(isobutyrylamino)-4,5dihydro-1H-benzo[g]indazole-3-carboxamide,
1-(4-(aminosulfonyl)phenyl]-8-{[4-(trifluoromethyl)benzoyl]amino}-4,5-dihydro-1H-benzo[g]indazole-3-carboxamide
1-[4-(aminosulfonyl)phenyl]-8-[(4-methoxybenzoyl) amino]-4,5-dihydro-1H-benzo[g]indazole-3-carboxamide,
1-[4-(aminosulfonyl)phenyl]-8-[(4-chlorobenzoyl) amino]-4,5-dihydro-1H-benzo[g]indazole-3-carboxamide,
1-[4-(aminosulfonyl)phenyl]-8-[(4-fluorobenzoyl) amino]-4,5-dihydro-1H-benzo[g]indazole-3-carboxamide,
1-[4-(aminosulfonyl)phenyl]-8-[(3,4-dimethoxybenzoyl) amino]-4,5-dihydro-1H-benzo[g]indazole-3-carboxamide,
1-[4-(aminosulfonyl)phenyl]-8-(2-furoylamino)4,5-dihydro-1H-benzo[g]indazole-3-carboxamide,
1-[4-(aminosulfonyl)phenyl]-8-[(thien-2-ylcarbonyl) amino]-4,5-dihydro-1H-benzo[g]indazole-3-carboxamide,
1-[4-(aminosulfonyl)phenyl]-8-(isonicotinoylamino)-4,5dihydro-1H-benzo[g]indazole-3-carboxamide,
8-[(1-adamantylcarbonyl)amino]-1-[4-(aminosulfonyl) phenyl]-4,5-dihydro-1H-benzo[g]indazole-3-carboxamide,
1-[4-(aminosulfonyl)phenyl]-8-[(phenylsulfonyl)amino]-4,5-dihydro-1H-benzo[g]indazole-3-carboxamide,
1-[4-(aminosulfonyl)phenyl]-8-{[3-(trifluoromethyl)benzoyl]amino}-4,5-dihydro-1H-benzo[g]indazole-3-carboxamide,
1-[4-(aminosulfonyl)phenyl]-8-[(3-methylbenzoyl) amino]-4,5-dihydro-1H-benzo[g]indazole-3-carboxamide,
1-[4-(aminosulfonyl)phenyl]-8-[(3-bromobenzoyl) amino]-4,5-dihydro-1H-benzo[g]indazole-3-carboxamide,
1-[4-(aminosulfonyl)phenyl]-8-{[(3-methoxyphenyl) acetyl]amino}-4,5-dihydro-1H-benzo[g]indazole-3-carboxamide,
1-[4(aminosulfonyl)phenyl]-8-[(pyridin-3-ylcarbonyl) amino]-4,5-dihydro-1H-benzo[g]indazole-3-carboxamide,
1-[4-(aminosulfonyl)phenyl]-8-[(2-chiorobenzoyl) amino]-4,5-dihydro-1H-benzo[g]indazole-3-carboxamide,
1-[4- (aminosulfonyl)phenyl]-8-{[(3-bromophenyl)sulfonyl]amino}-4,5-dihydro-1H-benzo[g]indazole-3carboxamide,
1-[4-(aminosulfonyl)phenyl]-8-{[(3-chlorophenyl)sulfonyl]amino}-4,5-dihydro-1H-benzo[g]indazole-3-carboxamide, 1-[4-(aminosulfonyt)phenyl]-8-[(3-cyanobenzoyl) amino]-4,5-dihydro-1H-benzo[g]indazole-3-carboxamide,
1-[4-(aminosulfonyl)phenyl]-8-{[(3-methylphenyl)sulfonyl]amino}-4,5-dihydro-1H-benzo[g]indazole-3-carboxamide,
1-[4-(aminosulfonyl)phenyl]-8-[(3-methoxybenzoyl) amino]-4,5-dihydro-1H-benzo[g]indazole-3-carboxamide,
1-[4-(aminosulfonyl)phenyl]-8-[(3-chlorobenzoyl) amino]-4,5-dihydro-1H-benzo[g]indazole-3-carboxamide,
1-[4-(aminosulfonyl)phenyl]-8-[(2-methoxybenzoyl) amino]-4,5-dihydro-1H-benzo[g]indazole-3-carboxamide,
1-[4-(aminosulfonyl)phenyl]-8-{[2-(trifluoromethyl)benzoyl]amino}-4,5-dihydro-1H-benzo[g]indazole-3-carboxamide,
1-[4-(aminosuifonyl)phenyl]-8-[(2-methylbenzoyl) amino]-4,5-dihydro-1H-benzo[g]indazole-3-carboxamide,
1-[4-(aminosulfonyl)phenyl]-8-[(2,6-dichlorobenzoyl) amino]-4,5-dihydro-1H-benzo[g]indazole-3-carboxamide,
1-[4-(aminosulfonyl)phenyl]-8-{[2-(trifluoromethoxy) benzoyl]amino}-4,5-dihydro-1H-benzo[g]indazole-3-carboxamide,
1-[4-(aminosulfonyl)phenyl]-8-[(2,3-dichlorobenzoyl) amino]-4,5-dihydro-1H-benzo[g]indazole-3-carboxamide,
1-[4-(aminosulfonyl)phenyl]-8-[(2-fluorobenzoyl) amino]-4,5-dihydro-1H-benzo[g]indazole-3-carboxamide,
1-4-(aminosulfonyl)phenyl]-8-{[(2-chloropyridin-3-yl) carbonyl]amino}-4,5-dihydro-1H-benzo[g]indazole-3-carboxamide,
1-[4-(aminosulfonyl)phenyl]-8-{[(2-chlorophenyl)sulfonyl]amino}-4,5dihydro-1H-benzo[g]indazole-3-carboxamide,
1-[4-(aminosulfonyl)phenyl]-8-[(2-bromobenzoyl) amino]-4,5-dihydro-1H-benzo[g]indazole-3-carboxamide,
8-[(2-chlorobenzoyl)amino]-1-{4-[(dimethylamino)sulfonyl]phenyl}-4,5-dihydro-1H-benzo[g]indazole-3-carboxamide,
8-[(2-chlorobenzoyl)amino]-1-[4-(methylsulfonyl)phenyl]-4,5-dihydro-1H-benzo[g]indazole-3-carboxamide, and
1-[3-(aminosulfonyl)phenyl]-8-[(2-chlorobenzoyl) amino]-4,5-dihydro-1H-benzo[g]indazole-3-carboxamide.

17. The method of claim 1 wherein said compound is a compound of the formula

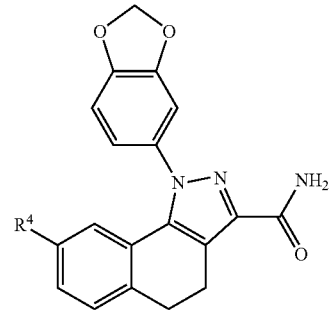

wherein

R⁴ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR¹³, SR⁸, SO₂N(R⁸)R⁸', NHR⁹, NHCOR⁹, NR⁹COR⁹, NHCO(OR⁹), NR⁹CO(OR⁹), NR⁸SO₂R¹⁰, NHSO₂N(R¹⁰)R¹⁰', NR⁶CON(R¹⁰)R¹⁰', COR⁹, CO₂R⁸, CON(R⁸)R⁸', wherein R⁸ and R⁸' may be taken together to form a 3–7 membered carbocyclic ring having 1 to 3 substituted or unsubstituted heteroatoms selected from S, SO, SO₂, O, N, and NR⁶, and wherein R¹⁰ and R¹⁰' be taken together to form a 3–7 membered carbocyclic ring having 1 to 3 substituted or unsubstituted heteroatoms selected from S, SO, SO₂, O, N, and NR⁸ wherein said aryl, heterocyclic, heteroaryl, or alkenyl are optionally substituted with R⁹;

R⁶ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R⁸ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁸' is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁹ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R¹⁰ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹⁰' is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹³ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of OR¹⁴, N(R¹⁴)R¹⁴', and glycols;

R¹⁴ is independently selected from the group consisting of hydrido, and lower alkyl; and R¹⁴' is independently selected from the group consisting of hydrido, and lower alkyl;

with the proviso that when R¹ is sulfamyl, then R⁴ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R⁴ is sulfamyl, then R¹ is not sulfamyl, halogen, alkyl, alkoxy, hydroxyl and haloalkyl;

or tautomers, carriers, prodrugs, or pharmaceutically acceptable salts thereof.

18. The method of claim 1 wherein said compound is a compound of the formula

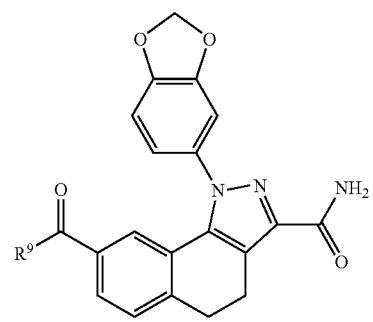

wherein

R⁹ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

or tautomers, carriers, prodrugs, or pharmaceutically acceptable salts thereof.

19. The method of claim 18 wherein said compound is selected from the group consisting of:

1-(1,3-benzodioxol-5-yl)-8-{[(2-chloropyridin-3-yl)carbonyl]amino}-4,5-dihydro-1H-benzo[g]indazole-3-carboxamide,
1-(1,3-benzodioxol-5-yl)-8-{[(2,5-dichloropyridin-3-yl)carbonyl]amino}-4,5-dihydro-1H-benzo[g]indazole-3-carboxamide,
1-(1,3-benzodioxol-5-yl)-8-{[2-chloro-4-(methylsulfonyl)benzoyl]amino}-4,5-dihydro-1H-benzo[g]indazole-3-carboxamide,
1-(1,3-benzodioxol-5-yl)-8-[(2,5-dichloroisonicotinoyl)amino]-4,5-dihydro-1H-benzo[g]indazole-3-carboxamide,
1-(1,3-benzodioxol-5-yl)-8-[(2-chloro-4-fluorobenzoyl)amino]-4,5-dihydro-1H-benzo[g]indazole-3-carboxamide,
1-(1,3-benzodioxol-5-yl)-8-[(2-chlorobenzoyl)amino]-4,5-dihydro-1H-benzo[g]indazole-3-carboxamide,
1-(1,3benzodioxol-5-yl)-8-[(2-chloro-4,5-difluorobenzoyl)amino]-4,5-dihydro-1H-benzo[g]indazole-3-carboxamide,
1-(1,3-benzodioxol-5-yl)-8-{[(2-chloro-6-methylpyridin-3-yl)carbonyl]amino}-4,5-dihydro-1H-benzo[g]indazole-3-carboxamide,
1-(1,3-benzodioxol-5-yl)-8-{[(6-chloro-1,3-benzodioxol-5-yl)carbonyl]amino}-4,5-dihydro-1H-benzo[g]indazole-3-carboxamide,
8-[(2-amino-6-chlorobenzoyl)amino]-1-(1,3-benzodioxol-5-yl)-4,5-dihydro-1H-benzo[g]indazole-3-carboxamide,
1-(1,3-benzodioxol-5-yl)-8-[(3-chloroisonicotinoyl)amino]-4,5-dihydro-1H-benzo[g]indazole-3-carboxamide,
8-4(3-amino-2-chlorobenzoyl)amino]-1-(1,3-benzodioxol-5-yl)-4,5-dihydro-1H-benzo[g]indazole-3-carboxamide hydrochloride,
8-[(5-amino-2-chlorobenzoyl)amino]-1-(1,3-benzodioxol-5-yl)-4,5-dihydro-1H-benzo[g]indazole-3-carboxamide,
1-(1,3-benzodioxol-5-yl)-8-[(2-chloro-5-nitrobenzoyl)amino]-4,5-dihydro-1H-benzo[g]indazole-3-carboxamide,
1-(1,3-benzodioxol-5-yl)-8-[(2-chloro-4,5-dimethoxybenzoyl)amino]-4,5-dihydro-1H-benzo[g]indazole-3-carboxamide,
1-(1,3-benzodioxol-5-yl)-8-[(2-chloro-3,4-dimethoxybenzoyl)amino]-4,5-dihydro-1H-benzo[g]indazole-3-carboxamide,
1-(1,3-benzodioxol-5-yl)-8-{[2-chloro-5-(methylsulfinyl)benzoyl]amino}-4,5-dihydro-1H-benzo[g]indazole-3-carboxamide,
1-(1,3-benzodioxol-5-yl)-8-[(2-bromobenzoyl)amino]-4,5-dihydro-1H-benzo[g]indazole-3-carboxamide,
1-(1,3-benzodioxol-5-yl)-8-({[2-(methylamino)pyridin-3-yl]carbonyl}amino)-4,5-dihydro-1H-benzo[g]indazole-3-carboxamide,
1-(1,3-benzodioxol-5-yl)-8-[(2-chloro-5-methoxybenzoyl)amino]-4,5-dihydro-1H-benzo[g]indazole-3-carboxamide,
8-[(4-acetylbenzoyl)amino]-1-(1,3-benzodioxol-5-yl)-4,5-dihydro-1H-benzo[g]indazole-3-carboxamide,
8-[(4-amino-2-chlorobenzoyl)amino]-1-(1,3-benzodioxol-5-yl)-4,5-dihydro-1H-benzo[g]indazole-3-carboxamide,
1-(1,3-benzodioxol-5-yl)-8-({[2-chloro-6-(trifluoromethyl)pyridin-3-yl]carbonyl}amino)-4,5-dihydro-1H-benzo[g]indazole-3-carboxamide,
1-(1,3-benzodioxol-5-yl)-8-[(2-chloro-4-methoxybenzoyl)amino]-4,5-dihydro-1H-benzo[g]indazole-3-carboxamide,
1-(1,3-benzodioxol-5-yl)-8-{[2-chloro-5-(dimethylamino)benzoyl]amino}-4,5-dihydro-1H-benzo[g]indazole-3-carboxamide,
1-(1,3-benzodioxol-5-yl)-8-[(2-chloro-4-nitrobenzoyl)amino]-4,5-dihydro-1H-benzo[g]indazole-3-carboxamide,
1-(1,3-benzodioxol-5-yl)-8-{[2-chloro-5-(methylsulfonyl)benzoyl]amino}-4,5-dihydro-1H-benzo[g]indazole-3-carboxamide,
1-(1,3-benzodioxol-5-yl)-8-{[(6-hydroxypyridin-3-yl)carbonyl]amino}-4,5-dihydro-1H-benzo[g]indazole-3-carboxamide,
1-(1,3-benzodioxol-5-yl)-8-{[(4-methyipyridin-3-yl)carbonyl]amino}-4,5-dihydro-1H-benzo[g]indazole-3-carboxamide,
1-(1,3-benzodioxol-5-yl)-8-[(2-methylbenzoyl)amino]-4,5-dihydro-1H-benzo[g]indazole-3-carboxamide,
1-(1,3-benzodioxol-5-yl)-8-[(2,5-dichlorobenzoyl)amino]-4,5-dihydro-1H-benzo[g]indazole-3-carboxamide,
1-(1,3-benzodioxol-5-yl)-8-{[2-chloro-5-(methylthio)benzoyl]amino}-4,5-dihydro-1H-benzo[g]indazole-3-carboxamide,
1-(1,3-benzodioxol-5-yl)-8-({2-chloro-5-[2-(dimethylamino)ethoxy]benzoyl}amino)-4,5-dihydo-1H-benzo[g]indazole-3-carboxamide,
1-(1,3-benzodioxol-5-yl)-8-[(2-nitrobenzoyl)amino]-4,5-dihydro-1H-benzo[g]indazole-3-carboxamide,
1-(1,3-benzodioxol-5-yl)-8-{[(4-methyl-1,2,3-thiadiazol-5-yl)carbonyl]amino}-4,5-dihydro-1H-benzo[g]indazole-3-carboxamide,
1-(1,3-benzodioxol-5-yl)-8-[(2,3-dichlorobenzoyl)amino]-4,5-dihydro-1H-benzo[g]indazole-3-carboxamide,
1-(1,3-benzodioxol-5-yl)-8-{[(3-chloro-6-morpholin-4-ylpyridin-2-yl)carbonyl]amino}-4,5-dihydro-1H-benzo[g]indazole-3-carboxamide,
1-(1,3-benzodioxol-5-yl)-8-[(2,4-dichlorobenzoyl)amino]4 5-dihydro-1H-benzo[g]indazole-3-carboxamide,
1-(1,3-benzodioxol-5-yl)-8-(isonicotinoylamino)-4,5-dihydro-1H-benzo[g]indazole-3-carboxamide,
1-(1,3-benzodioxol-5-yl)-8-[(5-methoxy-2-nitrobenzoyl)amino]-4,5-dihydro-1H-benzo[g]indazole-3-carboxamide,
1-(1,3-benzodioxol-5-yl)-8-[(3-hydroxy-2-methylbenzoyl)amino]-4,5-dihydro-1H-benzo[g]indazole-3-carboxamide,
1-(1,3-benzodioxol-5-yl)-8-[(1-oxidoisonicotinoyl)amino]-4,5-dihydro-1H-benzo[g]indazole-3-carboxamide,
1-(1,3-benzodioxol-5-yl)-8-(3-furoylamino)-4,5-dihydro-1H-benzo[g]indazole-3-carboxamide,
8-[(3-amino-4-chlorobenzoyl)amino]-1-(1,3-benzodioxol-5-yl)-4,5-dihydro-1H-benzo[g]indazole3-carboxamide,
1-(1,3-benzodioxol-5-yl)-8-{[(2-methylpyridin-3-yl)carbonyl]amino}-4,5-dihydro-1H-benzo[g]indazole-3-carboxamide, 1-(1,3-benzodioxol-5-yl)-8-({2-chloro-4-[(N,N-dimethylglycyl)amino]benzoyl}amino)-4,5-dihydo-1H-benzo[g]indazole-3-carboxamide,
1-(1,3-benzodioxol-5-yl)-8-{[(3,6-dichloropyridin-2-yl)carbonyl]amino}-4,5-dihydro-1H-benzo[g]indazole-3-carboxamide,
1-(1,3-benzodioxol-5-yl)-8-{[2-(trifluoromethoxy)benzoyl]amino}-4,5-dihydro-1H-benzo[g]indazole-3-carboxamide,
1-(1,3-benzodioxol-5-yl)-8-{[(6-hydroxypyridin-2-yl)carbonyl]amino}-4,5-dihydro-1H-benzo[g]indazole-3-carboxamide, and
1-(1,3-benzodioxol-5-yl)-8-[(4-cyanobenzoyl)amino]-4,5-dihydro-1H-benzo[g]indazole-3-carboxamide.

20. The method of claim 1 wherein said compound is a compound of the formula

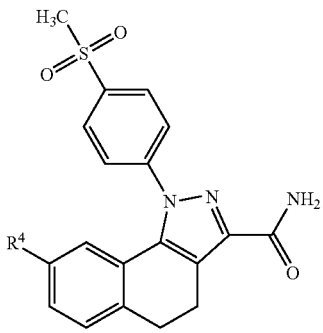

wherein
$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;
$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;
$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;
$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;
$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;
$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic,
$R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic,
$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;
$R^{14}$ is independently selected from the group consisting of hydrido, and lower alkyl; and
$R^{14'}$ is independently selected from the group consisting of hydrido, and lower alkyl;
with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;
or tautomers, carriers, prodrugs, or pharmaceutically acceptable salts thereof.

21. The method of claim 20 wherein said compound is selected from the group consisting of:
8-amino-1-[4-(methylsulfonyl)phenyl]-4,5-dihydro-1H-benzo[g]indazole-3-carboxamide hydrochloride,
1-[4-(methylsulfonyl)phenyl]-8-{[2-(trifluoromethyl)benzoyl]amino}-4,5-dihydro-1H-benzo[g]indazole-3-carboxamide,
8-[(2-methylbenzoyl)amino]-1-[4-(methylsulfonyl)phenyl]-4,5-dihydro-1H-benzo[g]indazole-3-carboxamide, 8-[(2-chlorobenzoyl)amino]-1-[4-(methylsulfonyl)phenyl]-4,5-dihydro-1H-benzo[g]indazole-3-carboxamide, 8-[(2,3-dichlorobenzoyl)amino]-1-[4-(methylsulfonyl)phenyl]-4,5-dihydro-1H-benzo[g]indazole-3-carboxamide, 8-[(2-fluorobenzoyl)amino]-1-[4-(methylsulfonyl)phenyl]-4,5-dihydro-1H-benzo[g]indazole-3-carboxamide, 8-{[(2-chloropyridin-3-yl)carbonyl]amino}-1-[4-(methylsulfonyl)phenyl]-4,5-dihydro-1H-benzo[g]indazole-3-carboxamide, 1-[4-(methylsulfonyl)phenyl]-8-[(1H-pyrazol-4-ylcarbonyl)amino]-4,5-dihydro-1H-benzo[g]indazole-3-carboxamide, 8-[(4-chloro-2-nitrobenzoyl)amino]-1-[4-(methylsulfonyl)phenyl]-4,5-dihydro-1H-benzo[g]indazole-3-carboxamide, 8-[(cyclobutylcarbonyl)amino]-1-[4-(methylsulfonyl)phenyl]-4,5-dihydro-1H-benzo[g]indazole-3-carboxamide, 8-[(2-methyl-3-nitrobenzoyl)amino]-1-[4-(methylsulfonyl)phenyl]-4,5-dihydro-1H-benzo[g]indazole-3-carboxamide, 8-[(2-chloro-6-fluorobenzoyl)amino]-1-[4-(methylsulfonyl)phenyl]-4,5-dihydro-1H-benzo[g]indazole-3-carboxamide, 8-[(2-chloro-3-nitrobenzoyl)amino]-1-[4-(methylsulfonyl)phenyl]-4,5-dihydro-1H-benzo[g]indazole-3-carboxamide, 8-[(5-bromo-2-chlorobenzoyl)amino]-1-[4-(methylsulfonyl)phenyl]-4,5-dihydro-1H-benzo[g]indazole-3-carboxamide, 8-{[2-chloro-5-(methylthio)benzoyl]amino}-1-[4-(methylsulfonyl)phenyl]-4,5-dihydro-1H-benzo[g]indazole-3-carboxamide, 8-{[(2-chloro-6-methylpyridin-3-yl)carbonyl]amino}-1-[4-(methylsulfonyl)phenyl]-4,5-dihydro-1H-benzo[g]indazole-3-carboxamide, 8-[(5-chloro-2-nitrobenzoyl)amino]-1-[4-(methylsulfonyl)phenyl]-4,5-dihydro-1H-benzo[g]indazole-3-carboxamide, 8-(benzoylamino)-1-[4-(methylsulfonyl)phenyl]-4,5-dihydro-1H-benzo[g]indazole-3-carboxamide, 1-[4-(methylsulfonyl)phenyl]-8-{[2-(methylthio)benzoyl]amino}-4,5-dihydro-1H-benzo[g]indazole-3-carboxamide, 8-[(3-methoxybenzoyl)amino]-1-[4-(methylsulfonyl)phenyl]-4,5-dihydro-1H-benzo[g]indazole-3-carboxamide, 8-[(4-methoxybenzoyl)amino]-1-[4-(methylsulfonyl)phenyl]-4,5-dihydro-1H-benzo[g]indazole-3-carboxamide, 8-[(4-cyanobenzoyl)amino]-1-[4-(methylsulfonyl)phenyl]-4,5-dihydro-1H-benzo[g]indazole-3-carboxamide, 8-{[(3,7-dimethylimidazo[1,2-a]pyridin-2-yl)carbonyl]amino}-1-[4-(methylsulfonyl)phenyl]-4,5-dihydro-1H-benzo[g]indazole-3-carboxamide, 8-{[(2-methylpyridin-3-yl)carbonyl]amino}-1-[4-(methylsulfonyl)phenyl]-4,5-dihydro-1H-benzo[g]indazole-3-carboxamide, 8-[(2,3-difluorobenzoyl)amino]-1-[4-(methylsulfonyl)phenyl]-4,5-dihydro-1H-benzo[g]indazole-3-carboxamide, 1-[4-(methylsulfonyl)phenyl]-8-[(2-nitrobenzoyl)amino]-4,5-dihydro-1H-benzo[g]indazole-3-carboxamide, 3-[({3-(aminocarbonyl)-1-[4-(methylsulfonyl)phenyl]-4,5-dihydro-1H-benzo[g]indazol-8-yl}amino)carbonyl]-2-methylphenyl acetate, 8-{[2-chloro-5-(methylsulfonyl)benzoyl]amino}-1-[4-(methylsulfonyl)phenyl]-4,5-dihydro-1H-benzo[g]indazole-3-carboxamide, 8-[(3-chloro-2-fluorobenzoyl)amino]-1-[4-(methylsulfonyl)phenyl]-4,5-dihydro-1H-benzo[g]indazole-3-carboxamide, 8-{[(4-chloropyridin-3-yl)carbonyl]amino}-1-[4-(methylsulfonyl)phenyl]-4,5-dihydro-1H-benzo[g]indazole-3-carboxamide 8-[(2,3-dimethylbenzoyl)amino]-1-[4-(methylsulfonyl)phenyl]-4,5-dihydro-1H-benzo[g]indazole-3-carboxamide, 8-[(2-chloro-4,5-dimethoxybenzoyl)amino]-1-[4-(methylsulfonyl)phenyl]-4,5-dihydro-1H-benzo[g]indazole-3-carboxamide, 1-[4-(methylsulfonyl)phenyl]-8-[(2-nitrobenzoyl)amino]-4,5-dihydro-1H-benzo[g]indazole-3-carboxamide, 8-[(2-chloro-4-nitrobenzoyl)amino]-1-[4-(methylsulfonyl)phenyl]-4,5-dihydro-1H-benzo[g]indazole-3-carboxamide, 8-[(5-methoxy-2-nitrobenzoyl)amino]-1-[4-(methylsulfonyl)phenyl]-4,5-dihydro-1H-benzo[g]indazole-3-carboxamide, 3-[({3-(aminocarbonyl)-1-[4-(methylsulfonyl)phenyl]-4,5-dihydro-1H-benzo[g]indazol-8-yl}amino)carbonyl]-4-nitrophenyl thiocyanate, 8-[(4,5-difluoro-2-nitrobenzoyl)amino]-1-[4-(methylsulfonyl)phenyl]-4,5-dihydro-1H-benzo[g]indazole-3-carboxamide, 8-[(4,5-dimethoxy-2-nitrobenzoyl)amino]-1-[4-(methylsulfonyl)phenyl]-4,5-dihydro-1H-benzo[g]indazole-3-carboxamide, 8-[(5-fluoro-2-nitrobenzoyl)amino]-1-[4-(methylsulfonyl)phenyl]-4,5-dihydro-1H-benzo[g]indazole-3-carboxamide, 1-[4-(methylsulfonyl)phenyl]-8-{[2-nitro-4-(trifluoromethyl)benzoyl]amino}-4,5-dihydro-1H-benzo[g]indazole-3-carboxamide, 8-[(5-methyl-2-nitrobenzoyl)amino]-1-[4-(methylsulfonyl)phenyl]-4,5-dihydro-1H-benzo[g]indazole-3-carboxamide, 8-[(3-methyl-2-nitrobenzoyl)amino]-1-[4-(methylsulfonyl)phenyl]-4,5-dihydro-1H-benzo[g]indazole-3-carboxamide, 8-[(2,4-dinitrobenzoyl)amino]-1-[4-(methylsulfonyl)phenyl]-4,5-dihydro-1H-benzo[g]indazole-3-carboxamide, 8-[(3-methylbenzoyl)amino]-1-[4-(methylsulfonyl)phenyl]-4,5-dihydro-1H-benzo[g]indazole-3-carboxamide, 8-{[(3-methoxyphenyl)acetyl]amino}-1-[4-(methylsulfonyl)phenyl]-4,5-dihydro-1H-benzo[g]indazole-3-carboxamide, 1-[4-(methylsulfonyl)phenyl]-8-[(phenylacetyl)amino]-4,5-dihydro-1H-benzo[g]indazole-3-carboxamide, 8-[(3-hydroxy-2-methylbenzoyl)amino]-1-[4-(methylsulfonyl)phenyl]-4,5-dihydro-1H-benzo[g]indazole-3-carboxamide, 8-[(2,5-dichlorobenzoyl)amino]-1-[4-(methylsulfonyl)phenyl]-4,5-dihydro-1H-benzo[g]indazole-3-carboxamide, 8-[(2-aminobenzoyl)amino]-1-[4-(methylsulfonyl)phenyl]-4,5-dihydro-1H-benzo[g]indazole-3-carboxamide, 8-(L-histidylamino)-1-[4-(methylsulfonyl)phenyl]-4,5-dihydro-1H-benzo[g]indazole-3-carboxamide,
8-(isonicotinoylamino)-1-[4-(methylsulfonyl)phenyl]-4,5-dihydro-1H-benzo[g]indazole-3-carboxamide,
8-[(2-chloro-5-nitrobenzoyl)amino]-1-[4-(methylsulfonyl)phenyl]-4,5-dihydro-1H-benzo[g]indazole-3-carboxamide,
8-[(5-amino-2-chlorobenzoyl)amino]-1-[4-(methylsulfonyl)phenyl]-4,5-dihydro-1H-benzo[g]indazole-3-carboxamide hydrochloride,
8-[(3-amino-4-chlorobenzoyl)amino]-1-[4-(methylsulfonyl)phenyl]-4,5-dihydro-1H-benzo[g]indazole-3-carboxamide,
8-[(4-amino-2-chlorobenzoyl)amino]-1-[4-(methylsulfonyl)phenyl]-4,5-dihydro-1H-benzo[g]indazole-3-carboxamide,
8-[(2-amino-5-chlorobenzoyl)amino]-1-[4-(methylsulfonyl)phenyl]-4,5-dihydro-1H-benzo[g]indazole-3-carboxamide,
8-[(3-amino-2-chlorobenzoyl)amino]-1-[4-(methylsulfonyl)phenyl]-4,5-dihydro-1H-benzo[g]indazole-3-carboxamide,
8-[(2-amino-4-chlorobenzoyl)amino]-1-[4-(methylsulfonyl)phenyl]-4,5-dihydro-1H-benzo[g]indazole-3-carboxamide,
8-[(2-amino-3-chlorobenzoyl)amino]-1-[4-(methylsulfonyl)phenyl]-4,5-dihydro-1H-benzo[g]indazole-3-carboxamide,
8-({2-chloro-5-[(N,N-dimethylglycyl)amino]benzoyl}amino)-1-[4-(methylsulfonyl)phenyl]-4,5-dihydro-1H-benzo[g]indazole-3-carboxamide hydrochloride,
8-{[2-chloro-5-(dimethylamino)benzoyl]amino}-1-[4-(methylsulfonyl)phenyl]-4,5-dihydro-1H-benzo[g]indazole-3-carboxamide,
8-[(5-azido-2-nitrobenzoyl)amino]-1-[4-(methylsulfonyl)phenyl]-4,5-dihydro-1H-benzo[g]indazole-3-carboxamide,
8-[(4-azidobenzoyl)amino]-1-[4-(methylsulfonyl)phenyl]-4,5-dihydro-1H-benzo[g]indazole-3-carboxamide,
8-{[(2,5-dichloropyridin-3-yl)carbonyl]amino}-1-[4-(methylsulfonyl)phenyl]-4,5-dihydro-1H-benzo[g]indazole-3-carboxamide,
8-{[2-chloro-5-(methylsulfinyl)benzoyl]amino}-1-[4-(methylsulfonyl)phenyl]-4,5-dihydro-1H-benzo[g]indazole-3-carboxamide, and
8-{[(6-chloro-1,3-benzodioxol-5-yl)carbonyl]amino}-1-[4-(methylsulfonyl)phenyl]-4,5-dihydro-1H-benzo[g]indazole-3-carboxamide.

22. The method of claim 1 wherein said compound is a compound of the formula

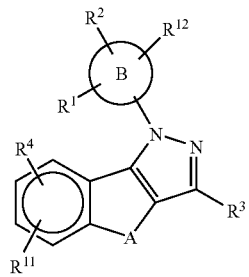

wherein
A is $(CH_2)_m$; wherein each $CH_2$ may be independently substituted with one or more substitution selected from the group consisting of: aryl, heteroaryl, alkanoyl, hydroxy, halogen, alkoxy, lower alkyl, amino, aminoalkyl, alkylamino, alkenyl, and alkynyl;
m is 1 to 4;
B is a 5 or 6 membered heteroaryl, aryl, saturated or unsaturated heterocyclic wherein said aryl, heteroaryl, or heterocyclic are optionally substituted with $R^1$, $R^2$, and $R^{12}$;
$R^1$ is halogen;
$R^2$ is selected from halogen, or hydrido;
$R^3$ is selected from the group consisting of: substituted or unsubstituted amidine, alkylamino, aminoalkyl, $CONHR^7$, $NH_2$, $NHCOR^6$, and $CH_2NHCOR^6$;
$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;
$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;
$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;
$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;
$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;
$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from hydrido or halogen;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, carriers, prodrugs, or pharmaceutically acceptable salts thereof.

23. The method of claim 22 wherein said compound is selected from the group consisting of:

8-{[2-chloro-5-(methylsulfinyl)benzoyl]amino}-1-(4-fluorophenyl)-4,5-dihydro-1H-benzo[g]indazole-3-carboxamide, 8-{[(2,5-dichloropyridin-3-yl)carbonyl]amino}-1-(4-fluorophenyl)-4,5-dihydro-1H-benzo[g]indazole-3-carboxamide, 8-[(2,5-dichloroisonicotinoyl)amino]-1-(4-fluorophenyl)-4,5-dihydro-1H-benzo[g]indazole-3-carboxamide, 8-{[(6-chloro-1,3-benzodioxol-5-yl)carbonyl]amino}-1-(4-fluorophenyl)-4,5-dihydro-1H-benzo[g]indazole-3-carboxamide, 8-{[(2-chloropyridin-3-yl)carbonyl]amino}-1-(3,4-difluorophenyl)-4,5-dihydro-1H-benzo[g]indazole-3-carboxamide, 8-{[(2-chloropyridin-3-yl)carbonyl]amino}-1-(4-fluorophenyl)-4,5-dihydro-1H-benzo[g]indazole-3-carboxamide, 8-{[2-chloro-4-(methylsulfonyl)benzoyl]amino}-1-(4-fluorophenyl)-4,5-dihydro-1H-benzo[g]indazole-3-carboxamide, 8-{[(2-chloro-6-methylpyridin-3-yl)carbonyl]amino}-1-(4-fluorophenyl)-4,5-dihydro-1H-benzo[g]indazole-3-carboxamide, 8-[(3-chloroisonicotinoyl)amino]-1-(4-fluorophenyl)-4,5-dihydro-1H-benzo[g]indazole-3-carboxamide hydrochloride, 8-[(3-amino-2-chlorobenzoyl)amino]-1-(4-fluorophenyl)-4,5-dihydro-1H-benzo[g]indazole-3-carboxamide, 8-{[(2-chloropyridin-3-yl)carbonyl]amino}-1-(2,4-difluorophenyl)-4,5-dihydro-1H-benzo[g]indazole-3-carboxamide, 8-[(2-chlorobenzoyl)amino]-1-(4-fluorophenyl)-4,5-dihydro-1H-benzo[g]indazole-3-carboxamide, 1-(4-fluorophenyl)-8-[(3-hydroxy-2-methylbenzoyl)amino]-4,5-dihydro-1H-benzo[g]indazole-3-carboxamide, 8-[(2-chlorobenzoyl)amino]-1-(2,4-difluorophenyl)-4,5-dihydro-1H-benzo[g]indazole-3-carboxamide, 8-[(4-amino-2-chlorobenzoyl)amino]-1-(4-fluorophenyl)-4,5-dihydro-1H-benzo[g]indazole-3-carboxamide, 8-[(2-chloro-4-methoxybenzoyl)amino]-1-(4-fluorophenyl)-4,5-dihydro-1H-benzo[g]indazole-3-carboxamide, 8-({[2-chloro-6-(trifluoromethyl)pyridin-3-yl]carbonyl}amino)-1-(4-fluorophenyl)-4,5-dihydro-1H-benzo[g]indazole-3-carboxamide, 8-{[2-chloro-5-(methylthio) benzoyl]amino}-1-(4-fluorophenyl)-4,5-dihydro-1H-benzo[g]indazole-3-carboxamide, 8-[(5-amino-2-chlorobenzoyl)amino]-1-(4-fluorophenyl)-4,5-dihydro-1H-benzo[g]indazole-3-carboxamide, 8-{[2-chloro-5-(dimethylamino)benzoyl]amino}-1-(4-fluorophenyl)-4,5-dihydro-1H-benzo[g]indazole-3-carboxamide, 8-[(2-chlorobenzoyl)amino]-1-(3,4-difluorophenyl)-4,5-dihydro-1H-benzo[g]indazole-3-carboxamide, 8-[(2,3-dichlorobenzoyl)amino]-1-(4-fluorophenyl)-4,5-dihydro-1H-benzo[g]indazole-3-carboxamide, 8-[(2-chloro-4,5-dimethoxybenzoyl)amino]-1-(4-fluorophenyl)-4,5-dihydro-1H-benzo[g]indazole-3-carboxamide, 1-(4-fluorophenyl)-8-[(2-methylbenzoyl)amino]-4,5-dihydro-1H-benzo[g]indazole-3-carboxamide, 8-[(2-chloro-3-nitrobenzoyl)amino]-1-(4-fluorophenyl)-4,5-dihydro-1H-benzo[g]indazole-3-carboxamide, 1-(4-fluorophenyl)-8-[(methylsulfonyl)amino]-4,5-dihydro-1H-benzo[g]indazole-3-carboxamide, 8-[(2-chlorobenzoyl)amino]-1-(3-chloro-4-fluorophenyl)-4,5-dihydro-1H-benzo[g]indazole-3-carboxamide, and 1-(4-fluorophenyl)-8-(isonicotinoylamino)-4,5-dihydro-1H-benzo[g]indazole-3-carboxamide.

24. The method of claim 1 wherein said compound is selected from the group consisting of:

8-[(2-chlorobenzoyl)amino]-1-(3-fluorophenyl)-4,5-dihydro-1H-benzo[g]indazole-3-carboxamide, 8-{[(2-chloropyridin-3-yl)carbonyl]amino}-1-(3-fluorophenyl)-4,5-dihydro-1H-benzo[g]indazole-3-carboxamide, 1-{4-[(allylamino)sulfonyl]phenyl}-8-[(2-chlorobenzoyl) amino]-4,5-dihydro-1H-benzo[g]indazole-3-carboxamide, 8-[(5-amino-2-chlorobenzoyl)amino]-1-[4-(ethylsulfonyl)phenyl]-4,5-dihydro-1H-benzo[g]indazole-3-carboxamide, 8-[(2-chlorobenzoyl)amino]-1-[4-(isopropylsulfonyl) phenyl]-4,5-dihydro-1H-benzo[g]indazole-3-carboxamide, 8-[(2-chlorobenzoyl)amino]-1-{4-[(1E)-3-hydroxybut-1-enyl]phenyl}-4,5-dihydro-1H-benzo[g]indazole-3-carboxamide, 8-{[5-(acetylamino)-2-chlorobenzoyl]amino}-1-[4-(ethylsulfonyl)phenyl]-4,5-dihydro-1H-benzo[g]indazole3-carboxamide, 8-{[(2-chloropyridin-3-yl)carbonyl]amino}-1-[4-(3-hydroxyprop-1-ynyl)phenyl]-4,5-dihydro-1H-benzo[g]indazole-3-carboxamide, 8-[(2-chlorobenzoyl)amino]-1-[4-(ethylsulfonyl)phenyl]-4,5-dihydro-1H-benzo[g]indazole-3-carboxamide, 8-[(2-chlorobenzoyl)amino]-1-{4-[(dimethylamino)sulfonyl]phenyl}-4,5-dihydro-1H-benzo[g]indazole-3-carboxamide, 1-[4-(aminosulfonyl)phenyl]-8-[(4-azidobenzoyl)amino]-4,5-dihydro-1H-benzo[g]indazole-3-carboxamide, 8-{[(2-chloropyridin-3-yl)carbonyl]amino}-1-(3,5-difluorophenyl)-4,5-dihydro-1H-benzo[g]indazole-3-carboxamide, 1-(4-aminophenyl)-8-[(2-chlorobenzoyl)amino]-4,5-dihydro-1H-benzo[g]indazole-3-carboxamide, 1-(3-aminophenyl)-8-[(2-chlorobenzoyl)amino]-4,5-dihydro-1H-benzo[g]indazole-3-carboxamide, 8-[(2-chlorobenzoyl)amino]-1-{4-[(2-chlorobenzoyl) amino]phenyl}-4,5-dihydro-1H-benzo[g]indazole-3-carboxamide, 8-[(2-chlorobenzoyl)amino]-1-[4-(1H-pyrrol-1-yl)phenyl]-4,5-dihydro-1H-benzo[g]indazole-3-carboxamide, 1-(4-{[(benzyloxy)acetyl]amino}phenyl)-8-[(2-chlorobenzoyl)amino]-4,5-dihydro-1H-benzo[g]indazole-3-carboxamide, 8-[(2-chlorobenzoyl)amino]-1-{4-[(5-{[(2,2-dimethylpropanoyl)oxy]amino}pentanoyl)amino]phenyl}-4,5-dihydro-1H-benzo[g]indazole-3-carboxamide, 8-[(2-chlorobenzoyl)amino]-1-[4-({[2-(dimethylamino) ethyl]amino}carbonyl)phenyl]-4,5-dihydro-1H-benzo[g]indazole-3-carboxamide hydrochloride, 1-(6-aminopyridin-3-yl)-8-[(3-chloroisonicotinoyl) amino]-4,5-dihydro-1H-benzo[g]indazole-3-carboxamide, 8-[(3-chloroisonicotinoyl)amino]-1-thien-2-yl-4,5-dihydro-1H-benzo[g]indazole-3-carboxamide, 8-[(3-chloroisonicotinoyl)amino]-1-thien-3-yl-4,5-dihydro-1H-benzo[g]indazole-3-carboxamide, 1-[4-(butylsulfonyl)phenyl]-8-[(2-chlorobenzoyl)amino]-4,5-dihydro-1H-benzo[g]indazole-3-carboxamide, 8-amino-1-[4-(ethylsulfonyl)phenyl]-4,5-dihydro-1H-benzo[g]indazole-3-carboxamide, 8-amino-1-[4-(propylsulfonyl)phenyl]-4,5-dihydro-1H-benzo[g]indazole-3-carboxamide, tert-butyl 3-[({3-(aminocarbonyl)-1-[4-(propylsulfonyl) phenyl]-4,5-dihydro-1H-benzo[g]indazol-8-yl}amino) carbonyl]-4-chlorophenylcarbamate, 8-[(2-chlorobenzoyl)amino]-1-{4-[(cyclopropylmethyl) sulfonyl]phenyl}-4,5-dihydro-1H-benzo[g]indazole-3-carboxamide, 8-[(2-chlorobenzoyl)amino]-1-[4-(methylsulfinyl)phenyl]-4,5-dihydro-1H-benzo[g]indazole-3-carboxamide, 8-[(2-chlorobenzoyl)amino]-1-(4-hydroxyphenyl)-4,5-dihydro-1H-benzo[g]indazole-3-carboxamide, 1-{4-[(1E)-3-amino-3-oxoprop-1-enyl]phenyl}-8-[(2-chlorobenzoyl)amino]-4,5-dihydro-1H-benzo[g]indazole-3-carboxamide, 8-[(2-chlorobenzoyl)amino]-1-(3-chlorophenyl)-4,5-dihydro-1H-benzo[g]indazole-3-carboxamide, 8-[(5-amino-2-chlorobenzoyl)amino]-1-[4-(propylsulfonyl)phenyl]-4,5-dihydro-1H-benzo[g]inazole-3-carboxamide trifluoroacetate, 8-[(2-chlorobenzoyl)amino]-1-phenyl-4,5-dihydro-1H-benzo[g]indazole-3-carboxamide, 8-[(2-chlorobenzoyl)amino]-1-(4-cyanophenyl)-4,5-dihydro-1H-benzo[g]indazole-3-carboxamide, 8-{[(6-chloro-1,3-benzodioxol-5-yl)carbonyl]amino}-1-(3-hydroxyphenyl)-4,5-dihydro-1H-benzo[g]indazole-3-carboxamide, 8-[(2-chlorobenzoyl)amino]-1-{4-[(methylamino)sulfonyl]phenyl}-4,5-dihydro-1H-benzo[g]indazole-3-carboxamide, 1-[4-(aminosulfonyl)phenyl]-8-[(1H-indol-2-ylcarbonyl) amino]-4,5-dihydro-1H-benzo[g]indazole-3-carboxamide, 8-[(2-chlorobenzoyl)amino]-1-{4-[(1E)-3-hydroxy-3-methylbut-1-enyl]phenyl}-4,5dihydro-1H-benzo[g]indazole-3-carboxamide, 8-[(5-amino-2-chlorobenzoyl)amino]-1-[4-(propylsulfonyl)phenyl]-4,5-dihydro-1H-benzo[g]indazole-3-carboxamide hydrochloride, 1-[4-(aminosulfonyl)phenyl]-8-[(methylsulfonyl)amino]-4,5-dihydro-1H-benzo[g]indazole-3-carboxamide, 8[(2-chlorobenzoyl)amino]-1-[4-(2,3-dihydroxypropoxy) phenyl]-4,5-dihydro-1H-benzo[g]indazole-3-carboxamide, 1-[4-(aminosulfonyl)phenyl]-8-{[(2-methylpyridin-3-yl) carbonyl]amino}-4,5-dihydro-1H-benzo[g]indazole3-carboxamide, 8[(2-chlorobenzoyl)amino]-1-(3-hydroxyphenyl)-4,5-dihydro-1H-benzo[g]indazole-3-carboxamide, 8-[(2-chlorobenzoyl)amino]-1-{4-[(methylsulfonyl) amino]phenyl}-4,5-dihydro-1H-benzo[g]indazole-3-carboxamide, 8-[(2-chlorobenzoyl)amino]-1-[4-(propylsulfonyl)phenyl]-4,5-dihydro-1H-benzo[g]indazole-3-carboxamide, 8-[(2-chlorobenzoyl)amino]-1-[4-(3-oxobutyl)phenyl]-4,5-dihydro-1H-benzo[g]indazole-3-carboxamide, 8-[(2-chlorobenzoyl)amino]-1-{4-[(E)-2-(methylsulfonyl)ethenyl]phenyl}-4,5-dihydro-1H-benzo[g]indazole-3-carboxamide, 8-[(2-chlorobenzoyl)amino]-1-{4-[(1E)-4-hydroxybut-1-enyl]phenyl}-4,5-dihydro-1H-benzo[g]indazole-3-carboxamide, 8-[(2-chlorobenzoyl)amino]-1-[4-(4-hydroxy-3-oxobutyl)phenyl]-4,5-dihydro-1H-benzo[g]indazole-3-carboxamide, 8-{[(2-chloropyridin-3-yl)carbonyl]amino}-1-{4-[(1Z)-3-hydroxyprop-1-enyl]phenyl}-4,5-dihydro-1H-benzo[g]indazole-3-carboxamide, 8-{[(2-chloropyridin-3-yl)carbonyl]amino}-1-{4-[(1E)-3-(methylamino)-3-oxoprop-1enyl]phenyl}-4,5-dihydro-1H-benzo[g]indazole-3-carboxamide, 8-{[(2-chloropyridin-3-yl)carbonyl]amino}-1-[4-(3-oxobutyl)phenyl]-4,5-dihydro-1H-benzo[g]indazole-3-carboxamide, 1-{4-[(1E)-3-amino-3-oxoprop-1-enyl]phenyl}-8-{[(2-chloropyridin-3-yl)carbonyl]amino}-4,5-dihydro-1H-benzo[g]indazole-3-carboxamide, 8-{[(2-chloropyridin-3-yl)carbonyl]amino}-1-{4-[(1E)-3-hydroxy-3-methylbut-1-enyl]phenyl}-4,5-dihydro-1H-benzo[g]indazole-3-carboxamide, 8-{[(2-chloropyridin-3-yl)carbonyl]amino}-1-{4-[(1E)-3-(dimethylamino)-3-oxoprop-1-enyl]phenyl}-4,5-dihydro-1H-benzo[g]indazole-3-carboxamide, 8-[(methylsulfonyl)amino]-1-[4-(3-oxobutyl)phenyl]-4,5-dihydro-1H-benzo[g]indazole-3-carboxamide, 1-{4-[(1E)-3-(methylamino)-3-oxoprop-1-enyl]phenyl}-8-[(methylsulfonyl)amino]-4,5-dihydro-1H-benzo[g]indazole-3-carboxamide, 8-[(2-chlorobenzoyl)amino]-1-{4-[(1E)-3-(dimethylamino)prop-1-enyl]phenyl}-4,5-dihydro-1H-benzo[g]indazole-3-carboxamide hydrochloride, 8-[(2-chlorobenzoyl)amino]-1-(4-{(1E)-3-[(2-methoxyethyl)amino]-3-oxoprop-1-enyl}phenyl)-4,5-dihydro-1H-benzo[g]indazole-3-carboxamide, 8-[(2-chlorobenzoyl)amino]-1-(4-{(1E)-3-[(2-furylmethyl)amino]-3-oxoprop-1-enyl}phenyl)-4,5-dihydro-1H-benzo[g]indazole-3-carboxamide, 8-[(2-chlorobenzoyl)amino]-1-{4-[(1E)-3-(methylamino)-3-oxoprop-1-enyl]phenyl}-4,5-dihydro-1H-benzo[g]indazole-3-carboxamide, 8-[(2-chlorobenzoyl)amino]-1-{4-[(1E)-3-(ethylamino)-3-oxoprop-1-enyl]phenyl}-4,5-dihydro-1H-benzo[g]indazole-3-carboxamide, 1-{4-[(1E)-3-(benzylamino)-3-oxoprop-1-enytlphenyl]-8-[(2-chlorobenzoyl)amino]-4,5-dihydro-1H-benzo[g]indazole-3-carboxamide, 8-amino-1-{4-[(1E)-3-(methylamino)-3-oxoprop-1-enyl]phenyl}-4,5-dihydro-1H-benzo[g]indazole-3-carboxamide, 1-{4-[(1E)-3-(dimethylamino)-3-oxoprop-1-enyl]phenyl}-8-[(methylsulfonyl)amino]-4,5-dihydro-1H-benzo[g]indazole-3-carboxamide, 8-[(2-chlorobenzoyl)amino]-1-[4-({[2-(dimethylamino)ethyl]amino}sulfonyl)phenyl]-4,5-dihydro-1H-benzo[g]indazole-3-carboxamide methanesulfonate, 8-[(2-chloro-5-nitrobenzoyl)amino]-1-(4-hydroxyphenyl)-4,5-dihydro-1H-benzo[g]indazole-3-carboxamide, 1-[4-(acetylamino)phenyl]-8-[(2-chlorobenzoyl)amino]-4,5-dihydro-1H-benzo[g]indazole-3-carboxamide, 8-[(2-chlorobenzoyl)amino]-1-(3-methylphenyl)-4,5-dihydro-1H-benzo[g]indazole-3-carboxamide, 8-[(5-amino-2-chlorobenzoyl)amino]-1-(4-hydroxyphenyl)-4,5-dihydro-1H-benzo[g]indazole-3-carboxamide, 8-[(2,3-dichlorobenzoyl)amino]-1-(3-fluorophenyl)-4,5-dihydro-1H-benzo[g]indazole-3-carboxamide, 8-{[(2-chloropyridin-3-yl)carbonyl]amino}-1-(4-hydroxyphenyl)-4,5-dihydro-1H-benzo[g]indazole-3-carboxamide, 8-{[(6-chloro-1,3-benzodioxol-5-yl)carbonyl]amino}-1-(4-hydroxyphenyl)-4,5-dihydro-1H-benzo[g]indazole-3-carboxamide, (2E)-3-(4-{3-(aminocarbonyl)-8-[(2-chlorobenzoyl)amino]-4,5-dihydro-1H-benzo[g]indazol-1-yl}phenyl)prop-2-enoic acid, 8-[(2-chlorobenzoyl)amino]-1-{4-[(E)-2-(1H-imidazol-1-yl)ethenyl]phenyl}-4,5-dihydro-1H-benzo[g]indazole-3-carboxamide, 8-[(2-chlorobenzoyl)amino]-1-(2-fluorophenyl)-4,5-dihydro-1H-benzo[g]indazole-3-carboxamide, 1-[4-(aminosulfonyl)phenyl]-8-[(3-formylbenzoyl)amino]-4,5-dihydro-1H-benzo[g]indazole-3-carboxamide, 1-[4-(aminosulfonyl)phenyl]-8-({[2-(methylamino)pyridin-3-yl]carbonyl}amino)-4,5-dihydro-1H-benzo[g]indazole-3-carboxamide, 8-{[2-chloro-5-(methylsulfinyl)benzoyl]amino}-1-(4-hydroxyphenyl)-4,5-dihydro-1H-benzo[g]indazole-3-carboxamide, 8-[(2-chlorobenzoyl)amino]-1-(4-methylphenyl)-4,5-dihydro-1H-benzo[g]indazole-3-carboxamide, 8-[(2-chlorobenzoyl)amino]-1-(4-nitrophenyl)-4,5-dihydro-1H-benzo[g]indazole-3-carboxamide, 8-[(2-chlorobenzoyl)amino]-1-{4-[(methoxyacetyl)amino]phenyl}-4,5-dihydro-1H-benzo[g]indazole-3-carboxamide, 8-[(2-chlorobenzoyl)amino]-1-(3,5-difluorophenyl)-4,5-dihydro-1H-benzo[g]indazole-3-carboxamide, 8-[(2-chlorobenzoyl)amino]-1-[4-(2-morpholin-4-ylethoxy)phenyl]-4,5-dihydro-1H-benzo[g]indazole-3-carboxamide, 8-{[(2-chloropyridin-3-yl)carbonyl]amino}-1-[4-(ethylsulfonyl)phenyl]-4,5-dihydro-1H-benzo[g]indazole-3-carboxamide, 8-{[(2-chloropyridin-3-yl)carbonyl]amino}-1-(4-vinylphenyl)-4,5-dihydro-1H-benzo[g]indazole-3-carboxamide, 1-(4-acetylphenyl)-8-{[(2-chloropyridin-3-yl)carbonyl]amino}-4,5-dihydro-1H-benzo[g]indazole-3-carboxamide, 8-{1(2-chloropyridin-3-yl)carbonyl]amino}-1-[4-(1-hydroxyethyl)phenyl]-4,5-dihydro-1H-benzo[g]indazole-3-carboxamide, 1-[4-(aminosulfonyl)phenyl]-8-[({2-[(2-hydroxyethyl)amino]pyridin-3-yl}carbonyl)amino]-4,5-dihydro-1H-benzo[g]indazole-3-carboxamide, 8-[(2-chlorobenzoyl)amino]-1-{4-[(2,2-dimethyl-1,3-dioxolan-4-yl)methoxy]phenyl}-4,5-dihydro-1H-benzo[g]indazole-3-carboxamide, 8-[(2-chlorobenzoyl)amino]-1-(4-chlorophenyl)-4,5-dihydro-1H-benzo[g]indazole-3-carboxamide, 1-[4-(aminosulfonyl)phenyl]-8-({[2-(isopropylamino)pyridin-3-yl]carbonyl}amino)-4,5-dihydro-1H-benzo[g]indazole-3-carboxamide, 1-{4-[(3-aminopropyl)sulfony]phenyl}-8-{[(2-chloropyridin-3-yl)carbonyl]amino}-4,5-dihydro-1H-benzo[g]indazole-3-carboxamide hydrochloride, 8-amino-1-[4-(aminosulfonyl)phenyl]-4,5-dihydro-1H-benzo[g]indazole-3-carboxamide, 8-[(2-chlorobenzoyl)amino]-1-[4-(trifluoromethyl)phenyl]-4,5-dihydro-1H-benzo[g]indazole-3-carboxamide, 8-[(2-chiorobenzoyl)amino]-1-[4-({[2-(dimethylamino)ethyl]amino}sulfonyl)phenyl]-4,5-dihydro-1H-benzo[g]indazole-3-carboxamide, 1-(4-bromophenyl)-8-[(2-chlorobenzoyl)amino]-4,5-dihydro-1H-benzo[g]indazole-3-carboxamide, 1-{4-[(3-aminopropyl)sulfonyl]phenyl}-8-[(2-chlorobenzoyl)amino]-4,5-dihydro-1H-benzo[g]indazole-3-carboxamide hydrochloride, tert-butyl 3-[({3-(aminocarbonyl)-1-[4-(ethylsulfonyl) phenyl]-4,5-dihydro-1H-benzo[g]indazol-8-yl}amino) carbonyl]-4-chlorophenylcarbamate,
1-[4-(aminosulfonyl)phenyl]-8-[({2-[(2-methoxyethyl) amino]pyridin-3-yl}carbonyl)amino]-4,5-dihydro-1H-benzo[g]indazole-3-carboxamide,
8-[(2-chlorobenzoyl)amino]-1-(4-isopropylphenyl)-4,5-dihydro-1H-benzo[g]indazole-3-carboxamide,
8-{[(2-chloropyridin-3-yl)carbonyl]amino}-1-(4-morpholin-4-ylphenyl)-4,5-dihydro-1H-benzo[g]indazole-3-carboxamide,
1-(4-bromophenyl)-8-[(2-methylbenzoyl)amino]-4,5-dihydro-1H-benzo[g]indazole-3-carboxamide,
8-amino-1-(4-bromophenyl)-4,5-dihydro-1H-benzo[g]indazole-3-carboxamide,
8-[(2-chlorobenzoyl)amino]-1-(2,4-difluorophenyl)-4,5-dihydro-1H-benzo[g]indazole-3-carboxamide,
8-[(3-chloroisonicotinoyl)amino]-1-(3,4-difluorophenyl)-4,5-dihydro-1H-benzo[g]indazole-3-carboxamide,
8-[(3-chloroisonicotinoyl)amino]-1-(3,5-difluorophenyl)-4,5-dihydro-1H-benzo[g]indazole-3-carboxamide,
8-[(2-chlorobenzoyl)amino]-1-(3-chloro-4-fluorophenyl)-4,5-dihydro-1H-benzo[g]indazole-3-carboxamide,
8-amino-1-{4-[(trifluoromethyl)sulfonyl]phenyl}-4,5-dihydro-1H-benzo[g]indazole-3-carboxamide,
8-[(3-chloroisonicotinoyl)amino]-1-{4-[(trifluoromethyl)sulfonyl]phenyl}-4,5-dihydro-1H-benzo[g]indazole-3-carboxamide hydrochloride,
8-{[(2-chloropyridin-3-yl)carbonyl]amino}-1-{4-[(trifluoromethyl)sulfonyl]phenyl}-4,5-dihydro-1H-benzo[g]indazole-3-carboxamide,
1-(4-chlorophenyl)-8-{[(4-chloropyridin-3-yl)carbonyl] amino}-4,5-dihydro-1H-benzo[g]indazole-3-carboxamide,
8-[(2-chlorobenzoyl)amino]-1-(3-methoxyphenyl)-4,5-dihydro-1H-benzo[g]indazole-3-carboxamide,
8-[(2-chlorobenzoyl)amino]-1-[4-(methylthio)phenyl]-4,5-dihydro-1H-benzo[g]indazole-3-carboxamide,
1-[4-(aminosulfonyl)phenyl]-8-[({2-[(3-hydroxypropyl) amino]pyridin-3-yl}carbonyl)amino]-4,5-dihydro-1H-benzo[g]indazole-3-carboxamide,
8-({[2-(allylamino)pyridin-3-yl]carbonyl}amino)-1-[4-(aminosulfonyl)phenyl]-4,5-dihydro-1H-benzo[g]indazole-3-carboxamide hydrate,
1-[4-(benzoylamino)phenyl]-8-[(2-chlorobenzoyl) amino]-4,5-dihydro-1H-benzo[g]indazole-3-carboxamide,
8-[(2-chlorobenzoyl)amino]-1-{4-[(E)-(2-oxodihydrofuran-3(2H)-ylidene)methyl]phenyl}-4,5-dihydro-1H-benzo[g]indazole-3-carboxamide,
8-[(2-chlorobenzoyl)amino]-1-[3'-(hydroxymethyl)-1,1'-biphenyl-4-yl]-4,5-dihydro-1H-benzo[g]indazole-3-carboxamide,
1-(3'-amino-1,1'-biphenyl-4-yl)-8-[(2-chlorobenzoyl) amino]-4,5-dihydro-1H-benzo[g]indazole-3-carboxamide,
4'-{3-(aminocarbonyl)-8-[(2-chlorobenzoyl)amino]-4,5-dihydro-1H-benzo[g]indazol-1-yl}-1,1'-biphenyl-3-carboxylic acid,
4'-{3-(aminocarbonyl)-8-[(2-chlorobenzoyl)amino]-4,5-dihydro-1H-benzo[g]indazol-1-yl}-1,1'-biphenyl-4-carboxylic acid,
8-[(2-chlorobenzoyl)amino]-1-(3',4'-dimethoxy-1,1'-biphenyl-4-yl)-4,5-dihydro-1H-benzo[g]indazole-3-carboxamide,
1-[4-(benzyloxy)phenyl]-8-{[(2-chloropyridin-3-yl)carbonyl]amino}-4,5-dihydro-1H-benzo[g]indazole-3-carboxamide,
8-{[(2-chloropyridin-3-yl)carbonyl]amino}-1-[4-(propylsulfonyl)phenyl]-4,5-dihydro-1H-benzo[g]indazole-3-carboxamide,
8-[(2-chlorobenzoyl)amino]-1-(3,4-dichlorophenyl)-4,5-dihydro-1H-benzo[g]indazole-3-carboxamide,
8-[(2-chlorobenzoyl)amino]-1-(4-pyridin-3-ylphenyl)-4,5-dihydro-1H-benzo[g]indazole-3-carboxamide,
8-amino-1-[4-(trifluoromethyl)phenyl]-4,5-dihydro-1H-benzo[g]indazole-3-carboxamide,
ethyl(2E)-3-(4-{3-(aminocarbonyl)-8-[(2-chlorobenzoyl) amino]-4,5-dihydro-1H-benzo[g]indazol-1-yl}phenyl) prop-2-enoate,
4-{3-(aminocarbonyl)-8-[(2-chlorobenzoyl)amino]-4,5-dihydro-1H-benzo[g]indazol-1-yl}benzoic acid,
3-({[3-(aminocarbonyl)-1-(3-fluorophenyl)-4,5-dihydro-1H-benzo[g]indazol-8-yl]amino}carbonyl)-2-methyiphenyl acetate,
8-[(2-chlorobenzoyl)amino]-1-[4-(3-furyl)phenyl]-4,5-dihydro-1H-benzo[g]indazole-3-carboxamide,
8-[(2-chlorobenzoyl)amino]-1-[4-(trifluoromethoxy)phenyl]-4,5-dihydro-1H-benzo[g]indazole-3-carboxamide,
8-[(2,3-dichlorobenzoyl)amino]-1-(3,5-difluorophenyl)-4,5-dihydro-1H-benzo[g]indazole-3-carboxamide,
8-[(2,3-difluorobenzoyl)amino]-1-(3-fluorophenyl)-4,5-dihydro-1H-benzo[g]indazole-3-carboxamide,
8-[(methylsulfonyl)amino]-1-[4-(methylthio)phenyl]-4,5-dihydro-1H-benzo[g]indazole-3-carboxamide,
8-[(3-chloroisonicotinoyl)amino]-1-[4-(methylthio)phenyl]-4,5-dihydro-1H-benzo[g]indazole-3-carboxamide hydrochloride,
8-{[(6-chloro-1,3-benzodioxol-5-yl)carbonyl]amino}-1-[4-(methylthio)phenyl]-4,5-dihydro-1H-benzo[g]indazole-3-carboxamide,
8-[(5-amino-2-chlorobenzoyl)amino]-1-[4-(methylthio) phenyl]-4,5-dihydro-1H-benzo[g]indazole-3-carboxamide hydrochloride,
1-[4-(methylsulfinyl)phenyl]-8-[(methylsulfonyl)amino]-4,5-dihydro-1H-benzo[g]indazole-3-carboxamide,
8-[(3-chloroisonicotinoyl)amino]-1-[4-(methylsulfinyl) phenyl]-4,5-dihydro-1H-benzo[g]indazole-3-carboxamide hydrochloride,
8-{[(6-chloro-1,3-benzodioxol-5-yl)carbonyl]amino}-1-[4-(methylsulfinyl)phenyl]-4,5-dihydro-1H-benzo[g] indazole-3-carboxamide,
8-[(5-amino-2-chlorobenzoyl)amino]-1-[4-(methylsulfinyl)phenyl]-4,5-dihydro-1H-benzo[g]indazole-3-carboxamide hydrochloride,
8-[(2-chlorobenzoyl)amino]-1-[4-(methylsulfinyl)phenyl]-4,5-dihydro-1H-benzo[g]indazole-3-carboxamide,
8-{[(2-chloropyridin-3-yl)carbonyl]amino}-1-[4-(methylsulfinyl)phenyl]-4,5-dihydro-1H-benzo[g]indazole-3-carboxamide,
8-amino-1-[4-(2,5-dihydro-1H-pyrrol-1-ylsulfonyl)phenyl]-4,5-dihydro-1H-benzo[g]indazole-3-carboxamide,
8-amino-1-[4-(morpholin-4-ylsulfonyl)phenyl]-4,5-dihydro-1H-benzo[g]indazole-3-carboxamide,
8-amino-1-{4-[(diprop-2-ynylamino)sulfonyl]phenyl}-4,5-dihydro-1H-benzo[g]indazole-3-carboxamide,
1-{4-[(dimethylamino)sulfonyl]phenyl}-8-[(methylsulfonyl)amino]-4,5-dihydro-1H-benzo[g]indazole-3-carboxamide, 8-[(2-chlorobenzoyl)amino]-1-{4-[(dimethylamino)sulfonyl]phenyl}-4,5-dihydro-1H-benzo[g]indazole-3-carboxamide, 8-[(2-chlorobenzoyl)amino]-1-[4-({[2-(dimethylamino)ethyl]amino}sulfonyl)phenyl]-4,5-dihydro-1H-benzo[g]indazole-3-carboxamide, 8-[(3-chlorobenzoyl)amino]-1-{4-[(dimethylamino)sulfonyl]phenyl}-4,5-dihydro-1H-benzo[g]indazole-3-carboxamide, 8-(acetylamino)-1-{4-[(dimethylamino)sulfonyl]phenyl}-4,5-dihydro-1H-benzo[g]indazole-3-carboxamide, 1-{4-[(diallylamino)sulfonyl]phenyl}-8-[(methylsulfonyl)amino]-4,5-dihydro-1H-benzo[g]indazole-3-carboxamide, 8-[(2-chlorobenzoyl)amino]-1-{4-[(diprop-2-ynylamino)sulfonyl]phenyl}-4,5-dihydro-1H-benzo[g]indazole-3-carboxamide, and 8-amino-1-[4-({[2-(dimethylamino)ethyl]amino}sulfonyl)phenyl]-4,5-dihydro-1H-benzo[g]indazole-3-carboxamide.

25. The method of claim 1 wherein said compound is selected from the group consisting of:

8-[(2-chlorobenzoyl)amino]-1-[6-(methylsulfonyl)pyridin-3-yl]-4,5-dihydro-1H-benzo[g]indazole-3-carboxamide, 8-[(2-chlorobenzoyl)amino]-1-pyridin-4-yl-4,5-dihydro-1H-benzo[g]indazole-3-carboxamide, 8-[(2-chlorobenzoyl)amino]-1-[5-(methylsulfonyl)pyridin-2-yl]-4,5-dihydro-1H-benzo[g]indazole-3-carboxamide, 8-[(2-chlorobenzoyl)amino]-1-pyridin-3-yl-4,5-dihydro-1H-benzo[g]indazole-3-carboxamide methanesulfonate, 8-[(2-chlorobenzoyl)amino]-1-pyridin-4-yl-4,5-dihydro-1H-benzo[g]indazole-3-carboxamide methanesulfonate, and 8-[(2-chlorobenzoyl)amino]-1-pyridin-3-yl-4,5-dihydro-1H-benzo[g]indazole-3-carboxamide.

26. The method of claim 1 wherein said compound is selected from the group consisting of:

1-(1,3-benzodioxol-5-yl)-8-{[(2-chloropyridin-3-yl)carbonyl]amino}-5,5-dimethyl-4,5-dihydro-1H-benzo[g]indazole-3-carboxamide and 1-(1,3-benzodioxol-5-yl)-8-[(3-chloroisonicotinoyl)amino]-5,5-dimethyl-4,5-dihydro-1H-benzo[g]indazole-3-carboxamide.

27. The method of claim 1 wherein said compound is a compound of the formula

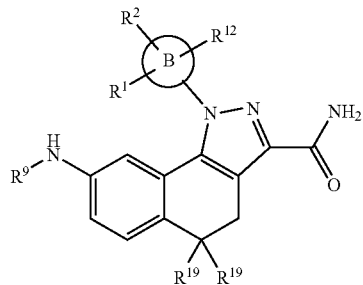

wherein

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COOF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $OON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, am inoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^9$ is selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylam inoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{12}$ is selected from the group consisting of: hydrido, halogen, alkyl, and alkoxy; and $R^{19}$ is independently selected from the group consisting of: hydroxy, halogen, alkoxy, lower alkyl, amino, aminoalkyl, alkylamino, alkenyl, and alkynyl;

or tautomers, carriers, prodrugs, or pharmaceutically acceptable salts thereof.

\* \* \* \* \*